United States Patent
Zonana et al.

(10) Patent No.: US 7,115,555 B2
(45) Date of Patent: Oct. 3, 2006

(54) HYPOHIDROTIC ECTODERMAL DYSPLASIA GENES AND PROTEINS

(75) Inventors: Jonathan Zonana, Portland, OR (US); Betsy M. Ferguson, Portland, OR (US); Denis Headon, Manchester (GB); Paul Overbeek, Houston, TX (US)

(73) Assignees: Baylor College of Medicine, Houston, TX (US); Oregon Health & Science University, Portland, OR (US)

( * ) Notice: Subject to any disclaimer, the term of this patent is extended or adjusted under 35 U.S.C. 154(b) by 522 days.

(21) Appl. No.: 09/729,658

(22) Filed: Dec. 4, 2000

(65) Prior Publication Data

US 2003/0023991 A1    Jan. 30, 2003

Related U.S. Application Data

(63) Continuation-in-part of application No. 09/342,681, filed on Jun. 29, 1999, now Pat. No. 6,355,782.

(60) Provisional application No. 60/112,366, filed on Dec. 15, 1998, provisional application No. 60/092,279, filed on Jul. 9, 1998.

(51) Int. Cl.
*A01N 37/18* (2006.01)
*C07K 16/00* (2006.01)
*C07K 14/00* (2006.01)
*A01K 67/00* (2006.01)

(52) U.S. Cl. .......................... 514/2; 530/390; 530/350; 800/8

(58) Field of Classification Search ................ 514/2; 530/390, 350; 800/8
See application file for complete search history.

(56) References Cited

U.S. PATENT DOCUMENTS 5,556,786 A   9/1996   Kere et al.
5,700,926 A   12/1997  Kere et al.
6,159,462 A * 12/2000  Matthews et al. ......... 424/85.1

OTHER PUBLICATIONS

Medline, Medical encylcopedia: Ectodermal dysplasia assessed May 12, 2004 at the nlm.nih.gov.*
Gaide and Schneider, Permanent correction of an inherited ectodermal dysplasia with recombinant EDA, Nature Medicine vol. (5), May 2003, pp. 614-618.*
Meng R.D. and El-Deiry, W.S. Tumor Suppressor Genes as Targets for Cancer Gene Therapy. 1999. Gene Therapy of Cancer,Chapter 1. pp. 3-18.*

Torchilin V.P. and Lukyanov A.N. Peptide and protein drug delviery to and itno tumors; challenges and solutions. DDT, Mar. 2003, vol. 8(6): p. 259-266.*
Drögemüller et al, X-linked anhidrotic ectodermal dysplasia (ED1) in men, mice, and cattle, Genet. Sel. Evol. 35 (Suppl. 1) (2003) S137-145.*
Smahi et al, The NF-KB signalling pathway in human disease, Human Molecular Genetics, 2002, vol. 11,No. 20, pp. 2371-2375.*
Headon & Overbeek, Involvement of a novel Tnf receptor homologue in hair follicle induction, Nature Genetics, vol. 22, 1999, pp. 370-374.*
Durmowicz,The EDA gene is atarget of, but does not regualte Wnt signaling, GENE, 2002, vol. 285, pp. 203-211.*
Ezer, S. et al.: "Anhidrotic ectodermal dysplasia (EDA) protein expressed in MCF-7 cells associates with cell membrane and induces rounding" Hum. Molec. Genetics, 1997, 6:1581-1587.
Ferguson, B. et al.: "Cloning of *Tabby*, the murine homolog of the human EDA gene: evidence for a membrane-associated protein with a short collagenous domain" Hum. Molec. Genetics, 1997, 6:1589-1594.
GenBank Accession No. AF004435.
Headon, D. et al.: "Involvement of a novel Tnf receptor homologue in hair follicle induction" Nature Genetics, 1999, 22:370-374.
Kere, J. et al.: "X-Linked anhidrotic (hypohidrotic) ectodermal dysplasia is caused by mutation in a novel transmembrane protein" Nature Genetics, 1996, 13:409-416.
Kumar, A. et al.: "Ectodermal dysplasia receptor activates the nuclear factor kappa B, c-Jun N-terminal kinase and cell death pathways and binds to ectodysplasmin A" J. Biol. Chem, 2000.
GenBank Accession No. U59227.
Majumder, K. et al.: "YAC rescue of downless locus mutations in mice" Mammalian Genome, 1998, 9:863-868.
Monreal, A. et al.: "Identification of a New Splice Form of the *EDA1* Gene Permits Detection of Nearly All X-Linked Hypohidrotic Ectodermal Dysplasia Mutations" Am. J. Hum. Genet., 1998, 63:380-389.
Pakula, et al.: "Genetic Analysis of Protein Stability and Function," Annu. Rev. Genet., 1989, 23:289-310.
Srivastava, A. et al.: "The Tabby phenotype is caused by mutation in a mouse homologue of the *EDA* gene that reveals novel mouse and human exons and encodes a protein (ectodysplasin-A) with collagenous domains" Proc. Natl. Acad. Sci. USA, 1997, 94:13069-13074.
GenBank Accession No. AF016628.
Yan, M. et al.: "Two-Amino Acid Molecular Switch in an Epithelial Morphogen That Regulates Binding to Two Distinct Receptors" Science, 2000, 290:523-527.

* cited by examiner

*Primary Examiner*—Dave Trong Nguyen
*Assistant Examiner*—Maria Marvich
(74) *Attorney, Agent, or Firm*—Klarquist Sparkman, LLP

(57) ABSTRACT

The DNA and amino acid sequences are disclosed for a ligand (EDA1-II) and receptor (dl in mice and DL in humans) involved in ectodermal dysplasia. Also disclosed are variant DNA and amino acid sequences, and therapeutic applications of the ligands and receptors.

10 Claims, 8 Drawing Sheets

```
EDA    1  MGYPEVERRELLPAAAPRERGSQGCGCGGAPARAGEGNSCL FLGFFGLSLALHLLTLCQ
TA        MGYPEVERREPLPAAAPRERGSQGCGCGGRGAPARAGEGNSCR LFLGFFGLSLALHLLTLCC
              *************************************   ******************

EDA   61  YLELRSELRRERGAESRLGGSGTPGTSGTLSSLGGLDPDSPITSHLGQPSPKQQPLEPGE
TA        YLELRSELRRERGTESRLGGPGAPGTSGTLSSPGSLDPVGPITRHLGQPSFQQQPLEPGE
          *************  ****  *  ******   * **  *** *****  *******

EDA  121  AALHSDSQDGHQ MALLNFFFPDEKPYSEEESRRVRRNKRSKSNEGADGPVKNKKGKKAG
TA        DPLPPESQDRHQ MALLNFFFPDEKAYSEEESRRVRRNKRSKSGEGADGPVKNKKGKKAG
             *  ****  *  *************  *********** ***************

EDA  181  PPGPNGPPGPPGPPGPQGPPGQGPPGIPGIPGTT VMGPPGPPGPPGPQGPPGPPGPGPSGAADK
TA        PPGPNGPPGPPGPPGPQGPPGQGPPGIPGIPGTT VMGPPGPPGPPGPQGPPGLQGPSGAADK
          ********************************* ***************      *******

EDA  241  AGTRENQPAVVHLQGQGSAIQVKNDLSGGVLNDWSRITMNPKVFKLHPRSGELEVLVDGT
TA        TGTRENQPAVVHLQGQGSAIQVKNDLSGGVLNDWSRITMNPKVFKLHPRSGELEVLVDGT
           ***********************************************************

EDA  301  YFIYSQVEVYYINFTDFASYEVVVDEKPFLQCTRSIETGKTNYNTCYTAGVCLLKARQKI
TA        YFIYSQVEVYYINFTDFASYEVVVDEKPFLQCTRSIETGKTNYNTCYTAGVCLLKARQKI
          ********************************************************* *

EDA  361  AVKMVHADISINMSKHTTFFGAIRLGEAPAS
TA        AVKMVHADISINMSKHTTFFGAIRLGEAPAS
          ******************************
```

FIG. 1

|       |   |   |   |   |   |   |   | • |   | • |   |   |   |   |
|-------|---|---|---|---|---|---|---|---|---|---|---|---|---|---|
|       | • |   |   |   |   |   | • | • |   | • |   | • |   |   |
| EDA   | L | E | V | L | V | D | G | T | Y | F | I | Y | S | Q | V | E | V |
| HuTNF | L | V | V | P | S | E | G | L | Y | L | I | Y | S | Q | V | L | F |
| CD40L | L | T | V | K | R | Q | G | L | Y | Y | I | Y | A | Q | V | T | F |
| LTα   | L | L | V | P | T | S | G | I | Y | F | V | Y | S | Q | V | V | F |
| LTβ   | L | A | L | P | Q | D | G | L | Y | Y | L | Y | C | L | V | G | Y |
| FAS   | L | V | I | N | E | A | G | L | Y | F | V | Y | S | K | V | Y | F |
| CD40L | L | T | V | K | R | Q | G | L | Y | Y | I | Y | A | Q | V | T | F |

FIG. 4

```
DL    1   MAHVGDCTQT  PWLPVLVVSL  MCSARAEYSN  CGENEYYNQT  TGLCQECPPC
          ::::::::    ::::::::::  :::::::: :  : ::::::  :  ::::::::::
dl    1   MAHVGDCKWM  SWLPVLVVSL  MCSAKAEDSN  CGENEYHNQT  TGLCQQCPPC

DL   51   GPGEEPYLSC  GYGTKDEDYG  CVPCPAEKFS  KGGYQICRRH  KDCEGFFRAT
          :::::::..:  :::::::..::  ::::::::::  ::::::::::  ::::::::::
dl   51   RPGEEPYMSC  GYGTKDDDYG  CVPCPAEKFS  KGGYQICRRH  KDCEGRRRAT

Dl  101   VLTPGDMEND  AECGPCLPGY  YMLENRPRNI  YGMVCYSCLL  APPNTKECVG
          ::::::::::  ::::::::::  ::::::::::  ::::::::::  ::::::::::
dl  101   VLTPGDMEND  AECGPCLPGY  YMLENRPRNI  YGMVCYSCLL  APPNTKECVG

DL  151   ATSGASANFP  GTSGSSTLSP  FQHAHKELSG  QGHLATALII  AMSTIFIMAI
          ::::  ::.   :::  ::::::  ::::::::::  ::::::::::  ::::::::::
dl  151   ATSGVSAHSS  STSGGSTLSP  FQHAHKELSG  QGHLATALII  AMSTIFIMAI

DL  201   AIVLIIMFYI  LKTKPSAPAC  CTSHPGKSVE  AQVSKDEEKK  EAPDNVVMFS
          ::::::::::  .::::::::::  : ::  ::::  : :   .    ::::  ::::::.  :
dl  201   AIVLIIMFYI  MKTKPSAPAC  CSSPPGKSAE  APANTHEEKK  EAPDSVVTFP

DL  251   EKDEFEKLTA  TSAKPTKSEN  DASSENEQLL  SRSVDSDEEP  APDKQGSPEL
          :   :: .:::   :    :    ::::  ::::::::::  ::::::::::  ::::::::::
dl  251   ENGEFQKLTA  TPTKTPKSEN  DASSENEQLL  SRSVDSDEEP  APDKQGSPEL

DL  301   CLLSLVHLAR  EKSATSNKSA  GIQSRRKKIL  DVYANVCGVV  EGLSPTELPF
          ::::::::::  :::  ::::::  ::::::::::  ::::::::::  ::::::::::
dl  301   CLLSLVHLAR  EKSVTSNKSA  GIQSRRKKIL  DVYANVCGVV  EGLSPTELPF

DL  351   DCLEKTSRML  SSTYNSEKAV  VKTWRHLAES  FGLKRDEIGG  MTDGMQLFDR
          ::::::::::  ::::::::::  ::::::::::  ::::::::::  ::::::::::
dl  351   DCLEKTSRML  SSTYNSEKAV  VKTWRHLAES  FGLKRDEIGG  MTDGMQLFDR

DL  401   ISTAGYSIPE  LLTKLVQIER  LDAVESLCAD  ILEWAGVVPP  ASQPHAAS
          ::::::::::  ::::::::::  ::::::::::  :: :   :::
dl  401   ISTAGYSIPE  LLTKLVQIER  LDAVESLCAD  ILEWAGVVPP  ASPPPAAS
```

FIG. 7

HYPOHIDROTIC ECTODERMAL DYSPLASIA GENES AND PROTEINS

This application is a continuation-in-part application of U.S. application Ser. No. 09/342,681, filed Jun. 29, 1999, now U.S. Pat. No. 6,355,782, issued on Mar. 12, 2002, and claims priority from U.S. Provisional Application No. 60/092,279 filed Jul. 9, 1998 and 60/112,366 filed Dec. 15, 1998.

ACKNOWLEDGEMENT OF GOVERNMENT SUPPORT

Some of the work described in this patent application was funded by a grant DE11311 from the National Institute of Dental Research, grants HL-49953 and AR-45316 from the National Institutes of Health and a grant from the National Foundation for Ectodermal Dysplasia. The government may have certain rights in this invention.

FIELD

This disclosure relates to nucleic acid sequences and proteins involved in hypohidrotic ectodermal dysplasia (HED) and the development of hair, teeth, and sweat glands.

BACKGROUND

Hereditary ectodermal dysplasia is an inherited disorder that affects the development of ectodermally derived structures, such as hair, teeth and sweat glands. The hidrotic form of the disease is characterized by poorly developed teeth and hair. The anhidrotic or hypohidrotic form of the disease further affects the development of sweat glands, which interferes with the ability to sweat, and the maintenance of thermoregulatory homeostasis. Both X-linked and autosomal dominant and recessive forms of the disease have been described.

X-linked hypohidrotic ectodermal dysplasia (XLHED; McKusick's number 305100), the most common form of the ectodermal dysplasias, results in the abnormal development of teeth, hair and eccrine sweat glands. Identification of the gene that is defective in this disease would help explain the molecular basis of XLHED, as well as the molecular mechanisms involved in normal tooth, hair and eccrine sweat gland development. Identification of the gene would also permit mutation testing for XLHED in potentially affected males and carrier females.

Heterozygote carriers of XLHED may have minor or moderate degrees of hypodontia, hypotrichosis and hypohidrosis, although many show no obvious clinical manifestations. This clinical variation, presumably caused by random X-inactivation (Lyonization), makes accurate diagnosis of carrier females difficult. Although indirect testing for carrier status is possible by linkage analysis in informative families (Zonana, 1993, *Semin Dermatol* 12:241–6), carrier detection by this method is impossible in families with single affected individuals, male or female, whose disorder may be the result of a de novo mutation. Detection of mutations within the EDA1 gene would also be advantageous in families with only a single affected sibship, because a rarer autosomal recessive form of the disorder (ARHED) is clinically indistinguishable from XLHED in affected males.

A gene identified as EDA1 was isolated by positional cloning (Kere et al., 1996, *Nature Genet.* 13:409–416). A single 858 bp cDNA, representing a full length transcript composed of two exons, was identified from an adult sweat gland cDNA library. In situ analysis showed that the EDA1 gene was expressed in hair follicles and the epidermis of adult skin. The putative gene product is a 135 amino acid protein, which has no clear homology to other proteins (see U.S. Pat. No. 5,700,926). The protein is predicted to contain a single transmembrane domain, and fractionation studies of transfected cell lines showed that the protein product is localized to the plasma membrane (Ezer et al., 1997, *Hum. Mol. Genet.* 6:1581–7). Yeast artificial chromosomes (YACs) containing at least a portion of the human EDA1 gene were disclosed in U.S. Pat. No. 5,556,786.

A syndrome similar to HED, with anhidrosis and absence of sweat glands, is known in the mouse, in which the mutant gene is called Tabby (Ta). Consistent with the map position in humans, the Ta gene has been mapped in the syntenically corresponding region in the X chromosome of the mouse (Brockdorff et al., 1991, *Genomics* 10:17–22). The Tabby phenotype is indistinguishable from that seen for mutations in downless, another spontaneous mouse mutation identified in the late 1950s on the A/H strain (Philips, 1960, *Mouse News Letter* 23:29). Tabby and downless mice have abnormally shaped or absent teeth (Grüneberg, 1965, *J. Embryol. Exp. Morph.* 14:137–59), missing sweat glands and absence of some hair types (Sundberg. 1994. The Downless (dl) and Sleek (D1$^{Sleek}$) mutations, Chromosome 10. In Maibach. H. I. (ed). Handbook of mouse mutations with skin and hair abnormalities. CRC Press, Inc., Boca Raton, Fla. 241–229.).

SUMMARY OF THE DISCLOSURE

The present disclosure has been made possible by the discovery that there are previously unidentified alternative transcripts of the EDA1 gene. The present disclosure includes an EDA1 cDNA splice-form (SEQ ID NO 1) that is homologous to the Ta cDNA (SEQ ID NO 3), and codes for a second isoform of the EDA1 protein (isoform II or EDA1-II). Nearly all of the mutations associated with XLHED are located within exons identified in this new splice-form. Also disclosed is a nucleic acid sequence encoding a human EDA1-II sequence (SEQ ID NOS 5–11), which encodes a 391 amino acid ligand protein (SEQ ID NO 2). EDA1-II is involved in hair, tooth, skin, and eccrine sweat gland morphogenesis. A form of the protein is present in humans, mice, cow and dog, and likely serves the same or nearly identical roles in each of these organisms.

Also provided herein are amino acid sequences of a receptor for the EDA1-II/Ta ligand, referred to as human downless (DL) and murine downless (dl), respectively. Murine and human cDNA and amino acid sequences for dl and DL receptors are provided in SEQ ID NOS 12, 19, 18 and 17.

Having provided the nucleotide sequence of EDA1-II, dl, and DL, correspondingly provided are the complementary DNA strands of these cDNA molecules and DNA molecules which hybridize under stringent conditions to these cDNA molecules, or their complementary strands. Such hybridizing molecules include DNA molecules differing only by minor sequence changes, including nucleotide substitutions, deletions and additions. Guidance about making such mutations, while maintaining biological activity of the proteins, is provided by the illustration of mutations that interfere with EDA1-II biological activity. Further guidance is provided by comparison of the sequences from different species, which illustrate highly conserved sequences.

Through the manipulation of the disclosed nucleotide and amino acid sequences by standard molecular biology techniques, variants of EDA1-II, dl and DL can be made which differ in precise amino acid sequence from the disclosed proteins, yet which maintain the basic functional characteristics of the disclosed proteins, or which are selected to differ in some characteristics from these proteins. Variants can also be made which interfere with receptor action, and therefore act as antagonists.

Provided herein are methods and compositions for increasing or decreasing the development of any cell or tissue of ectodermal origin, such as hair, teeth, skin, and/or sweat glands, by altering EDA1-II activity in a cell or tissue. EDA1-II activity can be increased or decreased using the EDA1-II, dl and DL gene, cDNA and protein sequences (and variants, polymorphisms and mutants thereof), as well as antisense molecules and specific binding agent disclosed herein alone or with a pharmaceutical carrier.

The present disclosure also provides a method for screening for compounds which increase or decrease development of hair follicles, sweat glands, teeth, or any other ectodermal tissue by determining whether a test compound binds to a DL or dl receptor in a cell expressing the receptor.

The foregoing and other objects, features, and advantages of the disclosure will become more apparent from the following detailed description of several embodiments which proceeds with reference to the accompanying figures.

BRIEF DESCRIPTION OF THE FIGURES

FIG. 1 is a sequence comparison of an EDA1-II (EDA) (SEQ ID NO 2) and Tabby (Ta) (SEQ ID NO 2) proteins. Amino acid identities are indicated by an asterisk (*). The transmembrane domain is boxed. A vertical line designates the start of the protein sequence unique to isoform II. The Gly-X-Y domain is indicated by boldface type, with the 2-amino acid interruption indicated by shadowed lettering. A blackened circle is shown above two potential N-linked glycosylation sites, and three C-terminal cysteines are indicated by underlining and boldface type.

FIG. 4 is a comparison of the sequences of the central β-sheet of EDA1-II (amino acids 291–309 of SEQ ID NO 2) compared with human tumor necrosis factor (Hu TNE, SEQ ID NO 123), lymphotoxin α (LTα, SEQ ID NO 124), lymphotoxin β (LTβ, SEQ ID NO 125), FAS (SEQ ID NO 126), and CD40-L (ligand, SEQ ID NO 127), which are all members of the TNF family of proteins. One dot over a column indicates conservation across all sequences. Two dots over a column indicates the G(x)Y (glycine and tyrosine residues) identified in all the TNF related proteins.

FIG. 7 is a comparison mouse dl (SEQ ID NO 19) and human DL (SEQ ID NO 17) amino acid sequences. (:) denotes identical residues; (.) identifies conserved residues. The cysteine-rich region (residues 30–71) is boxed and shaded with cysteines in bold; the potential transmembrane domain (residues 190–211) is underlined. The open box (residues 410–431) identifies the potential death domain region.

SEQUENCE LISTING

Figure 2:
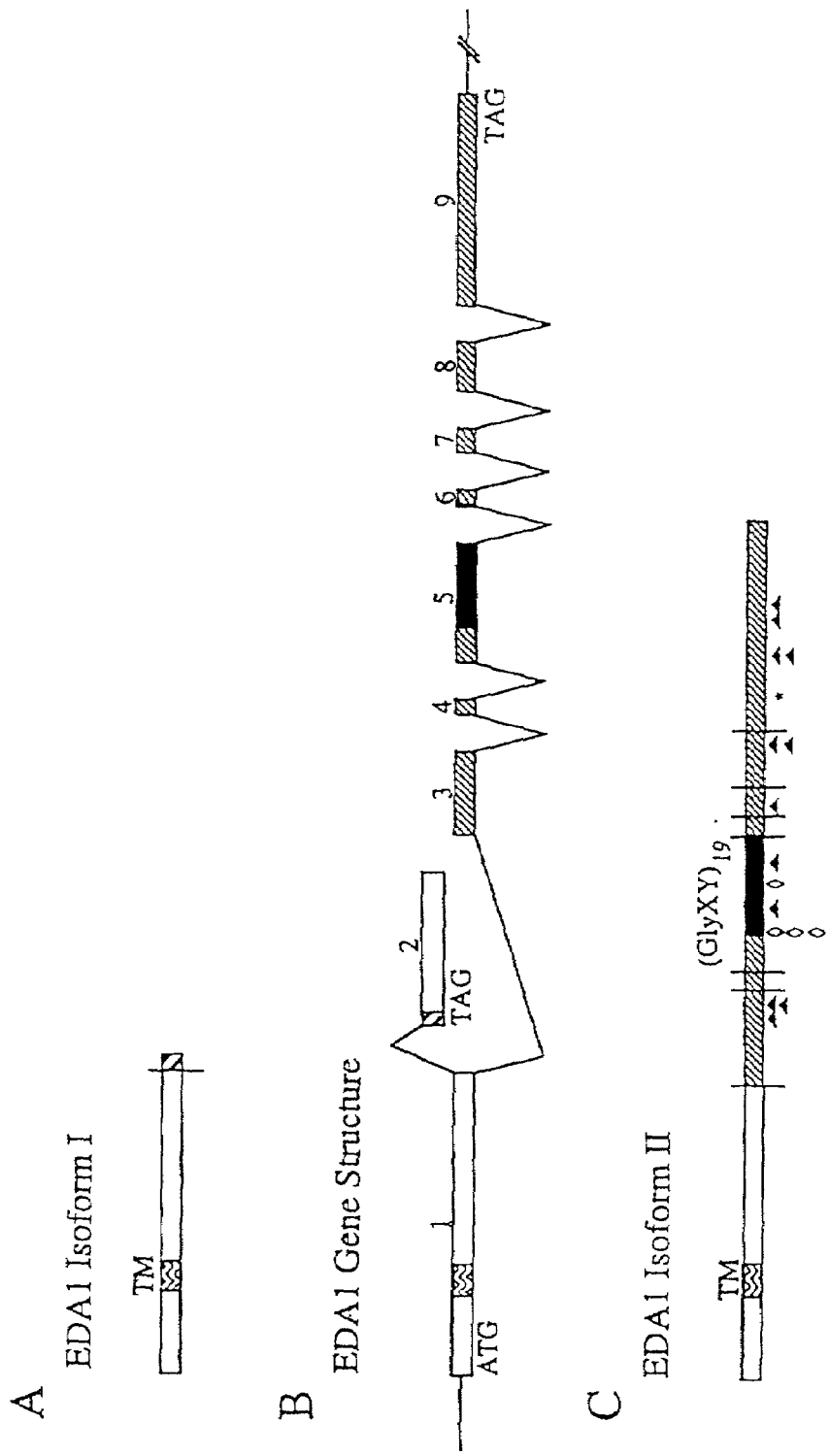
FIG. 2 is a schematic diagram of the gene structure and predicted protein products of the EDA1 isoforms I and II. The protein products of the two splice forms are depicted in panels A and C. The vertical lines separate protein regions encoded by different exons. Transmembrane ("TM") and collagen-like (Gly-X-Y) domains are shown. The relative positions of the mutations identified in the specification are depicted in panel C, with missense mutations indicated by blackened triangles, deletions indicated by unblackened diamonds, and a nonsense mutation indicated by an asterisk (*). Mutations in exon 1 are not included in this figure. The EDA1 gene structure is depicted in panel B, with the numbered boxes representing exons and the connecting lines representing intronic regions. The start and stop codons are indicated by ATG and TAG, respectively.

The nucleic and amino acid sequences in the accompanying sequence listing are shown using standard letter abbreviations for nucleotides, and three letter code for amino acids. Only one strand of each nucleic acid sequence is shown, but the complementary strand is understood as included by any reference to the displayed strand.

SEQ ID NO 1 shows a cDNA sequence of a human EDA1-II, including portions of 3' and 5' noncoding regions (GenBank Accession No. AF060999).

SEQ ID NO 2 shows an amino acid sequence of a human EDA1-II protein (GenBank Accession No. AAC36302).

SEQ ID NO 3 shows a cDNA sequence of Tabby (Ta), including portions of the 3' and 5' noncoding regions (GenBank Accession No. AF004435).

SEQ ID NO 4 shows an amino acid sequence of a murine Ta protein (GenBank Accession No. AAB88122).

SEQ ID NOS 5–11 are sequences of EDA1-II exons 3 (GenBank Accession No. AF060992), 4 (GenBank Accession No. AF060993), 5 (GenBank Accession No. AF060994), 6 (GenBank Accession No. AF060995), 7 (GenBank Accession No. AF060996), 8 (GenBank Accession No. AF060997) and 9 (GenBank Accession No. AF060998), respectively, with 3' and 5' flanking intronic sequences.

SEQ ID NO 12 shows a cDNA sequence of a mouse dl gene (GenBank Accession No. AF160502).

SEQ ID NO 13 shows an open reading frame of a mouse dl gene.

SEQ ID NO 14 shows an open reading frame of SEQ ID NO 1 (EDA1-II).

SEQ ID NO 15 shows an open reading frame of SEQ ID NO 2 (Ta).

SEQ ID NO 16 shows an open reading frame of a human DL cDNA (GenBank Accession No. AF130988)

SEQ ID NO 17 shows an amino acid sequence of a human DL protein.

SEQ ID NO 18 shows a cDNA sequence of a human DL, including the 5' and 3' UTR.

SEQ ID NO 19 shows an amino acid sequence of a murine dl protein.

SEQ ID NOS 20–21 show PCR primers used to amplify exon 5 of EDA1-II.

SEQ ID NOS 22–29 show oligonucleotide primers that can be used for diagnosis of ectodermal dysplasia.

SEQ ID NOS 30–33 show PCR primers used to screen a BAC library.

SEQ ID NOS 34–45 show PCR primers used to clone a murine dl gene.

SEQ ID NOS 46–73 show PCR primers used to clone a human DL gene.

SEQ ID NOS 74–93 show primers used for mutation screening of a human DL gene using SSCP analysis.

SEQ ID NOS 94–116 show human DL exons 1–12 with partial flanking genomic sequences (GenBank Accession NOS. AF130989–AF130996).

SEQ ID NOS 117 and 118 show oligonucleotide primers that can be used for diagnosis of ectodermal dysplasia.

SEQ ID NOS 119–122 show oligonucleotide primers that can be used to amplify the TNF homology domain of a mouse dl using nested PCR.

SEQ ID NO 123 shows a portion of a human tumor necrosis factor protein.

SEQ ID NO 124 shows a portion of a human lymphotoxin α protein.

SEQ ID NO 125 shows a portion of a human lymphotoxin β protein.

SEQ ID NO 126 shows a portion of a human FAS protein.

SEQ ID NO 127 shows a portion of a human CD40-L protein.

DETAILED DESCRIPTION OF SEVERAL EMBODIMENTS

Abbreviations and Terms

The following explanations of terms and methods are provided to better describe the present disclosure and to guide those of ordinary skill in the art in the practice of the present disclosure. As used herein and in the appended claims, the singular forms "a" or "an" or "the" include plural references unless the context clearly dictates otherwise. For example, reference to "a protein" includes a plurality of such proteins and reference to "the antibody" includes reference to one or more antibodies and equivalents thereof known to those skilled in the art, and so forth.

Unless explained otherwise, all technical and scientific terms used herein have the same meaning as commonly understood to one of ordinary skill in the art to which this disclosure belongs.

Allele Specific Oligonucleotide (ASO) Analysis: A method which can be used to determine if a mutation is present in a gene. In this method, probes or primers are designed to hybridize selectively to either the normal or mutant allele. These probes are used, with two other probes, to amplify the sequences across the mutation site, for example using PCR. The amplified DNA is applied to nitrocellulose, for example using slot-blotting. The nitrocellulose filter is then hybridized with the normal or mutant probe. The probe can be radiolabeled or labeled with a chemiluminescent compound.

The resulting autoradiographs are analyzed to determine if a subject's amplified DNA is normal, deleted, or if both sequences are present. If only the normal sequence is present, then the subject does not have that specific mutation. If only the mutant sequence is detected, the subject is homozygous or hemizygous for the mutation which causes ectodermal dysplasia (ED). If both sequences are present, the subject is heterozygous for the mutation which causes ED, and is therefore a carrier.

cDNA (Complementary DNA): A piece of DNA lacking internal, non-coding segments (introns) and regulatory sequences which determine transcription. cDNA can be synthesized in the laboratory by reverse transcription from messenger RNA extracted from cells.

Chemical Synthesis: An artificial means by which one can make a protein or peptide, for example as described in EXAMPLE 28.

Deletion: The removal of a sequence of a nucleic acid, for example DNA, the regions on either side being joined together.

DNA: Deoxyribonucleic acid. DNA is a long chain polymer which comprises the genetic material of most living organisms (some viruses have genes comprising ribonucleic acid, RNA). The repeating units in DNA polymers are four different nucleotides, each of which comprises one of the four bases, adenine, guanine, cytosine and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

Dideoxy Fingerprinting (ddF): Another method which can be used to determine if a mutation is present in a gene. This method is a hybrid between dideoxy sequencing and SSCP that can detect the presence of single base and other sequence changes in PCR-amplified segments. ddF involves a Sanger sequencing reaction with one dideoxynucleotide, followed by nondenaturing gel electrophoresis. The approximate locations of the sequence changes could be determined from the ddF pattern. Genomic DNA is amplified as in SSCP with the same primer sets. Analysis can be performed manually with radioactive labeling or by fluorescent techniques on an automated sequencer.

dl and DL cDNA: A dl (murine) or DL (human) cDNA is functionally defined as a cDNA molecule which, if transferred into and expressed in a cell, modulates the development of hair follicles, teeth, sweat glands and/or any other tissue of ectodermal origin, for example increasing or inhibiting such development. In other embodiments, when dl or DL cDNA is transfected into cells from some subjects (or patients) with autosomal recessive HED, restores the normal phenotype. In other or additional embodiments, dl and DL receptor cDNAs are activated by binding to a Ta or EDA1-II ligand, respectively, to increase or decrease development of hair follicles, teeth, and/or sweat glands. dl and DL cDNA can be derived by reverse transcription from the mRNA encoded by dl and DL genes, respectively and lacks internal non-coding segments and transcription regulatory sequences present in a dl or DL gene, respectively. Includes sequence variants, fragments, polymorphisms, and fusions thereof.

dl or DL Gene: A gene which encodes a dl or DL protein, respectively, which is a receptor for the Ta and EDA1-II ligand, respectively. Mutant forms of dl are associated with murine downless mutations. Mutant forms of DL are associated with HED, such as autosomal forms of the disease. A dl or DL gene includes the various sequence polymorphisms and allelic variants that exist within and between species. The human DL gene is abbreviated DL, and the murine gene is abbreviated dl.

dl and DL Protein: A protein encoded by a dl or DL gene or cDNA, respectively. In one embodiment, dl and DL protein includes the full-length dl or DL transcript (SEQ ID NOS:19 and 17, respectively), as well as shorter peptides which retain the ability to increase or decrease the development of hair follicles, teeth, sweat glands and/or any other tissue of ectodermal origin. This definition includes natural allelic variants in the disclosed sequences, as well as the protein of any species, and variant, fragment, or fusion peptides which retain the ability to increase or decrease development of hair follicles, teeth and/or sweat glands, in any species. Non-limiting specific examples include mouse, rat, chicken, rabbit, cat, and human. In particular examples, the proteins provided by the disclosure encode dl and DL receptors of mammalian origin. In other or additional embodiments, the dl or DL protein increases or promotes the development of hair follicles, teeth, sweat glands and/or any other tissue of ectodermal origin, for example as described in EXAMPLE 19. In other embodiments, antagonists of a dl or DL protein decrease the development of hair follicles, teeth, sweat glands and/or any other tissue of ectodermal origin, for example as described in EXAMPLE 20.

EDA1-II Activity: The activity of an agent in which the growth and/or development of hair follicles, teeth, sweat glands (such as eccrine sweat glands) and/or any other tissue of ectodermal origin (for example skin epidermis) is affected. Agents include, but are not limited to EDA1-II, dl, and DL proteins (including mimetics), nucleic acids (including DNA, RNA, and antisense molecules), specific binding agents, agonists, and antagonists, including variants, polymorphisms, fusions, and fragments thereof, disclosed herein. In one embodiment, EDA1-II activity is said to be enhanced when EDA1-II, dl, and DL proteins, nucleic acids, specific binding agents, agonists, and/or antagonists promote or increase the growth and/or development of hair follicles, teeth, sweat glands and/or any other tissue of ectodermal origin by a certain amount, for example by at least 10%. In other embodiments, EDA1-II activity is said to be reduced when EDA1-II, dl, and DL proteins, nucleic acids, specific binding agents, agonists, and/or antagonists decrease or inhibit the growth and/or development of hair follicles, teeth, sweat glands and/or any other tissue of ectodermal origin by a certain amount, for example by at least 10%.

Assays which can be used to determine if an agent has EDA1-II enhancing or reducing activity are described herein, for example in EXAMPLES 19 and 20. For example, a proposed EDA1-II secreted peptide (amino acids 133–391) can be assessed for its ability to increase hair follicle development by the intradermal injection or topical application of the protein to the skin or tails of newborn tabby mice. Functional protein activity would be detected by the induction of hair growth. Alternatively or in addition, the protein or polypeptide can be applied to skin dissected from mouse embryos, and the number of hair follicles calculated as described by Yan et al. (*Science* 290:523–7, 2000, herein incorporated by reference). Alternatively or in addition, the protein can be applied to or injected into the footpads of newborn tabby mice, with subsequent monitoring of sweat gland development. Alternatively or in addition the truncated protein can be applied to or expressed in an in vitro tooth organ culture system, and determine whether developmental changes occur (which are not expected in the absence of a functional protein). Similar assays can be used to determine if any agent disclosed herein can decrease the growth and/or development of hair follicles, teeth, sweat glands and/or any other tissue of ectodermal origin (for example skin epidermis). Any of these assays can be modified by using in vivo expression an EDA1-II, dl, or DL gene, and variants, fusions, and fragments thereof, instead of applying/injecting purified proteins.

EDA1-II cDNA: The EDA1-II cDNA is functionally defined as a cDNA molecule which, when transfected into and expressed in a cell, modulates the development of hair follicles, teeth, sweat glands and/or any other tissue of ectodermal origin. In other embodiments, when EDA1-II cDNA is transfected into a cell from some subjects with XLHED, restores the normal phenotype. EDA1-II cDNA can be derived by reverse transcription from mRNA encoded by an EDA1-II gene and lacks internal non-coding segments and transcription regulatory sequences present in an EDA1-II gene. Includes sequence variants, fragments, polymorphisms, and fusions thereof.

EDA1-II Gene: A gene which encodes for a EDA1-II protein which is a ligand for the DL receptor protein. Mutant forms of EDA1-II are associated with HED, such as X-linked forms of the disease. An EDA1-II gene includes the various sequence polymorphisms and allelic variants that exist in the species in question.

EDA1-II Protein: A protein encoded by an EDA1-II gene or cDNA. In one embodiment, an EDA1-II protein includes a full-length transcript (SEQ ID NO: 2), as well as shorter peptides which retain the ability to increase or decrease (such as inhibit) the development of hair follicles, teeth, sweat glands and/or any other tissue of ectodermal origin. In additional or alternative embodiments, an EDA1-II protein is believed to bind as an agonist to a DL receptor and activate signal transduction that promotes the development of hair follicles, sweat glands and/or teeth. The protein includes natural allelic variants in the disclosed sequences, as well as the protein of any species, and variant peptides which retain the ability to increase or decrease growth of hair follicles, teeth and/or sweat glands, in species such as mouse, rat, chicken, rabbit, cat, and human. In particular examples, the proteins provided by the disclosure encode an EDA1-II ligand of mammalian origin. In other or additional embodiments, the EDA1-II protein increases or promotes the growth of hair follicles, teeth, sweat glands and/or any other tissue of ectodermal origin, for example as described in EXAMPLE 19. In other embodiments, antagonists of an EDA1-II protein decrease or inhibit the growth of hair follicles, teeth, sweat glands and/or any other tissue of ectodermal origin, for example as described in EXAMPLE 20.

HED: Hypohidrotic ectodermal dysplasia, which can include X-linked and autosomal forms of the disease.

Isolated: An isolated nucleic acid has been substantially separated or purified away from other nucleic acid sequences in the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids.

Mammal: This term includes both human and non-human mammals. Similarly, the terms "patient," "subject," and "individual" includes both human and veterinary subjects.

Mutant DL/dl gene: A mutant form of a DL/dl gene which in some embodiments is associated with disease. In one embodiment the disease is ectodermal dysplasia. In another embodiment, the disease is autosomal recessive HED.

Mutant DL/dl RNA: The RNA transcribed from a mutant DL/dl gene.

Mutant DL/dl Protein: The protein encoded by a mutant DL/dl gene.

Mutant EDA1-II Gene: A mutant form of the EDA1-II gene which in some embodiments is associated with disease. In one embodiment the disease is ectodermal dysplasia. In another embodiment, the disease is XLHED.

Mutant EDA1-II RNA: The RNA transcribed from a mutant EDA1-II gene.

Mutant EDA1-II Protein: The protein encoded by a mutant EDA1-II gene.

Normal Cells: Non-tumor, non-malignant cells.

Oligonucleotide: A linear polynucleotide sequence of up to about 200 nucleotide bases in length, for example a polynucleotide (such as DNA or RNA) which is at least about 6 nucleotides, for example at least 15, 50, 100 or 200 nucleotides long.

Operably Linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

ORF (Open Reading Frame): A series of nucleotide triplets (codons) coding for amino acids without any termination codons. These sequences are usually translatable into a peptide.

Ortholog: Two nucleotide sequences are orthologs of each other if they share a common ancestral sequence and diverged when a species carrying that ancestral sequence split into two species. Orthologous sequences are also homologous sequences.

PCR (Polymerase Chain Reaction): Describes a technique in which cycles of denaturation, annealing with primer, and then extension with DNA polymerase are used to amplify the number of copies of a target DNA sequence.

Probes and Primers: Nucleic acid probes and primers can readily be prepared based on the amino acid sequences provided herein. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al., *Molecular Cloning: A Laboratory Manual*, Cold Spring Harbor Laboratory Press (1989) and Ausubel et al., *Current Protocols in Molecular Biology*, Greene Publishing Associates and Wiley-Intersciences (1987).

Primers are short nucleic acids, such as DNA oligonucleotides about at least 15 nucleotides in length. Primers can be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by PCR or other nucleic-acid amplification methods known in the art.

Methods for preparing and using probes and primers are described, for example, in Sambrook et al. (*Molecular Cloning: A Laboratory Manual*, Cold Spring Harbor Laboratory Press, 1989), Ausubel et al., 1987, and Innis et al., *PCR Protocols, A Guide to Methods and Applications*, 1990, Innis et al. (eds.), 21–27, Academic Press, Inc., San Diego, Calif. PCR primer pairs can be derived from a known sequence, for example, by using computer programs intended for that purpose such as Primer (Version 0.5, © 1991, Whitehead Institute for Biomedical Research, Cambridge, Mass.).

One of skill in the art will appreciate that the specificity of a particular probe or primer increases with its length. Thus, for example, a primer comprising 21 consecutive nucleotides of a human EDA1-II or DL cDNA or gene will anneal to a target sequence such as an EDA1-II or DL gene homolog (such as a Ta or dl gene) contained within a genomic DNA library with a higher specificity than a corresponding primer of only 15 nucleotides. Thus, to obtain greater specificity, probes and primers can be selected that comprise at least 1, 25, 30, 35, 40, 50 or more consecutive nucleotides of the EDA1-II, dl or DL cDNA or gene sequences disclosed herein.

The disclosure thus includes isolated nucleic acid molecules that comprise specified lengths of the disclosed EDA1-II, dl or DL cDNA or gene sequences. Such molecules can comprise at least 20, 21, 25, 30, 35, 40 or 50 consecutive nucleotides of these sequences and can be obtained from any region of the disclosed sequences. By way of example, the cDNA and gene sequences can be apportioned into halves or quarters based on sequence length, and the isolated nucleic acid molecules can be derived from the first or second halves of the molecules, or any of the four quarters. In particular, the DNA sequences may code for a unique portion of EDA1-II isoform (amino acid residues 133–391, as numbered in FIG. 1), or a ligand binding region of dl or DL.

Polynucleotide: A linear nucleic acid sequence of any length. Therefore, a polynucleotide includes molecules which are at least 15, 50, 100, 200 (oligonucleotides) and also nucleotides as long as a full length cDNA.

Promoter: An array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

Purified: The term purified does not require absolute purity; rather, it is intended as a relative term. Thus, for example, a purified EDA1-II protein preparation is one in which the protein is more pure than the protein in its natural environment within a cell. For example, a preparation of an EDA1-II protein is purified if the protein represents at least 50%, for example at least 70%, of the total protein content of the preparation.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

RT: Room temperature

Sample: Biological samples containing genomic DNA, cDNA, RNA, or protein obtained from the cells of a subject, such as those present in peripheral blood, urine, saliva, tissue biopsy, surgical specimen, fine needle aspriates, amniocentesis samples and autopsy material.

Sequence Identity/Similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (e.g., human and mouse sequences), compared to species more distantly related (e.g., human and C. elegans sequences). Typically, EDA1-II and DL orthologs are at least 50% identical at the nucleotide level and at least 50% identical at the amino acid level when comparing orthologous sequences.

Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:23744, 1988; Higgins & Sharp, CABIOS 5:151–3, 1989; Corpet et al., Nuc. Acids Res. 16:10881–90, 1988; Huang et al. Computer Appls. in the Biosciences 8, 155–65, 1992; and Pearson et al., Meth. Mol. Bio. 24:307–31, 1994. Altschul et al., J. Mol. Biol. 215:403–10, 1990, presents a detailed consideration of sequence alignment methods and homology calculations.

The NCBI Basic Local Alignment Search Tool (BLAST) (Altschul et al., J. Mol. Biol. 215:403–10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 70%, 75%, 80%, 85%, 90%, 92%, 95%, 98%, 99% sequence identity. When less than the entire sequence is being compared for sequence identity, homologs will typically possess at least 75% sequence identity over short windows of 10–20 amino acids, and can possess sequence identities of at least 85%, 90%, 95% or 98% depending on their identity to the reference sequence. Methods for determining sequence identity over such short windows are described at the NCBI web site.

Homologs of the disclosed EDA1-II protein are typically characterized by possession of at least 95%, or at least 98% sequence identity counted over the full-length alignment with the disclosed amino acid sequence using the NCBI Basic Blast 2.0, gapped blastp with databases such as the nr or swissprot database. Queries searched with the blastn program are filtered with DUST (Hancock and Armstrong, 1994, Comput. Appl. Biosci. 10:67–70). Other programs use SEG.

Homologs of the disclosed dl and DL proteins are typically characterized by possession of at least 70% sequence identity counted over the full-length alignment with the disclosed amino acid sequences using the NCBI Blast 2.0, or using the manual alignment as described above. Proteins with even greater similarity to the dl and DL sequences will show increasing percentage identities when assessed by this method, such as at least 75%, 80%, 85%, 90%, 95% or even 98% sequence identity. When less than the entire sequence is being compared for sequence identity, homologs will typically possess at least 75% sequence identity over short windows of 10–20 amino acids, and can possess sequence identities of at least 85%, 90%, 95% or even 98% depending on their similarity to the reference sequence.

One of skill in the art will appreciate that these sequence identity ranges are provided for guidance only; it is possible that strongly significant homologs could be obtained that fall outside the ranges provided. Provided herein are the peptide homologs described above, as well as nucleic acid molecules that encode such homologs.

One indication that two nucleic acid molecules are closely related is that the two molecules hybridize to each other under stringent conditions. Stringent conditions are sequence-dependent and are different under different environmental parameters. Nucleic acid molecules that hybridize under stringent conditions to a EDA1-II, DL, or dl gene sequence typically hybridize to a probe based on either an entire EDA1-II, DL, or dl gene or selected portions of the gene, respectively, under conditions described in EXAMPLE 21.

Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous peptides can, for example, possess at least 75%, 80%, 90%, 95%, 98%, or 99% sequence identity determined by this method. When less than the entire sequence is being compared for sequence identity, homologs can, for example, possess at least 75%, 85% 90%, 95%, 98% or 99% sequence identity over short windows of 10–20 amino acids. Methods for determining sequence identity over such short windows can be found at the NCBI web site. One of skill in the art will appreciate that these sequence identity ranges are provided for guidance only; it is possible that significant homologs or other variants can be obtained that fall outside the ranges provided.

An alternative (and not necessarily cumulative) indication that two nucleic acid sequences are substantially identical is that the polypeptide which the first nucleic acid encodes is immunologically cross reactive with the polypeptide encoded by the second nucleic acid.

Single-Stranded Conformation Polymorphism (SSCP) Analysis: A method which can be used to determine if a mutation is present in a gene. In this method, mutations are detected by analyzing the conformational change in a DNA due to the mutation. Briefly, genomic DNA is isolated from a subject and the region containing the mutation is amplified, for example using PCR. The primers used in the PCR reaction can be radiolabeled to label the DNA fragments, or the DNA can be directly visualized by silver staining. The resulting fragments are electrophoresed on a polyacrylamide gel. The bands from the normal sample will have a different electrophoretic mobility than the mutant or carrier samples. The samples are analyzed as described above for ASO analysis.

Specific Binding Agent: An agent that binds substantially only to a defined target. An EDA1-II, dl or DL specific binding agent binds substantially only the EDA1-II, dl or DL protein, respectively.

The terms "anti-EDA1-II antibodies" and "anti-dl or DL antibodies" encompasses monoclonal and polyclonal antibodies specific for an EDA1-II, dl or DL protein, respectively, i.e., which bind substantially only to an EDA1-II, dl or DL protein, respectively, when assessed using the methods described below, as well as immunologically effective portions ("fragments") thereof Antibodies disclosed herein can be polyclonal antibodies, monoclonal antibodies (mAb) (or immunologically effective portions thereof) and humanized mAbs (or immunologically effective portions thereof). Immunologically effective portions of mAbs include Fab, Fab', F(ab')$_2$ Fabc, Fv portions as well as any other agent capable of specifically binding to an EDA1-II, Dl, or dl protein (or the other disclosed proteins). Antibodies can also be produced using standard procedures as described in EXAMPLE 23, and as described in Harlow and Lane (*Antibodies: A Laboratory Manual*. 1988).

The determination that a particular agent binds substantially only to an EDA1-II, dl or DL protein can be made using or adapting routine procedures. For example, western blotting can be used to determine that a specific binding agent, such as a mAb, binds substantially only to the protein (Harlow and Lane, *Antibodies: A Laboratory Manual.* 1988).

Subject: Living multicellular vertebrate organisms, a category which includes, both human and veterinary subjects for example, mammals, rodents, and birds.

Therapeutically Effective Amount: An amount sufficient to achieve a desired biological effect, for example an amount that is effective to increase or decrease (such as inhibit) the growth and/or development of hair follicles, teeth, sweat glands and/or any tissue of ectodermal origin. In particular examples, it is a concentration of EDA1-II, dl and/or DL protein, nucleic acid, specific binding agent, agonist, and/or antagonist, effective to increase or decrease the growth and/or development of hair follicles, teeth, sweat glands and/or any tissue of ectodermal origin in a tissue, such as a tissue in a subject to whom it is administered. In other examples, it is an amount effective to increase the growth and/or development of hair follicles, teeth, sweat glands and/or any tissue of ectodermal origin by more than a desired amount. In other examples, it is an amount of EDA1-II, dl and/or DL antagonist effective to decrease the growth and/or development of hair follicles, teeth, sweat glands and/or any tissue of ectodermal origin by more than a desired amount.

In one embodiment, the therapeutically effective amount also includes a quantity of EDA1-II, dl and/or DL protein sufficient to achieve a desired effect in a subject being treated. In another or additional embodiment, the therapeutically effective amount also includes a quantity of EDA1-II, dl and/or DL nucleic acid sufficient to achieve a desired effect in a subject being treated. For instance, these can be an amount necessary to improve signs and/or symptoms a disease such as HED, for example by increasing the growth and/or development of hair follicles, teeth, sweat glands and/or any tissue of ectodermal origin.

In yet other embodiments, the therapeutically effective amount also includes a quantity of EDA1-II, dl and/or DL antagonist (such as a protein, specific binding agent, or nucleic acid) sufficient to achieve a desired effect in a subject being treated. For instance, this can be the amount necessary to improve signs and/or symptoms a disease such as hirsutism, ectopic teeth or breast cancer, for example by decreasing the development of hair follicles, teeth, or epithelial cells.

An effective amount of EDA1-II and/or dl/DL agent can be administered in a single dose, or in several doses, for example daily, during a course of treatment. However, the effective amount of EDA1-II, dl, and/or DL agent will be dependent on the source of EDA1-II, dl, and/or DL applied (i.e. EDA1-II, dl, and/or DL protein isolated from a cellular extract versus a chemically synthesized and purified EDA1-II, dl, and/or DL L, protein or a variant or fragment that may not retain full EDA1-II, dl, and/or DL activity), the subject being treated, the severity and type of the condition being treated, and the manner of administration of EDA1-II, dl, and/or DL. For example, a therapeutically effective amount of EDA1-II and/or dl/DL protein can vary from about 0.01 mg/kg body weight to about 1 g/kg body weight.

The EDA1-I, dl, and DL proteins, nucleic acids, and specific binding agents disclosed herein have equal application in medical and veterinary settings. Therefore, the general term "subject being treated" is understood to include all animals (e.g. humans, apes, dogs, cats, horses, and cows) that require an increase or decrease of the growth and/or development of hair follicles, teeth, and/or sweat glands susceptible to EDA1-II, dl, and/or DL-mediated modulation.

Therapeutically Effective Dose: A dose sufficient to increase or decrease (such as inhibit) the growth and/or development of hair follicles, teeth, sweat glands and/or any tissue of ectodermal origin, resulting in a regression of a pathological condition, or which is capable of relieving signs or symptoms caused by the condition, such as HED, hirsutism, breast cancer and ectopic teeth.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Transgenic Cell: Transformed cells which contain foreign, non-native DNA.

Tumor: A neoplasm

Variants or Fragments or Fusion Proteins: The production of EDA1-II, dl, and/or DL proteins can be accomplished in a variety of ways (for example see EXAMPLES 22, 27, 28 and 36). DNA sequences which encode for a protein or fusion protein, or a fragment or variant of a protein, can be engineered to allow the protein to be expressed in eukaryotic cells, bacteria, insects, and/or plants. To obtain expression, the DNA sequence can be altered and operably linked to other regulatory sequences. The final product, which contains the regulatory sequences and the therapeutic protein, is referred to as a vector. This vector can be introduced into eukaryotic, bacteria, insect, and/or plant cells. Once inside the cell the vector allows the protein to be produced.

A fusion protein comprising a protein, such as EDA1-II, dl, or DL (or variants, polymorphisms, mutants, or fragments thereof) linked to other amino acid sequences that do not inhibit the desired activity of the EDA1-II, dl, or DL protein, for example the ability to increase or decrease growth and/or development of hair follicles, teeth and/or sweat glands. In one embodiment, the other amino acid sequences are no more than 10, 20, 30, or 50 amino acid residues in length.

One of ordinary skill in the art will appreciate that the DNA can be altered in numerous ways without affecting the biological activity of the encoded protein. For example, PCR can be used to produce variations in the DNA sequence which encodes EDA1-II, dl, and/or DL. Such variants may be variants that are optimized for codon preference in a host cell that is to be used to express the protein, or other sequence changes that facilitate expression.

Vector: A nucleic acid molecule as introduced into a host cell, thereby producing a transformed host cell. A vector can include nucleic acid sequences that permit it to replicate in the host cell, such as an origin of replication. A vector can also include one or more selectable marker genes and other genetic elements known in the art.

XLHED: X-linked hypohydrotic ectodermal dysplasia.

Additional definitions of terms commonly used in molecular genetics can be found in Benjamin Lewin, *Genes V* published by Oxford University Press, 1994 (ISBN 0-19-854287-9); Kendrew et al (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The present disclosure provides a method of increasing or decreasing the development of any cell or tissue of ectodermal origin. In one embodiment, a method for increasing or decreasing hair follicle development, tooth development, or sweat gland development in a tissue by altering EDA1-II activity in the tissue is disclosed. In another embodiment, the method can be used to increase or decrease the development of skin epidermis by altering EDA1-II activity in the tissue. In one embodiment, increasing tooth development can be achieved in a subject directly, or alternatively in tissue culture (artificial) conditions, with subsequent introduction of teeth into a subject, such as a human.

Disclosed herein is a method of increasing hair follicle development, tooth development, or sweat gland development in a tissue by increasing EDA1-II activity in the tissue. In one embodiment, EDA1-II activity is increased by administering an EDA1-II nucleic acid or protein to the tissue, increasing EDA1-II expression in the tissue, and/or increasing EDA1-II sensitivity of the tissue. The EDA1-II tissue sensitivity can be increased by enhancing EDA1-II expression or activity in the tissue. In one embodiment, enhancing EDA1-II expression in a tissue consists of introducing in the tissue an expression vector encoding EDA1-II, such as an expression vector containing a DNA sequence. In particular embodiments, the DNA sequence consists of a nucleic acid sequence having at least 70%, 80%, 85%, 90%, 92%, 95%, 98% or 99% identity to SEQ ID NO: 1, which enhances EDA1-II activity in the tissue. In another embodiment, the DNA sequence is SEQ ID NO: 1, or subsequences thereof such as the C terminal 240 amino acid residues, such as residues 133–391, or 239–391.

In yet another embodiment, EDA1-II activity is increased by administering a DL or dl DNA or protein to the tissue, increasing DL or dl expression in the tissue, or increasing DL or dl sensitivity of the tissue. DL or dl sensitivity can be increased in the tissue by enhancing DL or dl expression or activity in the tissue. In one embodiment, enhancing DL or dl expression in the tissue consists of introducing an expression vector encoding DL or dl in the tissue. The expression vector can consist of a DNA sequence, such as a DNA sequence consisting of a nucleic acid sequence having at least 70%, 80%, 85%, 90%, 92%, 95%, 98% or 99% identity to SEQ ID NO: 12 or 18 which enhances EDA1-II activity in the tissue. In another embodiment, the DNA sequence is the nucleic acid sequence shown in SEQ ID NO: 12 or 18.

In another embodiment, EDA1-II activity is increased by administering an EDA1-II protein, such as a recombinant protein, to a cell or tissue. In particular embodiments, the EDA1-II protein has at least 95%, 98%, or 99% identity to SEQ ID NO: 2 and enhances EDA1-II activity in the cell or tissue. In another embodiment, the protein sequence is the sequence shown in SEQ ID NO: 2. In an alternative embodiment, increasing EDA1-II activity consists of administering DL or dl protein, such as a recombinant protein, to a cell or tissue. In one embodiment, the amino acid sequence of DL or dl protein has at least 70%, 80%, 85%, 90%, 92%, 95%, 98% or 99% identity to SEQ ID NO: 17 or 19 and enhances EDA1-II activity in the tissue. In yet other embodiments, the protein sequence is the sequence shown in SEQ ID NO: 17 or 19.

In yet another embodiment, EDA1-II activity is increased by administering a DL or dl specific binding agent to a cell or tissue. In one embodiment, the DL or dl specific binding agent is a polyclonal antibody, monoclonal antibody or fragment of a monoclonal antibody.

Also disclosed herein is a method of decreasing hair follicle development, tooth development, or sweat gland development in a tissue by decreasing EDA1-II activity in the tissue. In one embodiment, EDA1-II activity is decreased by administering a EDA1-II antisense molecule, specific binding agent or antagonist, which decreases EDA1-II expression in the tissue, or decreases EDA1-II sensitivity of a cell or tissue. EDA1-II sensitivity can be decreased by decreasing EDA1-II expression or activity in a cell or tissue, for example, by introducing an EDA1-II antisense molecule, an EDA1-II specific binding agent or an EDA1-II antagonist in the cell or tissue. In one embodiment, EDA1-II expression or activity is decreased by introducing in a cell or tissue a sequence having at least 70%, 80%, 85%, 90%, 92%, 95%, 98% or 99% identity to SEQ ID NO: 17 or 19, or consists of amino acids 1–183 of SEQ ID NO: 17, which reduces EDA1-II activity in the cell or tissue. In another embodiment, EDA1-II expression or activity is decreased by introducing in a cell or tissue a DL or dl antagonist.

The present disclosure are provides compositions consisting of a therapeutically effective amount of a nucleic acid or protein having EDA1-II activity and a pharmaceutically acceptable carrier. In particular embodiments, the protein having EDA1-II activity is an analogue, derivative or mimetic of the protein having EDA1-II activity. Also disclosed herein is a composition consisting of a therapeutically effective amount of an EDA1-II antagonist, a dl antagonist, a DL antagonist, a sequence consisting of amino acids 1–183 of SEQ ID NO: 17, or an EDA1-II specific binding agent and a pharmaceutically acceptable carrier. In addition, a composition consisting of a DL specific binding agent, dl specific binding agent, or EDA1-II specific binding agent, and a pharmaceutically acceptable carrier is disclosed. Any of the compositions disclosed herein can contain one or more other compounds which increase or decrease hair follicle development, tooth development, or sweat-gland development. The compositions disclosed herein can be used to increase or decrease hair follicle development, tooth development, or sweat gland development in a cell or tissue, such as in a cell or tissue of a subject suffering from an ectodermal disease.

Also provided herein is an antisense oligonucleotide which hybridizes to an RNA or a plus strand of an EDA1-II nucleic acid, a dl nucleic acid, or a DL nucleic acid and which reduces EDA1-II activity. In one embodiment, a therapeutically effective amount of the antisense oligonucleotide is present in composition with a pharmaceutically acceptable carrier. Such a composition can be used in a subject in whom decreased hair follicle development, tooth development, or sweat gland development is desired.

The methods and compositions disclosed herein can be used to treat a subject suffering from an ectodermal disease, such as XLHED, autosomal HED, or alopecia. In other embodiments, the methods disclosed herein can be used to treat a subject suffering from hirsutism, burns (for example in skin grafts) or other trauma of the skin such as surgery. In particular embodiments the methods and compositions disclosed herein can be used to increase the growth of mammary epithelial tissue, for example for reconstructive or cosmetic purposes. In other embodiments, the methods and compositions disclosed herein can be used for promoting or maintaining differentiation of breast epithelium. Alternatively, methods that decrease ectodermal development, are useful for inhibiting breast epithelial cell proliferation, for example as a therapeutic approach to slow or to inhibit the spread of breast cancer malignancies.

A method of screening for compounds which increase or decrease development of hair follicles, sweat glands, or teeth by determining whether a test compound, for example chemical compounds or polypeptides, binds to a DL or dl receptor in a cell expressing the receptor is also disclosed herein. In one embodiment, the method consists of transforming a cell with an expression vector consisting of a nucleic acid encoding a DL or dl receptor, culturing the transformed cell under conditions that allow expression of the DL or dl receptor, assaying the transformed cell for binding of the test compound, and determining whether the test compound binds to the DL or dl receptor with high specificity. In a particular embodiment, the method further consists of comparing an extent of binding of the test compound with an extent of binding of other compounds known to bind to the DL or dl receptor, wherein the additional compounds are naturally-occurring and synthetic DL or dl receptor agonists and antagonists, such as an EDA1-II ligand. In one embodiment, the EDA1-II ligand comprises a sequence having 95%, 98%, or 99% identity to SEQ ID NO: 2. In a particular embodiment, the test compound binds to the receptor with a $K_D$ of less than about $10^{-6}$ M. In yet another embodiment, the method further comprises determining if the test compound is an agonist or antagonist of the DL or dl receptor.

EXAMPLE 1

Cloning of Human EDA1 Isoform II (EDA1-II)

This example discloses the methods used to clone an EDA1 cDNA splice-form that is homologous to the murine Ta cDNA. This novel splice form codes for a putative, second isoform of the EDA1 protein (isoform II). Cloning of the Ta gene (GenBank Accession No. AF004435) was previously disclosed (Ferguson et al., 1997, *Hum. Molec. Genet.* 6:1589–94, hereby incorporated by reference in its entirety).

A human cDNA library constructed with mRNA isolated from 20–22 week fetal liver tissue was obtained from Clontech, Inc. (Palo Alto, Calif.). PCR primers were derived from the homologous murine gene, Tabby, and are published (see Table 1 in the erratum Monreal et al., 1998, *Am. J. Hum. Genet.* 63:1253–55, which corresponds to the publication Monreal et al., 1998, *Am. J. Hum. Genet.* 63:380–9, both hereby incorporated by reference in their entirety). PCR reactions for cDNA amplifications included 16.6 mM $(NH_4)SO_4$, 67 mM Tris (pH 8.8), 6.7 mM $MgC_2$, 170 µg/ml BSA, 6.7 µM EDTA and 10 mM BME, 10 ng of cDNA, 12.5 pM of each primer, 25 nM of dNTPs and 0.75 units of AmpliTaq polymerase (Perkin-Elmer, Inc., Foster City, Calif.). Reactions were cycled at 92° C. for 30 seconds, 58° C. for 30 seconds, and 72° C. for 1 minute, for 32 cycles. PCR products were electrophoresed on agarose gel, purified using GeneClean (Bio101, Inc.) and sequenced using Taq DyeDeoxy Terminators (Applied Biosystems). Sequencing reactions were run on a Model 373A DNA sequencer (Applied Biosystems). Alignments of nucleotide and protein sequences were performed using FASTA (Pearson et al., 1994, *Methods in Molecular Biology* 24:307–31). Nucleic acid sequence similarity searches were performed using the BLAST program against the non-redundant sequence and EST databases of the National Center for Biotechnology Information (Altschul et al., 1990, *J. Mol. Biol.*, 215:403–10).

With the exception of exons 1–3, PCR amplification between all exons was achieved using 1 unit of $rT^{th}$ DNA Polymerase, XL (Perkin-Elmer, Inc.) in a reaction mixture with 1× Buffer 2, 1 mM $Mg(OAc)_2$ and 800 µM dNTPs, 30 pM of each primer and 10 ng of the human YAC DNA template, yWXD1341. Intron sizes were estimated by agarose gel electrophoresis of the PCR products. DNA primer sequences are previously described (see Table 1 in the erratum Monreal et al., 1998, *Am. J. Hum. Genet.* 63:1253–55). The reactions were heated to 94° C. for 1 minute and 60° C. for 5 minute for a total of 30 cycles followed by a 10 minute incubation at 72° C. Vectorette PCR was used to obtain intron sequence flanking exon 3 (Arnold and Hodgson, 1991, *PCR Methods Appl* 1:39–42). PCR products containing the intron/exon boundaries were sequenced as described above. Exons 2, 3 and 9 were physically mapped using human YACs yWXD1851, yWXD 3583 and yWXD1341, obtained from American Type Culture Collection (Manassas, Va.). Amplification of the exons from these YACs was performed using the Taq PCR conditions described above.

Using these methods, a EDA1 cDNA (SEQ ID NO 14) which encodes a novel isoform of the EDA1 protein (isoform II) was obtained. The 1.5 kb human cDNA included 610 bp of sequence that was identical to the first exon of a previously identified 0.8 kb EDA1 cDNA (Kere et al., 1996, *Nature Genet.* 13:409–416), followed by 930 bp of unique DNA sequence. This cDNA included a 1173 bp open reading frame, followed by 160 bp of 3' UTR. No polyadenylation signal sequence was identified.

The EDA1-II cDNA (SEQ ID NO 1) encodes a 391 residue protein (SEQ ID NO 2), 256 amino acids of which are encoded by new exons. EDA1-II is 94% identical to Tabby (SEQ ID NO 4), and includes a collagen-like domain with 19 repeats of a Gly-X-Y motif, interrupted by two amino acids between repeats 11 and 12 (FIG. 1). The full-length EDA1-II transcript can include a longer 3' UTR, because no polyadenylation signal sequence was identified, and Northern analysis indicates the transcript is 5–6 kb in length. The Tabby transcript is also 5–6 kb in length and has a 3' UR of approximately 3.5 kb.

The exon boundaries and flanking sequences of all introns were established using either inter-exon or vectorette PCR amplification, followed by direct sequencing of the intron/exon junctions (see Table 2 in the erratum Monreal et al., 1998, *Am. J. Hum. Genet* 63:1253–55 and GenBank accession NOS. AF060992 and AF060998). Seven new exons were identified in the EDA1 gene (FIG. 2). These new exons (4–9) are within close proximity to one another, with introns ranging from 1 kb to 5 kb in length.

The intron between exon 1 and exon 3 is estimated to be at least 300 kb, as deduced by the analysis of YACs previously mapped to the EDA1 region (YACs yWXD1850, yWXD3583 and yWXD1341 map from centromere to telomere and 5' to 3' of EDA1.) (Srivastava et al., 1996, *Am. J. Hum. Gen.* 58:126–32). By Southern (Ferguson et al., 1997, *Hum. Mol. Genet.* 6:1589–94) and PCR analysis, exons 3–9 localize to yWXD1341, but not to yWXD1850 or yWXD3583. The previously identified exon 2 (Kere et al., 1996, *Nature Genet.* 13:409–16), not present in this spliceform, is present on all three YAC clones. Therefore, the newly identified exons are 3' and telomeric to exon 2 and map at least 300 kb from exon 1. The exon boundaries of EDA1 and Tabby genes are completely conserved.

EXAMPLE 2

Structure of EDA1-II

The EDA/Ta proteins (FIG. 1) can be divided into five domains. Listed from N- to C-terminus they are: a cytoplasmic domain (residues 1–41), a transmembrane domain (residues 42–60), an extracellular domain with furin cleavage site (residues 61–179, with potential furin cleavage site at residues 153–156-RVRR), a collagen-like domain (residues 180–238) and a TNF domain (residues 239–391).

The EDA1-II protein is related to the TNF family of proteins and includes a single transmembrane domain and, like EDA1 isoform I (EDA1-I), is believed to be a cell surface protein with a type II orientation (the C-terminus projecting extracellularly) (Ezer et al., 1997, *Hum. Mol. Genet.* 6:1581–7). A predicted collagen domain (Gly-X-Y)$_{19}$ may form a triple helix with either itself or the collagen domain of other proteins, resulting in the formation of either homo-trimeric or hetero-trimeric complexes. Three cysteine residues present in the C-terminal domains of the mouse and human proteins may stabilize such trimeric complexes. Therefore, it may be possible to interfere with EDA1-II function by introducing C-terminally truncated EDA1-II, such as amino acids 153 to 239. It is believed that EDA1-II plays a role in intercellular signaling, either as a membrane-bound or soluble ligand. In addition, it may function in cell adhesion or cell migration through interactions with the extracellular matrix. Other membrane-associated proteins with collagen domains include collagen XIII and XVII, macrophage scavenger receptor, and a bacteria binding macrophage receptor.

A 94% sequence identity was observed between EDA1-II and Tabby proteins. In the C-terminal 211 amino acids, which begin with the Gly-X-Y domain, only a single, conservative substitution at position 241 is present. This conservation in the C-terminus indicates that it is important in protein function and may interact with other highly-conserved proteins. Less conservation is observed between residues 1–180, particularly 1–163, and at residues 11, 28, 41, 74, 81, 83, 93, 95, 99, 100, 104, 111, 112, 121, 122, 124, 125, 126, 130, 145 and 163. Hence the region from residues 74–126, and such as 81–126, 93–126 and 93–112 are distinguishable from Tabby.

The biologically active domains of the EDA1-II protein are within approximately the C-terminal 240 amino acids, such as residues 133–391, such as residues 239–391 of EDA1-II). It is believed that the minimal domain of EDA1-II with functional activity is the TNF-like domain (residues 239–391), the domain likely to bind to and activate the receptor protein (see EXAMPLES 7–11). A more conservative choice of functional peptide begins at the furin recognition sequence and continues through the C-terminus (residues 153–391), which is believed to be the native, secreted form of the protein. Sequence variations of the potential furin cleavage site (RVRR, 153–156) cause a loss of protein function, indicating that secretion of the protein is essential, at least for biological activity of the protein as it is produced by the body (but which may not be true for exogenous forms of the protein, for example, those produced by recombinant methods and applied exogenously, for example topically). This region is presumably recognized and cleaved by the furin protease, and this event is required to make active EDA1-II. If excess peptide from this region, preferably in a recognizable, but non-hydrolysable form, were applied to the skin it could compete with the wild type EDA1-II, greatly reducing its processing efficiency and reducing signaling. See for example the fusing of protease recognition sites to proteins known to be protease inhibitors (see *Biochem. J.* 1997, 326:507–14). A similar technique could be adapted to the present disclosure by cloning the putative EDA1-II cleavage sequence (e.g. residues 145 to 165) into such a protein.

The structural conservation of the collagen-like domain (180–238) is believed to be important, because changes that alter the Gly-Xxx-Yyy repeated sequence appear to lose function, as do changes that shorten the domain by 12 amino acids. Sequence conservation between the mouse and human sequences highlight the importance of the TNF domain. Changes likely to disrupt the folding of the protein, in particular by changes in the proposed central β-sheet (291–309), are likely to cause loss of function. FIG. 4 illustrates the sequence of the central β-sheet in several members of the TNF family. A comparison of these sequences provides information about substitutions that may be made in the EDA1-II sequence without changing the structure of the central β-sheet. The amino acids conserved across the TNF family (indicated by dots above the column) are likely more critical in the structure and function of the molecule, and would not be the first candidates for mutation when it is desired to preserve biological activity.

The aligned sequences of EDA1-II and the other members of the TNF family, however, illustrate that the second amino acid residue (E) may be substituted with V, L, A or T (as in the aligned positions within the central β-sheet of the other members of the TNF family), while retaining biological activity. Substitutions for other residues of the central β sheet could also be made based on the variation of the residues in the aligned positions of the other members of the TNF family. Once mutations in the EDA1-II sequence are made, convenient assays are used to determine whether the mutant peptide retains EDA1-II biological activity, as described in EXAMPLES 19 and 20.

EXAMPLE 3

Expression Analysis of EDA1-II

This example describes methods used to examine the expression pattern of EDA1-II. Similar methods can be used to determine the expression pattern of EDA1-II, or variants, mutants, fusions, or fragments thereof, in any tissue.

Human Multi-Tissue Northern blots I and IV (Clontech, Inc.) were hybridized with a $^{32}$P labeled PCR product that included exon 1 to exon 9 (PCR primers shown in Table 1 of the erratum Monreal et al., 1998, *Am. J. Hum. Genet.* 63:1253–55). The filters were hybridized and washed according to the manufacturer's recommendations. The signals were visualized using Kodak X-Omat film with an exposure time of three days.

Northern analysis of RNA isolated from several human tissues (brain, heart, placenta, lung, liver, muscle, kidney, pancreas, spleen, thymus, prostate, testis, uterus, small intestine, colon, and leukocytes), hybridized with exons 1–9 of the cDNA, detected a 5–6 kb transcript. No additional hybridization was observed with longer exposures. The most abundant signal was detected in RNA isolated from adult heart, pancreas, prostate and uterus. Weaker signal was observed in RNA isolated from muscle, spleen, thymus, testis and small intestine.

To identify any rare, alternative EDA1 splice products in the fetal liver library, the cDNA was amplified with DNA primers between exon 1 and exons 3, 5, 7 or 9. All PCR products analyzed had identical sequences, with no differences in exon usage. To identify splice products that contain exon 1 but not the novel exons, the library was PCR amplified using primers from either exon 1 or exon 3, directed in the 3' direction, in combination with library vector primers. All PCR products generated using the exon 1 primer had corresponding products produced with the exon 3 primer, indicating that all cDNAs with exon 1 sequences also have exon 3 sequences. Similarly, all cDNAs with exon 3 contain exon 1 sequences, since 5'-directed primers from exon 1 or exon 3, in combination with vector primers, generated corresponding PCR products.

Since Ta cDNA was isolated in two forms, which varied by the presence or absence of nucleotides 958–1000, it was determined whether the human cDNA might also have a 42 bp variant. Primers closely flanking the 42 bp region were used to amplify the human cDNA library. Only a single 190 bp cDNA product, which included the 42 bp variable region, was identified. Analysis of the intron/exon boundaries shows that these 42 bp are contiguous with exon 8 in genomic DNA and thus do not represent a separate exon, but rather result from the use of an alternate splice donor site.

It is believed that this novel cDNA, EDA1-II, represents the major EDA1 transcript, since only a single hybridization band was detected by Northern analysis. The transcript is expressed in a variety of organs not clinically associated with HED, indicating that the EDA1-II protein may serve a redundant function in some tissues. No other EDA1 splice-products were identified, including the original 0.8 kb full-length transcript encoding EDA1 isoform I.

In mice, only the 5 kb homologous cDNA, and variants thereof, have been identified. One variant appears to result from the use of a cryptic splice donor site at the 3' end of exon 7, while two others include portions of intron 1 or intron 2 and are missing all downstream exons. Since 95% of XLHED mutations were detected within the newly identified exons (EXAMPLES 4 AND 5), isoform II is believed to be important in the biological activity of the protein, and indicates that there are no additional exons in the EDA1 gene critical for normal development.

EXAMPLE 4

Mutation Analysis of the EDA1 Gene in Subjects with XLHED

Affected males from 18 unrelated families with presumed X-linked hypohidrotic ectodermal dysplasia (XLHED) were selected for mutation analysis of the EDA1 gene. Their genomic DNAs were previously extracted and analyzed for mutations within exons 1 and 2 of the EDA1 gene, but none were found (Ferguson et al., 1998, *J. Med. Genet.* 35:112–5). All affected males had the classic XLHED phenotype including tooth, hair and sweat gland abnormalities. Ten families showed vertical transmission of the trait with two or more affected generations. Eight families had a single affected generation, with two affected brothers in three of the families, and a single affected male in five. None of the families was consanguineous or had severely affected females. Where applicable, DNA samples from other family members were studied to determine if the variants detected represented de novo mutations.

Exons were amplified from genomic DNA using primers previously described (see Table 1 in the erratum Monreal et al., 1998, *Am. J. Hum. Genet.* 63:1253–55) and the reactions conditions described above with AmpliTaq Polymerase. Amplicons were designed to include at least 28 base pairs (bp) of 3' and 5' flanking intronic regions. PCR products were treated with Shrimp Alkaline Phosphatase and Exonuclease I (Amersham, Inc.) to remove primers and excess nucleotides, and DNAs were sequenced using RediVu Thermosequenase Kit (Amersham, Inc.). Sequencing reactions were visualized by electrophoretic separation on an 8% polyacrylamide gel, and subsequent exposure on Kodak X-Omat film for 1–3 days. DNA sequence variants were verified by automated sequencing of the opposing strand using an ABI Model 373A sequencer (Applied Biosystems, Inc.).

Allele specific oligonucleotide (ASO) analysis was performed to detect polymorphisms in an unaffected population and to identify de novo mutations in a subset of families as described previously (Ferguson et al., 1998, *J. Med. Genet.* 35:112–5, herein incorporated by reference). One exception, the G1136A mutation (see Table 1), was analyzed by restriction digestion of PCR amplified exon 8 DNAs using BanI (New England Biolabs, Inc.). In all cases, genomic DNA samples from 40 control individuals, representing 60 X chromosomes, were analyzed. The de novo status of Del 794–829 in families ED1050 and ED 1204 was established by PCR amplifying exon 5 sequences, using primers 5' AGAAAGCAGGACCTCCTGG 3' (SEQ ID NO 20) and 5' CTCTCAGGATCACCCACTC 3' (SEQ ID NO 21), and separating the products on a 3% agarose gel (SeaKem, Inc.).

DNA changes were confirmed in 17 individuals (Table 1). Four individuals have genomic deletions, two of which also produced frameshift mutations. Twelve individuals have a single base pair change, predicted to generate a missense mutation, and one person has a base pair substitution that creates a premature termination codon.

TABLE 1

EDA1 Mutations in XLHED Patients

| Family | Sequence Change | Exon | Predicted Effect[a] |
|---|---|---|---|
| ED1081 | C704T | 3 | R155C |
| ED1095[b] | C707T | 3 | R156C |
| ED1039 | G708A | 3 | R156H |
| ED1011 | C867T | 5 | P209L |
| ED1019 | G912C | 5 | G224A |
| ED1050 | Del 794-829 | 5 | Del 185-196 |
| ED1204[b] | Del 794-829 | 5 | Del 185-196 |
| ED1018 | Del 803-830 | 5 | Del 188-197, FS 198, Ter 280 |
| ED1097[b] | Del 904-938 | 5 | Del 221-233, FS 234, Ter 240 |
| ED1197 | A996T | 7 | H252L |
| ED1007 | G1136A | 8 | G299S |
| ED1002 | G1136A | 8 | G299S |
| ED1001 | G1202T | 9 | E321Ter |
| ED1021 | G1285A | 9 | A349T |
| ED1126[b] | G1285A | 9 | A349T |
| ED1073 | C1308A | 9 | A356D |
| ED1022 | G1311C | 9 | R357P |

[a]FS = frameshift; Ter = termination. [b]De novo mutation.

Figure 3:
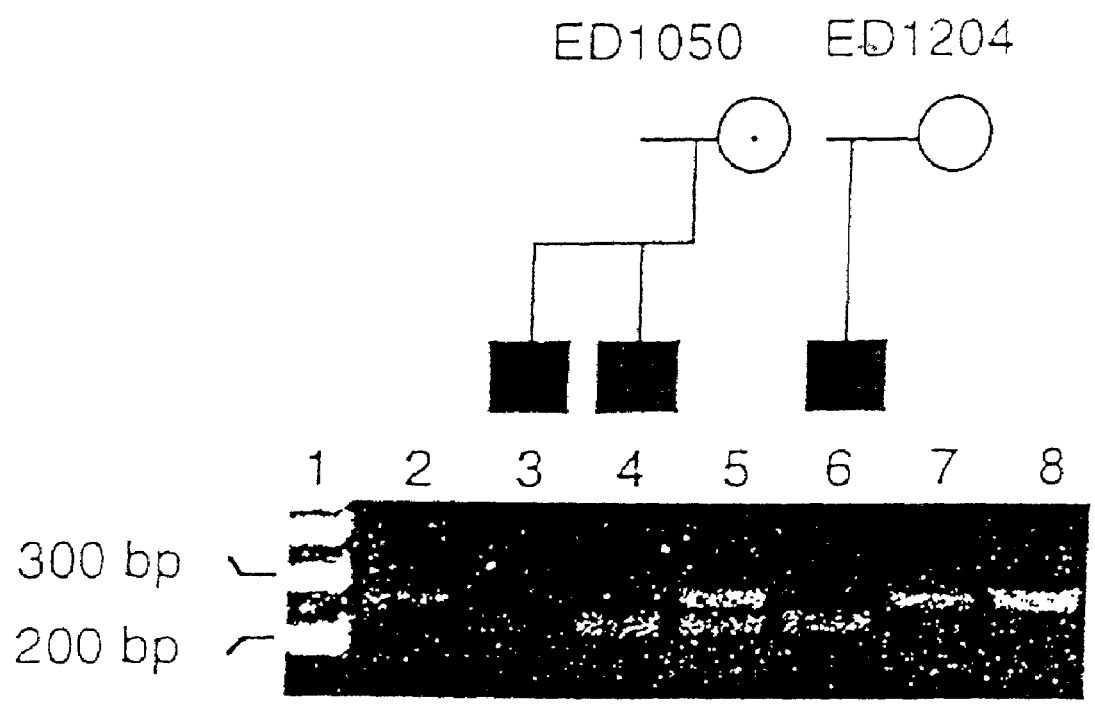
FIG. 3 is a digital image of an agarose-gel analysis of EDA1-II Del794-829. Circles represent females, with a dot indicating XLHED carrier status. Blackened boxes represent affected males. Molecular size markers are shown in lane 1, and control DNAs from unrelated, unaffected males are shown in lanes 2 and 8.

To determine if any of the putative missense mutations identified were present in an unaffected population, and thus likely to be a non-pathogenic polymorphism, ASO hybridization was used to survey 60 X chromosomes. None of the variants were present in the control population. Three presumed mutations (Del 794–829, G1136A and G1285A) were each identified twice among the 18 affected individuals. In two of these cases (Del 794–829 and G1285A), a de novo mutation was found in one of the families (ED1204 and ED1126), arguing against inheritance from a common ancestor (FIG. 3). Additional sequence variants were identified within intronic regions. Because these changes did not affect the splice recognition sites, and were present in unaffected individuals, they were classified as non-pathogenic polymorphisms.

EXAMPLE 5

Functional Implications of Identified Mutations

Some identified EDA1-II mutations are shown above in Table 1. Mutations were identified within exons 3–9 of EDA1-II in 94.4% of the families studied (17/18). Coupled with the previous mutation analysis of exon 1, which found mutations in only 7–8% of XLHED families (Ferguson et al., 1998, *J Med Genet* 35:112–5), it is estimated that 95% of mutations in XLHED patients are located within the 1173 bp coding region of EDA1-II. Additional mutations may be located in the remaining 3' UTR sequence, in regulatory elements, in unsequenced intronic regions, or may include large genomic rearrangements that are undetectable with the techniques used herein.

Although the identified mutations are heterogeneous, more than half of the individuals (11/18) had changes within the coding regions of exons 5 and 9. These two exons account for about 40% of the ORF. Six mutations were detected in exon 5, including 4 deletions 28–36 bp long. Exon encodes the Gly-X-Y domain, and deletions within it may be enriched because of the high frequency of repeated sequences. Indeed, one deletion identified in two unrelated families (Del 794–829), is flanked by a 17 bp repeated sequence containing just two nucleotide differences. This deletion may truncate the collagen domain of the protein, but otherwise leave the protein intact. If the mutant protein is stable, it indicates the collagen domain is required for normal protein function.

Two missense mutations may also perturb the collagen domain. In one case, the glycine of a Gly-X-Y triplet is substituted by an alanine. In another, a third position Pro (Gly-X-Pro) is substituted by a Leu. The third position Pro plays an important role in stabilizing the collagen helix (Brodsky and Shah, 1995, *Faseb J.* 9:1537–46). The coding region of exon 9 also contains a disproportionate share of mutations (all missense). Three changes cluster within an eight amino acid region, indicating the importance of this domain for protein stability or function. Also, this region overlaps with the C-terminal cysteine domain, which may stabilize intermolecular associations.

A mutation identified twice in exon 8, G1136A, is located within the 42 bp region previously found to be deleted in one of the Ta splice-forms (Ferguson et al, 1997, *Hum. Mol Genet.* 6:1589–94). Therefore, the 14 amino acid region encoded by the sequence is important in at least some, if not all, tissues.

EXAMPLE 6

Diagnostic Applications

Linkage-based molecular diagnostic testing for XLHED has been available for approximately 10 years and can significantly improve carrier risk estimates (Zonana et al. 1988, *Am J. Hum. Genet.* 43:75–85; Zonana et al, 1992, *Am. J. Hum. Genet.* 51:1036–46; Zonana et al., 1989 *J. Pediatr.* 114:392–9). However, linkage analysis is limited to families with two or more affected individuals, and multiple family members must be available and cooperative. However, using the EDA1-II sequence disclosed herein, and direct mutation screening, approximately 95% of mutations can be detected in individuals with presumed XLHED.

The finding that approximately half of all identifiable mutations are within exon 5 and the coding region of exon 9 indicates that initial analysis of these two exons would provide the most efficient approach in a mutation detection protocol. Since these two coding regions are relatively small (181 bp and 252 bp), they are amenable to direct sequencing, screening by SSCP (Sheffield et al., 1993, *Genomics* 16:325–32) dideoxy-fingerprinting (ddF) (Liu et al., 1996, *Hum. Mol. Genet.* 5:107–14), or by other mutation detection methods (Grompe, 1993, *Nature Genet.* 5:111–7). Amplification of exon 5 may reveal deletions large enough to be detectable by agarose gel analysis, as observed in four families in FIG. 3. If no mutations are present in exons 5 and 9, screening or sequencing exons 1, 3, 7 and 8 can be done and may yield an additional 40% of mutations. No mutations were detected in exons 4 and 6; however, they represent only about 5% of the coding sequence, and analysis of a larger set of patients may reveal mutations in these exons as well. In families where mutations are not detected, linkage analysis can still be used when the family is informative.

Primers are disclosed that can be used for diagnosis of XLHED. These include primers for amplification and sequencing of the intron regions of exon 3, 5, and 9. Exon 3: 5'-TATGTTGGCTATGACTGACTGAGTGG-3' (SEQ ID NO 22) and 5'-CCCTACCAAGAAGGTAGTTC-3' (SEQ ID NO 23). Exon 5: 5'-AAAAAGTAACACTGATC-CTATTT-3' (SEQ ID NO 117) or 5'-AGAAAGCAGGAC-CTCCTGG-3' (SEQ ID NO 118) as a forward primer with 5'-CTCTCAGGATCACCCACTCCTG-3' (SEQ ID NO 24) as a reverse primer. Exon 9: 5'-TGTCAATTCACCACAGG- GAG-3' (SEQ ID NO 25) and 5'-GAATCTAGGATG-CAGGGGC-3' (SEQ ID NO 26). Primers can also be used to directly distinguish common mutations in Exon 3: normal sequence 5'-TATTGCGGCGAACACG-3' (SEQ ID NO 27); altered sequence 5'-TATTGCAGCGAACACG-3' (SEQ ID NO 28); and altered sequence 5'-TATTGCGGCAAAA-CACG-3' (SEQ ID NO 29).

Five families had a negative family history and an unaffected mother, and thus were potentially informative as to whether the mutation was de novo. In all five families the mutations (3 deletions and 2 missense) were de novo, thus arising either during oogenesis or postzygotically. There appears to be an equal rate of mutation during oogenesis and spermatogenesis. The autosomal recessive form of the disorder is infrequent compared to the X-linked form. Review of clinical features showed no obvious phenotype/genotype correlation between individuals with missense mutations, and those with deletions truncating the collagen domain, nor those with frameshift mutations that may yield either an abnormal truncated protein or no protein at all. This is similar to the previous analysis of mutations within exon 1, which showed no difference in phenotype between patients with missense mutations and those with exon deletions or frameshifts (Ferguson et al., 1998, *J. Med. Genet.* 35:112–5; Kere et al., 1996, *Nature Genet.* 13:409–16).

The availability of direct testing for XLHED mutations is a significant advance in diagnostic capabilities. It allows carrier detection in families with only a single affected male, and helps differentiate the X-linked disorder from the rarer, autosomal recessive form of the disorder. It is also helpful in distinguishing sporadic carriers of XLHED from females with an autosomal dominant form of isolated hypodontia (Arte et al., 1996, *J. Dent. Res.* 75:1346–52). Testing will also be useful in the diagnosis of XLHED in affected male infants, such as in sporadic cases, before abnormal tooth and hair involvement is apparent. Early diagnosis can avert the significant morbidity and mortality associated with the disorder due to uncontrolled hypothermia (Clarke et al., 1987, *Arch. Dis. Child* 62:989–96). Additional methods that can be used for diagnosis are disclosed in EXAMPLES 24, 25, and 26.

EXAMPLE 7

Cloning of Murine dl

Two original families of mouse mutants, called downless$^{Jackson}$ (recessive inheritance) and Downless$^{Sleek}$ (dominant inheritance ) due to their poor hair growth, arose spontaneously during the 1960's and 1970's (Soafer, 1973, *Dev. Biol.* 34:289–96; Crocker and Cattanach 1979, *Genet. Res.* 34:231–8). The routine process of introduction of foreign DNA (transgene) into a fertilized embryo resulted in deletion of the gene responsible for the downless phenotype by the transgene. Mice carrying this deletion are called OVE 1B, and have the full range of anhidrotic ectodermal dysplasia symptoms. The presence of the transgene in the OVE 1B mice allowed identification of large fragments of mouse DNA (YACs) deleted in the OVE 1B family. YAC D9 (Majumder et al. 1998, *Mammalian Genome* 9:863–8, incorporated by reference), completely cured the mutants. The sequence from YAC D9 was used to identify similar large fragments of mouse DNA, called BACs, that overlap YAC D9. The BAC most similar to YAC D9 was used to identify specific cDNAs from developing skin, each a candidate for the gene.

BAC Library Screening and DNA Preparation

Two sets of oligonucleotides were designed based on the known YAC D9 sequence: Oligo 27209 ATCATGGCTGT-GCACTCTAG (SEQ ID NO 30) and Oligo 27210 ACCTACTGCATGTCTGTGGA (SEQ ID NO 31); Oligo 27213 CACATGCTCAGTGTTGTCCA (SEQ ID NO 32) and Oligo 27214 ACACAGGCTCAGTCATGCGG (SEQ ID NO 33).

Both primer pairs were used for primary screening of pooled BAC clones by PCR. Positive clones were identified by filter hybridization to [α-$^{32}$P]-dCTP labeled PCR product of the oligos used in the primary screen. BACs were grown in chloramphenicol-containing medium and BAC DNA isolated using QIAGEN plasmid DNA purification columns. Elution buffer was heated to 65° C. and multiple elutions performed. DNA was precipitated with isopropanol, washed with 70% ethanol, and dissolved in 10 mM Tris buffer (pH 8).

cDNA Selection

The cDNA selection protocol was a modification of Segre et al. (*Genomics* 28: 549–59, 1995). DNA was purified using QIAGEN PCR purification columns after each enzymatic step listed below. BAC 508K21 was digested using Alu I, Hae III, and Rsa I restriction enzymes in separate reactions. The pre-annealed oligonucleotide linkers: 5'-biotin-GCG-GTGACCCGGGAGATCTGAATTC-3' (SEQ ID NO 34) and 5'-phosphate-GAATTCAGATC 3' (SEQ ID NO 35), were ligated onto the BAC digestion fragments at about 50-fold molar excess to generate PCR amplifiable DNA fragments with inverted repeats at their termini. The biotinylated oligonucleotide, SEQ ID NO 34, was used to prime the PCR amplification of the DNA pool. The conditions were: 65° C. for 5 minutes (1 cycle); 94° C. for 45 seconds, 72° C. for 2.5 minutes (20 cycles).

The resulting biotinylated PCR product was used as driver in the hybridizations. To prepare the cDNA tester for hybridization polyA$^+$ RNA was isolated from a pool of E13, 17, and P0 skin. Double-stranded cDNA was synthesized (cDNA synthesis kit, Gibco) and digested with Alu I, Hae III, and Rsa I. Non-biotinylated linkers of different sequence to those ligated to the driver population were added to the fragments: CTGAGCGGAATTCGTGAGACC (SEQ ID NO 36) and phosphate-GGTCTCACGAATTCCGCT-CAGTT (SEQ ID NO 37). The cDNA pool was amplified by PCR (using cDNA-1) under the same cycle conditions described for the BAC DNA amplification.

Prior to selection, 1 µg driver DNA was denatured by boiling and blocked by overnight prehybridization to 2 µg Cot1 DNA plus 8 µg shorn OVE 1B/1B genomic DNA in the following buffer conditions: 0.75 M NaCl, 20 mM sodium phosphate pH 7.2, 5 mM EDTA, 5× Denhardt's solution and 0.1% SDS at 65° C. For the first round of enrichment 1 µg amplified BAC DNA was denatured by boiling, added to the prehybridized cDNA, and allowed hybridize at 65° C. for three days in a total volume of 20 µl. Biotinylated driver and annealed cDNAs were immobilized on streptavidin coated magnetic beads (Dynal) and unannealed cDNA was removed by washing with 0.1×SSC, 0.1% SDS at 65° C. After washing, the annealed, selected cDNAs were eluted from the biotinylated driver using 50 mM NaOH, neutralized with 1M Tris pH7.5, and PCR amplified using SEQ ID NO 36 under the following cycle conditions: 94° C. for 45 seconds, 64° C. for 45 seconds, 72° C. for 1.25 minutes (30 cycles).

This amplified, selected cDNA was subjected to a second round of enrichment by driver hybridization, washing, and amplification as above. The amplified cDNA from this second enrichment was ligated into pT-Adv (Clontech) and transformed into *E. coli*. Bacteria were grown on gridded plates prior to further analysis. One clone, cDS 446, was used for further analyses.

cDNA Library Construction and Screening

Poly A+ RNA was isolated from E17.5 fetal skin of OVE 951 mice and used as template to prepare the cDNA library. Using the lambda ZAP-cDNA synthesis kit (Stratagene) the library was plated and screened using [$\alpha$-$^{32}$P]-dCTP labeled cDS446, following kit manufacturer's instructions.

RT-PCR and RACE cDNA was prepared from newborn skin RNA using the SuperScript II kit according to manufacturer's instructions (Gibco BRL). The oligos used to amplify the downless$^{Jackson}$ mutated region from mutant cDNA were: Oligo 28756 AGTGAGAATGATGCCTCC (SEQ ID NO 38) and Oligo 28762 GCCTTTGTTCAGTCATAGG (SEQ ID NO 39). The PCR conditions were: 94° C. for 2 minutes (1 cycle); 94° C. for 30 seconds, 58° C. for 45 seconds, 72° C. for 1.5 minutes (34 cycles); and 72° C. for 15 minutes (1 cycle). SEQ ID NO 38 was used to directly sequence the RT-PCR product.

Rapid amplification of cDNA ends (RACE) was performed by synthesizing YAC D9 cured E17.5 skin cDNA using random primers (SuperScript II kit, Gibco BRL), and then 3' dC tailing the first strand cDNA using terminal transferase (Gibco BRL). PCR amplification was performed using: Oligo 10S CCTGAGAGCTCTTTGTGAG (SEQ ID NO 40) and Anchored oligo dG CGGGATCCTC-GAGGGGGGGGGGGGGGGGH (SEQ ID NO 41). The PCR conditions were: 94° C. for 2 minutes (1 cycle); 94° C. for 30 seconds, 58° C. for 45 seconds, 72° C. for 2 minutes (40 cycles); 72° C. 10 minutes (1 cycle). The PCR product was sequenced using antisense Oligo 28753 AAGCA-GAGCTCCACAATC (SEQ ID NO 42).

Dl$^{Sleek}$ cDNA was prepared for 3' RACE by generating first strand cDNA using oligodTVN:
GGCCGCTCTGGACAGGATAT-GTTTTTTTTTTTTTTTVN (SEQ ID NO 43) primer (SuperScript II kit, Gibco). PCR was performed on the first strand reaction product using: 5' GGAACAGTCAAGAGC-GAGTT (SEQ ID NO 44) and Oligo dT nested GCGGATC-CAGGCCGCTCTGGACAGGATATG (SEQ ID NO 45) under the following conditions: 94° C. for 2 minutes (1 cycle); 94° C. for 30 seconds, 58° C. for 45 seconds, 72° C. for 1.75 minutes (36 cycles); 72° C. 15 minutes (1 cycle). The PCR product was directly sequenced using SEQ ID NO 38.

All DNA sequencing was performed using the standard automated method. All PCR products were purified prior to sequencing using the QIAGEN PCR purification or QIAEX II gel purification kits according to manufacturer's instructions.

Using similar techniques, allelic variations of the dl DNA, which encodes the dl receptor that is absent in downless mice, can also be detected in humans, mice, or other mammals. The disclosure therefore includes DNA sequences that include allelic variations in the sequence.

The ORF of the cDNA sequence of the murine downless gene, dl (SEQ ID NO: 13), and the corresponding amino acid sequence (SEQ ID NO: 19) were obtained. The dl cDNA of SEQ ID NO: 12 is 3720 nucleotides, encodes a protein (SEQ ID NO: 19) of 448 amino acids, and is maintained in the pBK-CMV plasmid. The dl protein is a novel tumor necrosis factor receptor homologue.

EXAMPLE 8

Expression Analysis of Murine dl

This example describes the methods used to study dl expression in mouse hair follicles and skin. Similar expression analysis can be performed in other mammals, for example humans, using the same techniques, to confirm a similar distribution of dl expression in those mammals.

For Northern analysis RNA was prepared from E17.5 skin of the various genotypes using the phenol/guanidium thiocyanate method (RNA STAT 60, Tel-Test). Each total RNA sample (300 μg) was polyA enriched (Messagemaker Kit, Gibco BRL) and precipitated with ethanol. The recovered RNA was separated on a formaldehyde containing agarose gel, transferred to a nylon membrane (Zeta Probe, Bio-Rad), and probed with [$\alpha$-$^{32}$P]-dCTP labeled dl 5' untranslated region and open reading frame in 0.5M sodium phosphate, 7% SDS at 65° C. overnight. Four post-hybridization washes were performed in 0.1×SSC, 0.1% SDS at 65° C. for 20 minutes each.

Genomic DNA for Southern analysis was isolated from proteaseK digested mouse tails, followed by phenol extraction and thanol precipitation. The isolated DNA was EcoRI digested, separated on a 1% agarose gel, and transferred to nylon membrane (Zeta Probe, Bio-Rad). Hybridization to the entire [$\alpha$-$^{32}$P]-dCTP labeled dl cDNA and subsequent washing was performed under the conditions described above for Northern blotting.

For in situ hybridization, tissue was fixed in 10% formalin for two days, then stored in 70% ethanol. Paraffin sections of mouse embryos were deparaffinized in xylene, rehydrated, treated with 20 mg/ml protease K, and refixed in 4% paraformaldehyde before prehybridization. Hybridization was carried out overnight at 50° C. Slides were washed in FSM (50% formalin, 2×SSC, 1 mM EDTA, 2-mercaptoethanol) for 1 hour, treated with 20 μg/ml RNAse A for 30 minutes, and washed in FSM for 2 hours before coating with silver emulsion (Kodak) and exposing for 2–4 weeks. The entire dl cDNA sequence was used to prepare [$^{35}$S]-UTP labeled antisense riboprobe using T7 RNA polymerase. Samples of dl$^{OVE1B}$ tissue were used as negative controls.

Whole mount in situ hybridization was performed using digoxigenin labeled riboprobe transcribed from a genomic DNA clone corresponding to the cDNA selected clone cDS446. The riboprobe was synthesized using the DIG RNA labeling kit (Boehringer Mannheim) according to manufacturer's instructions. Embryos were fixed in 4% paraformaldehyde, bleached, and stored in methanol. For hybridization the samples were rehydrated, treated with proteaseK, and hybridized at 65° C. overnight. Embryos were then washed in 5×SSC, 1% SDS, 50% formamide at 65° C. for 30 minutes, treated with 100 μg/ml RNase A for 30 minutes, and washed in 2×SSC, 0.1% Tween 20, 50% formamide for 30 minutes. Hybridized riboprobe was detected using the DIG Nucleic Acid Detection kit (Boehringer Mannheim) according to manufacturer's instructions.

The murine dl gene is completely deleted in OVE 1B mice and at least partially present in YAC D9. Murine dl is expressed in developing skin and adult hair follicles, as determined by in situ hybridization, and is mutated in both downless$^{Jackson}$ and Downless$^{Sleek}$ mice, confirming that it is the gene responsible for these phenotypes. The expression pattern of dl is consistent with it specifying which cells are to become hair follicles, and in adult skin it is expressed by the cells at the very base of the hair follicle which surround the dermal papillae (growth regulation center). The lack of hair follicle development and the slow rate of hair growth in both mouse mutants and human ED patients indicates a role for this receptor in promoting hair follicle development and hair growth throughout life. The ability to block or enhance the activity of this receptor should allow control over these processes and be of major clinical and cosmetic relevance. Knowledge of the dl cDNA and protein sequence, and its human homolog DL (see EXAMPLE 9), allows screening for and designing molecules that modulate dl receptor activity by enhancing or inhibiting its function.

The dl mRNA in fetal mouse skin was detected by Northern blotting. The dl gene is active in normal (wild type) and YAC D9-cured mutants at this stage, and the receptor is made by the downless$^{Jackson}$ mice. The Downless$^{Sleek}$ mice have an altered form of the transcript that is smaller than the wild-type version, while the OVE 1B mice do not have the transcript.

Southern hybridization demonstrated that the dl gene is absent from the OVE 1B genome and altered in Downless$^{Sleek}$ mice. The YAC D9 cured mutants received many copies of the gene. The murine dl mutation in downless$^{Jackson}$ mice is due to a single nucleotide difference between the wild type and mutant cDNAs at nucleotide 1135 (SEQ ID NO: 13). This mutation results in glutamate 379 (SEQ ID NO: 19) of the wild type protein being changed to lysine in the mutant. The position of the dl mutation in downless$^{Sleek}$ mice is more severe. Up to nucleotide 964 (SEQ ID NO 13) the wild type and mutant sequences are the same. After this nucleotide, the Downless$^{Sleek}$ mRNA is completely different from the wild type cDNA.

In situ hybridization was used to identify the locations of dl expression in the skin. At embryonic day 15, the dl transcript is detected in the basal layer of the epidermis of a fetal mouse, and at elevated levels in the developing hair follicle buds in sectioned skin. Analysis of dl expression over the whole mouse fetus at embryonic day 15 demonstrated that dl is expressed in developing hair follicles at a high level, and at a lower level in the rest of the skin. Expression of dl was also observed in other tissues such as the lung and kidney. The dl transcript is present in the cells at the base follicle that surround the dermal papillae (growth signaling center). Some dl expression was detected in the sebaceous glands.

EXAMPLE 9

Cloning and Analysis of Human DL

This example describes methods used to clone, sequence and analyze the human DL receptor, a homolog of murine dl.

RNA isolated from human fetal skin of 11 week estimated gestational age (EGA) was reverse transcribed using 25U of MMuLV reverse transcriptase (New England Biolabs) and random hexamer primers (Pharmacia) to provide first strand cDNA used for both 3' RACE experiments, and inter-exon amplification. To obtain the initial human homologous sequence, total human genomic DNA was amplified and sequenced using primers designed from mouse dl cDNA sequence: 5'-TGGTGTCTCTGATGTGC-3' (SEQ ID NO: 46), and 5'-ACAGTGGCCCGGAAGAAG-3'(SEQ ID NO: 47). Primers derived from human sequence and primers from additional mouse cDNA sequences, each in a hemi-nested PCR reaction (SEQ ID NOS: 48 and 49 then SEQ ID NOS: 50 and 49), were used to amplify exons 3–12 from human cDNA.

The 5' end of the gene was determined by 5'-RACE. A reverse transcriptase reaction on total RNA from human fetal (11 wk EGA) skin was performed using a human gene specific primer: 5'-TCAGCGTCATTCTCCATGTC-3' (SEQ ID NO: 51). The product was dA-tailed using terminal transferase (Gibco) and the cDNA amplified using 5'-CTAGACTCGAGAATTCGCGGCCGCACTAGT$_{(17)}$-3' (SEQ ID NO: 52) and SEQ ID NO:53. The resulting product was amplified twice, first with 5'-CTAGACTCGAGAATTCG-3' (SEQ ID NO: 54) and 5'-TAGTCCTCGTCTTTGGTGCC-3' (SEQ ID NO: 55), and subsequently with SEQ ID NO: 56 and 57. For cycle sequencing, all PCR products were recovered from a 2% agarose gel, purified using GeneClean (Bio101), and sequenced on a Perkin Elmer ABI 373 stretch sequencer using the BigDye™ terminator kit. A human fetal heart cDNA library of 20–25 weeks gestation (Clontech, Inc.) containing 2–4×10$^5$ plaques was screened using a radioactively labeled murine dl cDNA probe.

DNA primers used to amplify the exons of human DL are shown in Table 2.

TABLE 2

DNA Primers Used for cDNA Amplification of human DL

| Exon | Forward Primer | Reverse Primer |
|---|---|---|
| 1–3 | GAGAATTCGCGGCCGCAC (56) | AGCCCCGTAGTCTGGTTGTA (57) |
| 3–4 | CTGCGGTGAGAACGAGTAC (48) | TCTGGTAGCCTCCTTTGGAA (53) |
| 4–12 | CTGCGGTGAGAACGAGTAC (48) | GGCAAGGTGGCGCCATGT* (49) |
|  | GGCACCAAAGACGAGGACTA (50) | GGCAAGGTGGCGCCATGT* (49) |

Primers shown in 5'-3' orientation.
SEQ ID NOS shown in parenthesis.
*mouse dl sequence Expression Analysis A Northern blot (Clontech, Inc.) containing RNA from human fetal tissues (17–24 week EGA) was hybridized with a radiolabeled probe containing exons 5–11. Nested primers from DL exons 11 and 12 (394 bp amplicon) were used to amplify by PCR a human craniofacial library made from embryos of 42–53 day gestation (5'-GCGTCGACAGTGAT-GAGGA-3' (SEQ ID NO: 58), 5'-CAGTCTTTTGGCAC-CACTCA-3' (SEQ ID NO: 59), then 5'-ACGTGTGTG-GAGTCGTGGA-3' (SEQ ID NO 60), 5'-CTCGTTGGATCCTTGGCTT-3' (SEQ ID NO: 61)).

RNA isolated from human fibroblast, keratinocyte (Clonetics), lymphoblast cell lines, and fetal skin (15 week EGA), was reverse transcribed and subsequently amplified in nested PCR reactions with primers from exons 4 and 6, yielding a 238 bp PCR product (SEQ ID NO: 50 and 5'-TACATGCTGGAGAACAGACC-3' (SEQ ID NO: 62); SEQ ID NO: 63 and 5'-TTGGCAGAAGCTCCTGAAGT-3' (SEQ ID NO: 64)). Control PCR reactions were conducted using primers derived from HPRT cDNA sequence (5'-TGCTCGAGATGTGATGAAGG-3' (SEQ ID NO: 65), 5'-AAGCAGATGGCCACAGAACT-3' (SEQ ID NO: 66)).

Physical Mapping and Isolation of Genomic Clones

The Genebridge hybrid panel (Research Genetics) was used for radiation hybrid mapping, screening with an STS designed from IVS-3 sequence (primers: SEQ ID NOS: 48 and 53). The results of the screening were analyzed on the Whitehead/MIT Genome Center web site. DNAs isolated from YACs (Research Genetics) previously localized to the region (Konrad et al., 1995, *Genomics* 30:514–20) were screened for the DL gene by amplification with the IVS-3 STS. An arrayed human BAC library (Research Genetics) was screened by PCR using the same STS.

Genomic Organization

When possible, the intron/exon boundaries were determined from genomic DNA by inter-exon PCR amplification. Primer sequences are shown in Table 3. The remaining boundaries were defined by either vectorette PCR or by direct cycle sequencing of the BACs.

morphogenesis (EXAMPLE 8). DL is not expressed in human lymphoblast or fibroblast cell lines, but is expressed in cultured neonatal epidermal keratinocytes.

Figure 6:
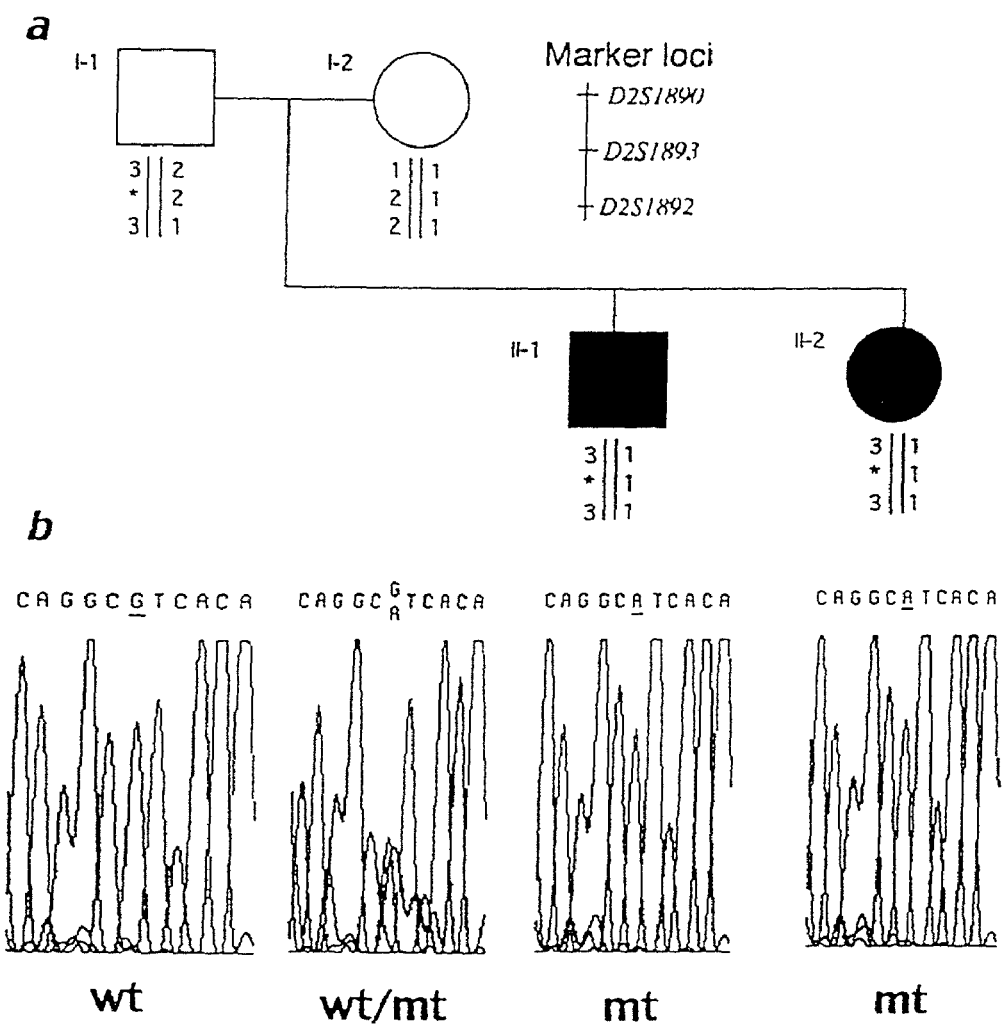
FIG. 6 is a schematic drawing representing the mutations observed in Family ED1237. (a) Pedigree with haplotypes showing lack of transmission of a D2S1893 allele from father to either affected child. (b) Partial sequence showing hemizygous wild type (wt) sequence in father (I-1), a heterozygous mother (I-2), and homozygous mutant (mt) sequence (266→A) in children (II-1 & II-2).

The ORF of human DL encodes a 448 amino acid protein (SEQ ID NO: 17), 91% identical to the dl protein (FIG. 6). The program TMpred predicts a single transmembrane domain with a type 1 membrane topology (N-terminus extracellular). Computer analysis using PSORTII predicts a possible N-terminal signal peptide for the murine dl protein, but no signal sequence is predicted for the human DL homolog, due to differences in non-conserved amino acids. As with the dl gene (EXAMPLE 8), a similarity search using protein-modeling programs pfscan and Pfam reveals a partial match (pfscan N=6.9) with the TNFR cysteine-rich region (Prosite—PS50050), in the ligand-binding region of these receptors. In addition, some similarity to a death domain (PS50017) was identified (Pfam E=5). Similar to members of the TNFR family, this potential domain resides in the carboxyterminal end of the protein, and may trimerize and interact with down-stream signal transducing proteins. Although individually the matches for each identified domain are not statistically significant, the occurrence and location of these two different domains within this predicted type 1 transmembrane protein indicates that it functions as a receptor and is related to the TNF-receptor family.

TABLE 3

Primers Used for Inter-Exon Amplification for Genomic Structure

| Exon | Forward Primer (5'-3') | Reverse Primer (5'-3') |
|---|---|---|
| 1–2 | Vectorette PCR | |
| 2–3 | GGAGAGGATGGCCCATGTG (67) | AGCCCCGTAGTCTGGTTGTA (57) |
| 3–4 | CTGCGGTGAGAACGAGTAC (48) | TCTGGTAGCCTCCTTTGGAA (53) |
| 4–5 | TTCCAAAGGAGGCTACCAGA (63) | CAGACCATGCCATAGATGTTC (68) |
| 5–6 | Vectorette PCR | |
| 6–8 | ACTTCAGGAGCTTCTGCCAA (69) | TCGTCCTTGCTCACTTGGG (70) |
| 8–9 | Vectorette PCR | |
| 9–10 | GGATGAATTTGAGAAGCTGAC (71) | CTGACTTGTTCGTGGTGGC (72) |
| 10–11 | GCGTCGACAGTGATGAGGA (47) | TCCACGACTCCACACACGT (73) |
| 11–12 | Vectorette PCR | |

All primers shown in the 5'-3' orientation.
SEQ ID NOS shown in parenthesis.

Results

Figure 5:
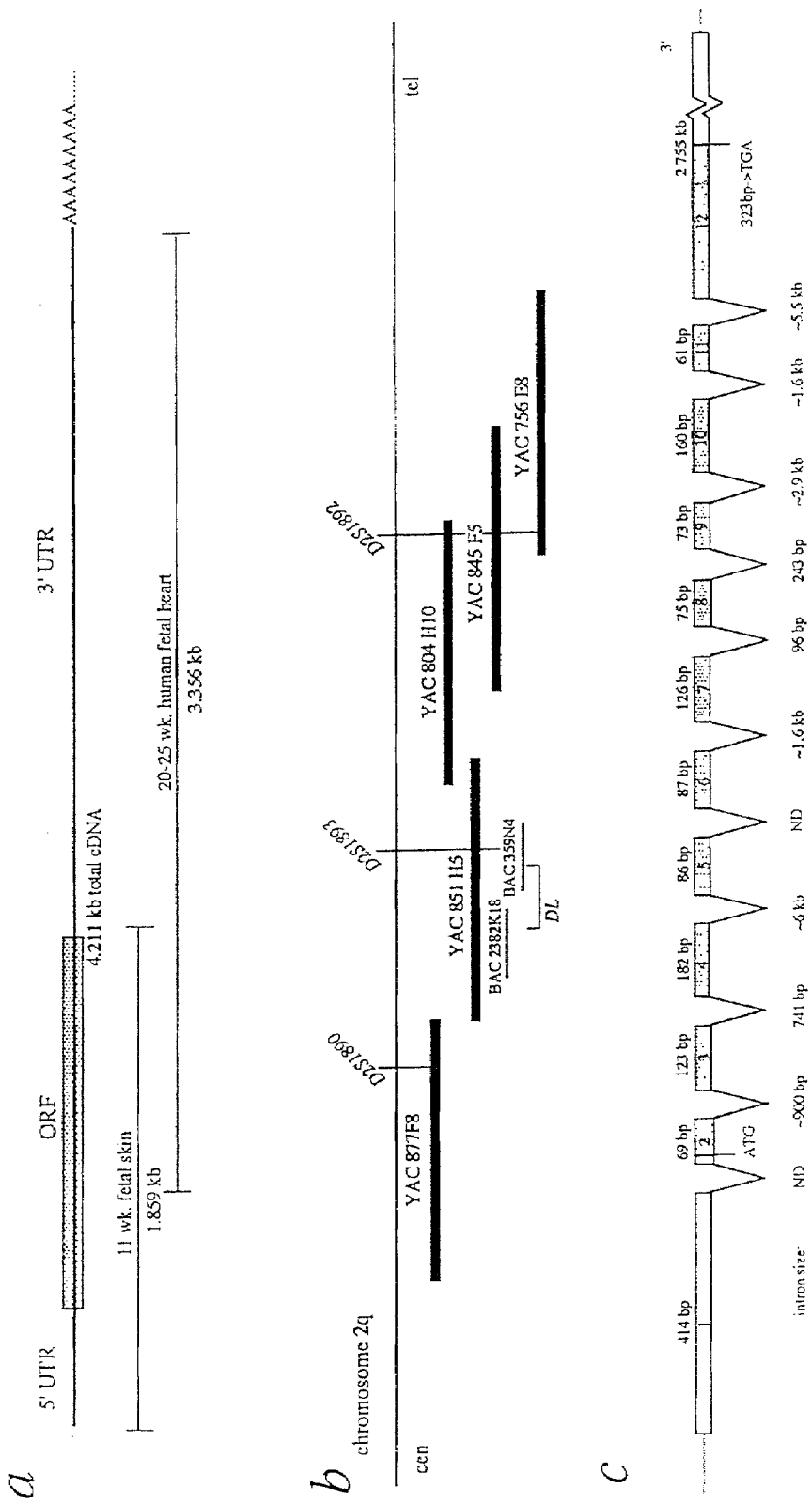
FIG. 5 is a schematic diagram illustrating the DL gene transcript, physical map and genomic organization. (a) cDNA from which the consensus sequence was constructed. (b) Physical map of the region with relevant genomic clones. BAC359N4, identified by a library screen, contains exons 2–12 and the 3' UTR. BAC2382K18, ascertained through data base searches, includes exon 1 plus the 5'UTR. The centromeric to telomeric orientation of the BACs and the candidate gene are unknown. Marker D2S1893 is either intragenic or 3' to the candidate gene. (c) Genomic structure with open reading frame shaded. The sizes of two introns were not determined (ND).

Using a cDNA from the murine dl gene (EXAMPLE 7), a single cDNA from a human fetal heart library was identified. Additional sequence information was obtained by RT-PCR using total RNA isolated from human fetal skin. The consensus sequence of the human gene (DL) contained an open reading frame (ORF) of 1,347 bp (SEQ ID NO: 16), preceded by a 432 bp 5'-untranslated region (UTR), and followed by a 2.3 kb 3'-UTR (FIG. 5).

Northern analysis revealed only a single 4.4 kb transcript in fetal kidney and lung. The DL gene is expressed in embryonic and fetal tissues during periods of hair follicle, eccrine sweat gland, and tooth bud formation, as shown by its expression in fetal skin at 11 and 15 weeks EGA, and from a 42 to 53 day human craniofacial cDNA library. This is consistent with in situ hybridization studies in mouse embryos showing expression of dl gene during follicular The human DL gene was localized to a position 10.1 cR from marker AFMA037YB9 (likelihood P>3.0) by radiation hybrid mapping, consistent with the independent localization of an homologous EST sequence (W73914) to reference interval D2S293–D2S121 (122.4–127.9 cM). Single families with autosomal dominant and recessive inheritance have been mapped to the 2q11–q13 region, which contains this interval. Genomic clones containing the gene were identified by screening both a human genomic BAC library and YACs from the region (FIG. 5B).

The DL genomic structure indicated the presence of twelve exons with flanking intronic sequences (FIG. 5C). The full coding sequence of a human DL gene is shown in Table 4, with exons 1–12 identified, and separated from the intervening sequences.

TABLE 4

Human DL Exon/Intron Sequence

| Description | Nucleotide Sequence |
| --- | --- |
| Exon 1 (5'UTR underlined) | TTTTTTTTTTT<u>GGGGGCAGACGGCCGAAGAGCCAGGTGTGCCAAGGTCA</u><br><u>TATGGCAGCAGGGCTGAACGTGCCCGCTCCAGCCTCTCCAGTGCTGGAA</u><br><u>GAGACCTCTAGATGGAGCAGGTGAGTTTGCAATTAGGGAAAGCCCCTC</u><br><u>GGCAAGGACTGAGTTTCCAAACTTGCAGACAGGGCAGGGAGCGGTCAA</u><br><u>GGAAGAGTTCCCGGGAAGCCCTTTAAACGGAAAGGAAGCGGGGCTAGT</u><br><u>GTCAGAGAGGTGTGACAGGTCCCAGTCAGCCCTGCTGGCCCCTAAGGA</u><br><u>CATAGAGTACCTGCTTCTGAGAGGGCTGCCACGGTGGCCACCTGTGAAG</u><br><u>CCTGTCACCCAGAACTGGATGGTACCTGACTTTCTTCATAGACCCATCTT</u><br><u>CTGCTGGGACTGAAGCTGACCTCCAACAGAAGCCAG</u>(94) |
| Intervening Sequence (IVS) 1 | GTAAGCCCTGGTCCTTTCCTCTGGTTTTCTAAACTCTTCAGCTGTGGCCG<br>AGACGGAGGTGTCATGGGCTGGGAGAGAGCTGGGTGCATTTTTGAAA<br>TGCATGTCATTTTTGGGTTGCGTTTGAA...GGTTTCNCCAAACCCTCTGA<br>GCACGAGAAACACAATCACTANCCTCGGGTTTAACCTTGGGCCCTCCGT<br>GTGCTCCTAGCCTCCTNTCAGGCTCCCTCCCAGGCATGGCTGCNAGGCT<br>GGGAAGGCCCCAGAGTCAGCCCAAGTGGCATGGGTNCAGCTTCAGCTT<br>CATGTCTGCTTTTCTTTTAGGATGTATAGTTTCCCCTCTGTTTGCTGGAA<br>GGCACCTTATATCCAGTGGGGTTAAATAAAGGTAGCCAGACCCCCGGCT<br>GGGGTGCTACCGCCAGTGCCCAGCTAATGACGCATNNNTTCAG(95) |
| Exon 2 (5'UTR underlined- remaining is coding) | <u>GTGAGCCCCTTGGGAGAGG</u>ATGGCCCATGTGGGGACTGCACGCAGAC<br>GCCCTGGCTCCCCGTCCTGGTG(96) |
| IVS 2 (SINE-MIR repeat- 112bp- italicized) | GTAAGTGGTCTGAGCCCCTTACCCCCACAGCACCCTCATCCTCATGATG<br>GTTGGA*CTGTTTCTTGGCCTCTTCAGCTGTAAAATGGGAATGCTGATCATAG*<br>*TCCCTCCTCCACAGGGTTCTTCTGAGGGTGAAATGAAACCAGGCCTGCAAAG*<br>*CACAGAACTCTGCCCCAGGCTGAAGTTACATTGATTTCGTTGGTAGCTCC*<br>CTTCATAGGGTCTCATGGATATAAACGTTCTTGATTGCTTGTTTGTGGTG<br>TGATACACACAGCCCTGTGTCTATGTGATGAGCTCATGCTTGGGGGCCG<br>CGCAGCTAAGAAAGACTTGGAAGACTCAGACCCCTACCCCCATCCTCCT<br>GGACACGCCGGTGTTCTGAGGAGCCACTGTATTAGAGGCTCAGTGGGG<br>GACAGGGGCGCCTCCTCCATGACCTTGGCAAGTGCGTTGATGAGGAGA<br>ACTCANAGCAGGCCTTGATGGTGGGATGGGGCTTGGCCAGCAGGGGTG<br>AAGGCAGGGTGGTTCTAGTGGGGGCTGGCCGTGCCCANGTGGATCAAC<br>CAGGAGCCACTGGAGACTTAACAGCAGTGAGCACTNACAAGCGGCACC<br>TTCCCAGACCGAGCCCCCAGCAGAGCCCCCACCGCAGGGCACCCCCTTC<br>CTATGTCAACCTTGGGGTCTTGCAGGAGTCACATGTGTTTCTAAGGAGG<br>TACGGAGGCCACAACACCCCCCTTTGTTGGCAG(97) |
| Exon 3 | GTGTCTCTGATGTGCTCAGCCCGAGCGGAATACTCAAACTGCGGTGAGA<br>ACGAGTACTACAAcCAGACTACGGGGCTGTGCCAGGAGTGCCCCCCGTG<br>TGGGCCGGGAGAGGAGCCCTACCTG(98) |
| IVS 4 | GTAAGGACCCAGCCCTCCTGGAGCCTGGTGCGCTCTCAGGGGAGGCCTC<br>CTGCTTGTGGCATTGTTGCCCTGAGCCTGCCTTGCTGTGTGAGGGGATG<br>CCAGGGTATATCAAACCAGCCGGTCACGCTCCCTGGACGTTGAGATTGA<br>TGGCAAGAGCTGCCGTGAGCCCAGGAATGGCACTCACCAGCTAAGCAT<br>TCATAAACAGATTTTTCAGGAGTTCTGAAATGTTTTTAAAGGATCACTTT<br>CCCACTCTACCCTGATTAAATGAGCGTCAGATCATCTGATTGGAAGCAG<br>GATTGAAATATTCTCCAGTACTAGTACATTTTTTCCTGAGTGCTGCATCT<br>CCCTCCGCCTCTGGGCAAGCTAAGCCTGAGTGTTCTGTTCAGCACTAAG<br>GGAAACCTCCGGGGTTT7CAGTGTCCGGTTCTTGTAGCAAGCTGAGGAAA<br>GTCAGATGCCAAGTGCTACCTGCACTGCCTGGGCATTCCAGCAGCTCGC<br>TGAATTCATCTCGGGGAGGCTCAGAAAAGGGGCAGCATCTGGAGCCTG<br>AGAGTGGCGAGGAGAGGGGCAAGCCCAGAGCATGAGCTGGTTCCTGGG<br>GGGTTTTGCAGTTAGGACAACTCAGGAAACCAAGGCCCGGCAAGAGTA<br>GCTTCTGGAGACAGCTGGCACGTCACTGCCCAAGGACTGTGGGCCGAG<br>TCCGTATGGTTTGGCTGCTGCACTCACCTGTGTCCCCTGTCCTCTTTCCC<br>TGGACAG(99) |
| Exon 4 | TCCTGTGGCTACGGCACCAAAGACGAGGACTACGGCTGCGTCCCCTGCC<br>CGGCGGAGAAGTTTTCCAAAGGAGGCTACCAGATATGCAGGCGTCACA<br>AAGACTGTGAGGGCTTCTTCCGGGCCACCGTGCTGACACCAGGGGACA<br>TGGAGAATGACGCTGAGTGTGGCCCTTGCCTCCCTGG(100) |
| IVS 5 | GTAAGCACAGGCCCTCCTGGCAAACCCTGGCATGCTTTCTGCAGAAAAC<br>CCCGAGGGGCTACGGGCAAGGACCTTGGGAACAGGGGTCATGGATACT<br>GCAGGCCTCGGTGCAGCCGCACACCTGGCCTTGGTCCCATCCCACAAGG<br>AGCAGCATCCAGGACGGAGAGTCCTGGCCCCTCCGGTGGACAGGCAGC<br>CCATCAGGCTCTGCCTCTGTGTCTCCTAAGTGGCATTAACCATCATAAT<br>ATCTTCTGACCACCAAAAGGAAACAAATTGCTTGAATACTTACAGTGCA<br>GTAGCCCATGTGAAACACTTTGGGAAAAAGAAAACTNNAATTTNATGC<br>AAAAAGCAGTATTTTNAGTATTCTGGNAACACTCTGGNNAANCTACTAA |

TABLE 4-continued

Human DL Exon/Intron Sequence

| Description | Nucleotide Sequence |
|---|---|
| | TAANNTANATNTG...AGAAAAGAAATATNANTGANGAGATTATGANNNC<br>GAAGNNAAGNNANGNANAANCANANNAGGNTNNAGAAAATGAGGTTG<br>NNAANGANTNATAANATAGNACANNGNTGATATNCATNGGAAAGTAA<br>ACNGCNTGAGNANNAGTGATTTGTGATNGCCAGGGTATTCNTNGAGGG<br>AAAACANGACTATTGGANCAGANNGTGNGGAAAGGNACAAACGNTGT<br>NTNANCATAGANAANNTAGAGTTGNTGGGTGGGCATTNNAANNAGCNG<br>GTAAAGAATAGCTTGNAAGTNGNCAAGGGGTNCCAGAGGCAANNNTA<br>ATGCCTATANATCCCATAAGNNTGCAGGCTANTGGNGANGGTGCTNAC<br>AAAGAGCATGTTCCTCCTCCAGGAAGGTCTGGCCTTNGTTGGTGTNACC<br>CCTGGGGGGCTAANCAGGCCNTACATGTGGGGGCACAGGGATATTTCT<br>GGTGNATGATGTGATGGCACACACACTAAACACAGCCACCAGAGAGAG<br>GAACCAGAAAGGGGCTGAGATCAAAAGAAAGGCCCACGTTGGCAGCTC<br>AATATTGTTAAAAGAATGCTCCATTTCAAGACAGGCTGAAACCCCAAG<br>GAAACTGAGTGGACAGAGCAGGTGACTGAGTGGGCGTGGCCTCATGCC<br>CGACTTGATTGTGGGCCTGCAGACTGGCCACCGTGCTCTCTGCACCAGT<br>CCCTGCCTGTGTGCTGTCCAGCTCACCTGTCTACTGTTTTGTCCTTGTGC<br>TCTCCNCCGTAG(101) |
| Exon 5 | CTACTACATGCTGGAGAACAGACCGAGGAACATCTATGGCATGGTCTG<br>CTACTCCTGCCTCCTGGCACCCCCAACACCAAGGAAT(102) |
| IVS 6<br>(SINE-MIR<br>repeat-<br>104bp-<br>italicized) | GTGAGTGTCTTTGTCCTTCCACCAGCACGGTATTTGTTCAGGCACGGAT<br>CTCTTTCACTACAGAGGGTGTAGGAAAGAGCCGGTCCTGGCACCTGGAC<br>AAGGTGAATCACAGTAACAGCACTAGTGAAAGTGCTCCTGTGGCCTGTC<br>CAGGCAGGTCTATGAAGGGAGGGGCGTTTGCCACATCTGAGC*CTTGAGT<br>CAGAGGCTGAGGTTCTAGTGCAGGTTGGCCACCAGCTACCTGACAAGTCAC<br>TTAACCTCCATGAGCCTCGGTTTTCTCATCGGTAATATGGGGGTGA*...AGAAA<br>GNACAATANCGATGACTCTTTAGGGTTCATTAAACAGTCTAAGAAATAC<br>AAATATTTAGCTCCCCTCAGCCATCACTGCCTCAGGCCCATTCATGATC<br>ATGAATCCAGATCCATGAGCTCTGTGGCAGCGTGCTTTGAAGGTGGAGC<br>TTCTCTGGATCATTTGAGGGACTCTATTTTGCCTTGCAG(103) |
| Exon 6 | GTGTGGGAGCCACTTCAGGAGCTTCTGCCAACTTCCCTGGCACCTCGGG<br>CAGCAGCACCCTGTCTCCCTTCCAGCACGCCCACAAAG(104) |
| IVS 7 | GTGAGGAGGGTGCTCAGGTATCGATCACCTGGAGTTAGGTGGTACTCG<br>GATGAAAGCTCAGAAGAGGAGAGGAAATGATCATGAGTGATGATTATG<br>GTGCGCTTCCCCACCTGGCCTCACCTCCCTAATGTAATTGAATGACATG<br>TTGCCCCCCGTGCAGGAAGTCATTATATCTGCAATCAGAGTTGATCCCT<br>CTATGGGTGTCCTGGGACCGCTGGGAGGTGCTGGTGGTGAAGGCGGGG<br>GCATAGCGGCAGGTGGACAGCACAGGCAGCTGCAAGCCCGGCCAGGAG<br>GAGAGACCAGGCGTCCTGGGCTTTGGTTTGGCCNGAGTTAACAGCAA<br>TTCTATCACTGGTTTTCATATAAACATGCTGACCATAGCACTTTAATATT<br>AACTTGCANAANGTNCATTTTCATTCTNCCTTAACCAGGGAAGANGGGA<br>TCGNGGAGGACCCCAANGTTTANTNTGCCTCTCACANTTAGNCCCCCAC<br>NTGGCTT...GNCNTNAAGGTTGCCAAAGCAGTAGNAGCGAGAAGCAAGC<br>TCCCCTTAGGAACAATNAGGTANCCCCAGAAAAAGTCTGGANAGGCCAA<br>GTCTGAGGGCAGCGAGCAGGGGTTGTGGGCAGTCCTGGTCTGGCAGCC<br>AAAACCAGCGCGNAGGATTTGGTTCTCAGTCTAAGCAAGCACCTCAGA<br>TTTCAGGGTTCCCTGAAAGCATCCCAGGGGCAGGGCCATTGCTTCCAGG<br>GGCCGGAGTCCTGGAGGGAAGACCAGCAGGGATCCTGAGCTCTGGGTC<br>ATTCATGCCTTCTCTCCACCCACAG(105) |
| Exon 7 | AACTCTCAGGCCAAGGACACCTGGCCACTGCCCTGATCATTGCAATGTC<br>CACCATCTTCATCATGGCCATCGCCATCGTCCTCATCATCATGTTCTACA<br>TCCTGAAGACAAAGCCCTCTGCCCCAG(106) |
| IVS 8 | GTGACGGCCCCCATGCGCCGGTGCCCTGCCTCCTGGACTCTCCGTCAAC<br>TCCCCCTGTCGGAGAGCCTGGCTGCTCACTCCCTCCTCTCTCCCCAG<br>(107) |
| Exon 8 | CCTGTTGCACCAGCCACCCGGGGAAGAGCGTGGAGGCCCAAGTGAGCA<br>AGGACGAGGAGAAGAAAGAGGCCCCAG(108) |
| IVS 9 | GTCTGTGAACCAGGGCTTCCACACACCATGTGCACGGTGCCCATCTCTG<br>GGTGGAGGGCGTTCCCAGAAGCAGCCTCCTCGCTGCTTCTGCTCTCACA<br>TGCTGAACCATACTGTGCTTACCGTGGGGTGGTGCCACACAGACACCGG<br>GCAGCTCTGCCCAACAGGAAGAGCAGGGTTGGGCTGAGCGCANAGCCA<br>TGAGCCAATTCTAACTCCTATCTCCCCAACCTCCCCATTTCCCTGCAG<br>(109) |
| Exon 9 | ACAACGTGGTGATGTTCTCCGAGAAGGATGAATTTGAGAAGCTGACAG<br>CAACTTCAGCAAAGCCCACCAAGAG(110) |

TABLE 4-continued

Human DL Exon/Intron Sequence

| Description | Nucleotide Sequence |
|---|---|
| IVS 10 | GTATGTGGAAGCCCCCACACCAAGCTGAACTGGGGTCCTGTGGATCCTG<br>AGCAGGGAGGGGTTNCCAGGGTGCAGCCGAGTGAACTGACAGGCTAGC<br>CTGGGACACTATGGGACGTTCGGCGACAGACAGTCCCCACCACCTCTT<br>TGCTGACTGGCAGGGGTCAGGTGGTGTGAGGAGCCTGTGGAAACAGCT<br>GCCTGCTGCTCTCGGGTCAGGCCCCTGTCCCTGCATCCTGCCAAATTCCC<br>TGGGCCTTCCTCCTTAACATCCGAATTCCTCATGCCCCTTCTCCAGACTG<br>GGAGGGCAGAACATAAAGCCAAGGATGCATGCCTGTTGCGGCCAACAC<br>ACCAGTACCACCCGTGCCGGTGCCAGTACTGCTGCCACCGTAATGCTGG<br>TAACAACCGTGGTGATGACGGCTAACAGCATTTGGTGCCTACTGCCCAC<br>CAAGTGCTGGGCTAGGGCTGTGAACACATCCTNCCTTCCACCAGCCCAN<br>GAGCAAGGTGCTTGGAATCATCCCTGGTTATAGGAATACCACACTGAG<br>GTATGGAAGTTGTCACTCGCCCAAAGTCACACACTAGTGAACACANGG<br>CTTGGGGTCCGAAGTCCANGCTCCCAANGAGCCACATGGNGNTAAANA.<br>..GGTNAGNCAGGGTCACCCCCCTAAGTTCCAAGAGGGGGGCTTTTCNAG<br>GCACAAAGGGTTCCATTNAGGTTCCCTTTTCAATGNCTTCCAGAGAGCC<br>AGCATGGATTTCAGCGCCAGCNGCATCCAATCTGTTTGCTTTAACATGA<br>AGACACCAGTTGAACTTGGGTGCTTACTGGGATTAAATACAGAGATCTA<br>GGACATATTCAATGAACCTTCACGGAGCATCCATTGTGTGTCAGGTAGC<br>AGGGAAGGAGAGGCCCGTGGATGCCTCCCACCCGCAGTGGCAGCCCCA<br>GCCCCTTAGACGCCTGCAGGTCACCCACCACGGACTTGTTTGTTTGGAA<br>AGAAGCAGGAAGCCACCGGTGTATGTCTCGTCTCATGTCCCCTGGTCCC<br>GTGCCCACAAGGTGCCCAGTAAACACCTGAAAAACAAGTCATTGCCCC<br>CCACTGTCCACAGCTGGGCAATGGACAAGTTCACCACAGGAGAACTTG<br>TCAGGGCTGCAGCCCCCCCAGGCACTGCTAATGACCATCGCTCTTGTTT<br>TTGCAG(111) |
| Exon 10 | CGAGAACGATGCCTCATCNGAGAATGAGCAGCTGCTGAGCCGGAGCGT<br>CGACAGTGATGAGGAGCCCGCCCCTGACAAGCAGGGCTCCCCGGAGCT<br>GTGCCTGCTGTCGCTGGTTCACCTGGCCAGGGAGAAGTCTGCCACCAGC<br>AACAAGTCAGCCGGG(112) |
| IVS 11 (Alu repeat-italicized) | GTGAGGCTCCTGCAGGTGCCATGATGAGCTGTGAGATGTGGCTCCCTCA<br>CAGCCGCAAGGACTAAAACTTTCTTATTGAATCAGCTCTCCTGCAAGAC<br>GGGGTGTTTCTCCCAGAAGTCCAAGATAGGAGACCTGGACAGTGACAA<br>GTTCACAGCAAGATAGTCAAAAGGGAAAAAAACCCTTTCGTTTTTGAG*T*<br>*TTTGTTTTTTTTTNGGNGATGANAGNCTNG*...(113) |
| Exon 11 | ATTCAAAGCCGGAGGAAAAAGATCCTCGATGTGTATGCCAACGTGTGT<br>GGAGTCGTGGAAG(114) |
| IVS 12 | ...AGAGTGGNNGAAGAGNGAAGGGAGGNGAAAAGGGGNGAGNGAGG<br>GAAGGAGGNGGGAANNNGGAGTGAGGGGGGGAAGGGGNAGAGNGGG<br>NGGNAGNGNGNGGNGAGNGGGANAGNGAAAGNAGTGAGANGGGAAG<br>GNANAGNGAGNAGGGGNNANGAGAAAGNGGGAGNGTAGGNGGCGAT<br>GNGNNNGGTNGAAATATTNANAGAAATTTTTTCAAATAATTTTTATTTC<br>ATTTAAATAATTTTTCAGTGTTGACCTTCTATTGACTGTGACTTGCAACA<br>TCTAACTGTGGCCATTGGTGTCTGTAG(115) |
| Exon 12 (3'UTR underlined) | GTCTTAGCCCGACGGAGCTGCCATTTGATTGCCTCGAGAAGACTAGCCG<br>AATGCTCAGCTCCACGTACAACTCTGAGAAGGCTGTTGTGaAAACGTGG<br>CGCCaCCTCGCCGAGAGCTTCGGCCTGAAGAGGGATGAGATTGGGGGC<br>ATGACAGACGCATGCAACTCTTTGACCGCATCAGCACGGCAGGCTAC<br>AGCATCCCTGAGCTACTCACAAAACTGGTGCAGATTGAGCGGCTGGAT<br>GCTGTGGAGTCCTTGTGTGCAGACATACTGGAGTGGGCGGGGTTGTGC<br>CACCTGCCTCCCAGCCACATGCTGCATCCTGA<u>AAAGCATGCCTGTGGGC</u><br><u>TGTCCTCCCAgGACAAGCCAAGGATCCAACGAGGGCTCTGGAGCTGTGA</u><br><u>GTGGTGCCAAAAGACTGCCAAGAATCaAGGCTTTTGTGATATGTCACCG</u><br><u>TATGCCTTAGGATGTTCAAGGAGCCAGACGAAATAAGGCCTGTCTTCCA</u><br><u>ATTTAACCAAAGATAAAGGACTAGAGCCGGGATACTTTCANATGCTCG</u><br><u>CCTGTACCTCACCAGGCAGAGTAAATATCTACTCACTCATACAGCCAGC</u><br><u>CCACCAGCCCACCATTAACTCACTGAACAATGAGACAATGTNGAGGAC</u><br><u>TCAAATGAATCAAACCCCGTGGGAATGACAGANTGAAGAATCTGGTCC</u><br><u>CTGTCTTTAAGGAGTTTGCACTCCAGTAGAAGACAGAAGGAACGTATGT</u><br><u>TTACAAACCACTTCACTGGAAGACGTCAAACAAGCTGAATGAAGGGGC</u><br><u>GCTTAGAAAACGTTAATAGAAGTTCTAAGCGGGAGATGACTCCCTACTG</u><br><u>GGATGATGAAGGATGGCATCCTAGTGAAGAAGCAGCTCAAACATTTTG</u><br><u>ATAAAATGGCAACAAAATGCAGACACCCTGCTCCAGGTATTATTTCAGG</u><br><u>TTTAGTACAAGTCTGTTAATACCCTATGTGGTTTCATTAGGATAACTTTT</u><br><u>TACCTATCCTTGAGGTCATCCATATTGTTACAGGCCTTCCAGTCAATAAT</u><br><u>GGAAGAGCTCACTCTATACAAAACCAATATGCAAGGCATGTGTTTGTCC</u><br><u>AAGCAATTGGATGTGTGCAGTAGCCAATTTCATTTACTGCATTACTCTTT</u><br><u>GGCCTGGGAACCCTGTGGTCTGCACTACATGTGAATGGCCTTCCACTTC</u><br><u>AAGTCTTAGGCAGATTTGACCTTTTAGGGGCAGCAATGCTGAAGGACAC</u><br><u>AGCAATTTAAATTATAATGTGTCAGGCTGTGTTTTCACTTCAAACATGT</u> |

TABLE 4-continued

Human DL Exon/Intron Sequence

| Description | Nucleotide Sequence |
|---|---|
| | ATGAGTAGTCAGCTGTAATTAGAGAAATGATGACTTCCTAAGAGTTCAG |
| | CCACGCATAATTCTAGATTTCAAGAGCATCTAAGACTTGTGGATTAGCC |
| | TCATGGCATGAGAGTTTCAGACTCAGCCTTCTGAGCCAGTCAGGGAAAG |
| | TGGAGTTCTGCAGCGCAAATGAGAGCCTGGGCTTGGTGTCGAGGGAGC |
| | TGGCTTCTAGTTGTGCCACCTTGGGCCTTGTCTTTTCCTCTCTCTGCCTCA |
| | GTTTCTCGTCTGCCAATGAGATGTTAGTTAGTGATTCTATAATTGGGGC |
| | AGGTAGGGTTCAGGTGAGCAAAAAGAAAGTGGAGCTATAGGAAATGCC |
| | AGGCCTTTGAGGTGCTCTATGGAAGTCAACACAGTGTGGTTTGTCCATT |
| | TAAATGGGAATAAAAACAGAAAAACTCAGACTTGGCATTTTCACAATA |
| | ACTGCAATGGTTTGACATAACATTTATAGGCAGAAAGTTAATAAACTGG |
| | CATTGTTCTTGGCATATTATTGTACTATCCCTGTAACTGCCAAGAGCTCA |
| | GGAGCCAGGCTAGTGATCACACCAGGGGTTAGAGTTCACTGCTGAACT |
| | CCCTGATGGCAGGTCTGTGTTTATTACTACATTAAAACAAAGTCTCTGA |
| | CTTATAAAGCGAGGTCGTAAAAATTACAAGTTGCATGACTGAAAAAAT |
| | GCTTTAGGGGGAAAATCAGTCATATCTTTAACACCAACAAGCAATTTCC |
| | CACCAACGAATGTAGTACATACTGTGAGAGGATCATAATGAGGTCCTG |
| | AATATTTAATATCATCATTTACTGTGTCTGTTTGCTGCTGTTTTTCGAAC |
| | CTATTTGGTTTACCCTGCAAGCTAAATACTCCACGGCAGANCTTAATTA |
| | TCCTTTTAATTCCTCTTTGAAATCCTGTGGTGCCCCCTTCCCCCTGCCTTG |
| | TGATGATGATGAGTGAGTCTCCCCTTAATTAGACTGCAAATGTCACTTG |
| | TGATGAGTGTGCCATTCCAGGATAACAGCTTGCACCCTCCTCAGAATGT |
| | TTTCAGCGAAAGAGTGGGGTGGCTGTTCTCTGCTCCTGGTGCTTTGGCC |
| | TCATTTCACACTATTAGAATTCTGGGGCTGTAAGGCCAGCCAGTGTCAG |
| | CTCATGTTCCATTGGCTCTCCACCTGCCATTTTTAGGGAGCTATTCCTTA |
| | TATAGTTACAAATTCCCTTGTCATTTACTTATTTGGAAACATGGGATTTA |
| | CTCTGACAAGCTTTAGCCTATGTTATGGGATTCAGAACAATGAGATCAT |
| | AATAATTCTCACTGACCAAAGCTGGGACTCCATCCTGCCATTTTTGTGT |
| | GGAGATATTCATAATTCTGCAATACTTTAAAACATTTAGAAAACACCCC |
| | AGGGTAGGTCTGTGGCCCTTANACAGTGAAAGTCTTAATTGGCAATATT |
| | ATTTTTGCTAATTCTGGATATATATAACNNATTATATTTATAAATCTCAA |
| | TAAACCCCATTTANTAAAAAAAAAAAAAAAAAAAAAAAA(116) |

SEQ ID NO shown in parenthesis.

EXAMPLE 10

Mutation Analysis of the DL Gene in Patients with HED

Kindreds

Clinical information for each family, with specific attention to dentition, sweating, scalp and body hair, as well as informed consent for blood sampling and DNA analyses, was obtained. Twelve families were included as having possible autosomal recessive inheritance based on affected sibships with unaffected parents and/or the presence of a fully manifesting affected female. Five of 12 families were consanguineous. Two kindreds had apparent dominant inheritance based on vertical transmission of the trait with males and females affected to a similar degree.

Linkage Analysis

Primer pairs were used for microsatellite ($CA_n$) markers (Research Genetics) to amplify genomic DNA utilising recommended conditions. The amplicons were subsequently electrophoresed on a 7.5% polyacrylamide gel and blotted as described previously (Zonana et al., 1992, Am. J. Hum. Genet. 51:1036–46, herein incorporated by reference). The membrane was then hybridized with a digoxygenin 3'-end labeled $CA_{(15)}$ oligonucleotide, and subsequently developed using the Genius™ System Nonradioactive Nucleic Acid Detection Kit (Boehringer Mannheim).

Mutation Analysis

Primers from intronic sequences flanking exons 2–11 and from the coding region of exon 12, were designed to amplify genomic DNA from one affected individual in each family. Ten amplicons containing the entire coding region and the intron/exon boundaries were analyzed. Each exon was amplified in a 25 µl PCR reaction containing 5–10 ng DNA, 2.5 µl of 10× buffer, 6.5 pmol each primer, 0.5 mM–1.5 mM $MgCl_2$, 0.2 mM dNTPs, and 0.02 U Taq DNA polymerase (Qiagen). The exons were amplified using the following PCR conditions: 95° C. for 30 seconds, 30 seconds at the annealing temperature (Exons 2, 5, 10: 58° C.; Exon 3, 53° C.; Exon 4, 7&8, 60° C.; Exons 6, 9, 11 and 12, 57° C.), and 1 minute at 72° C., for 30–33 cycles.

After confirmation of amplification on a 2% agarose gel, products larger than 200 bp were restriction digested to obtain products between 70 bp and 205 bp (Exon3-BsrBI, Exon4-BanI, Exons7/8-HindII, Exon10-SalI, Exon12-XhoI, BsrBI). Amplicons or their restriction digest products were analyzed by single-strand-conformation-polymorphism-analysis (SSCP).

DNA from relevant family members, plus 50 control individuals (100 chromosomes), were tested for the presence of the variants by the appropriate method; electrophoresis on agarose gel, SSCP (see Table 5 for primers used) or ASO analysis. Putative mutations co-segregated with the disorder in each family and were absent in the control population.

TABLE 5

Primers used for Exon Amplification for Mutation Screening By SSCP

| Exon | Forward Primer (5'-3') | Reverse Primer (5'-3') |
|---|---|---|
| 2 | AAATAAAGGTAGCCAGACCC (74) | GTAAGGGGCTCAGACCAGT (75) |
| 3 | CATGTGTTTCTAAGGAGGTAC (76) | CAACAATGCCACAAGCAGGA (77) |
| 4 | GTCCGTATGGTTTGGCTGC (78) | GCCAGGGTTTGCCAGGAG (79) |
| 5 | GTCCAGCTCACCTGTCTCT (80) | ACCGGCTCTTTCCTACACC (81) |
| 6 | TGGAGCTTCTCTGGATCATTT (82) | AACTCCAGGTGATCGATACC (83) |
| 7–8a | CTGGGTCATTCATGCCTTCT (84) | ATGGTGTGTGGAAGCCCTG (85) |
| 9 | CATGAGCCAATTCTAACTCCT (86) | CAGGACCCCAGTTCAGCTT (87) |
| 10 | CCCAGGCACTGCTAATGAC (88) | CCACATCTCACAGCTCATCA (89) |
| 11 | TTTCTACTGTTGCCCCTTTCT (90) | CCCAGCCCTTCATGTCAGT (91) |
| 12 | TCTATTGACTGTGACTTGCA (92) | CTCGTTGGATCCTTGGCTT (93) | a Includes IVS 7.
SEQ ID NO shown in parenthesis.

To identify families whose disorder may map to the candidate region, three microsatellite markers were chosen for haplotype analysis. One marker (D2S1893) locus is present on the same YAC (851H5) as the candidate gene, while two others (D2S1890 and D2S1892) flank it (FIG. 7b). The disorder and marker loci showed co-segregation in seven of twelve families with recessive inheritance. The genomic DNAs from these families were analyzed for mutations by SSCP. Two families displayed dominant inheritance, and their disorder co-segregated with the markers. Affected individuals from these families had better heat tolerance and fuller scalp hair than individuals from families with recessive inheritance. Recessive families not co-segregating with the candidate locus may have mutations in the human ortholog of the murine crinkled (cr) gene.

Seven variants, two of which were detected in the control population were identified and are shown in Table 6. Both dominant families and three recessive families had putative mutations. A single change was found in each dominant family, involving a base pair transition in exon 12. One, a nonsense mutation (Arg358Ter, where Ter stands for termination), if translated, would truncate the predicted cytoplasmic portion of the protein. This is similar to the effect of the dominant mutation (Dl$^{slk}$) in the mouse, which truncates the protein prior to the possible death domain (EXAMPLE 8). Previous experiments demonstrated that co-expression of a truncated TNFR with a wild-type receptor results in a dominant negative effect on function (Fisher et al., 1995, Cell 81:935–46; Tartaglia and Goeddel, 1992, J. Biol. Chem. 267:4304–7), presumably due to lack of homo-trimerization of the death domains. The variant in the second family, a non-conserved missense mutation (Arg420Gln), is also in the predicted cytoplasmic portion of the protein within the potential death domain. Dominant negative mutations have also been described in the FAS antigen, a member of the TNFR family, in patients with autoimmune lymphoproliferative syndrome (Bettinardi et al., 1997, Blood 89:902–9; Infante et al., 1998, J. Pediat. 133:629–33).

TABLE 6

DL gene variants detected

| Family | Sequence Change | Exon | Predicted Effect |
|---|---|---|---|
| Putative Mutations | | | |
| ED1206 (AR) | IVS2 −25 to −8 del (homozygous) | — | reduction of poly-pyrimidine tract of acceptor splice site |
| ED1237 (AR) | 266 G→A 175-356 del* | 4 | Arg 89 His |
| ED1238 (AR) | 259 T→C (homozygous) | 4 | Cys 87 Arg |
| ED1012 (AD) | 1072 C→T (heterozygous) | 12 | Arg 358 Ter |
| ED1029 (AD) | 1259 G→A (heterozygous) | 12 | Arg 420 Gln |
| Polymorphisms | | | |
| | 1056 C→T | 12 | Cys 352 Cys |
| | 750 C→T | 9 | Ser 250 Ser |

*deletion includes at least exon 4 but exact size is unknown. AR = autosomal recessive; AD = autosomal dominant Both affected individuals from families with known consanguinity were homozygous for their putative mutations, and their parents were heterozygous. One had an 18 bp deletion at the 3' end of IVS-2. The deletion alters 7 of the 10 bp that constitute a polypyrimidine stretch at the acceptor splice site, reducing the number of pyrimidines from 8 to 3. The importance of an intact polypyrimidine tract for normal splicing is supported by experimental evidence and splice-site mutations described in human disorders (Beldjord et al., 1988, Nucleic Acids Res. 16:4927–35; Coolidge et al., 1997, Nucleic Acids Res. 25:888–96). The deletion may result in skipping of exon 3 or use of an alternative splice site.

In the other family, a homozygous Cys87 Arg mutation results in a non-conservative change in the extracellular domain, possibly affecting intra- or inter-chain disulfide bond formation. The two affected siblings in the third family (non-consanguineous) appeared to be homozygous for a 266G→A mutation, which results in a non-conservative change (Arg89His) in the extracellular domain. The affected children were heterozygous at flanking polymorphic loci, but failed to inherit a paternal allele at the D2S1893 locus (FIG. 6). Sequencing revealed the mother to be heterozygous for the variant, while their father was hemizygous wild-type (FIG. 6). Thus, the affected individuals are compound heterozygotes, with their paternally inherited allele containing a large deletion of indeterminate size.

In summary, mutations in DL produce both recessive loss of function and dominant negative affects. The DL protein may function as a multimeric receptor and is related to the TNFR family. Ectodysplasin-A, an abnormal protein in X-linked hypohidrotic ectodermal dysplasia, shows a highly significant match (pfscan N=9.9) in its extracellular domain with the TNF family profile (FIG. 4).

EXAMPLE 11

Analysis of dl and DL Protein Sequences

Figure 8:
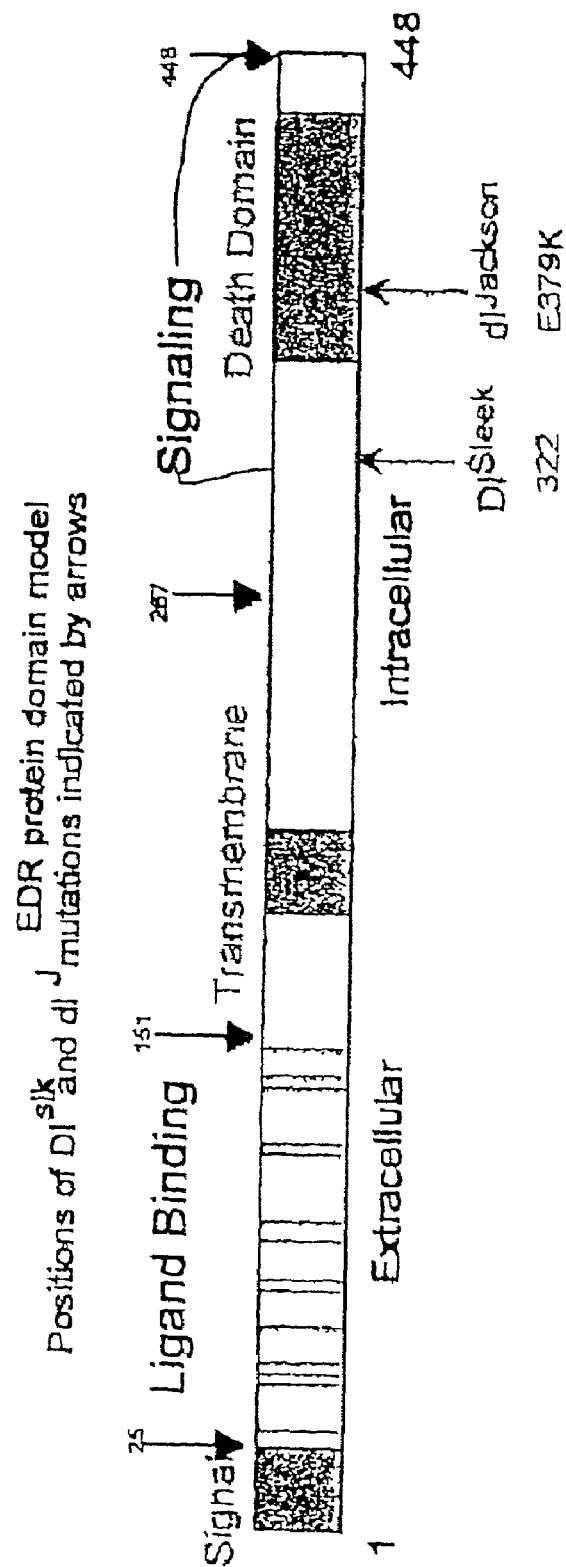
FIG. 8 is a schematic diagram illustrating domains of dl and DL receptor proteins.

The amino acid sequences of a mouse dl and human DL protein are aligned and compared in FIG. 7, and a schematic diagram of the proteins is shown in FIG. 8. The signal sequence of dl (FIG. 7, first 24 residues) is involved in insertion of the protein into the plasma membrane in an appropriate orientation, but the signal sequence is cleaved before the receptor becomes functional. This type of signal sequence is found in many proteins, and although it serves a function in protein localization, this sequence is not a unique characteristic of the protein, and can be substituted by other signal sequences. In vitro assays used to determine binding of the receptor to a ligand do not require the signal sequence. Hence, in some embodiments of the dl sequence, the signal sequence is absent. No signal sequence was predicted for DL, due to differences in non-conserved amino acids.

The predicted ligand binding region of dl and DL are amino acids 25–151 in FIG. 7, although the minimal binding region may be smaller. The cysteine-rich region (residues 30–71), the potential transmembrane domain (residues 190–211) and the potential death domain (residues 410–431) are shown in FIG. 7. Amino acids conserved between DL and dl are less likely candidates for mutations in variant peptides that retain biological activity. However, some amino acids do not appear to be crucial by sequence comparison (e.g. residues 25, 28, 37, 46, 51, 58 and 67). However, Cys residues in the binding region, and spacing between them, are believed important.

The binding region can be subdivided into a TNF receptor type fold (the region containing the first six Cys residues (amino acids 25 to 71) and the remainder of the sequence (amino acids 72 to 151). Either domain may individually bind ligand (Chen et al., 1995, *J. Biol. Chem.* 270:2874–8; Corcoran et al., 1994, *Eur. J. Biochem.* 223:831–40). Protein domain prediction was performed using PSORTII as described by Chen et al. (*J. Biol. Chem.* 270:2874–8, 1995). Sequences containing the ligand binding domain, or subregions of the binding domain, can be used in assays to detect binding of agonists or antagonists to the receptor.

The potential transmembrane domain (FIG. 8) is underlined in FIG. 7, and extends from residues 195 to 211. This region is not believed to have properties unique to DL or dl proteins. A similar domain is found in many proteins, and replacement of the transmembrane domain with that of another protein may have no significant effect on the biological activity of a DL or dl protein.

Regions immediately upstream and downstream of the transmembrane domain (such as residues 155 to 194, such as 155 to 165, and residues 212 to 266, such as 222 to 266) are not well conserved between human and mouse, and therefore are likely regions in which mutations can be made to produce variant proteins that preserve the biological activity of DL or dl.

The domain from about residue 300 to 448 is believed to be more critical to the function of DL and dl proteins. The dl or DL intracellular signaling domain is believed to include mouse and human amino acid residues 267–448 of SEQ ID NOS 19 and 17, respectively. This domain is conserved between mouse and human, and homology searches indicate that this region is similar to important signaling regions of other receptors. Moreover, both of the known mouse mutations that destroy gene function are in this region.

EXAMPLE 12

Expression Pattern of dl and Ta in Normal Mouse Development

Cloning of DL and dl genes makes it possible to follow their expression during development, such as tooth, hair, and sweat gland development, and to compare the expression with that of Ta/EDA1-II. This example describes experiments used to compare wild-type dl and Ta expression during tooth development in mice. Similar methods can be used to analyze DL, dl, EDA1-II and Ta expression patterns in any tissue, such as hair follicles, from any organism.

To prepare embryonic tissue, mutant and wildtype heads from E10 to E18 mice were wax embedded and sectioned at 5 µm. Sections were split over 5–10 slides and prepared for radioactive in situ hybridization, TUNEL staining or Eosin/ Haemotoxylin staining. To prepare adult tissue, eight-week old adult jaws were dissected out and boiled to remove soft tissue. Jaws were photographed and the teeth removed to allow assessment of root and crown development.

Radioactive $^{35}$S in situ hybridization procedures were performed as described by Wilkinson (*In situ hybridization: a practical approach.* Oxford. Oxford University Press. 1995) with modifications described by Tucker et al. (*Development* 126:221–8, 1999). Antisense probes were generated from mouse cDNA clones. Ta was linearized with Xba1 and transcribed with T7. Dl was linearized with BssH1 and transcribed with T7. p21 was linearized with BamHI and transcribed with T7. Fgf-4 was linearized with Xmn1, and transcribed with SP6. Wnt10B was linearized with Xho1 and transcribed with T3. Shh was linearized with EcoR1 and transcribed with T7, and Bmp-4 was linearized with EcoR1 and transcribed with SP6.

Expression of dl during early tooth development was followed by in situ hybridization. dl was first observed in the oral epithelium at E10, a stage prior to thickening of the dental epithelium. Expression was strongest in the maxillary arch epithelium, with mandibular arch expression not appearing until E10.5. At the same stage dl expression in the apical ectodermal ridge of the limb was strong. Dl expression was restricted at E11 to the thickening dental epithelium, and clearly observed by E12, when invagination of the epithelium starts to occur at sites of tooth development.

Ta expression was weak but detectable in tooth epithelium at E12. Ta expression was clearest in the incisor region on the medial (distal) side of the epithelial thickening. In contrast, dl was expressed more laterally (proximally) within the thickening. The situation appears similar in molars, although the expression of Ta is weaker. This is the earliest expression shown for Ta. Ta may be expressed earlier, but at levels not detected by in situ hybridization.

At E13, the bud stage, dl expression became restricted to the epithelial cells at the tip of the bud, the region encompassing enamel knot precursor cells. The enamel knot is a transient structure consisting of a cluster of non-dividing cells at the site of the future first cusp, and is associated with cuspal initiation in both incisors and molars (Butler, 1956, *Biol. Rev.* 31:30–70). To determine if dl was marking these cells its expression was compared to p21, a cyclin dependent kinase inhibitor thought to be the earliest marker of the future enamel knot. In reciprocal sections, dl and p21 expression in molar tooth germs corresponded exactly.

At E14, the cap stage, dl was strongly expressed in the enamel knot of both the incisor and molar and was excluded from other regions of epithelium. Expression was also observed in whisker follicles. At this stage Ta was expressed at the collar of the developing cap in the outer enamel epithelium and a restricted region of the oral epithelium. The expression patterns of Ta and dl are almost complementary at this stage in the epithelium. This is more obvious in the incisor region, with Ta expressed in the epithelial cells nearest to the oral cavity and dl expressed in the epithelial cells nearest to the dental mesenchyme. Ta expression was also observed in the forming glands of the face, such as the serous nasal glands and in the developing bone and cartilage. These glands are absent or reduced and the skull and facial bones dysmorphic in Tabby mice (Grüneberg, 1971, *J. Embryol. Exp. Morph.* 25:1–19) and in XLHED patients (Kere et al., 1996, *Nature Genet.* 13:409–416; Montonen et al., 1998, *J. Histochem. Cytochem.* 46:281–9). The distinct expression patterns of Ta and dl were also observed at E18, with dl expressed in the inner enamel epithelial cells, and Ta expressed in the outer enamel epithelium.

EXAMPLE 13

Expression Pattern of dl and Ta in Tabby and Lef-1 Mutant Mice

This example describes experiments used to determine dl and Ta expression patterns in mutant mice, using the methods described in EXAMPLE 12.

In E13.5 Tabby mice, dl expression was normal, indicating that the induction of dl is not reliant on the presence of active Ta protein. At E13.5, a smaller tooth germ is only just evident. Therefore, dl is expressed prior to Ta in the oral epithelium. Both dl and Ta expression were normal in Lef-1 mutant tooth buds at E13 (the stage when tooth development is arrested in Lef-1 mutants) indicating that in tooth development Lef-1 is not upstream of the Ta-EDA1-II/dl-DL pathway.

EXAMPLE 14

Phenotypic Defects During Tooth Development in Downless

This example describes the phenotypic defects in downless mice. There are two spontaneous mutants for downless, $dl^{Jackson}$ (homozygous) and $Dl^{Sleek}$ (heterozygous). $Dl^{Sleek}/+$ and $dl^J/dl^J$ mice have the same phenotype. The $dl^J$ mutation is caused by a single base pair change resulting in a glutamate to Lys substitution within the predicted death domain (Headon and Overbeek, 1999, *Nature Gen.* 22:370–4). $Dl^{Sleek}$ mice produce a truncated transcript. The Sleek mutation is thought to act as a dominant negative, binding to the ligand and wildtype receptor but lacking the cytoplasmic sequences required for signal transduction.

Teeth in $dl^{Jackson}$ and $Dl^{Sleek}$ mice were examined eight weeks after birth. In the mutant mice, all incisor and molar teeth were present. Although the incisors were of normal shape and size, the molars, particularly the first, were reduced in size compared to wild-type mice, and had a flattened appearance. Instead of the deep cusps observed in wild-type mice, very shallow depressions were present. In downless, only three of the normal eight cusps formed in the first upper molars and four of the normal seven cusps in the lower first molars.

No obvious differences were evident between $dl^{Jackson}$ and $Dl^{Sleek}$ adult molar teeth. The defects were identical to those previously described for $Dl^{Sleek}$ (Sofaer et al., 1977, *Arch. Oral Biol.* 22:299–301), and Tabby (Grüneberg, 1965, *J. Embryol. Exp. Morph.* 14:137–59; Grüneberg, 1966, *J. Embryol. Exp. Morph.* 15:223–44), and were similar to those observed in XLHED patients (Crawford et al., 1991, *J. Med. Genet.* 28:181–5).

During embryogenesis, the development of $dl^{Jackson}$ teeth was relatively normal up to the cap stage E14–E15. At this stage the enamel knot was not apparent. However, the overall size of the tooth germs appeared normal.

EXAMPLE 15

Conversion of the Enamel Knot into an Enamel Rope in Downless

To further investigate the enamel knot defect, the expression of genes associated with this signaling center were compared between wildtype and $dl^{Jackson}$ mice. dl is an early marker for the developing enamel knot. At E13, when the enamel knot starts to form, p21 and dl are expressed at the tips of the buds in the molar region. In downless, expression of p21 and dl was diffuse and spread throughout the invaginating epithelium. This effect was most obvious in the maxillary molars. The expression of p21 was downregulated in the buds when compared to normal levels seen in other structures such as the tongue. The surrounding condensing mesenchymal cells appeared relatively normal as shown by the expression of Bmp-4, a gene believed to be responsible for induction of the early enamel knot at the bud stage. The expression was slightly more diffuse, especially in the upper molar but by E14.5 however, expression appeared normal in the mesenchyme.

By E15, when the wild-type knot is visible as a clustering of cells, mutant cells fail to adopt their usual distribution and instead form an elongated sheet of cells termed the "enamel rope." Expression of dl was at wild-type levels but stretched as an elongated band of cells. This was also observed for Fgf-4, which is usually only expressed at the center of the enamel knot (Jernvall et al., 1994, *Int. J. Dev. Biol.* 38:463–9), and for Shh, which is usually expressed over a slightly larger area, correlating with the non-dividing cells (Vaahtokari et al., 1996, *Mech. Dev.* 54, 39–43). Expression of Wnt10b, which overlaps with Shh in the enamel knot, was similarly affected and extended in an elongated epithelial structure very different from the enamel knot. These changes were observed in all $dl^{Jackson}$ embryos examined with some variation in the extent of the enamel rope. Such variation may relate to the variation in the severity of cusp defects reported. Thus, enamel knot cells are formed but their organization is dramatically affected by the absence of dl protein. The expression of Bmp-4 in the condensing mesenchyme was normal in mutant tooth germs, but expression in epithelial cells overlying this region was similar to Shh, Fgf-4, and Wnt10b. Ta expression in the collar region of the tooth is normal, indicating that Ta does not need functional dl protein to maintain its expression pattern. The levels of expression of the enamel knot markers was normal, compared to controls. This is in contrast to the Tabby mutant mice, where expression is at a lower (reduced) level.

At E18 the secondary enamel knots form in the molars, above where additional cusps develop. Incisors do not develop secondary knots, as predicted by their monocuspid morphology. The secondary knots are highlighted by the expression of Fgf-4, which moves from the center of the tooth to the site of two new cusps (Jernvall et al., 1994, *Int. J. Dev. Biol.* 38:463–9). The presence of secondary enamel knots was compared in wildtype and downless mutant mice. Instead of two compact groups of cells expressing Fgf-4 at the position of the new knots, Fgf-4 is expressed in a band between the normal two sites. Thus no normal secondary enamel knots were formed, explaining the reduced number of cusps observed in downless adult teeth. Ta expression was normal. Overall, the tooth germs at E18 appeared smaller than the wildtype.

The disruption of the enamel knot into an enamel rope in downless mice correlates with cusp defects in developing teeth, directly linking the need for the enamel knot with cusp morphogenesis. The limited defect observed in incisor teeth, compared to molars, indicates that the enamel knot formed in incisor teeth has a slightly different role to that in the multicuspid molars. In normal development, the cusps that start to from first become the highest, with subsequently forming cusps being progressively smaller (Jernvall, 1995, *Acta Zool. Fennica* 198:1–61). The abnormal areas in the lower molars of the downless mutant are generally those that develop late, such as L1 (lingual cusp 1) (Sofaer, 1969, *J. Embryol. Exp. Morph.* 22:207–27). Such later developing cusps may be more susceptible to a general reduction in size and complexity of the whole crown. The upper molars, however, do not fit in with this pattern, with loss of B3 (buccal cusp 3) occurring frequently, despite the early development of this cusp (Grüneberg, 1965, *J. Embryol. Exp. Morph.* 14:137–59). Because cusps form in downless mutants indicates that the signaling functions of enamel knot cells are partially retained as shown by the expression of Fgf-4, Shh and Wnt10b. The abnormal shape of the structure may slightly alter the action of these signalling factors leading to abnormal cusp formation.

Although the adult phenotypes of Tabby and downless are identical, defects during tooth development are very different. In Tabby there is a recognizable but small enamel knot (Pispa et al., 1999, *Dev. Biol.* 216:521–34). In downless the knot is absent, but enamel knot cells are organized into a different shape, an enamel rope, showing altered expression of signaling factors (Shh, Fgf-4, Bmp-4, Wnt10b). That these two different defects lead to almost identical phenotypes of small teeth with reduced cusps, indicates that the enamel knot fails to function effectively in both cases.

A defect in cell adhesion is believed to generate the downless enamel knot defect. Absence of functional dl may result in failure of cells destined to form the enamel knot to adhere together, resulting in a flattened sheet-like structure. The possibility that dl/DL is expressed on the same cells as Ta/EDA1-II is consistent with a cell-cell adhesion mechanism. EGF, which partially rescues the Tabby mutant phenotype, also induces cell rounding in epithelial cells by counteracting the adhesive function of E-cadherin (Hoschuetzy et al., 1994, *J. Cell Biol.* 127:1375–80). Thus EGF, working with Lef-1, is believed to induce rounding of cells in the enamel knot, in the absence of Ta/EDA1-II. This indicates that the Ta/EDA1-II/dl/DL pathway(s) runs independently of the EGF/Lef-1 pathway. Such a parallel pathway was suggested in hair follicles (Headon and Overbeek, 1999, *Nature Gen.* 22:370–4). Further support is provided by the observation that dl and Ta expression is normal in Lef1 knockout mice, despite the potential Lef-1 binding site in the Ta promoter. In addition to a defect in cell adhesion, loss of functional dl protein may also lead to other secondary defects, such as a decrease in the ability of the enamel knot to stimulate proliferation.

EXAMPLE 16

Tabby and Downless Interact In Vitro

To further investigate the ability of the Ta/EDA1-II ligand and the dl/DL receptor to interact, fusion proteins were generated and purified, and their ability to immunoprecipitate together was assessed. Similar methods can be used to determine if polymorphisms, mutants, fragments, fusions or other Ta/EDA1-II and dl/DL variants interact, or to determine if the ligand and receptor interact with other proteins. In addition, these methods can be used to determine if other compounds, bind with high specificity to the dl/DL receptor.

A Ta fusion protein was constructed by fusing the extracellular domain of Ta (residues 1–183) to the hinge and Fc portion of human IgG1. hFas (residues 1–170), hTRAIL-R2 (residues 1–212) and 4-1BB (residues 1–186) were also expressed as Ig fusion proteins. cDNA for the TNF homology domain of murine dl was amplified by nested PCR from mouse lung cDNA using primer pairs 5'-GGATTCCAG-GAACAACTGTTATGG-3' (SEQ ID NO 119) with 5'-CCTACACACAGCAAGCACCTTAGAG-3' (SEQ ID NO 120); and 5'-GTCGACGAAAATCAGCCAGCTG-3' (SEQ ID NO 121) with 5'-AAGCTTCTAGGATG-CAGGGGC-3' (SEQ ID NO 122). The TNF homology domain of dl (residues 245–391) was cloned 3' of the haemaglutinin signal peptide and of a Flag tag. Flag-tagged hFasL (residues 103–281), hTRAIL (residues 95–281) and h4-1BBL (residues 85–253) were also used. Construction, expression and purification were performed as described by Schneider (*Meth. Enzymol.* 322:325–45, 2000) herein incorporated by reference.

The receptors:FC (0.5 µg each), were mixed with the Flag-ligands (about 200 ng) in 1 ml of PBS, and immunoprecipitated with 5 µl of Protein A-Sepharose for one hour at 4° C. Beads were loaded on mini-columns, washed twice with 400 µl of PBS and eluted with 15 µl of 0.1 M citrate-NaOH pH 2.7. Eluates were neutralized with Tris-HCl pH 8.5, resolved on 12% acrylamide gels and co-precipitating ligands detected by western blotting using anti-Flag M2Ab (1 µg/µl), horse radish peroxidase-coupled anti-mouse antibodies and ECL. The same blot was subsequently reprobed with horse radish peroxidase-coupled anti-human antibodies to reveal receptors:Fc.

Using recombinant, soluble forms of Ta and dl, a strong and specific interaction was observed, comparable to those of three other pairs of ligands and receptors of the TNF family, namely Fas/FasL, TRAIL-R2/TRAIL and 4-1BB/4-1BBL. Recombinant dl migrated as a double band, which may be the result of differential N-glycosylation. dl did not interact with 22 other receptors of the TNFR family, and Ta:Fc failed to immunoprecipitate 12 other ligands of the TNF family.

In another embodiment, an EDA1-II ligand can be used to quantitatively assay DL receptor binding affinity. The Ta ligand can be used for dl. Membranes from dl or DL transfected CHO cells (LC-7) are incubated with increasing concentrations of ($^{125}$I)-EDA1-II in a final volume of 0.2 mL binding buffer (50 mM Hepes, pH 7.4, 10 mM NaCl, 1 mM $MgCl_2$, 2.5 mM $CaCl_2$, 0.1% bovine serum albumin, 0.025% bacitracin) containing 1 mg wheat germ agglutinin-coated SA beads (Amersham). Iodinated peptide can be synthesized using the chloramine T method. Assays are performed in 96-well plates (OptiPlate, Caberra Packard) and the mixtures incubated with shaking for 1 hour. Bound ligand-associated radioactivity is determined by scintillation proximity (Nelson, 1987, *Anal. Biochem.* 165:287; Bosworth and Towers, 1989, *Nature* 341:167) using a TopCount microplate scintillation counter (Canberra packard). Concentrations of free ligand are calculated by subtracting the amount of specifically-bound ligand from the total amount of radioligand added.

A Scatchard analysis may be performed to determine whether the radiolabeled monoiodo-peptide displays saturable and displaceable binding to membranes of dl- or DL-expressing transfected cells, by determining the $K_D$ (slope of Scatchard line=$-1/K_D$) and a $B_{max}$ (Scatchard line abscissa intercept) of membrane protein. $K_D$ can be determined as in Munson, Principles of Pharmacology (Chapman & Hall), 1995, Chapter 1.

These experiments can be used to determine if EDA1-II, including variant EDA1-II peptides with deletions, substitutions, mutations, or insertions, bind saturably to the DL receptor with high-affinity, by determining the $K_D$ of the variant peptide. Similar methods can be used to determine if any compound of interest, for example naturally-occurring or synthetic dl or DL receptor agonists and antagonists, bind saturably to the receptor with high-affinity. Iodinated peptides and compounds that bind with high affinity to the receptor with high affinity can also be used as a radioligand to detect and quantify dl or DL receptor levels.

To determine if a peptide or compound binds with high affinity, $K_D$ is calculated as described above. For example, a compound or variant peptide having a $K_D$ less than about $10^{-6}$ M, for example $10^{-9}$ M, such as 2 nM or 20 nM, is considered a compound or peptide suitable for further investigation in biological assays of hair development, tooth development, sweat gland development and/or skin growth stimulation or inhibition.

EXAMPLE 17

Soluble Forms of Downless Phenocopy the Tabby Tooth Phenotype

Purified dl:Fc was dissolved in DMEM with glutamax (Gibco BRL) +3% fetal calf serum (FCS) and 50 μg/ml apotransferin to give a final concentration of 50 ng/ml soluble receptor. Mandibular molar regions were dissected out from E12.5 embryos of the CD-1 strain. Noon on the day on which the plugs were detected was considered as E0.5. Molar explants were cultured on membrane filters on metal grids following the Trowel technique as modified by Saxén (Trowel, 1959, *Exp. Cell Res.* 16:118–47; Saxén, 1966, *J. Exp. Zool.* 162:269–94; both herein incorporated by reference) in a standard incubator at 37° C. with an atmosphere of 5% $CO_2$ in air and 100% humidity. All solutions contained penicillin and streptomycin at 20 IU/ml. After three days, the explants were washed in ice-cold methanol for one minute then fixed in fresh 4% paraformaldehyde for one hour at RT. Cultures were then washed, taken through an ethanol series and embedded for sectioning.

The effect of adding soluble forms of dl to explant cultures of mandibular molars at E12.5 was tested. At this stage the tooth germ is visible as a deep thickening, and no defects are obvious in downless or Tabby mice. The cultures were left for three days to develop to the cap stage, when the enamel knot becomes prominent.

The resulting tooth germs had small enamel knots, which expressed sonic hedgehog at a greatly diminished extent. Fgf-4 expression was completely lost compared to control cultures. The reduction of Shh expression was noticeable along the longitudinal axis, as indicated by counting the number of sections showing gene expression. In controls, Shh expression lasted for at least 60 μm, while dl expression in the treated cultures appeared across only 30 μm. The loss of Fgf-4 may indicate a delay in development of the treated cultures, when compared to controls, since Fgf-4 is expressed in the enamel knot after Shh. The expression of other genes not associated with the enamel knot, for example Lhx7, were unaffected by the treatment indicating that the soluble dl receptor was not having a non-specific effect. This phenotype is very similar to the Tabby phenotype (Pispa et al., 1999, *Dev. Biol.* 216:521–34). Therefore, tooth germs treated with soluble dl receptor developed small Tabby-like enamel knots, rather than the enamel ropes of the downless mutant. That soluble dl can phenocopy Tabby indicates that in the cultures it is blocking endogenous Tabby protein.

EXAMPLE 18

Apoptosis Is not Affected in Downless Mutant Tooth Germs

The death domain, which is disrupted in $dl^{Jackson}$ mutants, is involved in the transduction of apoptotic signals (Ashkenaz and Dixit, 1998, *Science* 281:1305–8). In addition, the enamel knot is a well-established localized site of apoptosis, which leads to its eventual silencing as a signaling center (Vaahtokari et at, 1996, *Development* 122:121–9). Apoptosis starts at the bud stage, correlated with first expression of the enamel knot cell marker p21 (Jernvall et al, 1998, *Development* 125:161–9). To determine if apoptosis was affected in downless mutants, the extent of apoptosis seen in bud stage tooth germs in wildtype and downless mice was compared using a TUNEL assay.

Apoptotic cells were localized by detecting DNA fragmentation. A digoxigenin-based modification of terminal deoxynucleotidyl transferase mediated labeling (TUNEL) was used for histological sections, using the protocols of Vaahtokari et al. (*Development* 122:121–9, 1996, herein incorporated by reference). Slides were counter-stained with malachite green or eosin.

There was no change in the number of apoptotic cells at the bud stage, indicating that the downless phenotype is not caused by a change in cell death within the tooth germs. That there is no change in cell death agrees with the observation that loss of dl does not result in an enlargement or loss of the enamel knot but rather a change in its shape. The death domain in dl may be involved in mediating more general protein-protein interactions.

EXAMPLE 19

Therapeutic Applications

EDA1-II and dl/DL proteins (including variants, fragments, fusions, and polymorphisms thereof) and nucleic acids encoding these proteins have several therapeutic applications. Proteins of the present disclosure include any native or recombinant EDA1-II and dl/DL protein purified from cells, and those synthesized chemically. Such therapies include, but are not limited to: stimulation of hair growth (treatment of baldness), inhibition of hair growth (treatment of hirsutism, see EXAMPLE 20), stimulation of skin (particularly epidermal) healing, stimulation of tooth growth, inhibition of tooth growth, such as ectopic teeth, treatment of disorders of glands such as sweat and sebaceous glands, stimulation of sweat gland development, selective elimination of sweat glands for cosmetic reasons and treatment of ectodermal dysplasias. The therapies disclosed herein can be used alone or in combination, depending on the condition of the subject to be treated.

Stimulation of growth in the hair follicles and epidermis (dl and DL are expressed in the hair matrix, the proliferating cells of the follicle) would help to advance healing of the skin in cases of trauma or burns. *Dev. Biol.* 1988, 130: 610–20. Outer root sheath cells of human hair follicle are able to regenerate a fully differentiated epidermis in vitro. In pigs, sweat glands can re-epithelialize damaged skin, thus their stimulation has therapeutic uses. *J. Invest Dermatol.* 1998, 110:13–9.

In one embodiment, EDA1-II and/or dl/DL is used to modulate hair growth, for example stimulate hair growth. In this embodiment, EDA1-II and/or dl/DL protein is produced, such as a full-length protein, a fusion protein, a variant protein, or a fragment thereof, for example residues 133–391, 153–391 or 239–391 of EDA1-II. Such proteins will retain hair growth promoting activity. Such activity can be tested as follows. The EDA1-II and/or dl/DL protein, for example a purified protein, is applied at concentrations ranging from 1 ng/ml to 1 g/ml, to the tails, bellies, and the area behind the ears of newborn tabby mice, wildtype mice and nude mice over a period of 6 weeks, and hair growth monitored. Various methods available for the appropriate delivery of the protein to hair follicles in human skin can be performed, for example as described by Hoffman (1998, *J Drug Target;* 5:67–74), Lieb et al. (1997, *J. Pharm. Sci.* 86:1022), Laurer et al. (1995, *Pharm. Res.* 12:179–86), and Illel (1997, *Crit. Rev. Ther. Drug Carrier Syst.* 14:207–19). In another example, protein is applied to skin dissected from mouse embryos and the number of epidermal downgrowths monitored using anti-kerain 5 staining (Yan et al., *Science* 290:523–7, 2000, herein incorporated by reference). Another example is topical daily application to a bald area of the human scalp. An increase in hair growth when the protein is applied compared to the administration of no protein, indicates the ability of the protein to stimulate hair growth. The increase in hair growth can be detected by hair density measurements which measure number of hairs per unit area.

In another embodiment, EDA1-II and/or dl/DL is used to modulate tooth growth, for example stimulate tooth growth in cases of tooth loss or of natural absence of teeth. In this embodiment, EDA1-II and/or dl/DL protein is produced, such as those described above. Such proteins will retain tooth-growth promoting activity. Such activity can be tested as follows. The EDA1-II and/or dl/DL protein, for example a purified protein, is applied at concentrations ranging from 1 ng/ml to 1 g/ml, to an in vitro tooth organ culture system, over a period of days or months (for example 1–7 days, or 1–3 months), and subsequent monitoring to determine whether developmental changes occur (which is not expected in the absence of a functional protein). An increase in tooth growth development, for example the presence of teeth (or portions of teeth), or regrowth of teeth, indicates the ability of the protein to stimulate tooth growth. EDA1-II and/or dl/DL protein can be used to stimulate tooth growth in subjects directly, or in tissue culture (artificial) conditions, with subsequent introduction of teeth into humans or other organisms.

In yet other embodiments, EDA1-II and/or dl/DL is used to modulate eccrine sweat gland development, for example to stimulate eccrine sweat gland development in individuals for whom the normal sweating mechanism is compromised by disease, trauma, burns or surgery. In this embodiment, EDA1-II and/or dl/DL protein is produced, such as those described above. Such proteins will retain eccrine sweat gland development promoting activity. Such activity can be tested as follows. The EDA1-II and/or dl/DL protein, for example a purified protein, is applied or injected at concentrations ranging from 1 ng/ml to 1 g/ml, into the footpads of newborn Tabby or normal mice over a period of 6 weeks, with subsequent monitoring of sweat gland development. An increase in the number of eccrine sweat glands when the EDA1-II and/or dl/DL protein is applied as compared to the administration of no protein, indicates the ability of the protein to stimulate eccrine sweat gland development. Particular examples would show an increase of at least 5%, 10%, 25% or more in the number of eccrine sweat glands. Also disclosed herein is a method of using EDA1-II and/or dl/DL to modulate epidermal growth, for example stimulate epidermal growth. In one embodiment such a method can be used to stimulate skin (particularly epidermal) healing in cases of trauma or burns. Such activity can be tested as follows. The skin of a mouse is wounded, and an EDA1-II and/or dl/DL protein, for example a purified protein, is applied topically, injected, or administered systemically at concentrations ranging from 1 ng/ml to 1 g/ml, into the wound site over a period of time, for example 6 weeks, for example using the method of Frank et al. (*J. Clini. Invest.* 106:501–9, 2000, herein incorporated by reference in its entirety), with subsequent monitoring of wound healing,. Two basic types of wounds can be created, for example, using the method of Wojcik et al. (*Mol. Cell. Biol.* 20:5248–55, 2000, herein incorporated by reference in its entirety). One is a "full thickness wound" that involves removal of a punch of epidermis and dermis. The other is "depilation" which involves stripping off the epidermal layers (using adhesive tape) and leaving the dermis behind. Methods for evaluating rate of wound healing include measuring the rates of re-epithelialisation, wound closure, local DNA synthesis and cell proliferation (for example using the method of Frank et al. (*J. Clini. Invest.* 106:501–9, 2000).

Any assay disclosed herein can be modified by using in vivo expression of an EDA1-II and/or dl/DL gene (including antisense molecules), and variants thereof, instead of applying/injecting purified proteins, for example using the techniques of Hoffinan (1998, *J Drug Target;* 5:67–74) Li and Hoffinan (1995, *Nat. Med.* 1:705) or Majumder et al. (*Mammalian Genome,* 9:863–8, 1998). Hair growth, tooth growth, and/or eccrine sweat gland development is monitored following therapy as described above.

In yet another embodiment, these assays can be modified by administration of antibodies which recognize EDA1-II and/or DL/dl, such as antibodies raised against the extracellular portion of DL/dl (residues 1–183). Such antibodies may function as agonists of DL/dl. These molecules, or any others that cause multimerization (such as dimerization or trimerization) of DL/dl proteins, may cause activation of the downstream pathway. Similarly, overexpression of DL/dl proteins can compensate for the absence of EDA1-II/Ta by causing spontaneous multimerization (e.g. trimerization)

through crowding of receptors. Hair growth, tooth growth, and/or eccrine sweat gland development is monitored following therapy as described above.

EXAMPLE 20

Antagonists of EDA1-II and dl/DL

Another therapeutic use for the disclosed EDA1-II and dl/DL proteins and nucleic acids is the development of EDA1-II and dl/DL antagonists. Antagonists of EDA1-II and dl/DL can be used to reduce hair growth, for example in the treatment of hirsutism, inhibit tooth development, such as ectopic teeth, to selectively eliminate sweat glands, for example on the upper lip or under the arm, and to inhibit breast epithelial cell proliferation, for example in the treatment of breast cancer.

In one embodiment, a non-functional form of an EDA1-II ligand serves as a dl/DL antagonist. In other embodiments, antagonists are generated by producing C-terminally truncated dl/DL proteins. Based upon mutation analysis, deletion of residues 358–448 in DL or residues 332–448 in dl, may generate dominant negative phenotypes, such that these proteins bind to wild-type receptors and/or ligands, but do not activate downstream components of the signaling pathway. Therefore, such peptides expressed or applied therapeutically may abrogate signaling in vivo. In another embodiment, secreted forms of the dl/DL extracellular domain (residues 1–183) may compete for available EDA1-II/Ta, and generate an apparent loss of signaling through DL/dl.

Antagonists of EDA1-II protein function can be generated by producing antibodies that bind to the TNF-like domain. Additionally, the EDA1-II protein can be modified to generate homodimers that bind to the dl/DL receptor without activating the receptor. Multimerization (e.g. trimerization) of the receptor, via multimerization (e.g. trimerization) of the ligand, is believed to activate the downstream pathway.

Screening of potential antagonists (and agonists) is facilitated by the knowledge that EDA1-II/Ta ligands interact at the DL/dl receptor. A labeled ligand or receptor (such as a radioactively labeled ligand or receptor) can be used to probe compounds or peptides arranged in an array on a substrate. The array can be used as a probe to determine which of the compounds or peptides hybridize to the labeled ligand or receptor. Such hybridized compounds or peptides can then be tested as described herein and in the mouse model for biological function.

To test the ability of the disclosed antagonists to reduce hair growth, the antagonist, which in one embodiment is the purified extracellular domain 1–183 of DL/dl (or nucleic acid encoding the antagonist), is administered to the tail and bellies of mice using the methods described above in EXAMPLE 19. Hair growth would be monitored following the therapy. A reduction in hair growth, as measured by hair density measurements, or by epidermal downgrowths, when the antagonist is applied compared to the administration of no antagonist, indicates the ability of the antagonist to reduce hair growth. In particular examples, antagonists that reduce hair density by 10% or more are selected.

An in vitro screening system can also be devised using a dl or DL cDNA to express the receptor on a cell surface. A promoter is selected that switches on a marker gene (such as an antibiotic resistance gene), in which the promotor is directly controlled by dl or DL signaling. When pools of compounds are added to the cells in culture, it can be determined which of the compounds activate the receptor, and therefore allow the cells to grow in the presence of an antibiotic that would otherwise kill the cell. A similar strategy can be used to screen for antagonists, which will switch off expression of a gene that usually activated in the presence of the promoter.

EXAMPLE 21

Production of DNA and Protein Sequence Variants

Disclosed herein are nucleotide sequences of several EDA1-II, dl, and DL cDNAs, and the corresponding amino acid sequences of EDA1-II, dl, and DL proteins encoded by these cDNAs. Distinctive functional characteristics of EDA1-II, dl and DL include, but are not limited to, their ability to modulate hair, tooth, and eccrine sweat gland development, for example stimulating or inhibiting hair, tooth and eccrine sweat gland development. These activities may readily be determined using the assays disclosed herein, for example those described in EXAMPLES 19 and 20. In some embodiments, an additional distinctive characteristic is the ability of EDA1-II/Ta to interact in vitro with DL/dl, using the assay described in EXAMPLE 16. In yet other embodiments, EDA1-II and DL have the distinct characteristic of being mutated in patients suffering from HED, as described in EXAMPLES 4 and 10.

Having presented the nucleotide sequences of human EDA1-II, murine dl and human DL cDNAs, and the corresponding amino acid sequences, this disclosure facilitates the creation of DNA molecules, and thereby proteins, derived from those disclosed but which vary in their precise nucleotide or amino acid sequence from those disclosed. Such variants can be obtained through standard molecular biology laboratory techniques and the sequence information disclosed herein.

Particular guidance about the structure of the proteins, and proposed variants, fragments, polymorphisms, and fusions that retain EDA1-II biological activity, are described herein (see EXAMPLES 2 and 11). In addition, specific mutations that decrease or even abolish biological activity of the ligand and receptor in humans and mice are disclosed to provide additional evidence of mutations that should be avoided when making variant peptides that retain biological activity (see EXAMPLES 4 and 10). This example provides additional general teaching about techniques for preparing variant DNA sequences that encode these and other peptide sequences.

EDA1-II, dl and DL variants, fragments, fusions, and polymorphisms will retain the ability to modulate hair, tooth, and eccrine sweat gland development, for example stimulating or inhibiting hair, tooth and/or eccrine sweat gland development. In particular embodiments, EDA1-II has at least 153 amino acids, for example at least 175, 200, or 300 amino acids. In other embodiments, a dl or DL protein has at least 126 amino acids, for example at least 140, 175, or 300 amino acids.

Variants and fragments of EDA1-II may retain at least 95%, 98%, or greater sequence identity to the EDA1-II amino acid sequences disclosed herein, and in particular embodiments at least this much identity to SEQ ID NO: 2. Variants and fragments of dl and DL retain at least 70%, 80%, 90%, 95%, 98%, or greater sequence identity to the dl and DL amino acid sequences disclosed herein, and in particular embodiments at least this much identity to SEQ ID NOS: 19 and 17, respectively.

Variant and fragment sequences maintain the functional activity of the EDA1-II, dl and DL proteins as defined herein. Such activity can be readily determined using the assays disclosed herein.

Variant DNA molecules include those created by standard DNA mutagenesis techniques, for example, M13 primer mutagenesis. Details of these techniques are provided in Sambrook et al. (In: *Molecular Cloning: A Laboratory Manual*, Cold Spring Harbor, N.Y., 1989, Ch. 15). By the use of such techniques, variants may be created which differ in minor ways from those disclosed. DNA molecules and nucleotide sequences which are derivatives of those specifically disclosed herein and which differ from those disclosed by the deletion, addition or substitution of nucleotides while still encoding a protein which possesses the functional characteristics of the EDA1-II, dl, and DL proteins, are comprehended by this disclosure.

Also within the scope of this disclosure are small DNA molecules derived from the disclosed DNA molecules. Small DNA molecules include oligonucleotides for use as hybridization probes or PCR primers. Small DNA molecules will comprise at least a segment of a EDA1-II, dl or DL cDNA and, for PCR, will comprise at least a 20, 30, 40 or 50 contiguous nucleotides of EDA1-II, dl or DL cDNAs (SEQ ID NOS: 1, 12, and 18, or their complementary strands). Longer nucleotide sequences provide greater specificity in hybridization or PCR applications than shorter sequences. Accordingly, superior results can be obtained using longer stretches of consecutive nucleotides.

DNA molecules and nucleotide sequences derived from disclosed DNA molecules described above can also be defined as DNA sequences which hybridize under stringent conditions to the DNA sequences disclosed, or fragments thereof. Hybridization conditions resulting in particular degrees of stringency vary depending upon the nature of the hybridization method and the composition and length of the hybridizing DNA used. Generally, the temperature of hybridization and the ionic strength (especially the $Na^+$ concentration) of the hybridization buffer determines hybridization stringency. Calculations regarding hybridization conditions required for attaining particular amounts of stringency are discussed by Sambrook et al. (*Molecular Cloning: A Laboratory Manual*, Cold Spring Harbor, N.Y., 1989, Chapters 9 and 11), herein incorporated by reference. By way of illustration, a hybridization experiment can be performed by hybridization of a DNA molecule (for example, a variant of a EDA1-II cDNA) to a target DNA molecule (for example, a EDA1-II cDNA) which has been electrophoresed in an agarose gel and transferred to a nitrocellulose membrane by Southern blotting (Southern, *J. Mol. Biol.* 98:503, 1975), a technique well known in the art.

Specific hybridization refers to the binding, duplexing, or hybridizing of a molecule only or substantially only to a particular nucleotide sequence when that sequence is present in a complex mixture (e.g. total cellular DNA or RNA). Specific hybridization may also occur under conditions of varying stringency.

Hybridization with a target probe labeled with $[^{32}P]$-dCTP is generally carried out in a solution of high ionic strength such as 6×SSC at a temperature that is about 5–25° C. below the melting temperature, $T_m$. For Southern hybridization experiments where the target DNA molecule on the blot contains 10 ng of DNA or more, hybridization is typically carried out for 6–8 hours using 1–2 ng/ml radiolabeled probe (specific activity equal to $10^9$ CPM/μg or greater). Following hybridization, the nitrocellulose filter is washed to remove background hybridization. Washing conditions should be as stringent as possible to remove background hybridization but retain a specific hybridization signal.

The term $T_m$ is the temperature (under defined ionic strength and pH) at which 50% of the target sequence remains hybridized to a perfectly matched probe or complementary strand. The $T_m$ of such a hybrid molecule may be estimated from the following equation (Bolton and McCarthy, *Proc. Natl. Acad. Sci. USA* 48:1390, 1962): $T_m$=81.5° C.−16.6($\log_{10}[Na^+]$)+0.41(% G+C)−0.63(% formamide)−(600/l); where l=the length of the hybrid in base pairs.

This equation is valid for concentrations of $Na^+$ in the range of 0.01 M to 0.4 M, and it is less accurate for calculations of $T_m$ in solutions of higher $[Na^+]$. The equation is also primarily valid for DNAs whose G+C content is in the range of 30% to 75%, and it applies to hybrids greater than 100 nucleotides in length (the behavior of oligonucleotide probes is described in Sambrook et al. (*Molecular Cloning: A Laboratory Manual*, Cold Spring Harbor, N.Y., 1989, Ch. 11).

Thus, by way of example, for a 150 base pair DNA probe derived from the open reading frame of a EDA1-II cDNA (with a hypothetical % GC=45%), a calculation of hybridization conditions required to give particular stringencies may be made as follows. Assuming the filter is washed in 0.3×SSC solution following hybridization; $[Na^+]$=0.045 M; % GC=45%; [formamide]=0; l=150 base pairs; $T_m$=81.5−16.6($\log_{10}[Na^+]$)+(0.41×45)−(600/150); so $T_m$=74.4° C.

The $T_m$ of double-stranded DNA decreases by 1–1.5° C. with every 1% decrease in homology (Bonner et al., *J. Mol. Biol.* 81:123, 1973). Therefore, for this example, washing the filter in 0.3×SSC at 59.4–64.4° C. will produce a stringency of hybridization equivalent to 90%; that is, DNA molecules with more than 10% sequence variation relative to the target cDNA (for example a EDA1-II cDNA) will not hybridize. Alternatively, washing the hybridized filter in 0.3×SSC at 65.4–68.4° C. yields a hybridization stringency of 94%; that is, DNA with more than 6% sequence variation relative to the target cDNA will not hybridize. The above example is given by way of theoretical illustration. One skilled in the art will appreciate that other hybridization techniques can be utilized and that variations in experimental conditions will necessitate alternative calculations for stringency.

Examples of stringent conditions are those under which DNA molecules with more than 25%, 15%, 10%, 6% or 2% sequence variation (also termed "mismatch") will not hybridize. Longer sequences hybridize specifically at higher temperatures. An example of stringent conditions is a salt concentration of at least about 0.01 to 1.0 M Na ion concentration (or other salts) at pH 7.0 to 8.3 and a temperature of at least about 30° C. for short probes (e.g. 10 to 50 nucleotides). Stringent conditions can also be achieved with the addition of destabilizing agents such as formamide. For example, conditions of 5×SSPE (750 mM NaCl, 50 mM Na phosphate, 5 mM EDTA, pH 7.4) at 25–30° C. are suitable for allele-specific probe hybridizations.

A perfectly matched probe has a sequence perfectly complementary to a particular target sequence. The test probe is typically perfectly complementary to a portion (subsequence) of the target sequence. The term "mismatch probe" refers to probes whose sequence is deliberately selected not to be perfectly complementary to a particular target sequence.

The degeneracy of the genetic code further widens the scope of the present disclosure as it enables major variations in the nucleotide sequence of a DNA molecule while maintaining the amino acid sequence of the encoded protein. For example, the second amino acid residue of a DL protein is Ala, encoded in a DL cDNA by the nucleotide codon triplet GCC. Because of the degeneracy of the genetic code, three other nucleotide codon triplets, GCG, GCT and GCA, also code for Ala. Thus, the nucleotide sequence of a DL cDNA could be changed at this position to any of these three codons without affecting the amino acid composition of the encoded protein or the characteristics of the protein. Based upon the degeneracy of the genetic code, variant DNA molecules may be derived from the cDNA molecules disclosed herein using standard DNA mutagenesis techniques as described above, or by synthesis of DNA sequences. DNA sequences which do not hybridize under stringent conditions to the cDNA sequences disclosed by virtue of sequence variation based on the degeneracy of the genetic code are also comprehended by this disclosure.

One skilled in the art will recognize that the DNA mutagenesis techniques described above may be used not only to produce variant DNA molecules, but also facilitate the production of proteins which differ in certain structural aspects from a EDA1-II, dl and DL protein, yet which proteins are clearly derivative of these proteins and which maintain the essential functional characteristic of the protein as defined above. Newly derived proteins may also be selected in order to obtain variations on the characteristic of the protein. Such derivatives include those with variations in amino acid sequence including minor deletions, additions and substitutions.

While the site for introducing an amino acid sequence variation is predetermined, the mutation per se need not be predetermined. For example, to optimize the performance of a mutation at a given site, random mutagenesis can be conducted at the target codon or region and the expressed protein variants screened for optimal activity. Techniques for making substitution mutations at predetermined sites in DNA having a known sequence as described above are well known.

Amino acid substitutions are typically of single residues; for example 1, 2, 3, 4, 5, 10 or more substitutions; insertions usually will be on the order of about from 1 to 10 amino acid residues; and deletions will range about from 1 to 30 residues. Substitutions, deletions, insertions or any combination thereof may be combined to arrive at a final construct. Obviously, the mutations that are made in the DNA encoding the protein must not place the sequence out of reading frame and will not create complementary regions that could produce secondary mRNA structure.

The simplest modifications involve the substitution of one or more amino acid residues (for example 2, 5 or 10 residues) for amino acid residues having similar biochemical properties. These so-called conservative substitutions are likely to have minimal impact on the activity of the resultant protein. Substitutional variants are those in which at least one residue in the amino acid sequence has been removed and a different residue inserted in its place. Such substitutions generally are conservative when it is desired to finely modulate the characteristics of the protein. Examples of amino acids which may be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

Substantial changes in function or immunological identity are made by selecting substitutions that are less conservative than those listed above, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Such variants can be readily selected for additional testing by performing an assay (such as those described in EXAMPLES 19 and 20) to determine if the variant increases or inhibits hair, tooth, and eccrine sweat gland development/growth. The ability of variant EDA1-II/Ta proteins to interact with DL/dl and vice versa can also be readily assayed as in EXAMPLE 16.

EXAMPLE 22

Recombinant Expression of Proteins

With the provision of a human EDA1-II (SEQ ID NO: 1), a murine dl (SEQ ID NO: 12), and human DL (SEQ ID NO: 18) cDNAs and amino acid sequences (SEQ ID NOS: 2, 19 and 17, respectively), as well as variants, fragments and fusions thereof, the expression and purification of the corresponding proteins by standard laboratory techniques is enabled. The purified protein may be used for functional analyses, antibody production, diagnosis, and patient therapy. Furthermore, DNA sequences of a EDA1-II, dl, and DL cDNA and mutant EDA1-II, dl and DL cDNAs, can be manipulated to understand the expression of the gene and function of its product. In this way, the underlying biochemical defect which results in the symptoms of HED can be established. Mutant versions of the cDNAs isolated to date, and others which can be isolated based upon information contained herein, can be studied to detect other alterations in expression patterns in terms of relative quantities, tissue specificity and functional properties of the encoded mutant protein.

Partial or fill-length cDNA sequences, which encode for a protein, can be ligated into bacterial expression vectors. Methods for expressing large amounts of protein from a cloned gene introduced into *Escherichia coli* can be utilized for the purification, localization and functional analysis of proteins. For example, fusion proteins consisting of amino terminal peptides encoded by a portion of the *E. coli* lacZ or trpE gene linked to EDA1-II, dl and/or DL proteins can be used to prepare polyclonal and monoclonal antibodies against these proteins. These antibodies can be used to purify proteins by immunoaffinity chromatography, in diagnostic assays to quantitate the levels of protein and to localize proteins in tissues and individual cells by immunofluorescence.

Proteins can also be produced in *E. coli* in large amounts for functional studies. Methods and plasmid vectors for producing fusion proteins and intact native proteins (or variants or fragments thereof) in bacteria are described in Sambrook et al. (*Molecular Cloning: A Laboratory Manual*, Cold Spring Harbor, N.Y., 1989, Ch. 17, herein incorporated by reference). Fusion proteins can be made in large amounts, are easy to purify, and can be used to elicit antibody response. Proteins can also be produced in bacteria by placing a strong, regulated promoter and an efficient ribosome binding site upstream of the cloned gene. If low levels of protein are produced, additional steps can be taken to increase protein production; if high levels of protein are produced, purification is relatively easy. Suitable methods are presented in Sambrook et al. (*Molecular Cloning: A Laboratory Manual*, Cold Spring Harbor, N.Y., 1989) and are well known in the art. Often, proteins expressed at high levels are found in insoluble inclusion bodies. Methods for extracting proteins from these aggregates are described by Sambrook et al. (*Molecular Cloning: A Laboratory Manual*, Cold Spring Harbor, N.Y., 1989, Ch. 17).

Vector systems suitable for the expression of lacZ fusion genes include the pUR series of vectors (Ruther and Muller-Hill, 1983, *EMBO J.* 2:1791), pEX1-3 (Stanley and Luzio, 1984, *EMBO J.* 3:1429) and pMR100 (Gray et al., 1982, *Proc. Natl. Acad. Sci. USA* 79:6598). Vectors suitable for the production of intact native proteins include pKC30 (Shimatake and Rosenberg, 1981, *Nature* 292:128), pKK177-3 (Amann and Brosius, 1985, *Gene* 40:183) and pET-3 (Studiar and Moffatt, 1986, *J. Mol. Biol.* 189:113). EDA1-II, dl, or DL fusion proteins can be isolated from protein gels, lyophilized, ground into a powder and used as an antigen. A DNA sequence can be transferred to other cloning vehicles, such as other plasmids, bacteriophages, cosmids, animal viruses and yeast artificial chromosomes (YACs) (Burke et al., 1987, *Science* 236:806–12). These vectors can be introduced into a variety of hosts including somatic cells, and simple or complex organisms, such as bacteria, fungi (Timberlake and Marshall, 1989, *Science* 244:1313–7), invertebrates, plants (Gasser and Fraley, 1989, Science 244:1293), and mammals (Pursel et al., 1989, *Science* 244:1281–8), which are rendered transgenic by the introduction of the heterologous EDA1-II, dl, or DL cDNA.

For expression in mammalian cells, the cDNA sequence can be ligated to heterologous promoters, such as the simian virus SV40, promoter in the pSV2 vector (Mulligan and Berg, 1981, *Proc. Natl. Acad. Sci. USA* 78:2072–6), and introduced into cells, such as monkey COS-1 cells (Gluzman, 1981, *Cell* 23:175–82), to achieve transient or long-term expression. The stable integration of the chimeric gene construct may be maintained in mammalian cells by biochemical selection, such as neomycin (Southern and Berg, 1982, *J. Mol. Appl. Genet.* 1:327–41) and mycophoenolic acid (Mulligan and Berg, 1981, *Proc. Natl. Acad. Sci. USA* 78:2072–6).

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR.

The cDNA sequence (or portions derived from it) or a mini gene (a cDNA with or without an intron and a promoter) may be introduced into eukaryotic expression vectors by conventional techniques. These vectors are designed to permit the transcription of the cDNA in eukaryotic cells by providing regulatory sequences that initiate and enhance the transcription of the cDNA and ensure its proper splicing and polyadenylation. Vectors containing the promoter and enhancer regions of SV40 or long terminal repeat (LTR) of Rous Sarcoma virus (RSV) and polyadenylation and splicing signal from SV40 are readily available (Mulligan and Berg, 1981, *Proc. Natl. Acad. Sci. USA* 78:2072–6; Gorman et al., 1982, *Proc. Natl. Acad. Sci USA* 78:6777–81). The level of expression of the cDNA can be manipulated with this type of vector, either by using promoters that have different activities (for example, the baculovirus pAC373 can express cDNAs at high levels in *S. frugiperda* cells (Summers and Smith, 1985, *Genetically Altered Viruses and the Environment*, Fields et al. (Eds.) 22:319–28, Cold Spring Harbor Laboratory Press, Cold Spring Harbor, N.Y.) or by using vectors that contain promoters amenable to modulation, for example, the glucocorticoid-responsive promoter from the mouse mammary tumor virus (Lee et al., 1982, *Nature* 294:228). Expression of the cDNA can be monitored in the recipient cells 24 to 72 hours after introduction (transient expression).

Some vectors contain selectable markers such as gpt Mulligan and Berg, 1981, *Proc. Natl. Acad. Sci. USA* 78:2072–6) or neo (Southern and Berg, 1982, *J. Mol. Appl. Genet.* 1:327–41) bacterial genes. These selectable markers permit selection of transfected cells that exhibit stable, long-term expression of the vector (and therefore the cDNA). Vectors can be maintained in the cells as episomal, freely replicating entities by using regulatory elements of viruses such as papilloma (Sarver et al., 1981, *Mol. Cell Biol.* 1:486) or Epstein-Barr (Sugden et al., 1985, *Mol. Cell Biol.* 5:410). Alternatively, cell lines that have integrated the vector into genomic DNA can be produced. Both types of cell lines continually produce the gene product. Cell lines that have amplified the number of copies of the vector (and therefore the cDNA as well) can be produced to create cell lines that produce high levels of the gene product (Alt et al., 1978, *J. Biol. Chem.* 253:1357).

The transfer of DNA into eukaryotic, such as human or other mammalian cells, is a conventional technique. The vectors are introduced into the recipient cells as pure DNA (transfection) by, for example, precipitation with calcium phosphate (Graham and vander Eb, 1973, *Virology* 52:466) strontium phosphate (Brash et al., 1987, *Mol. Cell Biol.* 7:2013), electroporation (Neumann et al, 1982, *EMBO J.* 1:841), lipofection (Felgner et al., 1987, *Proc. Natl. Acad. Sci USA* 84:7413), DEAE dextran (McCuthan et al., 1968, *J. Natl. Cancer Inst.* 41:351), microinjection (Mueller et al., 1978, *Cell* 15:579), protoplast fusion (Schafner, 1980, *Proc. Natl. Acad. Sci. USA* 77:2163–7), or pellet guns (Klein et al., 1987, *Nature* 327:70). Alternatively, the cDNA can be introduced by infection with virus vectors, for example retroviruses (Bernstein et al., 1985, *Gen. Engrg* 7:235) such as adenoviruses (Ahmad et al., 1986, *J. Virol.* 57:267) or Herpes (Spaete et al., 1982, *Cell* 30:295).

These eukaryotic expression systems can be used for studies of the EDA1-II, dl and DL genes, and mutant forms of these genes, the encoded protein and mutant forms of these proteins. Such uses include, for example, the identification of regulatory elements located in the 5' region of the EDA1-II, dl or DL gene on genomic clones that can be isolated from genomic DNA libraries using the information contained herein. Eukaryotic expression systems can be used to study the function of the normal protein, portions of the protein, or naturally occurring or artificially produced mutant proteins. Naturally occurring mutant proteins exist in patients with HED, while artificially produced mutant proteins can be designed using site directed mutagenesis, for example to determine the function of any amino acid in the protein by mutating the nucleotide coding for that amino acid.

Using the above techniques, expression vectors containing the EDA1-II, dl or DL gene, or cDNA sequence or fragments, variants, fusions, or mutants thereof, can be introduced into any cell, including mammalian or non-mammalian cell. The choice of cell is determined by the purpose of the treatment. For example, monkey COS cells (Gluzman, 1981, Cell 23:175–82) that produce high levels of the SV40 T antigen and permit the replication of vectors containing the SV40 origin of replication. Chinese hamster ovary (CHO), mouse NIH 3T3 fibroblasts or human fibroblasts or lymphoblasts can be used.

One method to express EDA1-II, dl and DL polypeptides from cloned cDNA sequences in mammalian cells is to use the cloning vector pXTI (Stratagene). This vector contains LTRs and a portion of gag from Moloney Murine Leukemia Virus (MMLV). The position of viral LTRs allows highly efficient, stable transfection of the region within the LTRS. The vector also contains the Herpes Simplex Thymidine Kinase promoter (TK) and a selectable neo gene conferring G418 resistance. Two unique restriction sites, BglII and XhoI, are directly downstream from the TK promoter. EDA1-II, dl or DL cDNA, including the entire open reading frame for a EDA1-II, dl or DL protein and the 3' untranslated region of the cDNA is cloned into one of the two unique restriction sites downstream from the promoter.

The ligated product is transfected into mouse NIH 3T3 cells using Lipofectin (Life Technologies, Inc.) according to the manufacturer's instructions. Positive transfectants are selected after growing the transfected cells in 600 pg/ml G418 (Sigma, St. Louis, Mo.). The protein is released into the supernatant and may be purified by standard immunoaffinity chromatography techniques using antibodies raised against the EDA1-II, dl or DL protein (see EXAMPLE 23).

Expression of the protein in eukaryotic cells can be used as a source of proteins to raise antibodies. The EDA1-II, dl or DL protein is extracted following release of the protein into the supernatant or, the cDNA sequence can be incorporated into a eukaryotic expression vector and expressed as a chimeric protein with, for example, β-globin or glutathione S-transferase (GST). Antibody to β-globin is used to purify the chimeric protein. Corresponding protease cleavage sites engineered between the β-globin gene and the cDNA are used to separate the two polypeptide fragments from one another after translation. One useful expression vector for generating β-globin chimeric proteins is pSG5 (Stratagene).

The recombinant vector then contains the selected DNA of the DNA sequences disclosed herein for expression in a suitable host. The DNA is operatively linked in the vector to an expression control sequence in the recombinant DNA molecule so that the EDA1-II, dl or DL polypeptide is expressed. The expression control sequence can be selected from the group consisting of sequences that control the expression of genes of prokaryotic or eukaryotic cells and their viruses and combinations thereof, such as the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

The host cell, which may be transfected with the vector disclosed herein, may be selected from the group consisting of: E. coli, Pseudomonas, B. subtilis, B. stearothermophilus or other bacilli; other bacteria; yeast; fungi; plant; insect; mouse or other animal; or human tissue cells.

It is appreciated that for mutant or variant EDA1-II, dl or DL DNA sequences, similar systems can be employed to express and produce the mutant or variant product.

EXAMPLE 23

Production and Use of Antibodies

Production of Antibodies

Monoclonal and/or polyclonal antibodies can be produced to any EDA1-II, dl or DL proteins, herein disclosed, including variants, fragments, fusions, and mutant forms thereof. Optimally, antibodies raised against the protein will specifically detect the protein. That is, antibodies raised against the protein (e.g. EDA1-II, dl or DL) recognize and bind the protein and but not substantially recognize or bind to other proteins found in human (or mouse) cells. The determination that an antibody specifically detects an EDA1-II, dl or DL protein is made using any standard immunoassay methods; for instance, Western blotting (Sambrook et al., 1989, Molecular Cloning: A Laboratory Manual, Cold Spring Harbor Laboratory, Cold Spring Harbor, N.Y.).

To determine that an antibody preparation (such as one produced in a mouse against an EDA1-II, dl or DL protein) specifically detects an EDA1-II, dl or DL protein by Western blotting, total cellular protein is extracted from human cells (for example, lymphocytes) and electrophoresed on a sodium dodecyl sulfate-polyacrylamide gel. The proteins are transferred to a membrane (for example, nitrocellulose) and the antibody preparation incubated with the membrane. After washing the membrane to remove non-specifically bound antibodies, the presence of specifically bound antibodies is detected by using an anti-mouse antibody conjugated to an enzyme such as alkaline phosphatase; application of substrate 5-bromo4-chloro-3-indolyl phosphate/nitro blue tetrazolium results in the production of a dense blue compound by immuno-localized alkaline phosphatase.

Antibodies which specifically detect the protein will, by this technique, be shown to bind to the protein band (e.g. the EDA1-II protein band, which localizes at a given position on the gel determined by its molecular weight and phosphorylation). Non-specific binding of the antibody to other proteins may occur and may be detectable as a weak signal on the Western blot. The non-specific nature of this binding is recognized by one skilled in the art by the weak signal obtained on the Western blot relative to the strong primary signal arising from the specific antibody-EDA1-II protein binding.

Substantially pure EDA1-II, dl and DL proteins suitable for use as an immunogen is isolated as herein described, for example at least 50% pure, for example at least 75% pure. Concentration of protein in the final preparation is adjusted, for example, by concentration on an Amicon filter device, to the level of a few µg/ml. Monoclonal or polyclonal antibody to the protein can then be prepared.

Monoclonal Antibody Production by Hybridoma Fusion

Monoclonal antibody to epitopes of a EDA1-II, dl or DL protein can be identified, isolated and prepared from murine hybridomas using the method of Kohler and Milstein (Nature 256:495, 1975) or derivative thereof. Briefly, a mouse is repetitively inoculated with a few µg of the selected protein over a period of a few weeks. The mouse is sacrificed and antibody-producing cells of the spleen isolated. The spleen cells are fused using polyethylene glycol with mouse myeloma cells, and the excess unfused cells destroyed by growth of the system on selective media comprising aminopterin (HAT media). The fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as described by Engvall (*Enzymol.* 70:419, 1980), and similar methods. Selected positive clones can be expanded and their monoclonal antibody product harvested for use. Detailed procedures for monoclonal antibody production are described in Harlow and Lane (*Antibodies: A Laboratory Manual.* 1988, Cold Spring Harbor Laboratory, New York). In addition, protocols for producing humanized forms of monoclonal antibodies (for therapeutic applications) and fragments of monoclonal antibodies are known in the art.

Polyclonal Antibody Production by Immunization

Polyclonal antiserum containing antibodies to heterogeneous epitopes of a single protein can be prepared by immunizing suitable animals with the expressed protein (EXAMPLE 22), which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis et al. (*J. Clin. Endocrinol. Metab.* 33:988–91, 1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony et al. (In: *Handbook of Experimental Immunology*, Wier, D. (ed.). Chapter 19. Blackwell. 1973). Plateau concentration of antibody is usually in the range of 0.1 to 0.2 mg/ml of serum (about 12 μM). Affinity of the antisera for the antigen is determined by preparing competitive binding curves, as described, for example, by Fisher (*Manual of Clinical Immunology*, Chapter 42. 1980).

Antibodies Raised against Synthetic Peptides

Another approach to raising antibodies against the EDA1-II, dl or DL protein is to use synthetic peptides synthesized on a commercially available peptide synthesizer based upon amino acid sequences of a EDA1-II, dl or DL protein, for example SEQ ID NOS: 2, 19, and 17, respectively. The chemical synthesis described in EXAMPLE 28 for example can be used to generate synthetic EDA1-II, dl and DL proteins.

Antibodies Raised by Injection of EDA1-II, dl or DL cDNA

Antibodies can be raised against the EDA1-II, dl or DL protein by subcutaneous injection of a DNA vector expressing an EDA1-II, dl or DL protein into an animal, such as mice. Delivery of the recombinant vector into the animal can be achieved using a hand-held form of the Biolistic system (Sanford et al., *Particulate Sci. Technol.* 5:27–37, 1987) described by Tang et al. (*Nature* 356:152–4, 1992). Expression vectors include recombinant vectors expressing EDA1-II dl or DL cDNA under transcriptional control of the human β-actin promoter or cytomegalovirus (CMV) promoter.

Antibody preparations prepared according to these protocols are useful in quantitative immunoassays to determine concentrations of antigen-bearing substances in samples; or semi-quantitatively or qualitatively to identify the presence of antigen in a sample.

Labeled Antibodies

Antibodies disclosed herein can be conjugated with a label for their direct detection (see Chapter 9, Harlow and Lane, *Antibodies: A Laboratory Manual.* 1988). The label, which can include, but is not limited to, a radiolabel, enzyme, fluorescent probe, or biotin, is chosen based on the method of detection available to the user.

Antibodies can be radiolabeled with iodine ($^{125}$I), which yields low-energy gamma and X-ray radiation. Briefly, 10 μg of protein in 25 μl of 0.5 M sodium phosphate (pH 7.50 is placed in a 1.5 ml conical tube. To this, 500 μC of Na$^{125}$I, and 25 μl of 2 mg/ml chloramine T is added and incubated for 60 seconds at room temperature. To stop the reaction, 50 μl of chloramine T stop buffer is added (2.4 mg/ml sodium metabisulfite, 10 mg/ml tyrosine, 10% glycerol, 0.1% xylene cyanol in PBS). The iodinated antibody is separated from the iodotyrosine on a gel filtration column. Antibodies disclosed herein can also be labeled with biotin, with enzymes such as alkaline phosphatase (AP) or horseradish peroxidase (HRP) or with fluorescent dyes. The method of producing these conjugates is determined by the reactive group on the label added.

Therapeutic Uses for Antibodies

Antibodies can be used as agonists or antagonists of the dl/DL. Assays to determine whether an antibody functions as an agonist or antagonist of the dl/DL receptor are described in Examples 19 and 20. Antibodies which recognize an EDA1-II ligand, may prevent EDA1-II from binding to the DL receptor. Such antibodies are antagonists of the DL receptor, which can be used to reduce hair follicle, tooth, epithelial cell proliferation, and/or sweat gland growth.

Alternatively, antibodies which recognize the dl or DL receptor may function as agonists of the receptor. These antibodies may cause a multimerization or crosslinking of the receptors, which in turn may activate the downstream pathway. Such antibodies can be used to stimulate the growth/development of hair follicles, teeth, epithelial cells and/or sweat glands.

EXAMPLE 24

Use of EDA1-II, dl and DL Nucleotide Sequences for Diagnosis

One application of the EDA1-II, dl and DL cDNA sequence information presented herein is in the area of genetic testing, carrier detection and prenatal diagnosis for HED, in both its autosomal and X-linked forms. Individuals carrying mutations in an EDA1-II, dl or DL gene (disease carrier or patients) can be detected at the DNA level using a variety of techniques. For such a diagnostic procedure, a sample containing DNA or RNA derived from the subject, is assayed for the presence of a mutant EDA1-II, DL or dl gene. Suitable samples include genomic DNA or RNA obtained from cells, such as those present in peripheral blood, urine, saliva, tissue biopsy, surgical specimen, fine needle aspirate specimen, amniocentesis samples and autopsy material. Mutations in an EDA1-II, dl or DL gene can be detected using SSCP (see EXAMPLES 6 and 10). Detection of a mutant EDA1-II, dl or DL gene or RNA can also be performed by other methods known in the art as described below.

In one embodiment, the detection technique utilizes the polymerase chain reaction amplification of reverse transcribed RNA (RT-PCR) of RNA isolated from cells, such as lymphocytes, followed by direct DNA sequence determination of the products. The presence of one or more nucleotide differences between the obtained sequence and a EDA1-II, dl or DL cDNA sequence presented herein, such as differences in the ORF portion of the nucleotide sequence, are indicative of a potential EDA1-II, dl or DL gene mutation. The phenotypes of subjects in whom the mutation is detected can be noted, and the same mutations in other subjects may predict a similar phenotype. If the cells (or the subject from whom the sample is taken) are normal, observed nucleotide differences are regarded as neutral, and the subject is not classified as a carrier or sufferer on the basis of this nucleotide difference. On the other hand, if the altered cDNA reveals an abnormal result in the assay, the nucleotide difference is regarded as a mutation rather than a neutral difference, the protein is an aberrant (or mutant) EDA1-II, dl or DL gene product, and the subject is classified as a sufferer or carrier.

Because of the diploid nature of the human genome, both copies of the EDA1-II, dl or DL gene may need to be examined to distinguish between carriers and sufferers. In females, if a single copy of the EDA1-II, dl or DL gene is mutated and the other copy is normal, the subject is classified as an XLHED carrier or heterozygote. In females, if both copies of the EDA1-II, dl or DL gene are mutated, the subject is classified as a sufferer. In males, only a single copy of the EDA1 and dl/DL gene exists, hence if it is mutated, the individual is a sufferer.

In another embodiment, DNA extracted from lymphocytes or other cells is used directly for amplification. Direct amplification from genomic DNA is appropriate for analysis of the entire EDA1-II and/or dl/DL gene including regulatory sequences located upstream and downstream from the open reading frame. Reviews of direct DNA diagnosis have been presented by Caskey (*Science* 236:1223–8, 1989) and by Landegren et al. (*Science* 242:229–37, 1989).

Further studies of EDA1-II and/or dl/DL genes isolated from HED patients may reveal particular mutations which occur at a high frequency within this population of individuals. In this case, rather than sequencing the entire EDA1-II and/or dl/DL gene, DNA diagnostic methods can be designed to detect the most common mutations, deletions, or variants, for example those described in EXAMPLES 6 and 11.

The detection of specific DNA mutations can be achieved by hybridization with specific oligonucleotides (Wallace et al., 1986, *Cold Spring Harbor Symp. Quant. Biol.* 51:257–61), direct DNA sequencing (Church and Gilbert, 1984, *Proc. Natl. Acad. Sci. USA.* 81:1991–5), restriction enzymes (Flavell et al., 1978, *Cell* 15:25; Geever et al., 1981, *Proc. Natl. Acad. Sci USA* 78:5081), discrimination on the basis of electrophoretic mobility in gels with denaturing reagent Myers and Maniatis, 1986, *Cold Spring Harbor Symp. Quant. Biol.* 51:275–84), RNase protection (Myers et al., 1985, *Science* 230:1242), chemical cleavage (Cotton et al., 1985, *Proc. Natl. Acad. Sci. USA* 85:4397–401), and ligase-mediated detection (Landegren et al., 1988, *Science* 241:1077).

Oligonucleotides specific to normal or mutant sequences can be chemically synthesized using commercially available machines, labeled radioactively with isotopes (such as $^{32}P$) or non-radioactively with tags such as biotin (Ward and Langer, *Proc. Natl. Acad. Sci. USA* 78:6633–57, 1981), and hybridized to individual DNA samples immobilized on membranes or other solid supports by dot-blot or transfer from gels after electrophoresis. The presence or absence of specific sequences are visualized by methods such as autoradiography or fluorometric (Landegren, et al., 1989, *Science* 242:229–37) or colorimetric reactions (Gebeyehu et al., 1987, *Nucleic Acids Res.* 15:4513–34).

Sequence differences between normal, variant, polymorphic, and mutant forms of EDA1-II and dl/DL genes can be revealed by direct DNA sequencing (Church and Gilbert, 1988, *Proc. Natl. Acad. Sci. USA* 81:1991–5). Cloned DNA segments can be used as probes to detect specific DNA segments. The sensitivity of this method is greatly enhanced when combined with PCR (Wrichnik et al., 1987, *Nucleic Acids Res.* 15:529–42; Wong et al., 1987, *Nature* 330:384–6; Stoflet et al., 1988, *Science* 239:491–4). In this approach, a sequencing primer which lies within the amplified sequence is used with double-stranded PCR product or single-stranded template generated by a modified PCR. The sequence determination is performed by conventional procedures with radiolabeled nucleotides or by automatic sequencing procedures with fluorescent tags. The absence of hybridization indicates a mutation in a particular region of the gene, or a deleted gene.

Sequence alterations may generate fortuitous or eliminate existing restriction enzyme recognition sites. Changes in restriction sites are revealed by using appropriate enzyme digestion followed by conventional gel-blot hybridization (Southern, 1975, *J. Mol. Biol.* 98:503). DNA fragments carrying the site (either normal or mutant) are detected by their reduction in size or increase of corresponding restriction fragment numbers. Genomic DNA samples may also be amplified by PCR prior to treatment with the appropriate restriction enzyme; fragments of different sizes are then visualized under UV light in the presence of ethidium bromide after gel electrophoresis.

Genetic testing based on DNA sequence can be achieved by detection of alteration in electrophoretic mobility of DNA fragments in gels with or without denaturing reagent. Small sequence deletions and insertions can be visualized by high-resolution gel electrophoresis. For example, a PCR product with small deletions is clearly distinguishable from a normal sequence on an 8% non-denaturing polyacrylamide gel (WO 91/10734; Nagamine et al, 1989, *Am. J. Hum. Genet.* 45:337–9). DNA fragments of different sequence compositions may be distinguished on denaturing formamide gradient gels in which the mobilities of different DNA fragments are retarded in the gel at different positions according to their specific partial-melting temperatures (Myers et al., 1985, *Science* 230:1242). Alternatively, a method of detecting a mutation comprising a single base substitution or other small change can be based on differential primer length in a PCR. For example, an invariant primer can be used in addition to a primer specific for a mutation. The PCR products of the normal and mutant genes are differentially detected in acrylamide gels.

In addition to conventional gel-electrophoresis and blot-hybridization methods, DNA fragments can be visualized by methods where individual DNA samples are not immobilized on membranes. The probe and target sequences may be both in solution, or the probe sequence can be immobilized (Saiki et al., 1989, *Proc. Nat. Acad. Sci. USA* 86:6230–4). A variety of detection methods, such as autoradiography involving radioisotopes, direct detection of radioactive decay (in the presence or absence of scintillant), spectrophotometry involving calorigenic reactions and fluorometry involved fluorogenic reactions, can be used to identify specific individual genotypes.

If more than one mutation is frequently encountered in EDA1-II and/or DL/dl genes, a system capable of detecting such multiple mutations can be used. For example, a PCR with multiple, specific oligonucleotide primers and hybridization probes can be used to identify all possible mutations at the same time (Chamberlain et al., 1988, *Nucl. Acids Res.* 16:1141–55). The procedure can involve immobilized sequence-specific oligonucleotides probes (Saiki et al., 1989, *Proc. Nat. Acad. Sci. USA* 86:6230–4).

A method suitable for detecting the presence of EDA-II and/or dl/DL genes disclosed herein is the use of high density oligonucleotide arrays (also known as "DNA chips") as described by Hacia et al. (*Nat. Genet.* 14:441–7, 1996).

The diagnostic assays disclosed herein may be assembled in the form of a diagnostic kit and may include, for example: hybridization with oligonucleotides; PCR amplification of the gene or a part thereof using oligonucleotide primers; RT-PCR amplification of the RNA or a part thereof using oligonucleotide primers; or direct sequencing of an EDA1-II and/or dl/DL gene of the subject's genome using oligonucleotide primers. The efficiency of these molecular genetic methods should permit a rapid classification of patients affected by mutations, deletions or variants of an EDA1-II and/or dl/DL gene.

EXAMPLE 25

Two Step Assay to Detect the Presence of EDA1-II and/or dl/DL Gene in a Sample

This example describes a method that can be used to determine if an EDA1-II and/or DL/dl gene is present in a sample, such as a sample obtained from a subject. A sample from a subject is processed using the method of Antonarakis et al. (*New Eng. J. Med.* 313:842–8, 1985), separated through a 1% agarose gel and transferred to a nylon membrane for Southern analysis. Membranes are UV cross linked at 150 mJ using a GS Gene Linker (Bio-Rad). An EDA1-II or dl/DL probe (for example, SEQ ID NOS: 1 and 16, respectively) is subcloned into pTZ18U. The phagemids are transformed into *E. coli* MV 1190 infected with M13KO7 helper phage (Bio-Rad, Richmond, Calif.). Single-stranded DNA is isolated according to standard procedures (Sambrook, et al. *Molecular Cloning: A Laboratory Manual*, Cold Spring Harbor, N.Y., 1989).

Blots are prehybridized for 15–30 minutes at 65° C. in 7% sodium dodecyl sulfate (SDS) in 0.5 M NaPO$_4$. The methods follow those described by Nguyen et al. (*BioTechniques* 13:116–23, 1992). The blots are hybridized overnight at 65° C. in 7% SDS, 0.5 M NaPO$_4$ with 25–50 ng/ml single stranded probe DNA. Post-hybridization washes consist of two 30 minute washes in 5% SDS, 40 mM NaPO$_4$ at 65° C., followed by two 30-minute washes in 1% SDS, 40 mM NaPO$_4$ at 65° C.

The blots are subsequently rinsed with phosphate buffered saline (pH 6.8) for five minutes at RT and incubated with 0.2% casein in PBS for five minutes. The blots are then preincubated for 5–10 minutes in a shaking water bath at 45° C. with hybridization buffer consisting of 6 M urea, 0.3 M NaCl, and 5× Denhardt's solution (see Sambrook et al., *Molecular Cloning. A Laboratory Manual*, Cold Spring Harbor, N.Y., 1989). The buffer is removed and replaced with 50–75 μl/cm² fresh hybridization buffer plus 2.5 nM of the covalently cross-linked oligonucleotide sequence complementary to the universal primer site (UP-AP, Bio-Rad). The blots are hybridized for 20–30 minutes at 45° C. and post hybridization washes are incubated at 45° C. as two 10 minute washes in 6 M urea, 1× standard saline citrate (SSC), 0.1% SDS and one 10 minute wash in 1×SSC, 0.1% Triton™X-100. The blots are rinsed for 10 minutes at RT with 1×SSC.

Blots are incubated for 10 minutes at RT with shaking in the substrate buffer consisting of 0.1 M diethanolarnine, 1 mM MgCl$_2$, 0.02% sodium azide, pH 10.0. Individual blots are placed in heat sealable bags with substrate buffer and 0.2 mM AMPPD (3-(2'-spiroadamantane)4-methoxy-4-(3'-phosphoryloxy)phenyl-1,2-dioxetane, disodium salt, Bio-Rad). After a 20 minute incubation at RT with shaking, excess AMPPD solution is removed. The blot is exposed to X-ray film overnight. Positive bands indicate the presence of the EDA1-II or dl/DL gene. Samples in which no hybridizing bands are observed lack the EDA1-II or dl/DL gene, indicating the possibility of disease such as HED, or an enhanced susceptibility to developing a disease such as HED in the future.

EXAMPLE 26

Quantitation of Proteins

An alternative or supplemental method of diagnosing HED sufferers/carriers is to quantitate the level of EDA1-II and/or dl/DL protein in the cells of a subject in which expression of the protein is expected. This diagnostic tool is useful for detecting reduced levels of EDA1-II and/or dl/DL protein resulting from, for example, mutations in promoter regions of an EDA1-II and/or dl/DL gene, or mutations within the coding region of the gene which produce nonfunctional polypeptides, such as truncated proteins. These diagnostic methods, in addition to those described in EXAMPLES 24–25, provide an enhanced ability to diagnose susceptibility to diseases caused by mutation or deletion of these genes, such as HED.

The availability of antibodies specific to EDA1-II or dl/DL protein (for example those described in EXAMPLE 23) facilitate quantitation of cellular EDA1-II and/or dl/DL protein using any immunoassay method known in the art (Harlow and Lane, *Antibodies: A Laboratory Manual.* 1988). Such assays permit detection of EDA1-II and/or dl/DL protein in a biological sample and quantitation of such proteins. Typical methods involve combining the sample with an EDA1-II and/or dl/DL specific binding agent, such as an anti-EDA1-II, dl or DL antibody, so that complexes form between the binding agent and the EDA1-II and/or dl/DL protein present in the sample, and then detecting or quantitating such complexes.

These assays can be performed with the EDA1-II and/or dl/DL specific binding agent immobilized on a support surface, such as in the wells of a microtiter plate or on a column. The sample is then introduced onto the support surface and allowed to interact with the specific binding agent so as to form complexes. Excess sample is removed by washing, and the complexes are detected with a reagent, such as a second anti-EDA1-II, dl or DL protein antibody that is conjugated with a detectable marker.

In another embodiment, the cellular proteins are isolated and subjected to SDS-PAGE followed by Western blotting. After resolving the proteins, the proteins are transferred to a membrane, which is probed with specific binding agents that recognize EDA1-II and/or DL/dl. The proteins are detected, for example with HRP-conjugated secondary antibodies, and quantitated.

In yet another assay, the level of EDA1-II and/or dl/DL protein in cells is analyzed using microscopy. Using specific binding agents which recognize EDA1-II and/or dl/DL samples can be analyzed for the presence of EDA1-II, dl or DL proteins. For example, frozen biopsied tissue sections are thawed at RT and fixed with acetone at −200° C. for five minutes. Slides are washed twice in cold PBS for five minutes each, then air-dried. Sections are covered with 20–30 µl of antibody solution (15–45 µg/ml) (diluted in PBS, 2% BSA at 15–50 µg/ml) and incubated at RT in a humidified chamber for 30 minutes. Slides are washed three times with cold PBS five minutes each, allowed to air-dry briefly (5 minutes) before applying 20–30 µl of the second antibody solution (diluted in PBS, 2% BSA at 15–50 µg/ml) and incubated at RT in humidified chamber for 30 minutes. The label on the second antibody may contain a fluorescent probe, enzyme, radiolabel, biotin, or other detectable marker. The slides are washed three times with cold PBS for five minutes each then quickly dipped in distilled water, air-dried, and mounted with PBS containing 30% glycerol. Slides can be stored at 4° C. prior to viewing.

For samples prepared for electron microscopy (versus light microscopy), the second antibody is conjugated to gold particles. Tissue is fixed and embedded with epoxy plastics, then cut into very thin sections (~1–2 µm). The specimen is then applied to a metal grid, which is then incubated in the primary anti-EDA1-II or dl/DL antibody, washed in a buffer containing BSA, then incubated in a secondary antibody conjugated to gold particles (usually 5–20 nm). These gold particles are visualized using electron microscopy methods.

For the purposes of quantitating the EDA1-II and/or dl/DL protein, a sample of the subject which includes cellular proteins, is used. Such a sample can be obtained from cells of the subject, such as those present in which expression of the protein has been detected. As described in EXAMPLE 3, for example, Northern analysis can be used to analyze EDA1-II expression in the heart, pancreas, prostate, testis or uterus, but its expression in the skin is clearly the most accessible and convenient source from which specimens can be obtained. Quantitation of EDA1-II and/or dl/DL protein is made by immunoassay and is compared to levels of the protein found in non-HED cells. A significant (such as 50% or greater) reduction in the amount of EDA1-II protein in the cells of a subject compared to the amount of EDA1-II protein found in non-XLHED cells indicates that the subject may be an XLHED sufferer or carrier. Correspondingly, a significant (such as 50% or greater) reduction in the amount of dl/DL protein in the cells of a subject compared to the amount of dl/DL protein found in non-autosomal HED cells would be indicate that the subject may be an autosomal HED sufferer or carrier.

EXAMPLE 27

Peptide Modifications

The peptides disclosed herein can be modified using a variety of chemical techniques to produce derivatives having essentially the same activity as the unmodified peptides, and optionally having other desirable properties. For example, carboxylic acid groups of the peptide, whether carboxyl-terminal or side chain, can be provided in the form of a salt of a pharmaceutically-acceptable cation or esterified to form a $C_1$–$C_{16}$ ester, or converted to an amide of formula $NR_1R_2$ wherein $R_1$ and $R_2$ are each independently H or $C_1$–$C_{16}$ alkyl, or combined to form a heterocyclic ring, such as a 5- or 6-membered ring. Amino groups of the peptide, whether amino-terminal or side chain, can be in the form of a pharmaceutically-acceptable acid addition salt, such as the HCl, HBr, acetic, benzoic, toluene sulfonic, maleic, tartaric and other organic salts, or may be modified to $C_1$–$C_{16}$ alkyl or dialkyl amino or further converted to an amide.

Hydroxyl groups of the peptide side chain can be converted to $C_1$–$C_{16}$ alkoxy or to a $C_1$–$C_{16}$ ester using well-recognized techniques. Phenyl and phenolic rings of the peptide side chain can be substituted with one or more halogen atoms, such as F, Cl, Br or I, or with $C_1$–$C_{16}$ alkyl, $C_1$–$C_{16}$ alkoxy, carboxylic acids and esters thereof, or amides of such carboxylic acids. Methylene groups of the peptide side chains can be extended to homologous $C_2$–$C_4$ alkylenes. Thiols can be protected with any one of a number of well-recognized protecting groups, such as acetamide groups. Those skilled in the art will also recognize methods for introducing cyclic structures into the peptides disclosed herein to select and provide conformational constraints to the structure that result in enhanced stability. For example, a carboxyl-terminal or amino-terminal cysteine residue can be added to the peptide, so that when oxidized the peptide will contain a disulfide bond, generating a cyclic peptide. Other peptide cyclizing methods include the formation of thioethers and carboxyl- and amino-terminal amides and esters.

To maintain a functional peptide, particular peptide variants will differ by only a small number of amino acids from the peptides disclosed herein. Such variants can have deletions (for example of 1–3 or more amino acids), insertions (for example of 1–3 or more residues), or substitutions that do not interfere with the desired activity of the peptides. Substitutional variants are those in which at least one residue in the amino acid sequence has been removed and a different residue inserted in its place. In particular embodiments, such variants have amino acid substitutions of single residues, for example 1, 3, 5 or even 10 substitutions in the full-length EDA1-II, dl or DL protein (SEQ ID NOS: 2, 19, and 17, respectively).

Peptidomimetic and organomimetic embodiments are also disclosed herein, whereby the three-dimensional arrangement of the chemical constituents of such peptido- and organomimetics mimic the three-dimensional arrangement of the peptide backbone and component amino acid sidechains in the peptide, resulting in such peptido- and organomimetics of the peptides of this disclosure having substantial specific hair, tooth, and sweat gland growth promoting and/or hair growth inhibiting activity. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press: Buffalo Grove, Ill., pp. 165–174 and *Principles of Pharmacology* (ed. Munson, 1995), chapter 102 for a description of techniques used in CADD.

EXAMPLE 28

Peptide Synthesis and Purification

The disclosed peptides (and variants, fusions, polymorphisms, fragments, and mutants thereof) can be chemically synthesized by any of a number of manual or automated methods of synthesis known in the art. For example, solid phase peptide synthesis (SPPS) is carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/hydroxybenzotriazole or 2-(1H-benzo-triazol-1-yl)-1,1,3,3-tetramethyluronium hexafluorophosphate/hydroxybenzotriazole (HBTU/HOBT), and using p-hydroxymethylphenoxymethylpolystyrene (HMP) or Sasrin resin for carboxyl-terminus acids or Rink amide resin for carboxyl-terminus amides.

Fmoc-derivatized amino acids are prepared from the appropriate precursor amino acids by tritylation and triphenylmethanol in trifluoroacetic acid, followed by Fmoc derivitization as described by Atherton et al. (*Solid Phase Peptide Synthesis*, IRL Press: Oxford, 1989).

Sasrin resin-bound peptides are cleaved using a solution of 1% TFA in dichloromethane to yield the protected peptide. Where appropriate, protected peptide precursors are cyclized between the amino- and carboxyl-termini by reaction of the amino-terminal free amine and carboxyl-terminal free acid using diphenylphosphorylazide in nascent peptides wherein the amino acid sidechains are protected.

HMP or Rink amide resin-bound products are routinely cleaved and protected sidechain-containing cyclized peptides deprotected using a solution comprised of trifluoroacetic acid (TFA), optionally also comprising water, thioanisole, and ethanedithiol, in ratios of 100:5:5:2.5, for 0.5–3 hours at RT.

Crude peptides are purified by preparative high pressure liquid chromatography (HPLC), for example using a Waters Delta-Pak C18 column and gradient elution with 0.1% TFA in water modified with acetonitrile. After column elution, acetonitrile is evaporated from the eluted fractions, which are then lyophilized. The identity of each product so produced and purified may be confirmed by fast atom bombardment mass spectroscopy (FABMS) or electrospray mass spectroscopy (ESMS).

EXAMPLE 29

Pharmaceutical Compositions and Modes of Administration

Various delivery systems for administering the therapies disclosed herein are known, and include encapsulation in liposomes, microparticles, microcapsules, expression by recombinant cells, receptor-mediated endocytosis (Wu and Wu, *J. Biol. Chem.* 1987,262:4429–32), and construction of therapeutic nucleic acids as part of a retroviral or other vector. Methods of introduction include, but are not limited to, intradermal, intramuscular, intraperitoneal, intravenous, subcutaneous, intranasal, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Pharmaceutical compositions can be introduced into the central nervous system by any suitable route, including intraventricular and intrathecal injection; intraventricular injection may be facilitated by an intraventricular catheter, for example, attached to a reservoir, such as an Ommaya reservoir.

In one embodiment, pharmaceutical compositions disclosed herein are delivered locally to the area in need of treatment, for example, by local infusion during surgery, topical application, e.g., in conjunction with a wound dressing after surgery, by injection, through a catheter, by a suppository or an implant, such as a porous, non-porous, or gelatinous material, including membranes, such as silastic membranes, or fibers. In one embodiment, administration can be by direct administration at a site where hair growth, tooth growth, epithelial, or sweat gland growth is desired. In other embodiments, administration can be by direct administration at a site where reduction of hair growth or epithelial tissue is desired.

The use of liposomes as a delivery vehicle is one delivery method of interest. The liposomes fuse with the target site and deliver the contents of the lumen intracellularly. The liposomes are maintained in contact with the target cells for a sufficient time for fusion to occur, using various means to maintain contact, such as isolation and binding agents. Liposomes can be prepared with purified proteins or peptides that mediate fusion of membranes, such as Sendai virus or influenza virus. The lipids may be any useful combination of known liposome forming lipids, including cationic lipids, such as phosphatidylcholine. Other potential lipids include neutral lipids, such as cholesterol, phosphatidyl serine, phosphatidyl glycerol, and the like. For preparing the liposomes, the procedure described by Kato et al. (*J. Biol. Chem.* 1991, 266:3361) can be used.

The present disclosure also provides pharmaceutical compositions which include a therapeutically effective amount of the EDA1-II, dl and/or DL protein, RNA, DNA, antisense molecule or specific-binding agent, alone or with a pharmaceutically acceptable carrier. Furthermore, the pharmaceutical compositions or methods of treatment can be administered in combination with other therapeutic treatments, such as other agents that promote hair, tooth, and sweat gland development, or agents that reduce hair growth.

Delivery Systems

The pharmaceutically acceptable carriers useful herein are conventional. *Remington's Pharmaceutical Sciences*, by Martin, Mack Publishing Co., Easton, Pa., 15th Edition (1975), describes compositions and formulations suitable for pharmaceutical delivery of the DNA, RNA, proteins, and specific-binding agents herein disclosed. In general, the nature of the carrier will depend on the mode of administration being employed. For instance, parenteral formulations usually comprise injectable fluids that include pharmaceutically and physiologically acceptable fluids such as water, physiological saline, balanced salt solutions, aqueous dextrose, sesame oil, glycerol, ethanol, combinations thereof, or the like, as a vehicle. The carrier and composition can be sterile, and the formulation suits the mode of administration. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The composition can be a liquid solution, suspension, emulsion, tablet, pill, capsule, sustained release formulation, or powder. For solid compositions (e.g., powder, pill, tablet, or capsule forms), conventional non-toxic solid carriers can include, for example, pharmaceutical grades of mannitol, lactose, starch, sodium saccharine, cellulose, magnesium carbonate, or magnesium stearate. The composition can be formulated as a suppository, with traditional binders and carriers such as triglycerides.

Embodiments of the disclosure comprising medicaments can be prepared with conventional pharmaceutically acceptable carriers, adjuvants and counterions as would be known to those of skill in the art.

The amount of the EDA1-II, dl and/or DL protein, RNA, DNA, antisense molecule or specific-binding agent effective in the treatment of a particular disorder or condition will depend on the nature of the disorder or condition, and can be determined by standard clinical techniques. In addition, in vitro assays can be employed to identify optimal dosage ranges (see EXAMPLES 19 and 20). The precise dose to be employed in the formulation will also depend on the route of administration, and the seriousness of the disease or disorder, and should be decided according to the judgment of the practitioner and each subject's circumstances. Effective doses can be extrapolated from dose-response curves derived from in vitro or animal model test systems.

The disclosure also provides a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration. Instructions for use of the composition can also be included.

The disclosure provides compositions of the EDA-1, dl, and/or DL peptides, for example a composition that is comprised of at least 90% of the peptide, variant, polymorphism, fusion, analog, derivative or mimetic in the composition. Such compositions are useful as therapeutic agents when constituted as pharmaceutical compositions with the appropriate carriers or diluents.

Administration of Nucleic Acid Molecules

In an embodiment in which an EDA1-II, dl, and/or DL nucleic acid (or fragment, variant, fusion, mutant, or polymorphism thereof) is employed to allow expression of the nucleic acid in a cell, for in gene therapy, the nucleic acid is delivered intracellularly (e.g., by expression from a nucleic acid vector or by receptor-mediated mechanisms). In an embodiment where the therapeutic molecule is a nucleic acid or antisense molecule, administration can be achieved by an appropriate nucleic acid expression vector which is administered so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., *Proc. Natl. Acad. Sci. USA* 1991, 88:1864–8), etc. Alternatively, the nucleic acid can be introduced intracellularly and incorporated within host cell DNA for expression, by homologous recombination.

The vector pcDNA, is an example of a method of introducing the foreign cDNA into a cell under the control of a strong viral promoter (CMV) to drive the expression. However, other vectors can be used (see EXAMPLES 22 and 31). Other retroviral vectors (such as pRETRO-ON, Clontech), also use this promoter but have the advantages of entering cells without any transfection aid, integrating into the genome of target cells ONLY when the target cell is dividing (as cancer cells do, especially during first remissions after chemotherapy) and they are regulated. It is also possible to turn on the expression of the EDA1-II, dl, and/or DL nucleic acid by administering tetracycline when these plasmids are used. Hence these plasmids can be allowed to transfect the cells, then administer a course of tetracycline with a course of chemotherapy to achieve better cytotoxicity.

Other plasmid vectors, such as pMAM-neo (Clontech) or pMSG (Pharmacia) use the MMTV-LTR promoter (which can be regulated with steroids) or the SV10 late promoter (PSVL, Pharmacia) or metallothionein-responsive promoter (PBPV, Pharmacia) and other viral vectors, including retroviruses. Examples of other viral vectors include adenovirus, AAV (adeno-associated virus), recombinant HSV, poxviruses (vaccinia) and recombinant lentivirus (such as HIV). These vectors achieve the basic goal of delivering into the target cell the cDNA sequence and control elements needed for transcription. The present disclosure includes all forms of nucleic acid delivery, including synthetic oligos, naked DNA, plasmid and viral, integrated into the genome or not.

Administration of Antibodies

In an embodiment where the therapeutic molecule is an antibody, such as an antibody that recognizes an EDA1-II, dl, or DL protein, administration may be achieved by direct injection, or by use of microparticle bombardment (e.g., a gene gun; Biolistic, Dupont), or coating with lipids or cell-surface receptors or transfecting agents. Similar methods can be used to administer a EDA1-II, dl, or DL protein, of fragments, fusions, or variants thereof.

EXAMPLE 30

Methods for Expressing EDA1-II, dl, and or DL In Vivo

The present disclosure provides methods of expressing EDA1-II, dl and/or DL in a cell or tissue in vivo. In one embodiment, transfection of the cell or tissue occurs in vitro. In this example, the cell or tissue (such as a graft) is removed from a subject and then transfected with an expression vector containing EDA1-II, dl or DL cDNA. The transfected cells will produce functional EDA1-II, dl or DL protein and can be reintroduced into the subject. In another embodiment, the EDA1-II, dl and/or DL nucleic acid is administered to the subject directly, and transfection occurs in vivo.

The EDA1-II, dl and/or DL sequences disclosed herein can be used in methods of treating a subject with HED such as a subject suffering from an EDA1-II, dl and/or DL gene deletion or mutation. Such a method would promote the development of hair, teeth, sweat glands and/or ectoderm in persons suffering from HED or defects in hair, tooth, sweat gland and/or skin development.

The scientific and medical procedures required for human cell transfection are now routine. The provision herein of EDA1-II, dl and DL cDNAs allows the development of human (and other mammals) in vivo gene expression based upon these procedures. Immunotherapy of melanoma patients using genetically engineered tumor-infiltrating lymphocytes (TILs) has been reported by Rosenberg et al. (*N. Engl. J. Med.* 323:570–8, 1990). In that study, a retrovirus vector was used to introduce a gene for neomycin resistance into TILs. A similar approach may be used to introduce the EDA1-II, dl and/or DL cDNA into patients affected by EDA1-II, dl or DL deletions or mutations.

In some embodiments, a method of treating subjects which under express functional EDA1-II, dl and/or DL, or in which greater functional EDA1-II, dl and/or DL expression is desired, is disclosed. These methods can be accomplished by introducing a gene coding for EDA1-II, dl and/or DL gene into a subject. A general strategy for transferring genes into donor cells is disclosed in U.S. Pat. No. 5,529,774, incorporated by reference. Generally, a gene encoding a protein having therapeutically desired effects is cloned into a viral expression vector, and that vector is then introduced into the target organism. The virus infects the cells, and produces the protein sequence in vivo, where it has its desired therapeutic effect. Zabner et al. (*Cell* 75:207–16, 1993).

It may only be necessary to introduce the genetic or protein elements into certain cells or tissues. For example, in the case of HED, introducing them into only the skin may be sufficient. However, in some instances, it may be more therapeutically effective and simple to treat all of a subject's cells, or more broadly disseminate the vector, for example by intravascular administration.

The nucleic acid sequence encoding at least one therapeutic agent is under the control of a suitable promoter. Suitable promoters which may be employed include, but are not limited to, the gene's native promoter, retroviral LTR promoter, or adenoviral promoters, such as the adenoviral major late promoter; the CMV promoter; the RSV promoter; inducible promoters, such as the MMTV promoter; the metallothionein promoter; heat shock promoters; the albumin promoter; the histone promoter; the a-actin promoter; TK promoters; B19 parvovirus promoters; and the ApoAI promoter. However the scope of the disclosure is not limited to specific foreign genes or promoters.

The recombinant nucleic acid can be administered to the subject by any method which allows the recombinant nucleic acid to reach the appropriate cells. These methods include injection, infusion, deposition, implantation, or topical administration. Injections can be intradermal or subcutaneous. The recombinant nucleic acid can be delivered as part of a viral vector, such as avipox viruses, recombinant vaccinia virus, replication-deficient adenovirus strains or poliovirus, or as a non-infectious form such as naked DNA or liposome encapsulated DNA, as further described in EXAMPLE 31.

EXAMPLE 31

Viral Vectors for In Vivo Gene Expression

Adenoviral vectors include essentially the complete adenoviral genome (Shenk et al., *Curr. Top. Microbiol. Immunol.* 111:1–39, 1984). Alternatively, the adenoviral vector is a modified adenoviral vector in which at least a portion of the adenoviral genome has been deleted. In one embodiment, the vector includes an adenoviral 5' ITR; an adenoviral 3' ITR; an adenoviral encapsidation signal; a DNA sequence encoding a therapeutic agent; and a promoter for expressing the DNA sequence encoding a therapeutic agent. The vector is free of at least the majority of adenoviral E1 and E3 DNA sequences, but is not necessarily free of all of the E2 and E4 DNA sequences, and DNA sequences encoding adenoviral proteins transcribed by the adenoviral major late promoter. In another embodiment, the vector is an adeno-associated virus (AAV) such as described in U.S. Pat. No. 4,797,368 (Carter et al.) and in McLaughlin et al. (*J. Virol.* 62:1963–73, 1988) and AAV type 4 (Chiorini et al. *J. Virol.* 71:6823–33, 1997) and AAV type 5 (Chiorini et al. *J. Virol.* 73:1309–19, 1999)

Such a vector can be constructed according to standard techniques, using a shuttle plasmid which contains, beginning at the 5' end, an adenoviral 5' ITR, an adenoviral encapsidation signal, and an E1 a enhancer sequence; a promoter (which may be an adenoviral promoter or a foreign promoter); a tripartite leader sequence, a multiple cloning site (which may be as herein described); a poly A signal; and a DNA segment which corresponds to a segment of the adenoviral genome. The DNA segment serves as a substrate for homologous recombination with a modified or mutated adenovirus, and may encompass, for example, a segment of the adenovirus 5' genome no longer than from base 3329 to base 6246. The plasmid can also include a selectable marker and an origin of replication. The origin of replication may be a bacterial origin of replication. A desired DNA sequence encoding a therapeutic agent can be inserted into the multiple cloning site of the plasmid.

The plasmid can be used to produce an adenoviral vector by homologous recombination with a modified or mutated adenovirus in which at least the majority of the E1 and E3 adenoviral DNA sequences have been deleted. Homologous recombination can be effected through co-transfection of the plasmid vector and the modified adenovirus into a helper cell line, such as 293 cells, by $CaPO_4$ precipitation. The homologous recombination produces a recombinant adenoviral vector which includes DNA sequences derived from the shuttle plasmid between the Not I site and the homologous recombination fragment, and DNA derived from the E1 and E3 deleted adenovirus between the homologous recombination fragment and the 3' ITR.

In one embodiment, the adenovirus is constructed by using a yeast artificial chromosome (or YAC) containing an adenoviral genome according to the method described in Ketner et al. (*Proc. Natl. Acad. Sci. USA*, 91:6186–90, 1994), in conjunction with the teachings contained herein. In this embodiment, the adenovirus YAC is produced by homologous recombination in vivo between adenoviral DNA and YAC plasmid vectors carrying segments of the adenoviral left and right genomic termini. A DNA sequence encoding a therapeutic agent then is cloned into the adenoviral DNA. The modified adenoviral genome then is excised from the adenovirus YAC to be used to generate adenoviral vector particles as herein described.

Adenoviral particles are administered in an amount effective to produce a therapeutic effect in a subject. The exact dosage of adenoviral particles to be administered is dependent upon a variety of factors, including the age, weight, and sex of the subject to be treated, and the nature and extent of the disease or disorder to be treated. The adenoviral particles may be administered as part of a preparation having a titer of adenoviral particles of at least $1 \times 10^{10}$ pfu/ml, and in general not exceeding $2 \times 10^{11}$ pfu/ml. The adenoviral particles can be administered in combination with a pharmaceutically acceptable carrier in a volume up to 10 ml. The pharmaceutically acceptable carrier may be, for example, a liquid carrier such as a saline solution, protamine sulfate (Elkins-Sinn, Inc., Cherry Hill, N.J.), or Polybrene (Sigma Chemical) as well as those described in EXAMPLE 29.

In another embodiment, the viral vector is a retroviral vector. Retroviruses can be used for in vivo gene expression because they have a high efficiency of infection and stable integration and expression (Orkin et al., 1988, *Prog. Med. Genet.* 7:130–42). The full length EDA1-II and/or dl/DL gene or cDNA can be cloned into a retroviral vector and driven from either its endogenous promoter or from the retroviral LTR. Examples of retroviral vectors which can be used include, but are not limited to, MMLV, spleen necrosis virus, and vectors derived from retroviruses such as RSV, Harvey Sarcoma Virus, avian leukosis virus, HIV, myeloproliferative sarcoma virus, and mammary tumor virus. The vector is generally a replication defective retrovirus particle.

Retroviral vectors are useful to effect retroviral-mediated gene transfer into eukaryotic cells. Retroviral vectors are generally constructed such that the majority of sequences coding for the structural genes of the virus are deleted and replaced by the gene(s) of interest. Most often, the structural genes (i.e., gag, pol, and env), are removed from the retroviral backbone using genetic engineering techniques known in the art. Examples include digestion with the appropriate restriction endonuclease or, in some instances, with Bal 31 exonuclease to generate fragments containing appropriate portions of the packaging signal.

Other viral transfection systems may also be utilized for this type of approach, including Vaccinia virus (Moss et al., 1987, *Annu. Rev. Immunol.* 5:305–24), Bovine Papinoma virus (Rasmussen et al., 1987, *Methods Enzymol.* 139: 642–54) or members of the herpes virus group such as Epstein-Barr virus (Margolskee et al., 1988, *Mol. Cell. Biol.* 8:2837–47). In another embodiment RNA-DNA hybrid oligonucleotides, as described by Cole-Strauss et al. (*Science* 273:1386–9, 1996) are used. This technique can allow for site-specific integration of cloned sequences, permitting accurately targeted gene replacement.

New genes can be incorporated into proviral backbones in several ways. In the most straightforward constructions, the structural genes of the retrovirus are replaced by a single gene which then is transcribed under the control of the viral regulatory sequences within the LTR. Retroviral vectors have also been constructed which can introduce more than one gene into target cells. Usually, in such vectors one gene is under the regulatory control of the viral LTR, while the second gene is expressed either off a spliced message or is under the regulation of its own, internal promoter. Alternatively, two genes may be expressed from a single promoter by the use of an Internal Ribosome Entry Site.

EXAMPLE 32

Method for Generating Mimetics

Also disclosed are biologically active molecules that mimic the action of EDA1-II, dl and/or DL proteins. The disclosure therefore includes synthetic embodiments of naturally-occurring peptides described herein, as well as mimetics (non-peptide organic molecules), derivatives (chemically functionalized peptide molecules obtained starting with the disclosed peptide sequences) and variants (homologs) of these peptides that specifically modulate hair, tooth and sweat gland development, for example increase hair follicle, tooth and sweat gland development or decrease hair follicle development. Each peptide of the disclosure is comprised of a sequence of amino acids, which may be either L- and/or D-amino acids, naturally occurring and otherwise. Compounds or other molecules which mimic EDA1-II, dl, and/or DL activity can be identified and/or designed.

Mimetics include molecules, such as an organic chemical compound, that mimic the activity of EDA1-II, dl, and/or DL. Peptidomimetic and organomimetic embodiments are within the scope of this term, wherein the three-dimensional arrangement of the chemical constituents of such peptido- and organomimetics mimic the three-dimensional arrangement of the peptide backbone and component amino acid sidechains in the peptide, resulting in such peptido- and organomimetics of the peptides having substantial specific inhibitory activity. For computer modeling applications, a pharmacophore is an idealized, three-dimensional definition of the structural requirements for biological activity. Peptido- and organomimetics can be designed to fit each pharmacophore with current computer modeling software (using computer assisted drug design). See Walters, *Computer-Assisted Modeling of Drugs*, in Klegerman & Groves, eds., 1993, Pharmaceutical Biotechnology, Interpharm Press: Buffalo Grove, Ill., pp. 165–174 and Principles of Pharmacology (ed. Munson, 1995), chapter 102 for a description of techniques used in computer assisted drug design.

Crystallography

To identify the amino acids that interact between a Ta/EDA1-II ligand and dl/DL receptor, the ligand is co-crystallized in the presence of a receptor protein, for example, DL/dl. One method that can be used is the hanging drop method. In this method, a concentrated salt, ligand and receptor protein solution is applied to the underside of a lid of a multiwell dish. A range of concentrations may need to be tested. The lid is placed onto the dish, such that the droplet "hangs" from the lid. As the solvent evaporates, a protein crystal is formed, which can be visualized with a microscope. This crystallized structure is subjected to X-ray diffraction or NMR analysis allowing amino acid residues that are in contact with one another to be determined. The amino acids in contact with one another establish a pharmacophore that can then be used to identify drugs that interact at that same site.

Identification of Drugs

Once these amino acids are identified, synthetic drug databases (which can be licensed from several different drug companies) can be screened to identify drugs that interact with the same amino acids of Ta/EDA1-II that dl/DL interacts with. Moreover, structure activity relationships and computer assisted drug design can be performed as described in Remington, *The Science and Practice of Pharmacy*, Chapter 28.

Designing Synthetic Peptides

Synthetic peptides can be designed from the sequence of an ligand (such as dl or DL) that interacts with a receptor, such as Ta or EDA1-II. Several different peptides can be generated from this region. This can be done with or without the crystallography data. However, once crystallography data is available, peptides can also be designed that bind better than Ta/EDA1-II.

Chimeric peptides can be expressed recombinantly as described herein. One advantage of synthetic peptides over the monoclonal antibodies is that they are smaller, and therefore diffuse easier, and are not as likely to be immunogenic. Standard mutagenesis of such peptides can also be performed to identify variant peptides having even greater EDA1-II biological activity.

After synthetic drugs or peptides that bind to a dl/DL receptor have been identified, their ability to modulate hair follicle, tooth, and sweat gland development, can be tested as described in EXAMPLES 19 and 20. Those that are positive would be good candidates for therapies, such as treatment of diseases including, but not limited to HED, or diseases or conditions in which the modulation of hair follicle, tooth, and/or sweat gland development is desired, for example the stimulation of such development, including conditions resulting from burns, trauma, surgery, or baldness, or for example reduction of such development, such as reducing hair growth in subjects suffering from hirsutism.

EXAMPLE 33

Disruption of EDA1-II and/or DL/dl Expression

This example describes methods that can be used to disrupt expression of EDA1-II and/or DL/dl. Such methods are useful when decreasing hair follicle, tooth, sweat gland and/or skin epidermis development is desired, for example decreasing hair growth in subjects suffering from hirsutism. The method can also be used to inhibit the development of teeth, such as ectopic teeth. The selective elimination of sweat glands can also be achieved, for example for cosmetic reasons. Some individuals may desire to reduce sweat gland activity, for example on the upper lip or under the arm. The method can also be used to inhibit breast epithelial cell proliferation, for example in the treatment of breast cancer. As shown in EXAMPLE 17, tooth germ development can be inhibited by administering soluble receptor for the ligand. Another approach to disrupting EDA1-II and/or DL/dl function or expression is to use antisense oligonucleotides.

To design antisense oligonucleotides, the mRNA sequence from the desired molecule, such as EDA1-II and/or DL/dl, is examined. Regions of the sequence containing multiple repeats, such as TTTTTTTT, are not as desirable because they will lack specificity. Several different regions can be chosen. Of those, oligos are selected by the following characteristics: those having the best conformation in solution; those optimized for hybridization characteristics; and those having less potential to form secondary structures. Antisense molecules having a propensity to generate secondary structures are less desirable.

Plasmids containing EDA1-II and/or DL/dl antisense sequences can be generated. For example, cDNA fragments or variants coding for EDA1-II and/or DL are PCR amplified. The nucleotides are amplified using Pfu DNA polymerase (Stratagene) and cloned in antisense orientation a vector, such as pcDNA vectors (InVitrogen, Carlsbad, Calif.). The nucleotide sequence and orientation of the insert can be confirmed by sequencing using a Sequenase kit (Amersham Pharmacia Biotech).

Generally, the term "antisense" refers to a nucleic acid capable of hybridizing to a portion of a EDA1-II and/or DL/dl RNA (such as mRNA) by virtue of some sequence complementarity. The antisense nucleic acids disclosed herein can be oligonucleotides that are double-stranded or single-stranded, RNA or DNA or a modification or derivative thereof, which can be directly administered to a cell, or which can be produced intracellularly by transcription of exogenous, introduced sequences.

The EDA1-II and/or DL/dl antisense nucleic acids are polynucleotides, and can be oligonucleotides (ranging from about 6 to about 100 oligonucleotides). In specific aspects, the oligonucleotide is about at least 10, 15, or 100 nucleotides, or a polynucleotide of at least 200 nucleotides. The antisense nucleic acids can be much longer. The nucleotide can be modified at the base moiety, sugar moiety, or phosphate backbone, and can include other appending groups such as peptides, or agents facilitating transport across the cell membrane (Letsinger et al., *Proc. Natl. Acad. Sci. USA* 1989, 86:6553–6; Lemaitre et al., *Proc. Natl. Acad. Sci. USA* 1987, 84:648–52; PCT Publication No. WO 88/09810) or blood-brain barrier (PCT Publication No. WO 89/10134), hybridization triggered cleavage agents (Krol et al., *BioTechniques* 1988, 6:958–76) or intercalating agents (Zon, *Pharm. Res.* 1988, 5:539–49).

In one embodiment, an EDA1-II and/or DL/dl antisense polynucleotide (including oligonucleotides) is provided, for example of single-stranded DNA. The EDA1-II and/or DL/dl antisense polynucleotide recognizes any species of EDA1-II and/or DL/dl. The antisense polynucleotide can be modified at any position on its structure with substituents generally known in the art. For example, a modified base moiety can be 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyarninomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl) uracil, and 2,6-diaminopurine.

In another embodiment, the polynucleotide includes at least one modified sugar moiety such as arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

In yet another embodiment, the polynucleotide is an α-anomeric oligonucleotide. An α-anomeric oligonucleotide forms specific double-stranded hybrids with complementary RNA in which, contrary to the usual β-units, the strands run parallel to each other (Gautier et al., *Nucl. Acids Res.* 1987, 15:6625–41). The oligonucleotide can be conjugated to another molecule, e.g., a peptide, hybridization triggered cross-linking agent, transport agent, or hybridization-triggered cleavage agent. Oligonucleotides can include a targeting moiety that enhances uptake of the molecule by cells. The targeting moiety can be a specific binding molecule, such as an antibody or fragment thereof that recognizes a molecule present on the surface of the cell, such as a hair follicle cell.

As an alternative to antisense inhibitors, catalytic nucleic acid compounds, such as ribozymes or anti-sense conjugates, can be used to inhibit gene expression. Ribozymes can be synthesized and administered to the subject, or can be encoded on an expression vector, from which the ribozyme is synthesized in the targeted cell (as in PCT publication WO 9523225, and Beigelman et al. *Nucl. Acids Res.* 1995, 23:4434–42). Examples of oligonucleotides with catalytic activity are described in WO 9506764. Conjugates of antisense with a metal complex, e.g. terpyridylCu (II), capable of mediating mRNA hydrolysis, are described in Bashkin et al., *Appl. Biochem Biotechnol.* 1995, 54:43–56.

Polynucleotides disclosed herein can be synthesized by standard methods, for example by use of an automated DNA synthesizer (Biosearch, Applied Biosystems, etc.). As examples, phosphorothioate oligos can be synthesized by the method of Stein et al. (*Nucl. Acids Res.* 1998, 16:3209), methylphosphonate oligos can be prepared by use of controlled pore glass polymer supports (Sarin et al., 1988, *Proc. Natl. Acad. Sci. USA* 85:7448–51). In a specific embodiment, an EDA1-II, dl, and/or DL antisense oligonucleotide comprises catalytic RNA, or a ribozyme (see PCT International Publication WO 90/11364, Sarver et al, *Science* 1990, 247:1222–5). In another embodiment, the oligonucleotide is a 2'-0-methylribonucleotide (Inoue et al., *Nucl. Acids Res.* 1987, 15:6131–48), or a chimeric RNA-DNA analogue (Inoue et al., *FEBS Lett.* 1987,215:327–330).

The antisense polynucleic acids disclosed herein comprise a sequence complementary to at least a portion of an RNA transcript of an EDA1-II and/or DL/dl gene, such as a human DL gene. However, absolute complementarity, although advantageous, is not required. A sequence can be complementary to at least a portion of an RNA, meaning a sequence having sufficient complementarily to be able to hybridize with the RNA, forming a stable duplex; in the case of double-stranded DL/dl antisense nucleic acids, a single strand of the duplex DNA may thus be tested, or triplex formation can be assayed. The ability to hybridize depends on the degree of complementarity and the length of the antisense nucleic acid. Generally, the longer the hybridizing nucleic acid, the more base mismatches with a EDA1-II and/or DL/dl RNA it may contain and still form a stable duplex (or triplex, as the case may be). One skilled in the art can ascertain a tolerable degree of mismatch by use of standard procedures to determine the melting point of the hybridized complex.

The relative ability of polynucleotides (such as oligonucleotides) to bind to complementary strands is compared by determining the $T_m$ of a hybridization complex of the poly/oligonucleotide and its complementary strand. Base stacking, which occurs during hybridization, is accompanied by a reduction in UV absorption (hypochromicity). A reduction in UV absorption indicates a higher $T_m$. The higher the $T_m$ the greater the strength of the binding of the hybridized strands. As close to optimal fidelity of base pairing as possible achieves optimal hybridization of a poly/oligonucleotide to its target RNA.

The amount of EDA1-II and/or DL/dl antisense nucleic acid which is effective in the treatment of a particular disease or condition depends on the nature of the disease or condition, and can be determined by standard clinical techniques. In one embodiment, it may be useful to use compositions to achieve sustained release of the EDA1-II and/or DL/dl antisense nucleic acids. In another embodiment, it may be desirable to utilize liposomes targeted via antibodies to specific identifiable hair follicle, tooth, epithelial cell, and/or sweat gland antigens (Leonetti et at. *Proc. Natl. Acad. Sci. USA* 1990, 87:2448–51; Renneisen et al. *J. Biol. Chem.* 1990, 265:16337–42).

EXAMPLE 34

Methods of Treatment Using Antisense Molecules

When EDA1-II and/or DL/dl levels are prematurely downregulated using antisense, hair follicle, tooth, sweat gland, and/or skin epidermis development may be decreased or inhibited. EDA1-II and/or DL/dl antisense oligonucleotides (EXAMPLE 33) can be used to disrupt cellular expression of a EDA1-II and/or DL/dl protein.

The subject suffering from a disease or condition in which reduction of hair follicle, tooth, and/or sweat gland development is desired, can be treated with a therapeutically effective amount of EDA1-II and/or DL/dl antisense molecule. After the EDA1-II and/or DL/dl antisense has taken affect (EDA1-II and/or DL/dl levels are downregulated), for example after 24–48 hours, the subject can be monitored for decreased of hair follicle, tooth, and/or sweat gland development, for example as described in EXAMPLES 19 and 20.

Prophylactic Treatments

The treatments disclosed herein can also be used prophylactically, for example to inhibit or prevent progression to of a disorder in which decreased of hair follicle, tooth, and/or sweat gland development is desired. Such administration is indicated where the treatment is shown to have utility for treatment or prevention of the disorder. The prophylactic use is indicated in conditions known or suspected of preceding progression to disorders associated with an undesired amount of hair, tooth, and/or sweat gland development, for example in diseases associated with EDA1-II and/or DL/dl expression. Such diseases include, but are not limited to hirsutism (also see EXAMPLE 20).

EXAMPLE 35

Cloning Genomic DNA

Having provided the isolated EDA1-II ligand sequence, and the mammalian dl and DL receptor sequences, this disclosure also includes genomic sequences from which these cDNAs are derived. The exon sequences of EDA-II are shown in SEQ ID NOS 5–11, and the exon/intron sequences of DL are shown in Table 5 (SEQ ID NOS 94–116).

Methods for cloning EDA1-II, dl and/or DL genomic DNA from any species, such as mammals, are known to those skilled in the art (Sambrook et al. *Molecular Cloning: A Laboratory Manual*, Cold Spring Harbor Laboratory Press, New York. 1989). Briefly, EDA1-II, dl and/or DL cDNA (full length or fragments thereof, for example SEQ ID NOS: 1, 12, and 18, respectively) is radiolabeled with Rediprime II (Amersham Pharmacia Biotech) as instructed by the manufacturer. The radiolabeled cDNA is used to screen a bacteriophage λgt11 genomic library. Genomic DNA of the resulting positive clones is isolated, purified and digested with appropriate restriction enzymes. Digested DNA is separated by agarose gel electrophoresis and blotted onto a nylon membrane. A Southern-Blot is performed using radioactive cDNA of EDA1-II, dl and/or DL to identify the exons. Bands that hybridized with the cDNA are isolated from the gel and sequenced. The resulting DNA sequence is analyzed by specific computer programs to identify the promoter region and exon/intron donor/acceptor sites.

EXAMPLE 36

Generation and Expression of Fusion Proteins

Methods for making fusion proteins are well known to those skilled in the art. For example U.S. Pat. No. 6,057,133 to Bauer et al. (herein incorporated by reference) discloses methods for making fusion molecules composed of human interleukin-3 (hIL-3) variant or mutant proteins functionally joined to a second colony stimulating factor, cytokine, lymphokine, interleukin, hematopoietic growth factor or IL-3 variant. U.S. Pat. No. 6,072,041 to Davis et al. (herein incorporated by reference) discloses the generation of fusion proteins comprising a single chain Fv molecule directed against a transcytotic receptor covalently linked to a therapeutic protein.

Similar methods can be used to generate fusion proteins comprising EDA1-II, DL and/or dl (or variants or fragments thereof) linked to other amino acid sequences. Linker regions can be used to space the two portions of the protein from each other and to provide flexibility between them. The linker region is generally a polypeptide of between 1 and 500 amino acids in length, for example less than 30 amino acid in length. The linker joining the two molecules can be designed to (1) allow the two molecules to fold and act independently of each other, (2) not have a propensity for developing an ordered secondary structure which could interfere with the functional domains of the two proteins, (3) have minimal hydrophobic or charged characteristic which could interact with the functional protein domains and (4)

provide steric separation of the two regions. Typically surface amino acids in flexible protein regions include Gly, Asn and Ser. Other neutral amino acids, such as Thr and Ala, can also be used in the linker sequence. Additional amino acids can be included in the linker due to the addition of unique restriction sites in the linker sequence to facilitate construction of the fusions. Other moieties can also be included, as desired. These can include a binding region, such as avidin or an epitope, such as a polyhistadine tag, which can be useful for purification and processing of the fusion protein. In addition, detectable markers can be attached to the fusion protein, so that the traffic of the fusion protein through a body or cell can be monitored conveniently. Such markers include radionuclides, enzymes, fluors, and the like.

Fusing of the nucleic acid sequences of EDA1-II, DL and/or dl (or variant or fragment thereof), with the nucleic acid sequence of another protein (or variant or fragment thereof), can be accomplished by the use of intermediate vectors. Alternatively, one gene can be cloned directly into a vector containing the other gene. Linkers and adapters can be used for joining the nucleic acid sequences, as well as replacing lost sequences, where a restriction site was internal to the region of interest. Genetic material (DNA) encoding one polypeptide, peptide linker, and the other polypeptide is inserted into a suitable expression vector which is used to transform prokaryotic or eukaryotic cells, for example bacteria, yeast, insect cells or mammalian cells (see EXAMPLE 22). The transformed organism is grown and the protein isolated by standard techniques, for example by using a detectable marker such as nickel-chelate affinity chromatography, if a polyhistadine tag is used. The resulting product is therefore a new protein, a fusion protein, which has a EDA1-II, DL and/or dl joined by a linker region to a second protein. To confirm that the fusion protein was expressed, the purified protein is subjected to electrophoresis in SDS-polyacrylamide gels, and transferred onto nitrocellulose membrane filters using established methods. The protein products can be identified by Western blot analysis using antibodies directed against the individual components, i.e., polyhistadine tag and EDA1-II, DL and/or dl (see EXAMPLE 23).

Having illustrated and described an EDA1-II isoform, a murine dl and a human DL cDNA, the proteins encoded by the cDNA, and modes of use of these biological molecules, it should be apparent to one skilled in the art that the disclosure can be modified in arrangement and detail without departing from such principles. In view of the many possible embodiments to which the principles of our disclosure may be applied, it should be recognized that the illustrated embodiments are only particular examples of the disclosure and should not be taken as a limitation on the scope of the disclosure. Rather, the scope of the disclosure is in accord with the following claims. We therefore claim as our invention all that comes within the scope and spirit of these claims.

We claim:

1. A method of increasing one or more of hair follicle development or sweat gland development in a newborn subject suffering from X-linked hypohidrotic ectodermal dysplasia (XLHED) or autosomal hypohidrotic ectodermal dysplasia (HED), comprising administering an amount of EDA1-II protein to the subject sufficient to promote one or more of hair follicle development or sweat gland development, wherein the EDA1-II protein comprises amino acids 239–391 of SEQ ID NO: 2 and can promote one or more of hair follicle development or sweat gland development in the subject.

2. The method of claim 1, wherein the method is a method of increasing hair follicle development.

3. The method of claim 1, wherein the method is a method of increasing sweat gland development.

4. The method of claim 1, wherein the EDA1-II protein is a recombinant protein.

5. The method of claim 1, wherein the EDA1-II protein comprises an amino acid sequence having at least 95% identity to SEQ ID NO: 2.

6. The method of claim 1, wherein the EDA1-II protein comprises an amino acid sequence having at least 98% identity to SEQ ID NO:2.

7. The method of claim 6, wherein the amino acid sequence comprises the sequence shown in SEQ ID NO: 2.

8. The method of claim 1, wherein the EDA1-II protein is a fusion protein.

9. The meted of claim 1, wherein administering an amount of EDA1-II protein to the subject comprises intraperitoneal administration.

10. The method of claim 1, wherein the EDA1-II protein consists of amino acids 239–391 of SEQ ID NO: 2.

* * * * *

UNITED STATES PATENT AND TRADEMARK OFFICE
CERTIFICATE OF CORRECTION

PATENT NO. : 7,115,555 B2
APPLICATION NO. : 09/729658
DATED : October 3, 2006
INVENTOR(S) : Zonana et al.

It is certified that error appears in the above-identified patent and that said Letters Patent is hereby corrected as shown below:

In the Specification:

Column 4, line 21, "(266→A)" should be --(266G→A)--.

Column 6, lines 54-55, "restores the normal phenotype" should be --the normal phenotype is restored--.

Column 8, line 16, "restores the normal phenotype" should be --the normal phenotype is restored--.

Column 11, line 28, "73:23744" should be --73:237-44--.

Column 13, line 16, "thereof Antibodies" should be --thereof. Antibodies--.

Column 13, line 22, "Dl" should be --DL--.

Column 13, lines 64-65, "symptoms a disease" should be --symptoms of a disease--.

Column 14, line 6, "symptoms a disease" should be --symptoms of a disease--.

Column 14, line 17, "DL L," should be --DL,--.

Column 14, line 24, "EDA1-I" should be --EDA1-II--.

Column 16, line 49 (specification page 17, line 36), "disclosure are provides" should be --disclosure provides--.

Column 18, line 39, "5 minute" should be --5 minutes--.

Column 19, line 2, "3′ UR" should be --3′ UTR--.

Column 23, line 12, Table 1, in the first column under the heading "Family," "ED1018" should be --ED1018$^{b}$--.

Column 23, line 62, "Exon encodes" should be --Exon 5 encodes--.

Column 26, line 55, "allowed hybridize" should be --allowed to hybridize--.

UNITED STATES PATENT AND TRADEMARK OFFICE
CERTIFICATE OF CORRECTION

PATENT NO. : 7,115,555 B2
APPLICATION NO. : 09/729658
DATED : October 3, 2006
INVENTOR(S) : Zonana et al.

It is certified that error appears in the above-identified patent and that said Letters Patent is hereby corrected as shown below:

Column 33, Table 4, under the heading "IVS 4,", the ninth line of the nucleotide sequence, "GGAAACCTCCGGGGTTT7CAGTGTCCGGTTCTTGTAGCAAGCTGAGGAAA" should be --GGAAACCTCCGGGGTTTCAGTGTCCGGTTCTTGTAGCAAGCTGAGGAAA--.

Column 37, Table 4, under the heading "Exon 12 (3 'UTR underlined)," the first line of the nucleotide sequence "GTCTTAGCCCGACGGAGCTGCCATTTGATTGCCTCGAGAAGACTAGCCG" should be --GTCTTAGCCCCACGGAGCTGCCATTTGATTGCCTCGAGAAGACTAGCCG--.

Column 37, Table 4, under the heading "Exon 12 (3 'UTR underlined)," the 21$^{st}$ line of the nucleotide sequence "TACCTATCCTTGAGGTCATCCATATTGTTACAGGCCTTCCAGTCAATAAT" should be --TACCTATCCTTGAGGTCATCCATATTCTTACAGGCCTTCCAGTCAATAAT--.

Column 41, Table 5, under the heading "Reverse Primer (5' - 3')," the first line "GTAAGGGGCTCAGACCAGT (75)" should be --GTAAGGGGCTCAGACCACT (75)--.

Column 43, line 53, "151)." should be --151))--.

Column 48, line 53, "M2Ab" should be --M2mAb--.

Column 50, line 38, "et at" should be --et al.--.

Column 52, line 53, "Hoffinan" should be --Hoffman--.

Column 52, line 54, "Hoffinan" should be --Hoffman--.

Column 55, line 23, "at least a 20," should be --at least 20,--.

Column 58, line 49, "fill-length" should be --full-length--.

Column 60, line 18-19, "gpt Mulligan" should be --gpt (Mulligan--.

Column 61, line 17, "LTRS" should be --LTRs--.

UNITED STATES PATENT AND TRADEMARK OFFICE
CERTIFICATE OF CORRECTION

PATENT NO.        : 7,115,555 B2
APPLICATION NO. : 09/729658
DATED             : October 3, 2006
INVENTOR(S)       : Zonana et al.

It is certified that error appears in the above-identified patent and that said Letters Patent is hereby corrected as shown below:

Column 61, line 29, "600 pg/ml" should be --600 μg/ml--.

Column 62, line 35, "5-bromo4-chloro-3-indolyl" should be --5-bromo-4-chloro-3-indolyl--.

Column 65, line 56, "reagent Myers" should be --reagent (Myers--.

Column 67, line 10, "Eda-II" should be --Eda1-II--.

Column 69, line 48, "would be indicate" should be --would indicate--.

Column 70 line 62-63, "polymorphismis" should be --polymorphisms--.

Column 73, line 24, "EDA-1" should be --EDA1-II--.

Column 74, line 4, "(PSVL," should be --(pSVL,--.

Column 74, line 5, "(PBPV," should be --(pBPV,--.

Column 75, line 21, "a-actin" should be --α-actin--.

Column 76, line 31, "termin" should be --termini--.

Column 77, line 10, "Papinoma" should be --Papilloma--.

Column 81, line 3, "complementarily" should be --complementarity--.

Column 81, line 36, "Leonetti et at." should be --Leonetti et al.,--.

Column 81, line 57, "decreased of hair" should be --decreased hair--.

Column 81, line 63, "progression to of" should be --progression of--.

Column 81, line 64, "decreased of hair" should be --decreased hair--.

Column 82, line 15, "EDA-II" should be --EDA1-II--.

UNITED STATES PATENT AND TRADEMARK OFFICE
CERTIFICATE OF CORRECTION

PATENT NO.      : 7,115,555 B2
APPLICATION NO. : 09/729658
DATED           : October 3, 2006
INVENTOR(S)     : Zonana et al.

It is certified that error appears in the above-identified patent and that said Letters Patent is hereby corrected as shown below:

In the Claims:

Column 171, line 64, claim 1, "hypobidrotic" should be --hypohidrotic--.

Column 174, line 3, claim 9, "meted" should be --method--.

Signed and Sealed this

Sixteenth Day of October, 2007

JON W. DUDAS
*Director of the United States Patent and Trademark Office*

```
                         SEQUENCE LISTING

<160> NUMBER OF SEQ ID NOS: 122

<210> SEQ ID NO 1
<211> LENGTH: 1574
<212> TYPE: DNA
<213> ORGANISM: Homo sapiens
<220> FEATURE:
<221> NAME/KEY: CDS
<222> LOCATION: (242)..(1417)

<400> SEQUENCE: 1
attccctcgg cgggccagcc tcccctctct cccgcccctc ctcctcccct tcccaccccct      60 cggagtagag ctgcacatgc ggctgctccc tgctccgtcc cgcccagcca ctgtcgcgca     120
ggaacgggtc cctgcagccc ccagccgatg gcaggacagt agccgcctgt cagaggtcgt     180
gaacggctga ggcagacgca gcggctcccg ggcctcaaga gagtgggtgt ctccggaggc     240 c atg ggc tac ccg gag gtg gag cgc agg gaa ctc ctg cct gca gca gcg     289
  Met Gly Tyr Pro Glu Val Glu Arg Arg Glu Leu Leu Pro Ala Ala Ala
  1               5                  10                  15 ccg cgg gag cga ggg agc cag ggc tgc ggg tgt ggc ggg gcc cct gcc      337
Pro Arg Glu Arg Gly Ser Gln Gly Cys Gly Cys Gly Gly Ala Pro Ala
            20                  25                  30 cgg gcg ggc gaa ggg aac agc tgc ctg ctc ttc ctg ggt ttc ttt ggc      385
Arg Ala Gly Glu Gly Asn Ser Cys Leu Leu Phe Leu Gly Phe Phe Gly
        35                  40                  45 ctc tcg ctg gcc ctc cac ctg ctg acg ttg tgc tgc tac cta gag ttg      433
Leu Ser Leu Ala Leu His Leu Leu Thr Leu Cys Cys Tyr Leu Glu Leu
    50                  55                  60 cgc tcg gag ttg cgg cgg gaa cgt gga gcc gag tcc cgc ctt ggc ggc      481
Arg Ser Glu Leu Arg Arg Glu Arg Gly Ala Glu Ser Arg Leu Gly Gly
65                  70                  75                  80
```

-continued

| | |
|---|---|
| tcg ggc acc cct ggc acc tct ggc acc cta agc agc ctc ggt ggc ctc<br>Ser Gly Thr Pro Gly Thr Ser Gly Thr Leu Ser Ser Leu Gly Gly Leu<br>               85                        90                        95 | 529 |
| gac cct gac agc ccc atc acc agt cac ctt ggg cag ccg tca cct aag<br>Asp Pro Asp Ser Pro Ile Thr Ser His Leu Gly Gln Pro Ser Pro Lys<br>             100                     105                     110 | 577 |
| cag cag cca ttg gaa ccg gga gaa gcc gca ctc cac tct gac tcc cag<br>Gln Gln Pro Leu Glu Pro Gly Glu Ala Ala Leu His Ser Asp Ser Gln<br>115                     120                     125 | 625 |
| gac ggg cac cag atg gcc cta ttg aat ttc ttc ttc cct gat gaa aag<br>Asp Gly His Gln Met Ala Leu Leu Asn Phe Phe Phe Pro Asp Glu Lys<br>    130                     135                     140 | 673 |
| cca tac tct gaa gaa gaa agt agg cgt gtt cgc cgc aat aaa aga agc<br>Pro Tyr Ser Glu Glu Glu Ser Arg Arg Val Arg Arg Asn Lys Arg Ser<br>145                     150                     155                     160 | 721 |
| aaa agc aat gaa gga gca gat ggc cca gtt aaa aac aag aaa aag gga<br>Lys Ser Asn Glu Gly Ala Asp Gly Pro Val Lys Asn Lys Lys Lys Gly<br>             165                     170                     175 | 769 |
| aag aaa gca gga cct cct gga ccc aat ggc cct cca gga ccc cca gga<br>Lys Lys Ala Gly Pro Pro Gly Pro Asn Gly Pro Pro Gly Pro Pro Gly<br>    180                     185                     190 | 817 |
| cct cca gga ccc cag gga ccc cca gga att cca ggg att cct gga att<br>Pro Pro Gly Pro Gln Gly Pro Pro Gly Ile Pro Gly Ile Pro Gly Ile<br>195                     200                     205 | 865 |
| cca gga aca act gtt atg gga cca cct ggt cct cca ggt cct cct ggt<br>Pro Gly Thr Thr Val Met Gly Pro Pro Gly Pro Pro Gly Pro Pro Gly<br>    210                     215                     220 | 913 |
| cct caa gga ccc cct ggc ctc cag gga cct tct ggt gct gct gat aaa<br>Pro Gln Gly Pro Pro Gly Leu Gln Gly Pro Ser Gly Ala Ala Asp Lys<br>225                     230                     235                     240 | 961 |
| gct gga act cga gaa aac cag cca gct gtg gtg cat cta cag ggc caa<br>Ala Gly Thr Arg Glu Asn Gln Pro Ala Val Val His Leu Gln Gly Gln<br>             245                     250                     255 | 1009 |
| ggg tca gca att caa gtc aag aat gat ctt tca ggt gga gtg ctc aat<br>Gly Ser Ala Ile Gln Val Lys Asn Asp Leu Ser Gly Gly Val Leu Asn<br>    260                     265                     270 | 1057 |
| gac tgg tct cgc atc act atg aac ccc aag gtg ttt aag cta cat ccc<br>Asp Trp Ser Arg Ile Thr Met Asn Pro Lys Val Phe Lys Leu His Pro<br>275                     280                     285 | 1105 |
| cgc agc ggg gag ctg gag gta ctg gtg gac ggc acc tac ttc atc tat<br>Arg Ser Gly Glu Leu Glu Val Leu Val Asp Gly Thr Tyr Phe Ile Tyr<br>    290                     295                     300 | 1153 |
| agt cag gta gaa gta tac tac atc aac ttc act gac ttt gcc agc tat<br>Ser Gln Val Glu Val Tyr Tyr Ile Asn Phe Thr Asp Phe Ala Ser Tyr<br>305                     310                     315                     320 | 1201 |
| gag gtg gtg gtg gat gag aag ccc ttc ctg cag tgc aca cgc agc atc<br>Glu Val Val Val Asp Glu Lys Pro Phe Leu Gln Cys Thr Arg Ser Ile<br>             325                     330                     335 | 1249 |
| gag acg ggc aag acc aac tac aac act tgc tat acc gca ggc gtc tgc<br>Glu Thr Gly Lys Thr Asn Tyr Asn Thr Cys Tyr Thr Ala Gly Val Cys<br>    340                     345                     350 | 1297 |
| ctc ctc aag gcc cgg cag aag atc gcc gtc aag atg gtg cac gct gac<br>Leu Leu Lys Ala Arg Gln Lys Ile Ala Val Lys Met Val His Ala Asp<br>355                     360                     365 | 1345 |
| atc tcc atc aac atg agc aag cac acc acg ttc ttt ggg gcc atc agg<br>Ile Ser Ile Asn Met Ser Lys His Thr Thr Phe Phe Gly Ala Ile Arg<br>    370                     375                     380 | 1393 |
| ctg ggt gaa gcc cct gca tcc tag attcccccat tttgcctctg tccgtgcccc<br>Leu Gly Glu Ala Pro Ala Ser<br>385                     390 | 1447 |

```
ttccctgggt ttgggagcca ggactcccaa aacctctaag tgctgctgtg gagtgaggtg    1507
tattggtgtt gcagccgcag agaaatgccc cattgttatt tattccccag tgactccagg    1567
gtgacaa                                                              1574
```

<210> SEQ ID NO 2
<211> LENGTH: 391
<212> TYPE: PRT
<213> ORGANISM: Homo sapiens

<400> SEQUENCE: 2

```
Met Gly Tyr Pro Glu Val Glu Arg Arg Glu Leu Leu Pro Ala Ala Ala
  1               5                  10                  15

Pro Arg Glu Arg Gly Ser Gln Gly Cys Gly Cys Gly Gly Ala Pro Ala
             20                  25                  30

Arg Ala Gly Glu Gly Asn Ser Cys Leu Leu Phe Leu Gly Phe Phe Gly
         35                  40                  45

Leu Ser Leu Ala Leu His Leu Leu Thr Leu Cys Cys Tyr Leu Glu Leu
 50                  55                  60

Arg Ser Glu Leu Arg Arg Glu Arg Gly Ala Glu Ser Arg Leu Gly Gly
 65                  70                  75                  80

Ser Gly Thr Pro Gly Thr Ser Gly Thr Leu Ser Ser Leu Gly Gly Leu
             85                  90                  95

Asp Pro Asp Ser Pro Ile Thr Ser His Leu Gly Gln Pro Ser Pro Lys
            100                 105                 110

Gln Gln Pro Leu Glu Pro Gly Glu Ala Ala Leu His Ser Asp Ser Gln
        115                 120                 125

Asp Gly His Gln Met Ala Leu Leu Asn Phe Phe Phe Pro Asp Glu Lys
130                 135                 140

Pro Tyr Ser Glu Glu Glu Ser Arg Arg Val Arg Arg Asn Lys Arg Ser
145                 150                 155                 160

Lys Ser Asn Glu Gly Ala Asp Gly Pro Val Lys Asn Lys Lys Lys Gly
                165                 170                 175

Lys Lys Ala Gly Pro Pro Gly Pro Asn Gly Pro Pro Gly Pro Pro Gly
            180                 185                 190

Pro Pro Gly Pro Gln Gly Pro Pro Gly Ile Pro Gly Ile Pro Gly Ile
        195                 200                 205

Pro Gly Thr Thr Val Met Gly Pro Pro Gly Pro Pro Gly Pro Pro Gly
    210                 215                 220

Pro Gln Gly Pro Pro Gly Leu Gln Gly Pro Ser Gly Ala Ala Asp Lys
225                 230                 235                 240

Ala Gly Thr Arg Glu Asn Gln Pro Ala Val Val His Leu Gln Gly Gln
                245                 250                 255

Gly Ser Ala Ile Gln Val Lys Asn Asp Leu Ser Gly Gly Val Leu Asn
            260                 265                 270

Asp Trp Ser Arg Ile Thr Met Asn Pro Lys Val Phe Lys Leu His Pro
        275                 280                 285

Arg Ser Gly Glu Leu Glu Val Leu Val Asp Gly Thr Tyr Phe Ile Tyr
    290                 295                 300

Ser Gln Val Glu Val Tyr Tyr Ile Asn Phe Thr Asp Phe Ala Ser Tyr
305                 310                 315                 320

Glu Val Val Val Asp Glu Lys Pro Phe Leu Gln Cys Thr Arg Ser Ile
                325                 330                 335

Glu Thr Gly Lys Thr Asn Tyr Asn Thr Cys Tyr Thr Ala Gly Val Cys
```

-continued

```
                    340                 345                 350
Leu Leu Lys Ala Arg Gln Lys Ile Ala Val Lys Met Val His Ala Asp
            355                 360                 365

Ile Ser Ile Asn Met Ser Lys His Thr Thr Phe Phe Gly Ala Ile Arg
370                 375                 380

Leu Gly Glu Ala Pro Ala Ser
385                 390

<210> SEQ ID NO 3
<211> LENGTH: 1661
<212> TYPE: DNA
<213> ORGANISM: Mus musculus
<220> FEATURE:
<221> NAME/KEY: CDS
<222> LOCATION: (142)..(1275)

<400> SEQUENCE: 3
tcaggaacgg gtccctgcag cccccagccg atggcaggac agtagtcgcc tgtcagggt      60 cgtgaaggac tgaggcagag gcagaggctc ccggagaggc agaggctccc gggcctcaga   120
tagtggttgt ctctggaggc c atg ggc tac cca gag gta gag cgc agg gaa     171
                        Met Gly Tyr Pro Glu Val Glu Arg Arg Glu
                        1               5                     10 ccc ctg cct gcg gca gcg cca agg gag cgg ggc agc cag ggc tgc ggc      219
Pro Leu Pro Ala Ala Ala Pro Arg Glu Arg Gly Ser Gln Gly Cys Gly
            15                  20                  25 tgt cgc ggg gcc cct gct cgg gcg ggc gaa ggg aac agc tgc cgg ctc      267
Cys Arg Gly Ala Pro Ala Arg Ala Gly Glu Gly Asn Ser Cys Arg Leu
        30                  35                  40 ttc ctg ggt ttc ttt ggc ctc tcg ctg gcc ctc cac ctg ctg acg ctg      315
Phe Leu Gly Phe Phe Gly Leu Ser Leu Ala Leu His Leu Leu Thr Leu
    45                  50                  55 tgc tgc tac cta gag ttg cgg tcc gaa ttg cgg cgg gaa cgg gga acc      363
Cys Cys Tyr Leu Glu Leu Arg Ser Glu Leu Arg Arg Glu Arg Gly Thr
60                  65                  70 gag tcc cgc ctc ggt ggc ccg ggt gct cct ggc acc tct ggc acc cta      411
Glu Ser Arg Leu Gly Gly Pro Gly Ala Pro Gly Thr Ser Gly Thr Leu
75                  80                  85                  90 agc agc cct ggg agc ctc gac ccg gtg ggt ccc atc acc cgc cac ctg      459
Ser Ser Pro Gly Ser Leu Asp Pro Val Gly Pro Ile Thr Arg His Leu
                95                  100                 105 ggg cag ccg tcc ttt caa cag cag cct ttg gaa ccg gga gaa gat cca      507
Gly Gln Pro Ser Phe Gln Gln Gln Pro Leu Glu Pro Gly Glu Asp Pro
            110                 115                 120 ctc ccc cct gag tcc cag gac cgg cac cag atg gcc ctc ctg aat ttc      555
Leu Pro Pro Glu Ser Gln Asp Arg His Gln Met Ala Leu Leu Asn Phe
        125                 130                 135 ttc ttt cct gat gaa aag gca tat tct gaa gag gaa agt agg cgt gtt      603
Phe Phe Pro Asp Glu Lys Ala Tyr Ser Glu Glu Glu Ser Arg Arg Val
    140                 145                 150 cgc cgc aat aag aga agc aaa agt ggt gaa gga gca gat ggt cct gtt      651
Arg Arg Asn Lys Arg Ser Lys Ser Gly Glu Gly Ala Asp Gly Pro Val
155                 160                 165                 170 aaa aac aag aaa aag gga aag aag gca ggg cca cct ggg ccc aac ggc      699
Lys Asn Lys Lys Lys Gly Lys Lys Ala Gly Pro Pro Gly Pro Asn Gly
                175                 180                 185 ccc cca gga cct cca gga cct ccg gga ccc cag gga cct cca ggg att      747
Pro Pro Gly Pro Pro Gly Pro Pro Gly Pro Gln Gly Pro Pro Gly Ile
            190                 195                 200 cca gga att cct ggg att cca gga aca act gtt atg gga cca cct ggc      795
```

-continued

```
                Pro Gly Ile Pro Gly Ile Pro Gly Thr Thr Val Met Gly Pro Pro Gly
                                205                 210                 215 cca cct ggc cct cct ggt cct caa gga ccc cct ggc ctc caa gga cct                 843
Pro Pro Gly Pro Pro Gly Pro Gln Gly Pro Pro Gly Leu Gln Gly Pro
    220                 225                 230 tct ggt gct gct gat aaa act gga act cgg gaa aat cag cca gct gtg                 891
Ser Gly Ala Ala Asp Lys Thr Gly Thr Arg Glu Asn Gln Pro Ala Val
235                 240                 245                 250 gtg cat ctg cag ggc caa ggg tca gca att caa gtc aaa aat gat ctt                 939
Val His Leu Gln Gly Gln Gly Ser Ala Ile Gln Val Lys Asn Asp Leu
                255                 260                 265 tca ggt gga gtg ctc aat gac tgg tct cgc atc act atg aac cct aag                 987
Ser Gly Gly Val Leu Asn Asp Trp Ser Arg Ile Thr Met Asn Pro Lys
            270                 275                 280 gtg ttt aaa cta cat ccc cgc agc ggg gag ctg gag gtc tac tac atc                1035
Val Phe Lys Leu His Pro Arg Ser Gly Glu Leu Glu Val Tyr Tyr Ile
        285                 290                 295 aac ttc act gac ttt gcc agc tac gag gtg gtg gtg gat gag aag ccc                1083
Asn Phe Thr Asp Phe Ala Ser Tyr Glu Val Val Val Asp Glu Lys Pro
    300                 305                 310 ttc ctg cag tgc acc cgc agc att gag aca ggg aag acc aac tac aac                1131
Phe Leu Gln Cys Thr Arg Ser Ile Glu Thr Gly Lys Thr Asn Tyr Asn
315                 320                 325                 330 act tgc tat act gca ggc gtg tgc ctc ctc aag gcc agg cag aaa atc                1179
Thr Cys Tyr Thr Ala Gly Val Cys Leu Leu Lys Ala Arg Gln Lys Ile
                335                 340                 345 gcc gtg aag atg gtg cac gct gac atc tct atc aat atg agc aag cac                1227
Ala Val Lys Met Val His Ala Asp Ile Ser Ile Asn Met Ser Lys His
            350                 355                 360 acc acc ttc ttc ggg gcc atc agg ctg ggc gaa gcc cct gca tcc tag                1275
Thr Thr Phe Phe Gly Ala Ile Arg Leu Gly Glu Ala Pro Ala Ser
        365                 370                 375 attctcccat tccatcctgg cccatgcccc tgccccaggt tgggagcca ggactcccag                1335 aacctctaag tgctgctgtg tgtggaatga ggtatactgg cgttgcagcc acaaagagaa              1395
atgccccatg ctatttattc cccagtgact ccaggatgac aaggcctatg tgacttccca              1455
gaaagacctt gagttgccag gacagttgac ggagcccag ggttgtcaag aagcagaacc               1515
ttcttaggct ccctgctgac tggcttatgg tgactcctca acccttaggt ccctcatcag              1575
atgtatcatt tgttgcacta aaatgaggat ccaagacagt aggccacaaa agaaaaggt               1635 gcactccaga ttctaggggt gatccg                                                   1661

<210> SEQ ID NO 4
<211> LENGTH: 377
<212> TYPE: PRT
<213> ORGANISM: Mus musculus

<400> SEQUENCE: 4

Met Gly Tyr Pro Glu Val Glu Arg Arg Glu Pro Leu Pro Ala Ala Ala
1               5                   10                  15

Pro Arg Glu Arg Gly Ser Gln Gly Cys Gly Cys Arg Gly Ala Pro Ala
            20                  25                  30

Arg Ala Gly Glu Gly Asn Ser Cys Arg Leu Phe Leu Gly Phe Phe Gly
        35                  40                  45

Leu Ser Leu Ala Leu His Leu Leu Thr Leu Cys Cys Tyr Leu Glu Leu
    50                  55                  60

Arg Ser Glu Leu Arg Arg Glu Arg Gly Thr Glu Ser Arg Leu Gly Gly
65                  70                  75                  80
```

```
Pro Gly Ala Pro Gly Thr Ser Gly Thr Leu Ser Ser Pro Gly Ser Leu
                85                  90                  95
Asp Pro Val Gly Pro Ile Thr Arg His Leu Gly Gln Pro Ser Phe Gln
            100                 105                 110
Gln Gln Pro Leu Glu Pro Gly Glu Asp Pro Leu Pro Pro Glu Ser Gln
        115                 120                 125
Asp Arg His Gln Met Ala Leu Leu Asn Phe Phe Pro Asp Glu Lys
    130                 135                 140
Ala Tyr Ser Glu Glu Glu Ser Arg Arg Val Arg Arg Asn Lys Arg Ser
145                 150                 155                 160
Lys Ser Gly Glu Gly Ala Asp Gly Pro Val Lys Asn Lys Lys Gly
                165                 170                 175
Lys Lys Ala Gly Pro Pro Gly Pro Asn Gly Pro Gly Pro Gly Pro Gly
            180                 185                 190
Pro Pro Gly Pro Gln Gly Pro Pro Gly Ile Pro Gly Ile Pro Gly Ile
        195                 200                 205
Pro Gly Thr Thr Val Met Gly Pro Gly Pro Pro Gly Pro Pro Gly Pro Gly
    210                 215                 220
Pro Gln Gly Pro Pro Gly Leu Gln Gly Pro Ser Gly Ala Ala Asp Lys
225                 230                 235                 240
Thr Gly Thr Arg Glu Asn Gln Pro Ala Val Val His Leu Gln Gly Gln
                245                 250                 255
Gly Ser Ala Ile Gln Val Lys Asn Asp Leu Ser Gly Gly Val Leu Asn
            260                 265                 270
Asp Trp Ser Arg Ile Thr Met Asn Pro Lys Val Phe Lys Leu His Pro
        275                 280                 285
Arg Ser Gly Glu Leu Glu Val Tyr Tyr Ile Asn Phe Thr Asp Phe Ala
    290                 295                 300
Ser Tyr Glu Val Val Asp Glu Lys Pro Phe Leu Gln Cys Thr Arg
305                 310                 315                 320
Ser Ile Glu Thr Gly Lys Thr Asn Tyr Asn Thr Cys Tyr Thr Ala Gly
                325                 330                 335
Val Cys Leu Leu Lys Ala Arg Gln Lys Ile Ala Val Lys Met Val His
            340                 345                 350
Ala Asp Ile Ser Ile Asn Met Ser Lys His Thr Thr Phe Phe Gly Ala
        355                 360                 365
Ile Arg Leu Gly Glu Ala Pro Ala Ser
    370                 375

<210> SEQ ID NO 5
<211> LENGTH: 630
<212> TYPE: DNA
<213> ORGANISM: Homo sapiens
<220> FEATURE:
<221> NAME/KEY: misc_feature
<222> LOCATION: (65)
<223> OTHER INFORMATION: n represents a, c, t, or g

<400> SEQUENCE: 5
acagtggggg ggaagatggg ctcagggttt agacacatca aacttaaggt acaggtagac     60
tgtgntatgg aaagatggtt ttttatgttg gctatgactg agtggggtca acctttgact    120
gatgtacttg taattttttac agatggccct attgaatttc ttcttccctg atgaaaagcc   180
atactctgaa gaagaaagta ggcgtgttcg ccgcaataaa agaagcaaaa gcaatgaagg    240
agcagatggt aagtctactc agttgatcct ttatcacttc tgaattattt gttagtaaaa    300
```

```
gtatccttttt aagaactacc ttcttggtag ggcatggtgg ctcacgcctg taatcctagc    360
actttgggag gcccacgcgg gcagatcact tgaggtgagg aattcaaaac cagcctggcc    420
aacatggtga aaccctgtct ctactaaaaa tacaaaaaaa attagccggg cctagtccca    480
gctgcttggg agactaaggc aggagaatcg cttgaaactg ggaggtagag gttgcagtga    540
gctgagactg tgccactgca ctccagcctg ggtgacagtg cgagactcca tctcaaaaaa    600
caaaaacaaa caaaaaaaaa cactacccttt                                    630

<210> SEQ ID NO 6
<211> LENGTH: 549
<212> TYPE: DNA
<213> ORGANISM: Homo sapiens

<400> SEQUENCE: 6
acccattccc tcaccccaaa gactgaagta gagagatttt tctccctagg gaagaatctt     60
ccttgaaact tttgtggcct caggagtcag aagacagaat ggggaggttt gatagttgga    120
tccttgccaa aagcctgacc cttggctgtg agactccctc aaatttgcag tgtcttgggg    180
atccctccta gtgactatct tagaaaataa acattttctg ttcatttcca atgacttaat    240
tatctatttt attttttctta taggcccagt taaaaacaag aaaaagggta agttcctgac    300
tttataaaat tgctgtcttg tcatatattt tctaaagtta gaagaaaaaa acaagagtgc    360 gattttttgta ttatattctt tcagcattgt ctgtctgtta ttttattcaa tcatatgtta    420
tcttcttgag tattgtagtt tctgaagaac aagaaatcat tcttcagtga tgattcacct    480 cttttcattct tccttgttct tctccctgcc cttctttta ttctttttttt tttttttttt    540 ttttttttt                                                           549

<210> SEQ ID NO 7
<211> LENGTH: 821
<212> TYPE: DNA
<213> ORGANISM: Homo sapiens

<400> SEQUENCE: 7
aatcccagca ttttgggagg ctgaggcagg cagatcaccc gaagtcagga gtttgagacc     60
aacctggccg acatggtgaa accccgtttt tactaaaaat acaaaaatta gcaggttgcg    120
gtggcaagcg cctgtaatcc cagttaatcc agaggctgag gcaggagaat tgcttgaacc    180
cgggaggtgg aggttgcagt gagccgagat tgtgccactg aactccagcc tgggcaacag    240
agcaggactc cgtctcaaaa aaaaagtaa cactgatcct attttttcagg aaagaaagca    300 ggacctcctg gacccaatgg ccctccagga cccccaggac ctccaggacc caggga ccc    360 ccaggaattc cagggattcc tggaattcca ggaacaactg ttatgggacc acctggtcct    420
ccaggtcctc ctggtcctca aggacccct ggcctccagg gaccttctgg tgagttcccc    480
tgtctctcca ccccaccagg tgcctttaaa gtactttagg agagcaggag tgggtgatcc    540
tgagagcagt ttcaaacggt ggagatgggg ttggtgtgca ataagggatg cagatctcct    600
agcccagtgt aaaactagga attggacaag ccagtagggc ctggcctgct ctagcttctt    660
atatctacca aactgtcaag gacaggccac ctgttcttgc cccatctcaa cccttctgtt    720
acaagccctc cctgactctt ggcctccctg tagtggacca gtaaaactca tatgagccag    780
agacagaggc cctggtggtt cacagggagt tccagtgggg a                        821

<210> SEQ ID NO 8
```

<211> LENGTH: 977
<212> TYPE: DNA
<213> ORGANISM: Homo sapiens

<400> SEQUENCE: 8

```
ttcacacagg gctcagcagt gttaccatgg ccacaagaga tggagttaga gatttttttt      60
caaccaatca ttccttaaat attgagcact ttctgtatac aaagagatat attgatacat     120
ggtcccttt cttatagagt ttatctccta gaggaagaga aacaaagaa acaagatatt      180
tacaaatagc agtgggctct atgaagaaaa ttaatagaaa gggagcaaaa cactagagaa     240
gccaatgcca ttgcctcagg gtcacacagt gatgggaatg ctctctcatt gttctccatg     300
ggtgcccggt ggggcttgcc ttgggctaat attggccaga gcaatactc agaagtttcc     360
ctgctgggtg ctgggcccac tgaagatgaa ggtcagggca ggaaacagaa ggggtgcact     420
ctgactcttc ctccagctct gagccctgga gaataaagct cagacagggc tggctgcagg     480
gagcatggct caccaccact agctgctcag gtgaggggaa aaggaagtca aaagattatg     540
ccctctgatt gtcctatcct attttgcagg tgctgctgat aaagctggaa ctcgagaaaa     600
ccaggttggc tggggattgc tctcttcctg ggtaggaggg aaagccacag gctagagcca     660
cctttaaatt agcttcttat tagatttcct gagctttatt tcatgagaac accccggaga     720
ttctgacggt tttcactcac agcccctcc catctctatg aatagaaaag ctttgcccca     780
gggcatgttt ttagctaagg aaagggtgtc ttgccaggat cattttcct cattccacag     840
gagaccccag gttcaccata gccaggccca gtagtcagct gaataagct gccagtcaga     900
cctattcacc tgagcctcca actccccaac caccccagac accttgccgg ctctcagacc     960
acctgggatc cggagct                                                   977
```

<210> SEQ ID NO 9
<211> LENGTH: 1048
<212> TYPE: DNA
<213> ORGANISM: Homo sapiens
<220> FEATURE:
<221> NAME/KEY: misc_feature
<222> LOCATION: (754)
<223> OTHER INFORMATION: n represents a, c, t, or g

<400> SEQUENCE: 9

```
cggttctcag accacctggg atccggagct gaagagttga agagtatgtc cttgaaaaac      60
agccaaccag ctccaggccc agcctagcct gggcgtctgc cttaatggcc tgaagagctc     120
ctcccagtct ttgagcttcc taatctgtct ctattggcag gttctactgc cttgccttgt     180
ctcatctcag cctcccttgc tacagctgtg tggccacagt gataaatcta cacagctgca     240
cagtgcttga cggcttgcag ggcaatttta tatccatcac ctcatttgat cttcagacat     300
ccctgtgaga gaggccagac attcttataa tccccatttt acagttaggg aaatgaggct     360
cagaggcatt acatttggtt gaggtcacat agctaggaag cggtagagct acaaaatcat     420
attaccctct agtagaaatg tagtcagtaa catcccaaga caggggagag ggatcagaat     480
tggattacaa tagaagacta gaaaccagga tggaaacatg ggactggtgg ctgagcaagc     540
agccattact catagtgact atctctatcc ttctcatcct gccagccagc tgtggtgcat     600
ctacagggcc aagggtcagc aattcaagtc aagaatggta agaatcaaaa taggctctct     660
cccaaagagg agcttctccc ctgcctcctc cccagcctcc aaataatcac ccagcctagt     720
tcctcccagg ccgctgaggt accgttggca tacnaagtca ttctttgctc catcatgccc     780
tctactggct gtcctgagca attgctggca tcaagaccag ttgctacacc caaattgctt     840
```

```
tagaatcact gatgacggag ctgaaaggga cttgagacat catctagccc aggcattctc      900
aggggatgga ggttatatca gagccaccat ggagatatgt gtagttagat taatattttc      960
acaatacaaa ttatagaaag taaaactatg taaaattaaa ttttcttgt ctgatctaca      1020 caggtgggca gacaggctgc atctctca                                          1048
```

<210> SEQ ID NO 10
<211> LENGTH: 831
<212> TYPE: DNA
<213> ORGANISM: Homo sapiens

<400> SEQUENCE: 10

```
attttgcctg tgcaggcccc ataacaacaa agaaaatagg gcagcatgcc cactctcatc       60
ctccaccggc aaattccagc taggaggtat tggttaaaga cccttccaga tgcaagggtc      120
aagaaaggaa ggataaagac agacaggcag agcccaggag ccctgaagca ggcctggcag      180
ctgctttaca aacagaacag cttctctgct ttcaaatgct cttcttaaag tttggccttc      240
taggctaccc tggttgcact gggatagggg tggggttgt gaactccttg gtatttattt       300
tctgttgcct cgattattct gacatgtact gagtgactgc cttctctcat actgagatct      360
ttcaggtgga gtgctcaatg actggtctcg catcactatg aaccccaagg tgtttaagct      420
acatccccgc agcggggagc tggaggtact ggtggacggc acctacttca tctatagtca      480
ggtagaagtg agtacggtct taggcctaac tcttcttata tccagaatgc agatccggtg      540
caggccacat aggggcactg tggagccagc caagaccatc caatggctaa cttcctgctt      600
tgggtgaggg ggtgggggga ccgcactggg agggagttga aaggaggaaa gagagagggg      660
gccagcttct tttgttttgt tttgtttgt ttttccctac ccaaatatta ttgaaaaact      720
gtgaaaaaga ccctcccaca ccctgccatc tgattccctc ctgcagggcc tcaggcccct      780
gtttaccctc tgagctgttt ggctgcactg ccaaacttga acttggtctc a               831
```

<210> SEQ ID NO 11
<211> LENGTH: 743
<212> TYPE: DNA
<213> ORGANISM: Homo sapiens
<220> FEATURE:
<221> NAME/KEY: misc_feature
<222> LOCATION: (302)
<223> OTHER INFORMATION: n represents a, c, t, or g

<400> SEQUENCE: 11

```
gcttcatgtc agggctgggg caggggtggg cgggggaaca ggggcacggt gaagctgcaa       60
atagggcatg gttcttagcc ttacagagtt tgcgacaagt gtgctgttgt aagaaaagtt      120
tgctcagcca gctgagcccc atggactagg ggaagaacaa tgcctgtcac ctgtcctttc      180
ctgttggcca gctagcacgc cttcacatgg cactgcccca tccatggggt atactaacag      240
ctcatctgag aagattctgt caattcacca cagggagggc cccccaccct ctctttcctc      300
tnttccccaa tcccttcttg ttgcctctca tcaggtatac tacatcaact tcactgactt      360
tgccagctat gaggtggtgg tggatgagaa gcccttcctg cagtgcacac gcagcatcga      420
gacgggcaag accaactaca acacttgcta taccgcaggc gtctgcctcc tcaaggcccg      480
gcagaagatc gccgtcaaga tggtgcacgc tgacatctcc atcaacatga gcaagcacac      540
cacgttcttt ggggccatca ggctgggtga agccctgca tcctagattc ccccattttg      600
cctctgtccg tgcccttcc ctgggtttgg gagccaggac tcccaaaacc tctaagtgct      660
```

```
gctgtggagt gaggtgtatt ggtgttgcag ccgcagagaa atgccccatt gttatttatt        720 cccccagtgac tccagggtga caa                                               743

<210> SEQ ID NO 12
<211> LENGTH: 3720
<212> TYPE: DNA
<213> ORGANISM: Mus musculus
<220> FEATURE:
<221> NAME/KEY: CDS
<222> LOCATION: (260)..(1606)
<221> NAME/KEY: misc_feature
<222> LOCATION: (2961)..(3673)
<223> OTHER INFORMATION: n represents a, c, t, or g

<400> SEQUENCE: 12
cagtccagac cgggaacagt caagagcgag ttcccgggag cccttcaaaa tagaaagtta         60
gttgcgctgg cagcagaggt gtgcctggcc gctgtcaccc ggctggcccc aggattgtgg        120
agctctgctt ttgagaggac accgacggac gcctgtgaag cctgcccccc atcccttacc        180
tgctcgcctt ctccgtagac ccatcttctg ctgggaaaag ctaacctcat tcgggtacca        240
ggtgtacttc aagagatc atg gcc cac gtc ggg gac tgc aaa tgg atg tcc         292
                    Met Ala His Val Gly Asp Cys Lys Trp Met Ser
                     1               5                  10 tgg ctc cca gtg ctg gtg gtg tct ctg atg tgc tca gcc aag gcg gag         340
Trp Leu Pro Val Leu Val Val Ser Leu Met Cys Ser Ala Lys Ala Glu
         15                  20                  25 gac tcc aac tgt ggt gag aac gaa tac cac aac cag act acc ggg ctg         388
Asp Ser Asn Cys Gly Glu Asn Glu Tyr His Asn Gln Thr Thr Gly Leu
     30                  35                  40 tgc cag cag tgt cct cca tgc aga cca ggg gag gag ccc tac atg tcc         436
Cys Gln Gln Cys Pro Pro Cys Arg Pro Gly Glu Glu Pro Tyr Met Ser
 45                  50                  55 tgt gga tac ggc act aaa gac gac gac tat ggc tgt gtg ccc tgc cct         484
Cys Gly Tyr Gly Thr Lys Asp Asp Asp Tyr Gly Cys Val Pro Cys Pro
 60                  65                  70                  75 gca gag aag ttc tcc aaa gga ggt tat cag ata tgc agg cgc cac aaa         532
Ala Glu Lys Phe Ser Lys Gly Gly Tyr Gln Ile Cys Arg Arg His Lys
             80                  85                  90 gac tgt gag ggc ttc ttc cgg gcc act gtg ctg aca cca gga gac atg         580
Asp Cys Glu Gly Phe Phe Arg Ala Thr Val Leu Thr Pro Gly Asp Met
         95                  100                 105 gaa aac gac gct gag tgt ggc cca tgt ctc cct ggc tac tac atg ctg         628
Glu Asn Asp Ala Glu Cys Gly Pro Cys Leu Pro Gly Tyr Tyr Met Leu
     110                 115                 120 gaa aac aga ccc agg aac atc tat ggc atg gtc tgc tac tcc tgt ctc         676
Glu Asn Arg Pro Arg Asn Ile Tyr Gly Met Val Cys Tyr Ser Cys Leu
 125                 130                 135 ttg gca cct ccc aac acc aag gaa tgt gtg gga gca act tct ggg gtt         724
Leu Ala Pro Pro Asn Thr Lys Glu Cys Val Gly Ala Thr Ser Gly Val
140                 145                 150                 155 tca gca cac tca tcc agc act tcc ggt ggc agc acc ttg tct ccc ttc         772
Ser Ala His Ser Ser Ser Thr Ser Gly Gly Ser Thr Leu Ser Pro Phe
             160                 165                 170 cag cat gct cac aaa gag ctc tca ggc caa gga cac ctg gcc acc gcc         820
Gln His Ala His Lys Glu Leu Ser Gly Gln Gly His Leu Ala Thr Ala
         175                 180                 185 ctg att att gcc atg tct acg atc ttc atc atg gcc att gcc atc gtc         868
Leu Ile Ile Ala Met Ser Thr Ile Phe Ile Met Ala Ile Ala Ile Val
     190                 195                 200 ctc atc atc atg ttc tac atc atg aag act aag ccg tca gct cca gcc         916
```

```
                Leu Ile Ile Met Phe Tyr Ile Met Lys Thr Lys Pro Ser Ala Pro Ala
                205                 210                 215 tgc tgt agc agt ccc cca gga aag agc gca gaa gcc cca gct aac aca        964
Cys Cys Ser Ser Pro Pro Gly Lys Ser Ala Glu Ala Pro Ala Asn Thr
220                 225                 230                 235 cac gag gag aaa aaa gag gcc cca gac agt gtg gtg acg ttc cct gag       1012
His Glu Glu Lys Lys Glu Ala Pro Asp Ser Val Val Thr Phe Pro Glu
                240                 245                 250 aat ggt gag ttc cag aag ctg aca gca aca ccc aca aag acc ccc aaa       1060
Asn Gly Glu Phe Gln Lys Leu Thr Ala Thr Pro Thr Lys Thr Pro Lys
            255                 260                 265 agt gag aat gat gcc tcc tct gag aac gag cag ttg cta agt cgc agt       1108
Ser Glu Asn Asp Ala Ser Ser Glu Asn Glu Gln Leu Leu Ser Arg Ser
        270                 275                 280 gtg gac agt gat gaa gag cca gcc ccg gac aag cag ggg tcc cca gag       1156
Val Asp Ser Asp Glu Glu Pro Ala Pro Asp Lys Gln Gly Ser Pro Glu
    285                 290                 295 cta tgt ctg ctg tcg cta gtt cac ctg gcc agg gag aag tct gtg acc       1204
Leu Cys Leu Leu Ser Leu Val His Leu Ala Arg Glu Lys Ser Val Thr
300                 305                 310                 315 agt aac aag tct gct ggg atc cag agc cgg agg aaa aag ata ctg gat       1252
Ser Asn Lys Ser Ala Gly Ile Gln Ser Arg Arg Lys Lys Ile Leu Asp
                320                 325                 330 gtg tat gcc aac gtg tgt ggt gtt gtt gaa ggt ctc agc ccc acc gag       1300
Val Tyr Ala Asn Val Cys Gly Val Val Glu Gly Leu Ser Pro Thr Glu
                335                 340                 345 ttg ccg ttt gac tgc ctt gag aag aca agc cga atg ctc agc tct aca       1348
Leu Pro Phe Asp Cys Leu Glu Lys Thr Ser Arg Met Leu Ser Ser Thr
            350                 355                 360 tac aac tct gag aag gcg gtc gtg aaa aca tgg cgc cac ctt gcc gag       1396
Tyr Asn Ser Glu Lys Ala Val Val Lys Thr Trp Arg His Leu Ala Glu
        365                 370                 375 agc ttt gga ctg aag agg gat gag att ggg ggc atg act gat ggc atg       1444
Ser Phe Gly Leu Lys Arg Asp Glu Ile Gly Gly Met Thr Asp Gly Met
380                 385                 390                 395 cag ctc ttt gac cgc atc agc acc gcg ggc tac agc atc cca gag ctg       1492
Gln Leu Phe Asp Arg Ile Ser Thr Ala Gly Tyr Ser Ile Pro Glu Leu
                400                 405                 410 ctc aca aag ttg gtg cag atc gag cgg ctg gat gct gtg gag tcc ttg       1540
Leu Thr Lys Leu Val Gln Ile Glu Arg Leu Asp Ala Val Glu Ser Leu
                415                 420                 425 tgt gca gac ata ttg gag tgg gct ggg gtt gta cca cct gcc tcc cca       1588
Cys Ala Asp Ile Leu Glu Trp Ala Gly Val Val Pro Pro Ala Ser Pro
            430                 435                 440 ccc cca gct gcg tcc tga agagttgtct tggactgtct tccctgggac              1636
Pro Pro Ala Ala Ser
    445 cagctgggga tccaatgaag tcacgaccga cagctgtgag tgatgctatc agactgccaa     1696 aactcaaggc atttcctggt gggtcactgt attccttagg ctgccctaag tagttcattg     1756 agcactcaaa tgaaccaaac catgtgggaa ggacacaggt gaagaatctg atcctgtctt     1816 ttaaggaggc acttagtgag agatgggagc atggtataga ccgtgttacc aaaacatcac    1876 ctaggcaaat gaagggatgc ttttttaaaa agtagcaaaa gttataaggg tgatagagtc    1936 tcaagggtt gaaagtggga acatcctaat gaagaaaata acttcaaggt tttagtaaaa    1996 cggttacaaa gtacaggcat cccacatcct tcatggcctc agacagagca tggtttgctg    2056 gcatgcccta tggtttcaga ggtaactcga cctgtgtttg cagtcacaca ccatggtata    2116
```

-continued

```
agccttgcag tcactagtgg aagaactcac catgtgtcac tgacatacaa ggcgtgtgtc    2176
tgtccagtca caagtgtggg cagatctggc ctccagcacc actcgcagcc acagcagtta    2236
caatgtcagg cttgtcttgc ttcaaaggga cgtgcgtcct atctagaaa ggaaatggtg     2296 acttgctcag agtttgacca tgcctgattc ctgggtgagg ctcgagtgag ttcaggcaca    2356
acatcctgag ccagtgaggg gtggtgcagc ccgagacgca gtacagagct ggggtctgag    2416
gtcctgggca ctgggagagt cattcaaagt gtctgtctcc tccagactta gcttctctta    2476
ggtgagagag gttggtattc acatctgtag tcaggaatgt tgaggctcca gtgagcgaaa    2536
gggtgagtga aagaacacgg aggcagaaga gaagaggcca gaggagcctc catgggtaa    2596 atacagtgtg ggtggccaca aaaatgaga gtcaagggaa acgcagccgc cattctcata    2656
taagggcaac tgtaggactg agcgtttaca gggcttataa acagccattg ctcttggcat    2716
attctcttac tgcacctgta actgccagga atgggagcc aaggaaactt ccccggcagg     2776
gggttaatgc caagctggct gctgggctcc ctcccagagc gctgactgca gagaatgctt    2836
cctttcagta aagctctggt ttagaaggcg gttgggtttt tttgttttac aaggcctatg    2896
actgaacaaa ggctttggag agcaatcagt ggtgtgttta aaaccatcaa gccatttccc    2956
accantgaat atagaccata ctgtgagagg accataatta ggtcctgaat ttttaatatg    3016
atcattttcc tgtgtctgtc tgtgcagtgt ttttttttt tttttaaag aaggcattta      3076 ctccattttg caagttaaat gtctgcttaa ttgtccttt aattcctgag accctgcagt     3136
gtcccttacc cctggtcttc cataatgacg ctgcgattcc ccttaattag acttgtaaat    3196
gtcatgcgtg atgagtgagc aggtcgagga cagcaggctc ttctccaact gtcattgtgc    3256
tgaagaatgg gcagctgcag ccagcggtgt gggctgccct ccattcacac taataggttt    3316
caaggcctga ggcagccagc atccttgttg tttcctagac tccctgcttg ctgctttagg    3376
ggagccagtt cccttgtcat ttaattaaca tggcaataaa ttctggnagg gttggttggc    3436
ttcagtgtgc tttgccaacc aacaagacca cagtgacttt tggtgaccaa tggtggaact    3496
ccacgctgcc atgtttgttt ggagactgtt attatttttt cagtaattaa aggtatttag    3556
taaacaccca agctaggttt gagggcctga gccagtgaag ttttaattgt gaatatttta    3616
tataattttg tttatgtaaa ttattatatt tttataagct caataaacat attgatnaaa    3676
agggaaaaaa aaaaaaaaaa aaaaaaaaaa aaaaaaaaaa aaaa                     3720
```

<210> SEQ ID NO 13
<211> LENGTH: 1347
<212> TYPE: DNA
<213> ORGANISM: Mus musculus
<220> FEATURE:
<221> NAME/KEY: CDS
<222> LOCATION: (1)..(1347)

<400> SEQUENCE: 13

```
atg gcc cac gtc ggg gac tgc aaa tgg atg tcc tgg ctc cca gtg ctg        48
Met Ala His Val Gly Asp Cys Lys Trp Met Ser Trp Leu Pro Val Leu
  1               5                  10                  15 gtg gtg tct ctg atg tgc tca gcc aag gcg gag gac tcc aac tgt ggt        96
Val Val Ser Leu Met Cys Ser Ala Lys Ala Glu Asp Ser Asn Cys Gly
             20                  25                  30 gag aac gaa tac cac aac cag act acc ggg ctg tgc cag cag tgt cct       144
Glu Asn Glu Tyr His Asn Gln Thr Thr Gly Leu Cys Gln Gln Cys Pro
         35                  40                  45 cca tgc aga cca ggg gag gag ccc tac atg tcc tgt gga tac ggc act       192
Pro Cys Arg Pro Gly Glu Glu Pro Tyr Met Ser Cys Gly Tyr Gly Thr
```

-continued

|  |  |
|---|---|
| ```
             50                  55                  60
aaa gac gac gac tat ggc tgt gtg ccc tgc cct gca gag aag ttc tcc
Lys Asp Asp Asp Tyr Gly Cys Val Pro Cys Pro Ala Glu Lys Phe Ser
 65                  70                  75                  80
``` | 240 |
| ```
aaa gga ggt tat cag ata tgc agg cgc cac aaa gac tgt gag ggc ttc
Lys Gly Gly Tyr Gln Ile Cys Arg Arg His Lys Asp Cys Glu Gly Phe
                 85                  90                  95
``` | 288 |
| ```
ttc cgg gcc act gtg ctg aca cca gga gac atg gaa aac gac gct gag
Phe Arg Ala Thr Val Leu Thr Pro Gly Asp Met Glu Asn Asp Ala Glu
                100                 105                 110
``` | 336 |
| ```
tgt ggc cca tgt ctc cct ggc tac tac atg ctg gaa aac aga ccc agg
Cys Gly Pro Cys Leu Pro Gly Tyr Tyr Met Leu Glu Asn Arg Pro Arg
            115                 120                 125
``` | 384 |
| ```
aac atc tat ggc atg gtc tgc tac tcc tgt ctc ttg gca cct ccc aac
Asn Ile Tyr Gly Met Val Cys Tyr Ser Cys Leu Leu Ala Pro Pro Asn
    130                 135                 140
``` | 432 |
| ```
acc aag gaa tgt gtg gga gcc act tct ggg gtt tca gca cac tca tcc
Thr Lys Glu Cys Val Gly Ala Thr Ser Gly Val Ser Ala His Ser Ser
145                 150                 155                 160
``` | 480 |
| ```
agc act tcc ggt ggc agc acc ttg tct ccc ttc cag cat gct cac aaa
Ser Thr Ser Gly Gly Ser Thr Leu Ser Pro Phe Gln His Ala His Lys
                165                 170                 175
``` | 528 |
| ```
gag ctc tca ggc caa gga cac ctg gcc acc gcc ctg att att gcc atg
Glu Leu Ser Gly Gln Gly His Leu Ala Thr Ala Leu Ile Ile Ala Met
                180                 185                 190
``` | 576 |
| ```
tct acg atc ttc atc atg gcc att gcc atc gtc ctc atc atg ttc
Ser Thr Ile Phe Ile Met Ala Ile Ala Ile Val Leu Ile Ile Met Phe
            195                 200                 205
``` | 624 |
| ```
tac atc atg aag act aag ccg tca gct cca gcc tgc tgt agc agt ccc
Tyr Ile Met Lys Thr Lys Pro Ser Ala Pro Ala Cys Cys Ser Ser Pro
    210                 215                 220
``` | 672 |
| ```
cca gga aag agc gca gaa gcc cca gct aac aca cac gag gag aaa aaa
Pro Gly Lys Ser Ala Glu Ala Pro Ala Asn Thr His Glu Glu Lys Lys
225                 230                 235                 240
``` | 720 |
| ```
gag gcc cca gac agt gtg gtg acg ttc cct gag aat ggt gag ttc cag
Glu Ala Pro Asp Ser Val Val Thr Phe Pro Glu Asn Gly Glu Phe Gln
                245                 250                 255
``` | 768 |
| ```
aag ctg aca gca aca ccc aca aag acc ccc aaa agt gag aat gat gcc
Lys Leu Thr Ala Thr Pro Thr Lys Thr Pro Lys Ser Glu Asn Asp Ala
                260                 265                 270
``` | 816 |
| ```
tcc tct gag aac gag cag ttg cta agt cgc agt gtg gac agt gat gaa
Ser Ser Glu Asn Glu Gln Leu Leu Ser Arg Ser Val Asp Ser Asp Glu
            275                 280                 285
``` | 864 |
| ```
gag cca gcc ccg gac aag cag ggg tcc cca gag cta tgt ctg ctg tcg
Glu Pro Ala Pro Asp Lys Gln Gly Ser Pro Glu Leu Cys Leu Leu Ser
    290                 295                 300
``` | 912 |
| ```
cta gtt cac ctg gcc agg gag aag tct gtg acc agt aac aag tct gct
Leu Val His Leu Ala Arg Glu Lys Ser Val Thr Ser Asn Lys Ser Ala
305                 310                 315                 320
``` | 960 |
| ```
ggg atc cag agc cgg agg aaa aag ata ctg gat gtg tat gcc aac gtg
Gly Ile Gln Ser Arg Arg Lys Lys Ile Leu Asp Val Tyr Ala Asn Val
                325                 330                 335
``` | 1008 |
| ```
tgt ggt gtt gtt gaa ggt ctc agc ccc acc gag ttg ccg ttt gac tgc
Cys Gly Val Val Glu Gly Leu Ser Pro Thr Glu Leu Pro Phe Asp Cys
                340                 345                 350
``` | 1056 |
| ```
ctt gag aag aca agc cga atg ctc agc tct aca tac aac tct gag aag
Leu Glu Lys Thr Ser Arg Met Leu Ser Ser Thr Tyr Asn Ser Glu Lys
            355                 360                 365
``` | 1104 |
| ```
gcg gtc gtg aaa aca tgg cgc cac ctt gcc gag agc ttt gga ctg aag
``` | 1152 |

```
Ala Val Val Lys Thr Trp Arg His Leu Ala Glu Ser Phe Gly Leu Lys
        370                 375                 380 agg gat gag att ggg ggc atg act gat ggc atg cag ctc ttt gac cgc      1200
Arg Asp Glu Ile Gly Gly Met Thr Asp Gly Met Gln Leu Phe Asp Arg
385                 390                 395                 400 atc agc acc gcg ggc tac agc atc cca gag ctg ctc aca aag ttg gtg      1248
Ile Ser Thr Ala Gly Tyr Ser Ile Pro Glu Leu Leu Thr Lys Leu Val
                405                 410                 415 cag atc gag cgg ctg gat gct gtg gag tcc ttg tgt gca gac ata ttg      1296
Gln Ile Glu Arg Leu Asp Ala Val Glu Ser Leu Cys Ala Asp Ile Leu
            420                 425                 430 gag tgg gct ggg gtt gta cca cct gcc tcc cca ccc cca gct gcg tcc      1344
Glu Trp Ala Gly Val Val Pro Pro Ala Ser Pro Pro Pro Ala Ala Ser
        435                 440                 445 tga                                                                   1347

<210> SEQ ID NO 14
<211> LENGTH: 1176
<212> TYPE: DNA
<213> ORGANISM: Homo sapiens
<220> FEATURE:
<221> NAME/KEY: CDS
<222> LOCATION: (1)..(1176)

<400> SEQUENCE: 14 atg ggc tac ccg gag gtg gag cgc agg gaa ctc ctg cct gca gca gcg       48
Met Gly Tyr Pro Glu Val Glu Arg Arg Glu Leu Leu Pro Ala Ala Ala
1               5                   10                  15 ccg cgg gag cga ggg agc cag ggc tgc ggg tgt ggc ggg gcc cct gcc       96
Pro Arg Glu Arg Gly Ser Gln Gly Cys Gly Cys Gly Gly Ala Pro Ala
                20                  25                  30 cgg gcg ggc gaa ggg aac agc tgc ctg ctc ttc ctg ggt ttc ttt ggc      144
Arg Ala Gly Glu Gly Asn Ser Cys Leu Leu Phe Leu Gly Phe Phe Gly
            35                  40                  45 ctc tcg ctg gcc ctc cac ctg ctg acg ttg tgc tgc tac cta gag ttg      192
Leu Ser Leu Ala Leu His Leu Leu Thr Leu Cys Cys Tyr Leu Glu Leu
        50                  55                  60 cgc tcg gag ttg cgg cgg gaa cgt gga gcc gag tcc cgc ctt ggc ggc      240
Arg Ser Glu Leu Arg Arg Glu Arg Gly Ala Glu Ser Arg Leu Gly Gly
65                  70                  75                  80 tcg ggc acc cct ggc acc tct ggc acc cta agc agc ctc ggt ggc ctc      288
Ser Gly Thr Pro Gly Thr Ser Gly Thr Leu Ser Ser Leu Gly Gly Leu
                85                  90                  95 gac cct gac agc ccc atc acc agt cac ctt ggg cag ccg tca cct aag      336
Asp Pro Asp Ser Pro Ile Thr Ser His Leu Gly Gln Pro Ser Pro Lys
                100                 105                 110 cag cag cca ttg gaa ccg gga gaa gcc gca ctc cac tct gac tcc cag      384
Gln Gln Pro Leu Glu Pro Gly Glu Ala Ala Leu His Ser Asp Ser Gln
            115                 120                 125 gac ggg cac cag atg gcc cta ttg aat ttc ttc ttc cct gat gaa aag      432
Asp Gly His Gln Met Ala Leu Leu Asn Phe Phe Phe Pro Asp Glu Lys
        130                 135                 140 cca tac tct gaa gaa gaa agt agg cgt gtt cgc cgc aat aaa aga agc      480
Pro Tyr Ser Glu Glu Glu Ser Arg Arg Val Arg Arg Asn Lys Arg Ser
145                 150                 155                 160 aaa agc aat gaa gga gca gat ggc cca gtt aaa aac aag aaa aag gga      528
Lys Ser Asn Glu Gly Ala Asp Gly Pro Val Lys Asn Lys Lys Lys Gly
                165                 170                 175 aag aaa gca gga cct cct gga ccc aat ggc cct cca gga ccc cca gga      576
Lys Lys Ala Gly Pro Pro Gly Pro Asn Gly Pro Pro Gly Pro Pro Gly
            180                 185                 190
```

-continued

| | | |
|---|---|---|
| cct cca gga ccc cag gga ccc cca gga att cca ggg att cct gga att<br>Pro Pro Gly Pro Gln Gly Pro Pro Gly Ile Pro Gly Ile Pro Gly Ile<br>              195                    200                    205 | | 624 |
| cca gga aca act gtt atg gga cca cct ggt cct cca ggt cct cct ggt<br>Pro Gly Thr Thr Val Met Gly Pro Pro Gly Pro Pro Gly Pro Pro Gly<br>210                    215                    220 | | 672 |
| cct caa gga ccc cct ggc ctc cag gga cct tct ggt gct gct gat aaa<br>Pro Gln Gly Pro Pro Gly Leu Gln Gly Pro Ser Gly Ala Ala Asp Lys<br>225                    230                    235                    240 | | 720 |
| gct gga act cga gaa aac cag cca gct gtg gtg cat cta cag ggc caa<br>Ala Gly Thr Arg Glu Asn Gln Pro Ala Val Val His Leu Gln Gly Gln<br>              245                    250                    255 | | 768 |
| ggg tca gca att caa gtc aag aat gat ctt tca ggt gga gtg ctc aat<br>Gly Ser Ala Ile Gln Val Lys Asn Asp Leu Ser Gly Gly Val Leu Asn<br>              260                    265                    270 | | 816 |
| gac tgg tct cgc atc act atg aac ccc aag gtg ttt aag cta cat ccc<br>Asp Trp Ser Arg Ile Thr Met Asn Pro Lys Val Phe Lys Leu His Pro<br>              275                    280                    285 | | 864 |
| cgc agc ggg gag ctg gag gta ctg gtg gac ggc acc tac ttc atc tat<br>Arg Ser Gly Glu Leu Glu Val Leu Val Asp Gly Thr Tyr Phe Ile Tyr<br>290                    295                    300 | | 912 |
| agt cag gta gaa gta tac tac atc aac ttc act gac ttt gcc agc tat<br>Ser Gln Val Glu Val Tyr Tyr Ile Asn Phe Thr Asp Phe Ala Ser Tyr<br>305                    310                    315                    320 | | 960 |
| gag gtg gtg gtg gat gag aag ccc ttc ctg cag tgc aca cgc agc atc<br>Glu Val Val Val Asp Glu Lys Pro Phe Leu Gln Cys Thr Arg Ser Ile<br>              325                    330                    335 | | 1008 |
| gag acg ggc aag acc aac tac aac act tgc tat acc gca ggc gtc tgc<br>Glu Thr Gly Lys Thr Asn Tyr Asn Thr Cys Tyr Thr Ala Gly Val Cys<br>              340                    345                    350 | | 1056 |
| ctc ctc aag gcc cgg cag aag atc gcc gtc aag atg gtg cac gct gac<br>Leu Leu Lys Ala Arg Gln Lys Ile Ala Val Lys Met Val His Ala Asp<br>355                    360                    365 | | 1104 |
| atc tcc atc aac atg agc aag cac acc acg ttc ttt ggg gcc atc agg<br>Ile Ser Ile Asn Met Ser Lys His Thr Thr Phe Phe Gly Ala Ile Arg<br>370                    375                    380 | | 1152 |
| ctg ggt gaa gcc cct gca tcc tag<br>Leu Gly Glu Ala Pro Ala Ser<br>385                    390 | | 1176 |

<210> SEQ ID NO 15
<211> LENGTH: 1134
<212> TYPE: DNA
<213> ORGANISM: Mus musculus
<220> FEATURE:
<221> NAME/KEY: CDS
<222> LOCATION: (1)..(1134)

<400> SEQUENCE: 15

| | | |
|---|---|---|
| atg ggc tac cca gag gta gag cgc agg gaa ccc ctg cct gcg gca gcg<br>Met Gly Tyr Pro Glu Val Glu Arg Arg Glu Pro Leu Pro Ala Ala Ala<br>1                    5                    10                    15 | | 48 |
| cca agg gag cgg ggc agc cag ggc tgc ggc tgt cgc ggg gcc cct gct<br>Pro Arg Glu Arg Gly Ser Gln Gly Cys Gly Cys Arg Gly Ala Pro Ala<br>              20                    25                    30 | | 96 |
| cgg gcg ggc gaa ggg aac agc tgc cgg ctc ttc ctg ggt ttc ttt ggc<br>Arg Ala Gly Glu Gly Asn Ser Cys Arg Leu Phe Leu Gly Phe Phe Gly<br>              35                    40                    45 | | 144 |
| ctc tcg ctg gcc ctc cac ctg ctg acg ctg tgc tgc tac cta gag ttg<br>Leu Ser Leu Ala Leu His Leu Leu Thr Leu Cys Cys Tyr Leu Glu Leu<br>50                    55                    60 | | 192 |

-continued

```
cgg tcc gaa ttg cgg cgg gaa cgg gga acc gag tcc cgc ctc ggt ggc      240
Arg Ser Glu Leu Arg Arg Glu Arg Gly Thr Glu Ser Arg Leu Gly Gly
 65                  70                  75                  80 ccg ggt gct cct ggc acc tct ggc acc cta agc agc cct ggg agc ctc      288
Pro Gly Ala Pro Gly Thr Ser Gly Thr Leu Ser Ser Pro Gly Ser Leu
                 85                  90                  95 gac ccg gtg ggt ccc atc acc cgc cac ctg ggg cag ccg tcc ttt caa      336
Asp Pro Val Gly Pro Ile Thr Arg His Leu Gly Gln Pro Ser Phe Gln
            100                 105                 110 cag cag cct ttg gaa ccg gga gaa gat cca ctc ccc cct gag tcc cag      384
Gln Gln Pro Leu Glu Pro Gly Glu Asp Pro Leu Pro Pro Glu Ser Gln
        115                 120                 125 gac cgg cac cag atg gcc ctc ctg aat ttc ttc ttt cct gat gaa aag      432
Asp Arg His Gln Met Ala Leu Leu Asn Phe Phe Phe Pro Asp Glu Lys
130                 135                 140 gca tat tct gaa gag gaa agt agg cgt gtt cgc cgc aat aag aga agc      480
Ala Tyr Ser Glu Glu Glu Ser Arg Arg Val Arg Arg Asn Lys Arg Ser
145                 150                 155                 160 aaa agt ggt gaa gga gca gat ggt cct gtt aaa aac aag aaa aag gga      528
Lys Ser Gly Glu Gly Ala Asp Gly Pro Val Lys Asn Lys Lys Lys Gly
                165                 170                 175 aag aag gca ggg cca cct ggg ccc aac ggc ccc cca gga cct cca gga      576
Lys Lys Ala Gly Pro Pro Gly Pro Asn Gly Pro Pro Gly Pro Pro Gly
            180                 185                 190 cct ccg gga ccc cag gga cct cca ggg att cca gga att cct ggg att      624
Pro Pro Gly Pro Gln Gly Pro Pro Gly Ile Pro Gly Ile Pro Gly Ile
        195                 200                 205 cca gga aca act gtt atg gga cca cct ggc cca cct ggc cct cct ggt      672
Pro Gly Thr Thr Val Met Gly Pro Pro Gly Pro Pro Gly Pro Pro Gly
210                 215                 220 cct caa gga ccc cct ggc ctc caa gga cct tct ggt gct gct gat aaa      720
Pro Gln Gly Pro Pro Gly Leu Gln Gly Pro Ser Gly Ala Ala Asp Lys
225                 230                 235                 240 act gga act cgg gaa aat cag cca gct gtg gtg cat ctg cag ggc caa      768
Thr Gly Thr Arg Glu Asn Gln Pro Ala Val Val His Leu Gln Gly Gln
                245                 250                 255 ggg tca gca att caa gtc aaa aat gat ctt tca ggt gga gtg ctc aat      816
Gly Ser Ala Ile Gln Val Lys Asn Asp Leu Ser Gly Gly Val Leu Asn
            260                 265                 270 gac tgg tct cgc atc act atg aac cct aag gtg ttt aaa cta cat ccc      864
Asp Trp Ser Arg Ile Thr Met Asn Pro Lys Val Phe Lys Leu His Pro
        275                 280                 285 cgc agc ggg gag ctg gag gtc tac tac atc aac ttc act gac ttt gcc      912
Arg Ser Gly Glu Leu Glu Val Tyr Tyr Ile Asn Phe Thr Asp Phe Ala
290                 295                 300 agc tac gag gtg gtg gtg gat gag aag ccc ttc ctg cag tgc acc cgc      960
Ser Tyr Glu Val Val Val Asp Glu Lys Pro Phe Leu Gln Cys Thr Arg
305                 310                 315                 320 agc att gag aca ggg aag acc aac tac aac act tgc tat act gca ggc     1008
Ser Ile Glu Thr Gly Lys Thr Asn Tyr Asn Thr Cys Tyr Thr Ala Gly
                325                 330                 335 gtg tgc ctc ctc aag gcc agg cag aaa atc gcc gtg aag atg gtg cac     1056
Val Cys Leu Leu Lys Ala Arg Gln Lys Ile Ala Val Lys Met Val His
            340                 345                 350 gct gac atc tct atc aat atg agc aag cac acc acc ttc ttc ggg gcc     1104
Ala Asp Ile Ser Ile Asn Met Ser Lys His Thr Thr Phe Phe Gly Ala
        355                 360                 365 atc agg ctg ggc gaa gcc cct gca tcc tag                             1134
Ile Arg Leu Gly Glu Ala Pro Ala Ser
```

<210> SEQ ID NO 16
<211> LENGTH: 1347
<212> TYPE: DNA
<213> ORGANISM: Homo sapiens
<220> FEATURE:
<221> NAME/KEY: CDS
<222> LOCATION: (1)..(1347)

<400> SEQUENCE: 16

| | | | | | | | | | | | | | | | | |
|---|---|---|---|---|---|---|---|---|---|---|---|---|---|---|---|---|
| atg | gcc | cat | gtg | ggg | gac | tgc | acg | cag | acg | ccc | tgg | ctc | ccc | gtc | ctg | 48 |
| Met | Ala | His | Val | Gly | Asp | Cys | Thr | Gln | Thr | Pro | Trp | Leu | Pro | Val | Leu | |
| 1 | | | | 5 | | | | | 10 | | | | | 15 | | |
| gtg | gtg | tct | ctg | atg | tgc | tca | gcc | cga | gcg | gaa | tac | tca | aac | tgc | ggt | 96 |
| Val | Val | Ser | Leu | Met | Cys | Ser | Ala | Arg | Ala | Glu | Tyr | Ser | Asn | Cys | Gly | |
| | | | 20 | | | | | 25 | | | | | 30 | | | |
| gag | aac | gag | tac | tac | aac | cag | act | acg | ggg | ctg | tgc | cag | gag | tgc | ccc | 144 |
| Glu | Asn | Glu | Tyr | Tyr | Asn | Gln | Thr | Thr | Gly | Leu | Cys | Gln | Glu | Cys | Pro | |
| | 35 | | | | | 40 | | | | | 45 | | | | | |
| ccg | tgt | ggg | ccg | gga | gag | gag | ccc | tac | ctg | tcc | tgt | ggc | tac | ggc | acc | 192 |
| Pro | Cys | Gly | Pro | Gly | Glu | Glu | Pro | Tyr | Leu | Ser | Cys | Gly | Tyr | Gly | Thr | |
| 50 | | | | | 55 | | | | | 60 | | | | | | |
| aaa | gac | gag | gac | tac | ggc | tgc | gtc | ccc | tgc | ccg | gcg | gag | aag | ttt | tcc | 240 |
| Lys | Asp | Glu | Asp | Tyr | Gly | Cys | Val | Pro | Cys | Pro | Ala | Glu | Lys | Phe | Ser | |
| 65 | | | | | 70 | | | | | 75 | | | | | 80 | |
| aaa | gga | ggc | tac | cag | ata | tgc | agg | cgt | cac | aaa | gac | tgt | gag | ggc | ttc | 288 |
| Lys | Gly | Gly | Tyr | Gln | Ile | Cys | Arg | Arg | His | Lys | Asp | Cys | Glu | Gly | Phe | |
| | | | | 85 | | | | | 90 | | | | | 95 | | |
| ttc | cgg | gcc | acc | gtg | ctg | aca | cca | ggg | gac | atg | gag | aat | gac | gct | gag | 336 |
| Phe | Arg | Ala | Thr | Val | Leu | Thr | Pro | Gly | Asp | Met | Glu | Asn | Asp | Ala | Glu | |
| | | | 100 | | | | | 105 | | | | | 110 | | | |
| tgt | ggc | cct | tgc | ctc | cct | ggc | tac | tac | atg | ctg | gag | aac | aga | ccg | agg | 384 |
| Cys | Gly | Pro | Cys | Leu | Pro | Gly | Tyr | Tyr | Met | Leu | Glu | Asn | Arg | Pro | Arg | |
| | 115 | | | | | 120 | | | | | 125 | | | | | |
| aac | atc | tat | ggc | atg | gtc | tgc | tac | tcc | tgc | ctc | ctg | gca | ccc | ccc | aac | 432 |
| Asn | Ile | Tyr | Gly | Met | Val | Cys | Tyr | Ser | Cys | Leu | Leu | Ala | Pro | Pro | Asn | |
| 130 | | | | | 135 | | | | | 140 | | | | | | |
| acc | aag | gaa | tgt | gtg | gga | gcc | act | tca | gga | gct | tct | gcc | aac | ttc | cct | 480 |
| Thr | Lys | Glu | Cys | Val | Gly | Ala | Thr | Ser | Gly | Ala | Ser | Ala | Asn | Phe | Pro | |
| 145 | | | | | 150 | | | | | 155 | | | | | 160 | |
| ggc | acc | tcg | ggc | agc | agc | acc | ctg | tct | ccc | ttc | cag | cac | gcc | cac | aaa | 528 |
| Gly | Thr | Ser | Gly | Ser | Ser | Thr | Leu | Ser | Pro | Phe | Gln | His | Ala | His | Lys | |
| | | | | 165 | | | | | 170 | | | | | 175 | | |
| gaa | ctc | tca | ggc | caa | gga | cac | ctg | gcc | act | gcc | ctg | atc | att | gca | atg | 576 |
| Glu | Leu | Ser | Gly | Gln | Gly | His | Leu | Ala | Thr | Ala | Leu | Ile | Ile | Ala | Met | |
| | | | 180 | | | | | 185 | | | | | 190 | | | |
| tcc | acc | atc | ttc | atc | atg | gcc | atc | gcc | atc | gtc | ctc | atc | atc | atg | ttc | 624 |
| Ser | Thr | Ile | Phe | Ile | Met | Ala | Ile | Ala | Ile | Val | Leu | Ile | Ile | Met | Phe | |
| | 195 | | | | | 200 | | | | | 205 | | | | | |
| tac | atc | ctg | aag | aca | aag | ccc | tct | gcc | cca | gcc | tgt | tgc | acc | agc | cac | 672 |
| Tyr | Ile | Leu | Lys | Thr | Lys | Pro | Ser | Ala | Pro | Ala | Cys | Cys | Thr | Ser | His | |
| 210 | | | | | 215 | | | | | 220 | | | | | | |
| ccg | ggg | aag | agc | gtg | gag | gcc | caa | gtg | agc | aag | gac | gag | gag | aag | aaa | 720 |
| Pro | Gly | Lys | Ser | Val | Glu | Ala | Gln | Val | Ser | Lys | Asp | Glu | Glu | Lys | Lys | |
| 225 | | | | | 230 | | | | | 235 | | | | | 240 | |
| gag | gcc | cca | gac | aac | gtg | gtg | atg | ttc | tcc | gag | aag | gat | gaa | ttt | gag | 768 |
| Glu | Ala | Pro | Asp | Asn | Val | Val | Met | Phe | Ser | Glu | Lys | Asp | Glu | Phe | Glu | |
| | | | | 245 | | | | | 250 | | | | | 255 | | |
| aag | ctg | aca | gca | act | cca | gca | aag | ccc | acc | aag | agc | gag | aac | gat | gcc | 816 |
| Lys | Leu | Thr | Ala | Thr | Pro | Ala | Lys | Pro | Thr | Lys | Ser | Glu | Asn | Asp | Ala | |

```
                          260                 265                 270
tca tcc gag aat gag cag ctg ctg agc cgg agc gtc gac agt gat gag           864
Ser Ser Glu Asn Glu Gln Leu Leu Ser Arg Ser Val Asp Ser Asp Glu
            275                 280                 285 gag ccc gcc cct gac aag cag ggc tcc ccg gag ctg tgc ctg ctg tcg           912
Glu Pro Ala Pro Asp Lys Gln Gly Ser Pro Glu Leu Cys Leu Leu Ser
    290                 295                 300 ctg gtt cac ctg gcc agg gag aag tct gcc acc agc aac aag tca gcc           960
Leu Val His Leu Ala Arg Glu Lys Ser Ala Thr Ser Asn Lys Ser Ala
305                 310                 315                 320 ggg att caa agc cgg agg aaa aag atc ctc gat gtg tat gcc aac gtg          1008
Gly Ile Gln Ser Arg Arg Lys Lys Ile Leu Asp Val Tyr Ala Asn Val
                325                 330                 335 tgt gga gtc gtg gaa ggt ctt agc ccc acg gag ctg cca ttt gat tgc          1056
Cys Gly Val Val Glu Gly Leu Ser Pro Thr Glu Leu Pro Phe Asp Cys
            340                 345                 350 ctc gag aag act agc cga atg ctc agc tcc acg tac aac tct gag aag          1104
Leu Glu Lys Thr Ser Arg Met Leu Ser Ser Thr Tyr Asn Ser Glu Lys
        355                 360                 365 gct gtt gtg aaa acg tgg cgc cac ctc gcc gag agc ttc ggc ctg aag          1152
Ala Val Val Lys Thr Trp Arg His Leu Ala Glu Ser Phe Gly Leu Lys
    370                 375                 380 agg gat gag att ggg ggc atg aca gac ggc atg caa ctc ttt gac cgc          1200
Arg Asp Glu Ile Gly Gly Met Thr Asp Gly Met Gln Leu Phe Asp Arg
385                 390                 395                 400 atc agc acg gca ggc tac agc atc cct gag cta ctc aca aaa ctg gtg          1248
Ile Ser Thr Ala Gly Tyr Ser Ile Pro Glu Leu Leu Thr Lys Leu Val
                405                 410                 415 cag att gag cgg ctg gat gct gtg gag tcc ttg tgt gca gac ata ctg          1296
Gln Ile Glu Arg Leu Asp Ala Val Glu Ser Leu Cys Ala Asp Ile Leu
            420                 425                 430 gag tgg gcg ggg gtt gtg cca cct gcc tcc cag cca cat gct gca tcc          1344
Glu Trp Ala Gly Val Val Pro Pro Ala Ser Gln Pro His Ala Ala Ser
        435                 440                 445 tga                                                                      1347

<210> SEQ ID NO 17
<211> LENGTH: 448
<212> TYPE: PRT
<213> ORGANISM: Homo sapiens

<400> SEQUENCE: 17

Met Ala His Val Gly Asp Cys Thr Gln Thr Pro Trp Leu Pro Val Leu
  1               5                  10                  15

Val Val Ser Leu Met Cys Ser Ala Arg Ala Glu Tyr Ser Asn Cys Gly
             20                  25                  30

Glu Asn Glu Tyr Tyr Asn Gln Thr Thr Gly Leu Cys Gln Glu Cys Pro
         35                  40                  45

Pro Cys Gly Pro Gly Glu Glu Pro Tyr Leu Ser Cys Gly Tyr Gly Thr
     50                  55                  60

Lys Asp Glu Asp Tyr Gly Cys Val Pro Cys Pro Ala Glu Lys Phe Ser
 65                  70                  75                  80

Lys Gly Gly Tyr Gln Ile Cys Arg Arg His Lys Asp Cys Glu Gly Phe
                 85                  90                  95

Phe Arg Ala Thr Val Leu Thr Pro Gly Asp Met Glu Asn Asp Ala Glu
            100                 105                 110

Cys Gly Pro Cys Leu Pro Gly Tyr Tyr Met Leu Glu Asn Arg Pro Arg
        115                 120                 125
```

```
Asn Ile Tyr Gly Met Val Cys Tyr Ser Cys Leu Leu Ala Pro Pro Asn
            130                 135                 140

Thr Lys Glu Cys Val Gly Ala Thr Ser Gly Ser Ala Asn Phe Pro
145                 150                 155                 160

Gly Thr Ser Gly Ser Ser Thr Leu Ser Pro Phe Gln His Ala His Lys
                165                 170                 175

Glu Leu Ser Gly Gln Gly His Leu Ala Thr Ala Leu Ile Ile Ala Met
            180                 185                 190

Ser Thr Ile Phe Ile Met Ala Ile Ala Val Leu Ile Ile Met Phe
        195                 200                 205

Tyr Ile Leu Lys Thr Lys Pro Ser Ala Pro Ala Cys Cys Thr Ser His
    210                 215                 220

Pro Gly Lys Ser Val Glu Ala Gln Val Ser Lys Asp Glu Glu Lys Lys
225                 230                 235                 240

Glu Ala Pro Asp Asn Val Val Met Phe Ser Glu Lys Asp Glu Phe Glu
                245                 250                 255

Lys Leu Thr Ala Thr Pro Ala Lys Pro Thr Lys Ser Glu Asn Asp Ala
            260                 265                 270

Ser Ser Glu Asn Glu Gln Leu Leu Ser Arg Ser Val Asp Ser Asp Glu
        275                 280                 285

Glu Pro Ala Pro Asp Lys Gln Gly Ser Pro Glu Leu Cys Leu Leu Ser
    290                 295                 300

Leu Val His Leu Ala Arg Glu Lys Ser Ala Thr Ser Asn Lys Ser Ala
305                 310                 315                 320

Gly Ile Gln Ser Arg Arg Lys Lys Ile Leu Asp Val Tyr Ala Asn Val
                325                 330                 335

Cys Gly Val Val Glu Gly Leu Ser Pro Thr Glu Leu Pro Phe Asp Cys
            340                 345                 350

Leu Glu Lys Thr Ser Arg Met Leu Ser Ser Thr Tyr Asn Ser Glu Lys
        355                 360                 365

Ala Val Val Lys Thr Trp Arg His Leu Ala Glu Ser Phe Gly Leu Lys
    370                 375                 380

Arg Asp Glu Ile Gly Gly Met Thr Asp Gly Met Gln Leu Phe Asp Arg
385                 390                 395                 400

Ile Ser Thr Ala Gly Tyr Ser Ile Pro Glu Leu Leu Thr Lys Leu Val
                405                 410                 415

Gln Ile Glu Arg Leu Asp Ala Val Glu Ser Leu Cys Ala Asp Ile Leu
            420                 425                 430

Glu Trp Ala Gly Val Val Pro Pro Ala Ser Gln Pro His Ala Ala Ser
        435                 440                 445

<210> SEQ ID NO 18
<211> LENGTH: 4235
<212> TYPE: DNA
<213> ORGANISM: Homo sapiens
<220> FEATURE:
<221> NAME/KEY: CDS
<222> LOCATION: (433)..(1779)

<400> SEQUENCE: 18
gggggcagac ggccgaagag ccaggtgtgc cagggaccta tggcagcagg gctgaacgtg      60
cccgctccag cctctccagt gctgggagag acctctagat ggtgcaggtg agtttgcaat     120
gagggaaagc ccctcggcaa ggactgagtt tccaaacttg cagacagggc agggagcggt     180
caaggaagag ttcccgggaa gcccttaaa cggaaaggaa gcggggctag tgtcagagag      240
```

```
gtgtgccagg tcccaggcag ccctgctgac ccctaaggac atagagtacc tgcttctgag     300
agggctgcca cggtggccac ctgtgaagcc tgtcacccag aactggatgg tacctgactt     360
tcttcataga cccatcttct gctgggactg aagctgacct ccaacagaag ccaggtgagc     420
ccttgggaga gg atg gcc cat gtg ggg gac tgc acg cag acg ccc tgg ctc     471
              Met Ala His Val Gly Asp Cys Thr Gln Thr Pro Trp Leu
               1               5                   10 ccc gtc ctg gtg gtg tct ctg atg tgc tca gcc cga gcg gaa tac tca       519
Pro Val Leu Val Val Ser Leu Met Cys Ser Ala Arg Ala Glu Tyr Ser
        15                  20                  25 aac tgc ggt gag aac gag tac tac aac cag act acg ggg ctg tgc cag       567
Asn Cys Gly Glu Asn Glu Tyr Tyr Asn Gln Thr Thr Gly Leu Cys Gln
 30                  35                  40                  45 gag tgc ccc ccg tgt ggg ccg gga gag gag ccc tac ctg tcc tgt ggc       615
Glu Cys Pro Pro Cys Gly Pro Gly Glu Glu Pro Tyr Leu Ser Cys Gly
                 50                  55                  60 tac ggc acc aaa gac gag gac tac ggc tgc gtc ccc tgc ccg gcg gag       663
Tyr Gly Thr Lys Asp Glu Asp Tyr Gly Cys Val Pro Cys Pro Ala Glu
             65                  70                  75 aag ttt tcc aaa gga ggc tac cag ata tgc agg cgt cac aaa gac tgt       711
Lys Phe Ser Lys Gly Gly Tyr Gln Ile Cys Arg Arg His Lys Asp Cys
         80                  85                  90 gag ggc ttc ttc cgg gcc acc gtg ctg aca cca ggg gac atg gag aat       759
Glu Gly Phe Phe Arg Ala Thr Val Leu Thr Pro Gly Asp Met Glu Asn
 95                 100                 105 gac gct gag tgt ggc cct tgc ctc cct ggc tac tac atg ctg gag aac       807
Asp Ala Glu Cys Gly Pro Cys Leu Pro Gly Tyr Tyr Met Leu Glu Asn
110                 115                 120                 125 aga ccg agg aac atc tat ggc atg gtc tgc tac tcc tgc ctc ctg gca       855
Arg Pro Arg Asn Ile Tyr Gly Met Val Cys Tyr Ser Cys Leu Leu Ala
                130                 135                 140 ccc ccc aac acc aag gaa tgt gtg gga gcc act tca gga gct tct gcc       903
Pro Pro Asn Thr Lys Glu Cys Val Gly Ala Thr Ser Gly Ala Ser Ala
            145                 150                 155 aac ttc cct ggc acc tcg ggc agc agc acc ctg tct ccc ttc cag cac       951
Asn Phe Pro Gly Thr Ser Gly Ser Ser Thr Leu Ser Pro Phe Gln His
        160                 165                 170 gcc cac aaa gaa ctc tca ggc caa gga cac ctg gcc act gcc ctg atc       999
Ala His Lys Glu Leu Ser Gly Gln Gly His Leu Ala Thr Ala Leu Ile
    175                 180                 185 att gca atg tcc acc atc ttc atc atg gcc atc gcc atc gtc ctc atc      1047
Ile Ala Met Ser Thr Ile Phe Ile Met Ala Ile Ala Ile Val Leu Ile
190                 195                 200                 205 atc atg ttc tac atc ctg aag aca aag ccc tct gcc cca gcc tgt tgc      1095
Ile Met Phe Tyr Ile Leu Lys Thr Lys Pro Ser Ala Pro Ala Cys Cys
                210                 215                 220 acc agc cac ccg ggg aag agc gtg gag gcc caa gtg agc aag gac gag      1143
Thr Ser His Pro Gly Lys Ser Val Glu Ala Gln Val Ser Lys Asp Glu
            225                 230                 235 gag aag aaa gag gcc cca gac aac gtg gtg atg ttc tcc gag aag gat      1191
Glu Lys Lys Glu Ala Pro Asp Asn Val Val Met Phe Ser Glu Lys Asp
        240                 245                 250 gaa ttt gag aag ctg aca gca act cca gca aag ccc acc aag agc gag      1239
Glu Phe Glu Lys Leu Thr Ala Thr Pro Ala Lys Pro Thr Lys Ser Glu
    255                 260                 265 aac gat gcc tca tcc gag aat gag cag ctg ctg agc cgg agc gtc gac      1287
Asn Asp Ala Ser Ser Glu Asn Glu Gln Leu Leu Ser Arg Ser Val Asp
270                 275                 280                 285
```

```
agt gat gag gag ccc gcc cct gac aag cag ggc tcc ccg gag ctg tgc      1335
Ser Asp Glu Glu Pro Ala Pro Asp Lys Gln Gly Ser Pro Glu Leu Cys
            290                 295                 300 ctg ctg tcg ctg gtt cac ctg gcc agg gag aag tct gcc acc agc aac      1383
Leu Leu Ser Leu Val His Leu Ala Arg Glu Lys Ser Ala Thr Ser Asn
            305                 310                 315 aag tca gcc ggg att caa agc cgg agg aaa aag atc ctc gat gtg tat      1431
Lys Ser Ala Gly Ile Gln Ser Arg Arg Lys Lys Ile Leu Asp Val Tyr
        320                 325                 330 gcc aac gtg tgt gga gtc gtg gaa ggt ctt agc ccc acg gag ctg cca      1479
Ala Asn Val Cys Gly Val Val Glu Gly Leu Ser Pro Thr Glu Leu Pro
        335                 340                 345 ttt gat tgc ctc gag aag act agc cga atg ctc agc tcc acg tac aac      1527
Phe Asp Cys Leu Glu Lys Thr Ser Arg Met Leu Ser Ser Thr Tyr Asn
350                 355                 360                 365 tct gag aag gct gtt gtg aaa acg tgg cgc cac ctc gcc gag agc ttc      1575
Ser Glu Lys Ala Val Val Lys Thr Trp Arg His Leu Ala Glu Ser Phe
                370                 375                 380 ggc ctg aag agg gat gag att ggg ggc atg aca gac ggc atg caa ctc      1623
Gly Leu Lys Arg Asp Glu Ile Gly Gly Met Thr Asp Gly Met Gln Leu
            385                 390                 395 ttt gac cgc atc agc acg gca ggc tac agc atc cct gag cta ctc aca      1671
Phe Asp Arg Ile Ser Thr Ala Gly Tyr Ser Ile Pro Glu Leu Leu Thr
            400                 405                 410 aaa ctg gtg cag att gag cgg ctg gat gct gtg gag tcc ttg tgt gca      1719
Lys Leu Val Gln Ile Glu Arg Leu Asp Ala Val Glu Ser Leu Cys Ala
        415                 420                 425 gac ata ctg gag tgg gcg ggg gtt gtg cca cct gcc tcc cag cca cat      1767
Asp Ile Leu Glu Trp Ala Gly Val Val Pro Pro Ala Ser Gln Pro His
430                 435                 440                 445 gct gca tcc tga aaagcatgcc tgtgggctgt cctcccagga caagccaagg          1819
Ala Ala Ser atccaacgag ggctctggag ctgtgagtgg tgccaaaaga ctgccaagaa tcaaggcttt    1879
tgtgatatgt caccgtatgc cttaggatgt tcaaggagcc agacgaaata aggcctgtct    1939
tccaatttaa ccaaagataa aggactagag ccgggatact ttcagatgct cgcctgtacc    1999
tcaccaggca gagtaaatat ctactcactc atacagccag cccaccagcc caccattaac    2059
tcactgaaca atgagacaat gttgaggact caaatgaatc aaaccccgtg ggaatgacag    2119
aagtgaagaa tctggtccct gtctttaagg agtttgcact ccagtagaag acagaaggaa    2179
cgtatgttta caaccactt cactggaaga cgtcaaacaa gctgaatgaa ggggcgctta     2239
gaaaacgtta atagaagttc taagcgggag atgactccct actgggatga tgaaggatgg    2299
catcctagtg aagaagcagc tcaaacattt tgataaaatg gcaacaaaat gcagacaccc    2359
tgctccaggt attatttcag gtttagtaca agtctgttaa tacccctatgt ggtttcatta   2419 ggataacttt ttacctatcc ttgaggtcat ccatattctt acaggccttc cagtcaataa    2479
tggaagagct cactctatac aaaaccaata tgcaaggcat gtgtttgtcc aagcaattgg    2539
atgtgtgcag tagccaattt catttactgc attactcttt ggcctgggaa ccctgtggtc    2599
tgcactacat gtgaatggcc ttccacttca gtcttaggca gatttgacct tttaggggca    2659
gcaatgctga aggacacagc aatttaaatt ataatgtgtc aggctgtgtt ttcacttcaa    2719
acatgtatga gtagtcagct gtaattagag aaatgatgac ttcctaagag ttcagccacg    2779
cataattcta gatttcaaga gcatctaaga cttgtggatt agcctcatgg catgagagtt    2839
tcagactcag ccttctgagc cagtcaggga aagtggagtt ctgcagcgca aatgagagcc    2899
```

```
tgggcttggt gtcgagggag ctggcttcta gttgtgccac cttgggcctt gtcttttcct   2959
ctctctgcct cagtttctcg tctgccaatg agatgttagt tagtgattct ataattgggg   3019
caggtagggt tcaggtgagc aaaaagaaag tggagctata ggaaatgcca ggcctttgag   3079
gtgctctatg gaagtcaaca cagtgtggtt tgtccattta aatgggaata aaacagaaa    3139 aactcagact tggcattttc acaataactg caatggtttg acataacatt tataggcaga   3199
aagttaataa actggcattg ttcttggcat attattgtac tatccctgta actgccaaga   3259
gctcaggagc caggctagtg atcacaccag gggttagagt tcactgctga actccctgat   3319
ggcaggtctg tgtttattac tacattaaaa caaagtctct gacttataaa gcgaggtcgt   3379
aaaaattaca agttgcatga ctgaaaaaat gctttagggg gaaaatcagt catatcttta   3439
acaccaacaa gcaatttccc accaacgaat gtagtacata ctgtgagagg atcataatga   3499
ggtcctgaat atttaatatc atcatttact gtgtctgttt gctgctgttt ttcgaaccta   3559
tttggtttac cctgcaagct aaatactcca cggcagagct taattatcct tttaattcct   3619
ctttgaaatc ctgtggtgcc cccttccccc tgccttgtga tgatgatgag tgagtctccc   3679
cttaattaga ctgcaaatgt cacttgtgat gagtgtgcca ttccaggata acagcttgca   3739
ccctcctcag aatgttttca gcgaaagagt gggggtggctg ttctctgctc ctggtgcttt   3799
ggcctcattt cacactatta gaattctggg gctgtaaggc cagccagtgt cagctcatgt   3859
tccattggct ctccacctgc catttttagg gagctattcc ttatatagtt acaaattccc   3919
ttgtcattta cttatttgga aacatgggat ttactctgac aagctttagc ctatgttatg   3979
ggattcagaa caatgagatc ataataattc tcactgacca aagctgggac tccatcctgc   4039
catttttgtg tggagatatt cataattctg caatactttta aaacatttag aaaacacccc   4099
agggtaggtc tgtggcccctt agacagtgaa gtcttaattg tcaatattat ttttgtctaa   4159
ttctgtatat atataactta ttatatttta taatctcaat aaacacatta ataaaaaaaa   4219
aaaaaaaaaa aaaaaa                                                    4235
```

<210> SEQ ID NO 19
<211> LENGTH: 448
<212> TYPE: PRT
<213> ORGANISM: Homo sapiens

<400> SEQUENCE: 19

```
Met Ala His Val Gly Asp Cys Thr Gln Thr Pro Trp Leu Pro Val Leu
 1               5                  10                  15

Val Val Ser Leu Met Cys Ser Ala Arg Ala Glu Tyr Ser Asn Cys Gly
             20                  25                  30

Glu Asn Glu Tyr Tyr Asn Gln Thr Thr Gly Leu Cys Gln Glu Cys Pro
         35                  40                  45

Pro Cys Gly Pro Gly Glu Glu Pro Tyr Leu Ser Cys Gly Tyr Gly Thr
     50                  55                  60

Lys Asp Glu Asp Tyr Gly Cys Val Pro Cys Pro Ala Glu Lys Phe Ser
 65                  70                  75                  80

Lys Gly Gly Tyr Gln Ile Cys Arg Arg His Lys Asp Cys Glu Gly Phe
                 85                  90                  95

Phe Arg Ala Thr Val Leu Thr Pro Gly Asp Met Glu Asn Asp Ala Glu
            100                 105                 110

Cys Gly Pro Cys Leu Pro Gly Tyr Tyr Met Leu Glu Asn Arg Pro Arg
        115                 120                 125

Asn Ile Tyr Gly Met Val Cys Tyr Ser Cys Leu Leu Ala Pro Pro Asn
```

-continued

```
            130                 135                 140
Thr Lys Glu Cys Val Gly Ala Thr Ser Gly Ala Ser Ala Asn Phe Pro
145                 150                 155                 160

Gly Thr Ser Gly Ser Ser Thr Leu Ser Pro Phe Gln His Ala His Lys
                165                 170                 175

Glu Leu Ser Gly Gln Gly His Leu Ala Thr Ala Leu Ile Ile Ala Met
                180                 185                 190

Ser Thr Ile Phe Ile Met Ala Ile Ala Ile Val Leu Ile Ile Met Phe
                195                 200                 205

Tyr Ile Leu Lys Thr Lys Pro Ser Ala Pro Ala Cys Cys Thr Ser His
210                 215                 220

Pro Gly Lys Ser Val Glu Ala Gln Val Ser Lys Asp Glu Lys Lys
225                 230                 235                 240

Glu Ala Pro Asp Asn Val Val Met Phe Ser Glu Lys Asp Glu Phe Glu
                245                 250                 255

Lys Leu Thr Ala Thr Pro Ala Lys Pro Thr Lys Ser Glu Asn Asp Ala
                260                 265                 270

Ser Ser Glu Asn Glu Gln Leu Leu Ser Arg Ser Val Asp Ser Asp Glu
                275                 280                 285

Glu Pro Ala Pro Asp Lys Gln Gly Ser Pro Glu Leu Cys Leu Leu Ser
290                 295                 300

Leu Val His Leu Ala Arg Glu Lys Ser Ala Thr Ser Asn Lys Ser Ala
305                 310                 315                 320

Gly Ile Gln Ser Arg Arg Lys Lys Ile Leu Asp Val Tyr Ala Asn Val
                325                 330                 335

Cys Gly Val Val Glu Gly Leu Ser Pro Thr Glu Leu Pro Phe Asp Cys
                340                 345                 350

Leu Glu Lys Thr Ser Arg Met Leu Ser Ser Thr Tyr Asn Ser Glu Lys
                355                 360                 365

Ala Val Val Lys Thr Trp Arg His Leu Ala Glu Ser Phe Gly Leu Lys
                370                 375                 380

Arg Asp Glu Ile Gly Gly Met Thr Asp Gly Met Gln Leu Phe Asp Arg
385                 390                 395                 400

Ile Ser Thr Ala Gly Tyr Ser Ile Pro Glu Leu Leu Thr Lys Leu Val
                405                 410                 415

Gln Ile Glu Arg Leu Asp Ala Val Glu Ser Leu Cys Ala Asp Ile Leu
                420                 425                 430

Glu Trp Ala Gly Val Val Pro Pro Ala Ser Gln Pro His Ala Ala Ser
                435                 440                 445
```

```
<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primers used to amplify exon 5 of
      EDA1-II.

<400> SEQUENCE: 20
agaaagcagg acctcctgg                                              19

<210> SEQ ID NO 21
<211> LENGTH: 19
<212> TYPE: DNA
<213> ORGANISM: Artificial Sequence
<220> FEATURE:
```

```
<223> OTHER INFORMATION: Description of Artificial Sequence:
      Oligonucleotide primers used to amplify exon 5 of
      EDA1-II.

<400> SEQUENCE: 21
ctctcaggat cacccactc                                                    19

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide primers that can be used to
      diagnose ED.

<400> SEQUENCE: 22
tatgttggct atgactgact gagtgg                                            26

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primers that can be used to
      diagnose ED.

<400> SEQUENCE: 23
ccctaccaag aaggtagttc                                                   20

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide primers that can be used to
      diagnose ED.

<400> SEQUENCE: 24
ctctcaggat cacccactcc tg                                                22

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primers that can be used to
      diagnose ED.

<400> SEQUENCE: 25
tgtcaattca ccacagggag                                                   20

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primers that can be used to
      diagnos ED.

<400> SEQUENCE: 26
gaatctagga tgcaggggc                                                    19
```

```
<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence:
      Oligonucleotide primers that can be used to
      diagnose ED.

<400> SEQUENCE: 27
tattgcggcg aacacg                                                        16

<210> SEQ ID NO 28
<211> LENGTH: 16
<212> TYPE: DNA
<213> ORGANISM: Artificial Sequence
<220> FEATURE:
<223> OTHER INFORMATION: Description of Artificial Sequence:
      Oligonucleotide primers that can be used to
      diagnose ED.

<400> SEQUENCE: 28
tattgcagcg aacacg                                                        16

<210> SEQ ID NO 29
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide primers that can be used to
      diagnose ED.

<400> SEQUENCE: 29
tattgcggca aaacacg                                                       17

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primers used to screen a BAC
      library.

<400> SEQUENCE: 30
atcatggctg tgcactctag                                                    20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primers used to screen a BAC
      library.

<400> SEQUENCE: 31
acctactgca tgtctgtgga                                                    20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primers used to screen a BAC
      library.
```

```
<400> SEQUENCE: 32
cacatgctca gtgttgtcca                                            20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primers used to screen a BAC
      library.

<400> SEQUENCE: 33
acacaggctc agtcatgcgg                                            20

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide primers used to clone a murine dl
      gene.

<400> SEQUENCE: 34
gcggtgaccc gggagatctg aattc                                      25

<210> SEQ ID NO 35
<211> LENGTH: 11
<212> TYPE: DNA
<213> ORGANISM: Artificial Sequence
<220> FEATURE:
<223> OTHER INFORMATION: Description of Artificial Sequence:
      Oligonucleotide primers used to clone a murine dl
      gene.

<400> SEQUENCE: 35
gaattcagat c                                                     11

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primers used to clone a murine dl
      gene.

<400> SEQUENCE: 36
ctgagcggaa ttcgtgagac c                                          21

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide primers used to clone a murine dl
      gene.

<400> SEQUENCE: 37
ggtctcacga attccgctca gtt                                        23

<210> SEQ ID NO 38
<211> LENGTH: 18
<212> TYPE: DNA
<213> ORGANISM: Artificial Sequence
```

```
<220> FEATURE:
<223> OTHER INFORMATION: Description of Artificial Sequence:
      Oligonucleotide primers used to clone a murine dl
      gene.

<400> SEQUENCE: 38
agtgagaatg atgcctcc                                                    18

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primers used to clone a murine dl
      gene.

<400> SEQUENCE: 39
gcctttgttc agtcatagg                                                   19

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primers used to clone a murine dl
      gene.

<400> SEQUENCE: 40
cctgagagct ctttgtgag                                                   19

<210> SEQ ID NO 41
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide primers used to clone a murine dl
      gene.

<400> SEQUENCE: 41
cgggatcctc gaggggggggg ggggggggh                                       29

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primers used to clone a murine dl
      gene.

<400> SEQUENCE: 42
aagcagagct ccacaatc                                                    18

<210> SEQ ID NO 43
<211> LENGTH: 39
<212> TYPE: DNA
<213> ORGANISM: Artificial Sequence
<220> FEATURE:
<223> OTHER INFORMATION: Description of Artificial Sequence:
      Oligonucleotide primers used to clone a murine dl
      gene.
<221> NAME/KEY: misc_feature
<222> LOCATION: (38)..(39)
<223> OTHER INFORMATION: n represents a, c, t, or g; v represents a, g,
      or c
```

-continued

```
<400> SEQUENCE: 43
ggccgctctg gacaggatat gttttttttt tttttttvn                           39

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primers used to clone a murine dl
      gene.

<400> SEQUENCE: 44
ggaacagtca agagcgagtt                                                20

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primers used to clone a murine dl
      gene.

<400> SEQUENCE: 45
gcggatccag gccgctctgg acaggatatg                                     30

<210> SEQ ID NO 46
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide primers that were used to clone
      human DL.

<400> SEQUENCE: 46
tggtgtctct gatgtgc                                                   17

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primers that were used to clone
      human DL.

<400> SEQUENCE: 47
acagtggccc ggaagaag                                                  18

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primers that were used to clone
      human DL.

<400> SEQUENCE: 48
ctgcggtgag aacgagtac                                                 19

<210> SEQ ID NO 49
<211> LENGTH: 18
<212> TYPE: DNA
<213> ORGANISM: Artificial Sequence
```

```
<220> FEATURE:
<223> OTHER INFORMATION: Description of Artificial Sequence:
      Oligonucleotide primers that were used to clone
      human DL.

<400> SEQUENCE: 49
ggcaaggtgg cgccatgt                                              18

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primers that were used to clone
      human DL.

<400> SEQUENCE: 50
ggcaccaaag acgaggacta                                            20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primers that were used to clone
      human DL.

<400> SEQUENCE: 51
tcagcgtcat tctccatgtc                                            20

<210> SEQ ID NO 52
<211> LENGTH: 46
<212> TYPE: DNA
<213> ORGANISM: Artificial Sequence
<220> FEATURE:
<223> OTHER INFORMATION: Description of Artificial Sequence:
      Oligonucleotide primers that were used to clone
      human DL.

<400> SEQUENCE: 52
ctagactcga gaattcgcgg ccgcactagt tttttttttt tttttt              46

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primers that were used to clone
      human DL.

<400> SEQUENCE: 53
tctggtagcc tcctttggaa                                            20

<210> SEQ ID NO 54
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide primers that were used to clone
      human DL.

<400> SEQUENCE: 54
ctagactcga gaattcg                                               17
```

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primers that were used to clone
      human DL.

<400> SEQUENCE: 55
tagtcctcgt ctttggtgcc                                                 20

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primers that were used to clone
      human DL.

<400> SEQUENCE: 56
gagaattcgc ggccgcac                                                   18

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primers that were used to clone
      human DL.

<400> SEQUENCE: 57
agccccgtag tctggttgta                                                 20

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primers that were used to clone
      human DL.

<400> SEQUENCE: 58
gcgtcgacag tgatgagga                                                  19

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primers that were used to clone
      human DL.

<400> SEQUENCE: 59
cagtcttttg gcaccactca                                                 20

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primers that were used to clone
      human DL.

```
<400> SEQUENCE: 60
acgtgtgtgg agtcgtgga                                              19

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primers that were used to clone
      human DL.

<400> SEQUENCE: 61
ctcgttggat ccttggctt                                              19

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primers that were used to clone
      human DL.

<400> SEQUENCE: 62
tacatgctgg agaacagacc                                             20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primers that were used to clone
      human DL.

<400> SEQUENCE: 63
ttccaaagga ggctaccaga                                             20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primers that were used to clone
      human DL.

<400> SEQUENCE: 64
ttggcagaag ctcctgaagt                                             20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primers that were used to clone
      human DL.

<400> SEQUENCE: 65
tgctcgagat gtgatgaagg                                             20

<210> SEQ ID NO 66
<211> LENGTH: 20
<212> TYPE: DNA
```

-continued

<213> ORGANISM: Artificial Sequence
<220> FEATURE:
<223> OTHER INFORMATION: Description of Artificial Sequence:
    Oligonucleotide primers that were used to clone
    human DL.

<400> SEQUENCE: 66
aagcagatgg ccacagaact                                          20

<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence:
    Oligonucleotide primers that were used to clone
    human DL.

<400> SEQUENCE: 67
ggagaggatg gcccatgtg                                           19

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence:
    Oligonucleotide primers that were used to clone
    human DL.

<400> SEQUENCE: 68
cagaccatgc catagatgtt c                                        21

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence:
    Oligonucleotide primers that were used to clone
    human DL.

<400> SEQUENCE: 69
acttcaggag cttctgccaa                                          20

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence:
    Oligonucleotide primers that were used to clone
    human DL.

<400> SEQUENCE: 70
tcgtccttgc tcacttggg                                           19

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence:
    Oligonucleotide primers that were used to clone
    human DL.

<400> SEQUENCE: 71
ggatgaattt gagaagctga c                                        21

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primers that were used to clone
      human DL.

<400> SEQUENCE: 72
ctgacttgtt cgtggtggc                                              19

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primers that were used to clone
      human DL.

<400> SEQUENCE: 73
tccacgactc cacacacgt                                              19

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primers that can be used for
      mutation screening of human DL.

<400> SEQUENCE: 74
aaataaaggt agccagaccc                                             20

<210> SEQ ID NO 75
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primers that can be used for
      mutation screening of human DL.

<400> SEQUENCE: 75
gtaaggggct cagaccact                                              19

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primers that can be used for
      mutation screening of human DL.

<400> SEQUENCE: 76
catgtgtttc taaggaggta c                                           21

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primers that can be used for mutation screening of human DL.

<400> SEQUENCE: 77
caacaatgcc acaagcagga                                       20

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primers that can be used for
      mutation screening of human DL.

<400> SEQUENCE: 78
gtccgtatgg tttggctgc                                        19

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primers that can be used for
      mutation screening of human DL.

<400> SEQUENCE: 79
gccagggttt gccaggag                                         18

<210> SEQ ID NO 80
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primers that can be used for
      mutation screening of human DL.

<400> SEQUENCE: 80
gtccagctca cctgtctct                                        19

<210> SEQ ID NO 81
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primers that can be used for
      mutation screening of human DL.

<400> SEQUENCE: 81
accggctctt tcctacacc                                        19

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primers that can be used for
      mutation screening of human DL.

<400> SEQUENCE: 82
tggagcttct ctggatcatt t                                     21

<210> SEQ ID NO 83
<211> LENGTH: 20

```
<212> TYPE: DNA
<213> ORGANISM: Artificial Sequence
<220> FEATURE:
<223> OTHER INFORMATION: Description of Artificial Sequence:
      Oligonucleotide primers that can be used for
      mutation screening of human DL.

<400> SEQUENCE: 83
aactccaggt gatcgatacc                                              20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primers that can be used for
      mutation screening of human DL.

<400> SEQUENCE: 84
ctgggtcatt catgccttct                                              20

<210> SEQ ID NO 85
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primers that can be used for
      mutation screening of human DL.

<400> SEQUENCE: 85
atggtgtgtg gaagccctg                                               19

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primers that can be used for
      mutation screening of human DL.

<400> SEQUENCE: 86
catgagccaa ttctaactcc t                                            21

<210> SEQ ID NO 87
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primers that can be used for
      mutation screening of human DL.

<400> SEQUENCE: 87
caggacccca gttcagctt                                               19

<210> SEQ ID NO 88
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primers that can be used for
      mutation screening of human DL.

<400> SEQUENCE: 88
```

| | |
|---|---|
| cccaggcact gctaatgac | 19 |

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence:
    Oligonucleotide primers that can be used for
    mutation screening of human DL.

<400> SEQUENCE: 89

| | |
|---|---|
| ccacatctca cagctcatca | 20 |

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence:
    Oligonucleotide primers that can be used for
    mutation screening of human DL.

<400> SEQUENCE: 90

| | |
|---|---|
| tttctactgt tgcccctttc t | 21 |

<210> SEQ ID NO 91
<211> LENGTH: 19
<212> TYPE: DNA
<213> ORGANISM: Artificial Sequence
<220> FEATURE:
<223> OTHER INFORMATION: Description of Artificial Sequence:
    Oligonucleotide primers that can be used for
    mutation screening of human DL.

<400> SEQUENCE: 91

| | |
|---|---|
| cccagccctt catgtcagt | 19 |

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence:
    Oligonucleotide primers that can be used for
    mutation screening of human DL.

<400> SEQUENCE: 92

| | |
|---|---|
| tctattgact gtgacttgca | 20 |

<210> SEQ ID NO 93
<211> LENGTH: 19
<212> TYPE: DNA
<213> ORGANISM: Artificial Sequence
<220> FEATURE:
<223> OTHER INFORMATION: Description of Artificial Sequence:
    Oligonucleotide primers that can be used for
    mutation screening of human DL.

<400> SEQUENCE: 93

| | |
|---|---|
| ctcgttggat ccttggctt | 19 |

<210> SEQ ID NO 94
<211> LENGTH: 425
<212> TYPE: DNA
<213> ORGANISM: Homo sapiens

<400> SEQUENCE: 94

```
ttttttttttt tgggggcaga cggccgaaga gccaggtgtg ccaaggtcat atggcagcag      60
ggctgaacgt gcccgctcca gcctctccag tgctggaaga gacctctaga tggagcaggt     120
gagtttgcaa ttagggaaag cccctcggca aggactgagt tccaaactt gcagacaggg      180 cagggagcgg tcaaggaaga gttcccggga agccctttaa acggaaagga agcggggcta     240
gtgtcagaga ggtgtgacag gtcccagtca gccctgctgg cccctaagga catagagtac     300
ctgcttctga gagggctgcc acggtggcca cctgtgaagc ctgtcaccca gaactggatg     360
gtacctgact tccttcatag acccatcttc tgctgggact gaagctgacc tccaacagaa     420
gccag                                                                 425

<210> SEQ ID NO 95
<211> LENGTH: 434
<212> TYPE: DNA
<213> ORGANISM: Homo sapiens
<220> FEATURE:
<221> NAME/KEY: misc_feature
<222> LOCATION: (1)..(434)
<223> OTHER INFORMATION: n represents a, c, t, or g

<400> SEQUENCE: 95
gtaagccctg gtcctttcct ctggttttct aaactcttca gctgtggccg agacggaggt      60
gtcatgggct gggagagagg ctgggtgcat ttttgaaatg catgtcattt ttgggttgcg     120
tttgaaggtt tcnccaaacc ctctgagcac gagaaacaca atcactancc tcgggtttaa     180
ccttgggccc tccgtgtgct cctagcctcc tntcaggctc cctcccaggc atggctgcna     240
ggctgggaag gccccagagt cagcccaagt ggcatgggtn cagcttcagc ttcatgtctg     300
cttttctttt aggatgtata gtttcccctc tgtttgctgg aaggcacctt atatccagtg     360
gggttaaata aaggtagcca gaccccggc tggggtgcta ccgccagtgc ccagctaatg     420
acgcatnnnt tcag                                                       434

<210> SEQ ID NO 96
<211> LENGTH: 70
<212> TYPE: DNA
<213> ORGANISM: Homo sapiens

<400> SEQUENCE: 96
gtgagcccct tgggagagga tggcccatgt gggggactgc acgcagacgc cctggctccc      60
cgtcctggtg                                                            70

<210> SEQ ID NO 97
<211> LENGTH: 722
<212> TYPE: DNA
<213> ORGANISM: Homo sapiens
<220> FEATURE:
<221> NAME/KEY: misc_feature
<222> LOCATION: (1)..(722)
<223> OTHER INFORMATION: n is a, c, t or g

<400> SEQUENCE: 97
gtaagtggtc tgagccccctt accccacag caccctcatc ctcatgatgg ttggactgtt      60
tcttggcctc ttcagctgta aatgggaat gctgatcata gtccctcctc cacagggttc      120
ttctgagggt gaaatgaaac caggcctgca aagcacagaa ctctgcccca ggctgaagtt     180
acattgattt cgttggtagc tcccttcata gggtctcatg gatataaacg ttcttgattg     240
cttgtttgtg gtgtgataca cacagccctg tgtctatgtg atgagctcat gcttgggggc     300
```

```
cgcgcagcta agaaagactt ggaagactca gaccccctacc cccatcctcc tggacacgcc      360
ggtgttctga ggagccactg tattagaggc tcagtggggg acaggggcgc ctcctccatg      420
accttggcaa gtgcgttgat gaggagaact canagcaggc cttgatggtg ggatggggct      480
tggccagcag gggtgaaggc agggtggttc tagtgggggc tggccgtgcc cangtggatc      540
aaccaggagc cactggagac ttaacagcag tgagcactna caagcggcac cttcccagac      600
cgagccccca gcagagcccc caccgcaggg cacccccttc ctatgtcaac cttggggtct      660
tgcaggagtc acatgtgttt ctaaggaggt acggaggcca caacaccccc ctttgttggc      720
ag                                                                     722

<210> SEQ ID NO 98
<211> LENGTH: 123
<212> TYPE: DNA
<213> ORGANISM: Homo sapiens

<400> SEQUENCE: 98
gtgtctctga tgtgctcagc ccgagcggaa tactcaaact gcggtgagaa cgagtactac       60
aaccagacta cggggctgtg ccaggagtgc ccccgtgtg ggccgggaga ggagccctac      120
ctg                                                                    123

<210> SEQ ID NO 99
<211> LENGTH: 740
<212> TYPE: DNA
<213> ORGANISM: Homo sapiens

<400> SEQUENCE: 99
gtaaggaccc agccctcctg gagcctggtg cgctctcagg ggaggcctcc tgcttgtggc       60
attgttgccc tgagcctgcc ttgctgtgtg aggggatgcc agggtatatc aaaccagccg      120
gtcacgctcc ctggacgttg agattgatgg caagagctgc cgtgagccca ggaatggcac      180
tcaccagcta agcattcata aacagatttt tcaggagttc tgaaatgttt ttaaaggatc      240
actttcccac tctaccctga ttaaatgagc gtcagatcat ctgattggaa gcaggattga      300
aatattctcc agtactagta cattttttcc tgagtgctgc atctcccctcc gcctctgggc      360 aagctaagcc tgagtgttct gttcagcact aagggaaacc tccggggttt cagtgtccgg      420
ttcttgtagc aagctgagga agtcagatg ccaagtgcta cctgcactgc ctgggcattc      480
cagcagctcg ctgaattcat ctcggggagg ctcagaaaag gggcagcatc tggagcctga      540
gagtggcgag gagaggggca agcccagagc atgagctggt tcctgggggg ttttgcagtt      600
aggacaactc aggaaaccaa ggcccggcaa gagtagcttc tggagacagc tggcacgtca      660
ctgcccaagg actgtgggcc gagtccgtat ggtttggctg ctgcactcac ctgtgtcccc      720
tgtcctcttt ccctggacag                                                  740

<210> SEQ ID NO 100
<211> LENGTH: 182
<212> TYPE: DNA
<213> ORGANISM: Homo sapiens

<400> SEQUENCE: 100
tcctgtggct acggcaccaa agacgaggac tacggctgcg tccccctgccc ggcggagaag       60 ttttccaaag gaggctacca gatatgcagg cgtcacaaag actgtgaggg cttcttccgg      120
gccaccgtgc tgacaccagg ggacatggag aatgacgctg agtgtggccc ttgcctccct      180
gg                                                                     182
```

-continued

```
<210> SEQ ID NO 101
<211> LENGTH: 1169
<212> TYPE: DNA
<213> ORGANISM: Homo sapiens
<220> FEATURE:
<221> NAME/KEY: misc_feature
<222> LOCATION: (1)..(1169)
<223> OTHER INFORMATION: n represents a, c, t, or g

<400> SEQUENCE: 101
gtaagcacag gccctcctgg caaaccctgg catgctttct gcagaaaacc ccgaggggct      60
acgggcaagg accttgggaa cagggqtcat ggatactgca ggcctcggtg cagccgcaca     120
cctggccttg gtcccatccc acaaggagca gcatccagga cggagagtcc tggcccctcc     180
ggtggacagg cagcccatca ggctctgcct ctgtgtctcc taagtggcca ttaaccatca     240
taatatcttc tgaccaccaa aaggaaacaa attgcttgaa tacttacagt gcagtagccc     300
atgtgaaaca ctttgggaaa aagaaaactn naatttnatg caaaaagcag tattttnagt     360
attctggnaa cactctggnn aanctactaa taanntanat ntgagaaaag aaatatnant     420
gangagatta tgannncgaa gnnaagnnan gnanaancan annaggntnn agaaaatgag     480
gttgnnaang antnataana tagnacanng ntgatatnca tnggaaagta aacngcntga     540
gnannagtga tttgtgatng ccagggtatt cntngaggga aaacangact attggancag     600
anngtgngga aaggnacaaa cgntgtntna ncataganaa nntagagttg ntgggtgggc     660
attnnaanna gcnggtaaag aatagcttgn aagtngncaa ggggtnccag aggcaannnt     720
aatgcctata natcccataa gnntgcaggc tantggngan ggtgctnaca aagagcatgt     780
tcctcctcca ggaaggtctg gccttngttg gtgtnacccc tgggggggcta ancaggccnt     840
acatgtgggg gcacagggat atttctggtg natgatgtga tggcacacac actaaacaca     900
gccaccagag agaggaacca gaaaggggct gagatcaaaa gaaaggccca cgttggcagc     960
tcaatattgt taaaagaatg ctccatttca agacaggctg aaaccccaag gaaactgagt    1020
ggacagagca ggtgactgag tgggcgtggc ctcatgcccg acttgattgt gggcctgcag    1080
actggccacc gtgctctctg caccagtccc tgcctgtgtg ctgtccagct cacctgtcta    1140
ctgttttgtc cttgtgctct ccnccgtag                                      1169

<210> SEQ ID NO 102
<211> LENGTH: 86
<212> TYPE: DNA
<213> ORGANISM: Homo sapiens

<400> SEQUENCE: 102
ctactacatg ctggagaaca gaccgaggaa catctatggc atggtctgct actcctgcct      60
cctggcaccc cccaacacca aggaat                                          86

<210> SEQ ID NO 103
<211> LENGTH: 484
<212> TYPE: DNA
<213> ORGANISM: Homo sapiens
<220> FEATURE:
<221> NAME/KEY: misc_feature
<222> LOCATION: (1)..(484)
<223> OTHER INFORMATION: n represents a, c, t, or g

<400> SEQUENCE: 103
gtgagtgtct ttgtccttcc accagcacgg tatttgttca ggcacggatc tctttcacta      60
```

```
cagagggtgt aggaaagagc cggtcctggc acctggacaa ggtgaatcac agtaacagca    120
ctagtgaaag tgctcctgtg gcctgtccag gcaggtctat gaaggagggg cgtttgcca     180 catctgagcc ttgagtcaga ggctgaggtt ctagtgcagg ttggccacca gctacctgac    240
aagtcactta acctccatga gcctcggttt tctcatcggt aatatggggg tgaagaaagn    300
acaatancga tgactcttta gggttcatta acagtctaa gaaatacaaa tatttagctc     360
ccctcagcca tcactgcctc aggcccattc atgatcatga atccagatcc atgagctctg    420
tggcagcgtg ctttgaaggt ggagcttctc tggatcattt gagggactct attttgcctt    480
gcag                                                                  484

<210> SEQ ID NO 104
<211> LENGTH: 87
<212> TYPE: DNA
<213> ORGANISM: Homo sapiens

<400> SEQUENCE: 104
gtgtgggagc cacttcagga gcttctgcca acttccctgg cacctcgggc agcagcaccc    60
tgtctccctt ccagcacgcc cacaaag                                        87

<210> SEQ ID NO 105
<211> LENGTH: 799
<212> TYPE: DNA
<213> ORGANISM: Homo sapiens
<220> FEATURE:
<221> NAME/KEY: misc_feature
<222> LOCATION: (1)..(799)
<223> OTHER INFORMATION: n represents a, c, t, or g

<400> SEQUENCE: 105
gtgaggaggg tgctcaggta tcgatcacct ggagttaggt ggtactcgga tgaaagctca    60
gaagaggaga ggaaatgatc atgagtgatg attatggtgc gcttcccac ctggcctcac     120 ctccctaatg taattgaatg acatgttgcc ccccgtgcag gaagtcatta tatctgcaat    180
cagagttgat ccctctatgg gtgtcctggg accgctggga ggtgctggtg gtgaaggcgg    240
gggcatagcg gcaggtggac agcacaggca gctgcaagcc cggccaggag gagagaccag    300
gcgtcctggg ctttggtttg gccgngagtt aacagcaatt ctatcactgg ttttcatata    360
aacatgctga ccatagcact ttaatattaa cttgcanaan gtncattttc attctnccctt   420 aaccagggaa gangggatcg nggaggaccc caangttan tntgcctctc acanttagnc     480
ccccacntgg cttgncntna aggttgccaa agcagtagna gcgagaagca agctcccctta  540 ggaacaatna ggtancccca gaaaaagtct gganaggcca agtctgaggg cagcgagcag    600
gggttgtggg cagtcctggt ctggcagcca aaaccagcgc gnaggatttg gttctcagtc    660
taagcaagca cctcagattt cagggttccc tgaaagcatc ccaggggcag ggccattgct    720
tccaggggcc ggagtcctgg agggaagacc agcagggatc ctgagctctg ggtcattcat    780
gccttctctc cacccacag                                                 799

<210> SEQ ID NO 106
<211> LENGTH: 126
<212> TYPE: DNA
<213> ORGANISM: Homo sapiens

<400> SEQUENCE: 106
aactctcagg ccaaggacac ctggccactg ccctgatcat tgcaatgtcc accatcttca    60
tcatggccat cgccatcgtc ctcatcatca tgttctacat cctgaagaca aagcccctctg   120
```

```
ccccag                                                                 126

<210> SEQ ID NO 107
<211> LENGTH: 96
<212> TYPE: DNA
<213> ORGANISM: Homo sapiens

<400> SEQUENCE: 107
gtgacggccc ccatgcgccg gtgccctgcc tcctggactc tccgtcaact cccctgtcg      60 gagagcctgg ctgctcactc cctcctctct ccccag                                96

<210> SEQ ID NO 108
<211> LENGTH: 75
<212> TYPE: DNA
<213> ORGANISM: Homo sapiens

<400> SEQUENCE: 108
cctgttgcac cagccacccg gggaagagcg tggaggccca agtgagcaag gacgaggaga      60
agaaagaggc cccag                                                       75

<210> SEQ ID NO 109
<211> LENGTH: 243
<212> TYPE: DNA
<213> ORGANISM: Homo sapiens
<220> FEATURE:
<221> NAME/KEY: misc_feature
<222> LOCATION: (1)..(243)
<223> OTHER INFORMATION: n represents a, c, t, or g

<400> SEQUENCE: 109
gtctgtgaac cagggcttcc acacaccatg tgcacggtgc ccatctctgg gtggagggcg      60
ttcccagaag cagcctcctc gctgcttctg ctctcacatg ctgaaccata ctgtgcttac     120
cgtggggtgg tgccacacag acaccgggca gctctgccca acaggaagag cagggttggg     180
ctgagcgcan agccatgagc caattctaac tcctatctcc ccaacctccc catttccctg     240
cag                                                                    243

<210> SEQ ID NO 110
<211> LENGTH: 73
<212> TYPE: DNA
<213> ORGANISM: Homo sapiens

<400> SEQUENCE: 110
acaacgtggt gatgttctcc gagaaggatg aatttgagaa gctgacagca acttcagcaa      60
agcccaccaa gag                                                         73

<210> SEQ ID NO 111
<211> LENGTH: 1174
<212> TYPE: DNA
<213> ORGANISM: Homo sapiens
<220> FEATURE:
<221> NAME/KEY: misc_feature
<222> LOCATION: (1)..(1174)
<223> OTHER INFORMATION: n represents a, c, t, or g

<400> SEQUENCE: 111
gtatgtggaa gccccacac caagctgaac tggggtcctg tggatcctga gcagggaggg       60
gttnccaggg tgcagccgag tgaactgaca ggctagcctg ggacactatg ggacgttcg      120 gcgacagaca gtccccacca cctctttgct gactggcagg ggtcaggtgg tgtgaggagc    180
```

```
ctgtggaaac agctgcctgc tgctctcggg tcaggcccct gtccctgcat cctgccaaat       240
tccctgggcc ttcctcctta acatccgaat tcctcatgcc ccttctccag actgggaggg       300
cagaacataa agccaaggat gcatgcctgt tgcggccaac acaccagtac cacccgtgcc       360
ggtgccagta ctgctgccac cgtaatgctg gtaacaaccg tggtgatgac ggctaacagc       420
atttggtgcc tactgcccac caagtgctgg gctagggctg tgaacacatc ctnccttcca       480
ccagcccang agcaaggtgc ttggaatcat ccctggttat aggaatacca cactgaggta       540
tggaagttgt cactcgccca aagtcacaca ctagtgaaca canggcttgg ggtccgaagt       600
ccangctccc aangagccac atgggngntaa anaggtnagn cagggtcacc ccctaagtt       660 ccaagagggg ggcttttcna ggcacaaagg gttccattna ggttcccttt tcaatgncttt       720 ccagagagcc agcatggatt tcagcgccag cngcatccaa tctgtttgct ttaacatgaa       780
gacaccagtt gaacttgggt gcttactggg attaaataca gagatctagg acatattcaa       840
tgaaccttca cggagcatcc attgtgtgtc aggtagcagg gaaggagagg cccgtggatg       900
cctcccaccc gcagtggcag ccccagcccc ttagacgcct gcaggtcacc caccacggac       960
ttgtttgttt ggaaagaagc aggaagccac cggtgtatgt ctcgtctcat gtcccctggt      1020
cccgtgccca caaggtgccc agtaaacacc tgaaaaacaa gtcattgccc cccactgtcc      1080
acagctgggc aatggacaag ttcaccacag gagaacttgt cagggctgca gccccccag       1140 gcactgctaa tgaccatcgc tcttgttttt gcag                                   1174

<210> SEQ ID NO 112
<211> LENGTH: 160
<212> TYPE: DNA
<213> ORGANISM: Homo sapiens
<220> FEATURE:
<221> NAME/KEY: misc_feature
<222> LOCATION: (1)..(160)
<223> OTHER INFORMATION: n represents a, c, t, or g

<400> SEQUENCE: 112
cgagaacgat gcctcatcng agaatgagca gctgctgagc cggagcgtcg acagtgatga        60
ggagcccgcc cctgacaagc agggctcccc ggagctgtgc ctgctgtcgc tggttcacct       120
ggccagggag aagtctgcca ccagcaacaa gtcagccggg                             160

<210> SEQ ID NO 113
<211> LENGTH: 226
<212> TYPE: DNA
<213> ORGANISM: Homo sapiens
<220> FEATURE:
<221> NAME/KEY: misc_feature
<222> LOCATION: (1)..(226)
<223> OTHER INFORMATION: n represents a, c, t, or g

<400> SEQUENCE: 113
gtgaggctcc tgcaggtgcc atgatgagct gtgagatgtg gctccctcac agccgcaagg        60
actaaaactt tcttattgaa tcagctctcc tgcaagacgg ggtgtttctc ccagaagtcc       120
aagataggag acctggacag tgacaagttc acagcaagat agtcaaaagg gaaaaaaacc       180
ctttcgtttt tgagttttgt tttttttttn ggngatgana gnctng                     226

<210> SEQ ID NO 114
<211> LENGTH: 61
<212> TYPE: DNA
<213> ORGANISM: Homo sapiens

<400> SEQUENCE: 114
```

| attcaaagcc ggaggaaaaa gatcctcgat gtgtatgcca acgtgtgtgg agtcgtggaa | 60 |
| g | 61 |

<210> SEQ ID NO 115
<211> LENGTH: 309
<212> TYPE: DNA
<213> ORGANISM: Homo sapiens
<220> FEATURE:
<221> NAME/KEY: misc_feature
<222> LOCATION: (1)..(309)
<223> OTHER INFORMATION: n represents a, c, t, or g

<400> SEQUENCE: 115

| agagtggnng aagagngaag ggaggngaaa aggggngag ngagggaagg aggngggaan | 60 |
| nnggagtgag gggggaagg ggnagagngg gnggnagngn gnggngagng gganagngaa | 120 |
| agnagtgaga nggaaggna nagngagnag gggnnangag aaagngggag ngtaggnggc | 180 |
| gatgngnnng gtngaaatat tnanagaaat tttttcaaat aatttttatt tcatttaaat | 240 |
| aatttttcag tgttgacctt ctattgactg tgacttgcaa catctaactg tggccattgg | 300 |
| tgtctgtag | 309 |

<210> SEQ ID NO 116
<211> LENGTH: 2781
<212> TYPE: DNA
<213> ORGANISM: Homo sapiens
<220> FEATURE:
<221> NAME/KEY: misc_feature
<222> LOCATION: (1)..(2781)
<223> OTHER INFORMATION: n represents a, c, t, or g

<400> SEQUENCE: 116

| gtcttagccc cacggagctg ccatttgatt gcctcgagaa gactagccga atgctcagct | 60 |
| ccacgtacaa ctctgagaag gctgttgtga aaacgtggcg ccacctcgcc gagagcttcg | 120 |
| gcctgaagag ggatgagatt gggggcatga cagacggcat gcaactcttt gaccgcatca | 180 |
| gcacggcagg ctacagcatc cctgagctac tcacaaaact ggtgcagatt gagcggctgg | 240 |
| atgctgtgga gtccttgtgt gcagacatac tggagtgggc ggggttgtg ccacctgcct | 300 |
| cccagccaca tgctgcatcc tgaaaagcat gcctgtgggc tgtcctccca ggacaagcca | 360 |
| aggatccaac gagggctctg gagctgtgag tggtgccaaa agactgccaa gaatcaaggc | 420 |
| ttttgtgata tgtcaccgta tgccttagga tgttcaagga gccagacgaa ataaggcctg | 480 |
| tcttccaatt taaccaaaga taaggacta gagccgggat actttcanat gctcgcctgt | 540 |
| acctcaccag gcagagtaaa tatctactca ctcatacagc cagcccacca gcccaccatt | 600 |
| aactcactga acaatgagac aatgtngagg actcaaatga atcaaacccc gtgggaatga | 660 |
| cagantgaag aatctggtcc ctgtctttaa ggagtttgca ctccagtaga agacagaagg | 720 |
| aacgtatgtt tacaaaccac ttcactggaa gacgtcaaac aagctgaatg aagggcgct | 780 |
| tagaaaacgt taatagaagt tctaagcggg agatgactcc ctactgggat gatgaaggat | 840 |
| ggcatcctag tgaagaagca gctcaaacat tttgataaaa tggcaacaaa atgcagacac | 900 |
| cctgctccag gtattattc aggtttagta caagtctgtt aatacccat gtggtttcat | 960 |
| taggataact ttttacctat ccttgaggtc atccatattc ttacaggcct tccagtcaat | 1020 |
| aatggaagag ctcactctat acaaaaccaa tatgcaaggc atgtgtttgt ccaagcaatt | 1080 |
| ggatgtgtgc agtagccaat ttcatttact gcattactct ttggcctggg aaccctgtgg | 1140 |

-continued

```
tctgcactac atgtgaatgg ccttccactt caagtcttag gcagatttga ccttttaggg    1200
gcagcaatgc tgaaggacac agcaatttaa attataatgt gtcaggctgt gttttcactt    1260
caaacatgta tgagtagtca gctgtaatta gagaaatgat gacttcctaa gagttcagcc    1320
acgcataatt ctagatttca agagcatcta agacttgtgg attagcctca tggcatgaga    1380
gtttcagact cagccttctg agccagtcag ggaaagtgga gttctgcagc gcaaatgaga    1440
gcctgggctt ggtgtcgagg gagctggctt ctagttgtgc caccttgggc cttgtctttt    1500
cctctctctg cctcagtttc tcgtctgcca atgagatgtt agttagtgat tctataattg    1560
gggcaggtag ggttcaggtg agcaaaaaga agtggagct ataggaaatg ccaggccttt    1620
gaggtgctct atggaagtca acacagtgtg gtttgtccat ttaaatggga ataaaaacag    1680
aaaaactcag acttggcatt ttcacaataa ctgcaatggt tgacataac atttataggc    1740 agaaagttaa taaactggca ttgttcttgg catattattg tactatccct gtaactgcca    1800
agagctcagg agccaggcta gtgatcacac caggggttag agttcactgc tgaactccct    1860
gatggcaggt ctgtgtttat tactacatta aaacaaagtc tctgacttat aaagcgaggt    1920
cgtaaaaatt acaagttgca tgactgaaaa atgctttag ggggaaaatc agtcatatct    1980
ttaacaccaa caagcaattt cccaccaacg aatgtagtac atactgtgag aggatcataa    2040
tgaggtcctg aatatttaat atcatcattt actgtgtctg tttgctgctg tttttcgaac    2100
ctatttggtt taccctgcaa gctaaatact ccacggcaga ncttaattat ccttttaatt    2160
cctctttgaa atcctgtggt gccccttcc ccctgccttg tgatgatgat gagtgagtct    2220
ccccttaatt agactgcaaa tgtcacttgt gatgagtgtg ccattccagg ataacagctt    2280
gcaccctcct cagaatgttt tcagcgaaag agtgggggtgg ctgttctctg ctcctggtgc    2340
tttggcctca tttcacacta ttagaattct ggggctgtaa ggccagccag tgtcagctca    2400
tgttccattg gctctccacc tgccattttt agggagctat tccttatata gttacaaatt    2460
cccttgtcat ttacttattt ggaaacatgg gatttactct gacaagcttt agcctatgtt    2520
atgggattca gaacaatgag atcataataa ttctcactga ccaaagctgg gactccatcc    2580
tgccattttt gtgtggagat attcataatt ctgcaatact ttaaaacatt tagaaaacac    2640
cccagggtag gtctgtggcc cttanacagt gaaagtctta attggcaata ttattttgc    2700 taattctgga tatatataac nnattatatt tataaatctc aataaacccc atttantaaa    2760
aaaaaaaaaa aaaaaaaaa a                                                2781
```

```
<210> SEQ ID NO 117
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide primers that can be used to
      diagnosis ED.

<400> SEQUENCE: 117
aaaaagtaac actgatccta ttt                                              23

<210> SEQ ID NO 118
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primers that can be used to
      diagnosis ED.
```

```
<400> SEQUENCE: 118
agaaagcagg acctcctgg                                                        19

<210> SEQ ID NO 119
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide primer that can be used to amplify
      TNF homology domain of mouse dl.

<400> SEQUENCE: 119
ggattccagg aacaactgtt atgg                                                  24

<210> SEQ ID NO 120
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide primer that can be used to amplify
      TNF homology domain of mouse dl.

<400> SEQUENCE: 120
cctacacaca gcaagcacct tagag                                                 25

<210> SEQ ID NO 121
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide primer that can be used to amplify
      TNF homology domain of mouse dl.

<400> SEQUENCE: 121
gtcgacgaaa atcagccagc tg                                                    22

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer that can be used to amplify
      TNF homology domain of mouse dl.

<400> SEQUENCE: 122
aagcttctag gatgcagggg c                                                     21
```